(12) United States Patent
Salunke et al.

(10) Patent No.: US 9,676,818 B2
(45) Date of Patent: Jun. 13, 2017

(54) TOLL-LIKE RECEPTOR 2-AGONISTIC LIPOPEPTIDES, AND METHOD OF MAKING THE SAME

(71) Applicant: University of Kansas, Lawrence, KS (US)

(72) Inventors: Deepak B. Salunke, Lawrence, KS (US); Xiaoqiang Guo, Lawrence, KS (US); Sunil A. David, Lawerence, KS (US)

(73) Assignee: University of Kansas, Lawrence, KS (US)

(*) Notice: Subject to any disclaimer, the term of this patent is extended or adjusted under 35 U.S.C. 154(b) by 1 day.

(21) Appl. No.: 14/761,805

(22) PCT Filed: Jan. 17, 2014

(86) PCT No.: PCT/US2014/011985
§ 371 (c)(1),
(2) Date: Jul. 17, 2015

(87) PCT Pub. No.: WO2014/113634
PCT Pub. Date: Jul. 24, 2014

(65) Prior Publication Data
US 2015/0337009 A1 Nov. 26, 2015

Related U.S. Application Data

(60) Provisional application No. 61/753,690, filed on Jan. 17, 2013.

(51) Int. Cl.
| | | |
|---|---|---|
| A61K 38/00 | (2006.01) | |
| C07K 5/068 | (2006.01) | |
| A61K 39/39 | (2006.01) | |
| C07K 14/705 | (2006.01) | |
| C07K 5/062 | (2006.01) | |
| A61K 39/00 | (2006.01) | |

(52) U.S. Cl.
CPC .......... C07K 5/06086 (2013.01); A61K 39/39 (2013.01); C07K 5/0606 (2013.01); C07K 14/705 (2013.01); A61K 38/00 (2013.01); A61K 2039/55516 (2013.01)

(58) Field of Classification Search
None
See application file for complete search history.

(56) References Cited

U.S. PATENT DOCUMENTS

| | | | |
|---|---|---|---|
| 3,710,795 | A | 1/1973 | Higuchi et al. |
| 5,232,913 | A | 8/1993 | Ohmori et al. |
| 5,262,564 | A | 11/1993 | Kun et al. |
| 6,011,020 | A | 1/2000 | Gold et al. |
| 2010/0285051 | A1 | 11/2010 | Lemoine et al. |

FOREIGN PATENT DOCUMENTS

| | | |
|---|---|---|
| WO | WO2011119759 | 9/2011 |
| WO | PCTCN2012084982 | 5/2014 |

OTHER PUBLICATIONS

Ouaissi, A. et al, "The trypanosoma cruzi Tc52-released protein induces human dentritic cell maturation, signals via toll-like receptor 2, and confers protection against lethal injection", Journal Immunology, 168:2:6366-6374, retrieved from the Internet Apr. 15, 2015, http://www.jimmunol.org/content/168/12/6366.full.pdf (2002).
Relyveld, E. et al, "Rational approaches to reduce adverse reactions in man to vaccines containing tetanus and diphtheria toxoids", Vaccine, 16:9-10:1016-1023, (1998).
Gupta, R. , "Aluminum compounds as vaccine adjuvants", Drug Delivery Rev., vol. 32, pp. 155-172, (1998).
Kumagai, Y. et al, "Pathogen recognition by innate receptors", Infect. Chemother., 14:2:86-92, (Apr. 2008).
Takeda, K. et al, "Using bioinformatics tools for the sequence analysis of immunoglobulins and T cell receptors: Toll Receptors", Current Protocols in Immunology, Chapter 14, Unit 14.12, pp. 2-12, (2007).
Akira, S. "Toll-like receptors and innate immunity", Adv. Immunol, vol. 78, pp. 1-56, (1902).
Akira, S. et al, "Toll-like receptors: critical proteins linking innate and acquired immunity", Nature Immunology, 2:8:675-680, (2001).
Cottalorda, A. et al, "TLR2 engagement on CD8 T cells lowers the threshold for optimal antigen-induced T cell activation", Eur. J. Immunol., vol. 36, pp. 1684-1693, (2006).
Kaisho, T. et al, "Toll-like receptors as adjuvant receptors", Biochim. Biophys. Acta, vol. 1589:1:1-13, (Feb. 13, 2002).
Agnihotri, G. et al, "Structure-activity relationships in toll-like receptor 2-agonists leading to simplified monoacyl lipopeptides", J. Med. Chem., vol. 54:23:8148-8160, (Dec. 8, 2011).
Ukani, R. et al, "Potent adjuvantic activity of a CCR1-agonistic Bis-Quinoline", Bioorg. Med. Chem. Lett., 22:1:293-295, (Jan. 1, 2012).
Jin, M. et al, "Crystal structure of the TLR1-TLR2 heterodimer induced by binding of a tri-acylated lipopeptide", Cell, vol. 130, pp. 1071-1082, (Sep. 21, 2007).
Kang, J. et al, "Structural biololgy of the toll-like receptor family", Annu. Rev. Biochem., vol. 80, pp. 917-941, (2011).
Shukla, N. et al, "Regioisomerism-dependent TLR7 agonism and antagonism in an imidazoquinoline", Bioorg. Med. Chem. Lett, 19:8:2211-2214, (Apr. 15, 2009).

(Continued)

*Primary Examiner* — Jeanette Lieb
(74) *Attorney, Agent, or Firm* — McHale & Slavin, P.A.

(57) ABSTRACT

The present disclosure is directed to a novel class of toll-like receptor 2-agonistic (TLR2) lipopeptide compounds having specific structures, and synthetic methods of making the compounds. These compounds provide high potency of agonistic activities with human, other than murine, TLR2, and are useful as vaccine adjuvants. Vaccines are perhaps one of the most successful medical interventions against infectious disease.

9 Claims, 14 Drawing Sheets

(56) References Cited

OTHER PUBLICATIONS

Wu, W. et al, "Structure-activity relationships in toll-like receptor-2 agonistic diacylthioglycerol lipipeptides", J. Med. Chem., vol. 53:8:3198-3213, (Apr. 22, 2010).
Shukla, N. et al, "Preliminary evaluation of a 3H imidazoquinoline library as dual TLR7/TLR8 antagonists", Bioorg. Med. Chem. 19:12:3801-3811, (Jun. 15, 2011).
Pullen, G. et al, "Antibody avidity determination by ELISA using thiocyanate elution", J. Immunol. Methods, vol. 86, pp. 83-87, (1986).
MacDonald, R. et al, "The measurement of relative antibody affinity by ELISA using thiocyanate elution", J. Immunol. Methods, vol. 106, pp. 191-194, (1988).
Jin, M. et al, "Structures of TLR-ligand complexes", Cur. Opin. Immunol., vol. 20, pp. 414-419, (2008).
Seyberth, T. et al, "Lipolanthionine peptides act as inhibitors of TLR2-medicated IL-8 secretion, synthesis and structure—activity relationships", J. Med. Chem., vol. 49, pp. 1754-1765, (2006).
Hood, J. et al, "Immunoprofiling toll-like receptor ligands Comparison of immunostimulatory and proinflammatory profiles in ex vivo human blood models", Human Vaccines, 6:4:322-335, (2010).
Krantz, D. et al, "Partial elucidation of an anti-hapten repertoire in BALB/c mice: comparative characterization of several monoclonal antifluorescyl antibodies", Molecular Immunology, 18:10:889-898, (1981).

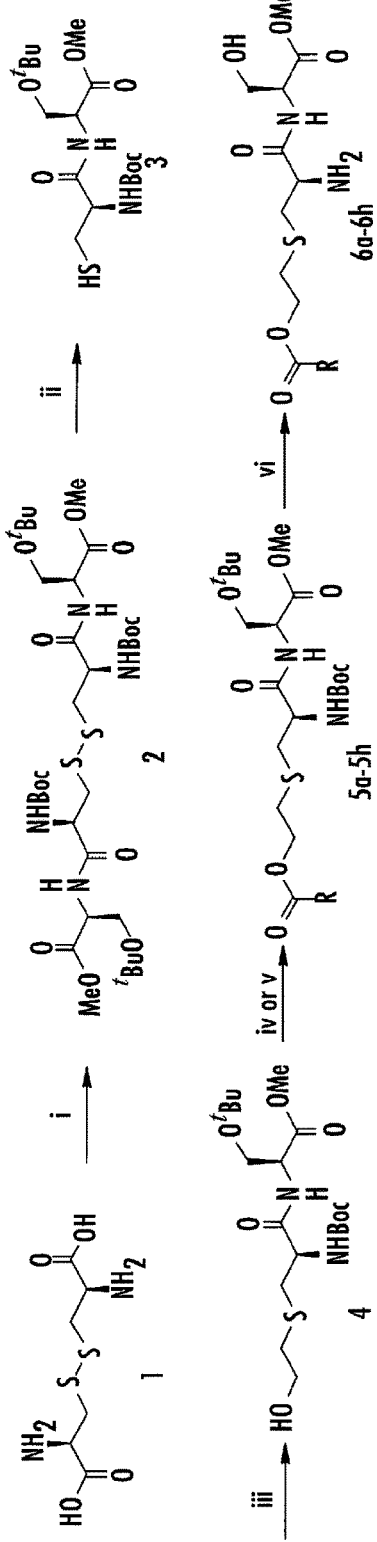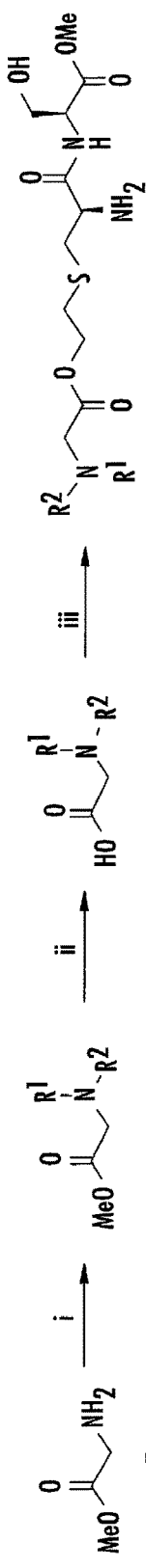
FIG. 7

GENERAL SCHEME 3:

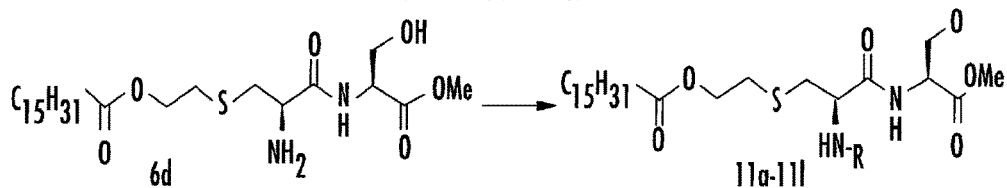

| COMPOUNDS | R | REAGENTS AND CONDITIONS |
|---|---|---|
| 11a | $-C_2H_5$ | $CH_3CHO, CH_3COOH, MP-CNBH_3, CH_2Cl_2$ |
| 11b | $-C_8H_{17}$ | $C_7H_{15}CHO, CH_3COOH, MP-CNBH_3, CH_2Cl_2$ |
| 11c | $-C_{16}H_{33}$ | $C_{16}H_{33}Br, Et_3N, CH_2Cl_2$ |
| 11d | $-COCH_3$ | $(CH_3CO)_2O, Et_3N, CH_2Cl_2$ |
| 11e | $-COC_3H_7$ | $C_3H_7COCl$, pyridine |
| 11f | $-COC_7H_{15}$ | $C_7H_{15}COCl$, pyridine |
| 11g | $-COC_{15}H_{31}$ | $C_{15}H_{31}COCl$, pyridine |
| 11h | $-COCF_3$ | $(CF_3CO)_2O, Et_3N, CH_2Cl_2$ |
| 11i | $-COCCl_3$ | $EDCl \cdot HCl, HOBt, CCl_3COOH, CH_2Cl_2$ |
| 11j | $-SO_2CH_3$ | $(CH_3SO_2)_2O, Et_3N, CH_2Cl_2$ |
| 11k | $-SO_2CF_3$ | $(CF_3SO_2)_2O, Et_3N, CH_2Cl_2$ |
| 11l | $-SO_2C_6H_4CH_3$ | $CH_3C_6H_4SO_2Cl, Et_3N, CH_2Cl_2$ |

GENERAL SCHEME 4:

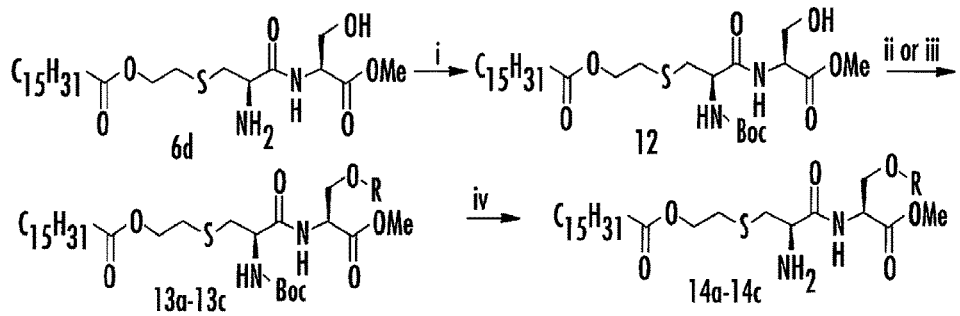

a, R=-$COCH_3$; b, R=-$COC_3CH_7$; c, R=-$COC_{15}H_{31}$

REAGENTS AND CONDITIONS: i. $(Boc)_2O, Et_3N, CH_2Cl_2$; FOR COMPOUND 13a: ii.$(CH_3CO)_2O$, PYRIDINE; FOR COMPOUND 13b-13c: iii. RCl, $Et_3N$, TH, iv. $CF_3COOH$.

FIG. 8

GENERAL SCHEME 8:
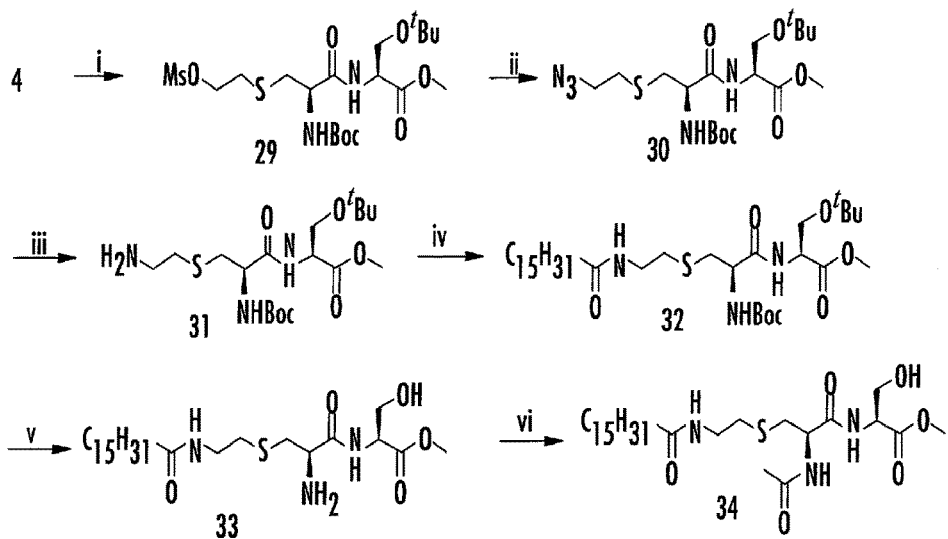
REAGENTS AND CONDITIONS: i. MsCl, Et₃N, DCM; ii PPH₃, THF, H₂O; iv. C₁₅H₃₁COCl, DCM; v. TFA; vi. Ac₂O, Et₃N, DCM
GENERAL SCHEME 9:
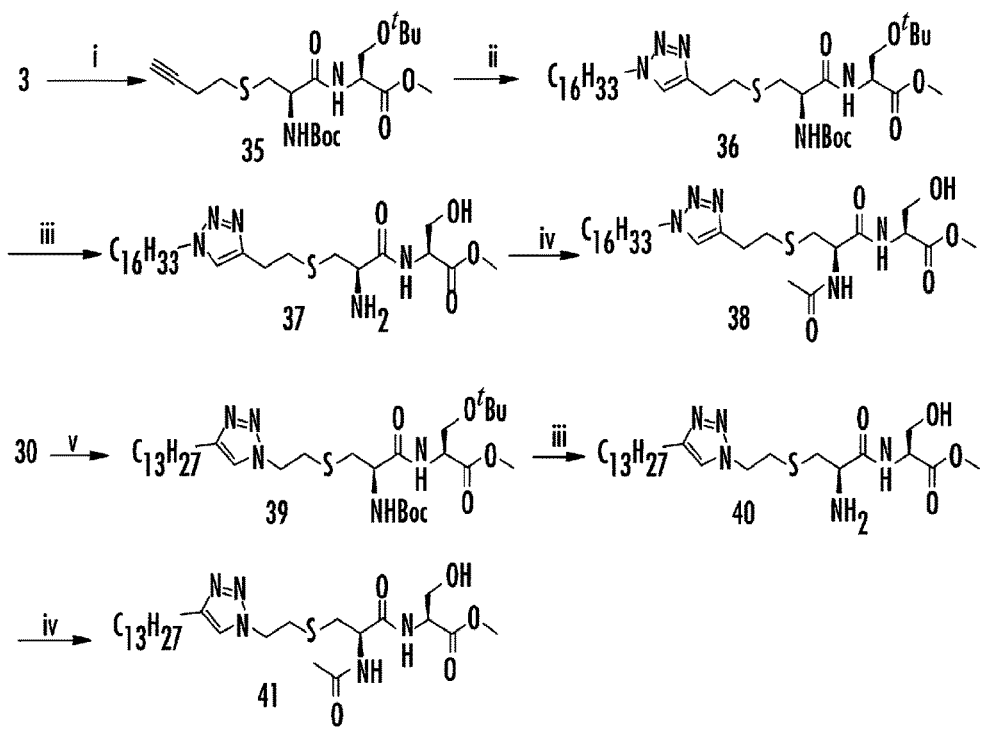
REAGENTS AND CONDITIONS: i. 4-BROMOBUT-1-YNE, Et₃N, DMF; ii 1-AZIDOHEXADECANE, CuSO₄, SODIUM ASCORBATE, THF, H₂O; iii. TFA; iv. Ac₂O, PYRIDINE, DCM; v. PENTADEC-1-YNE, CuSO₄, SODIUM ASCORBATE, THF, H₂O
FIG. 11

GENERAL SCHEME 10:
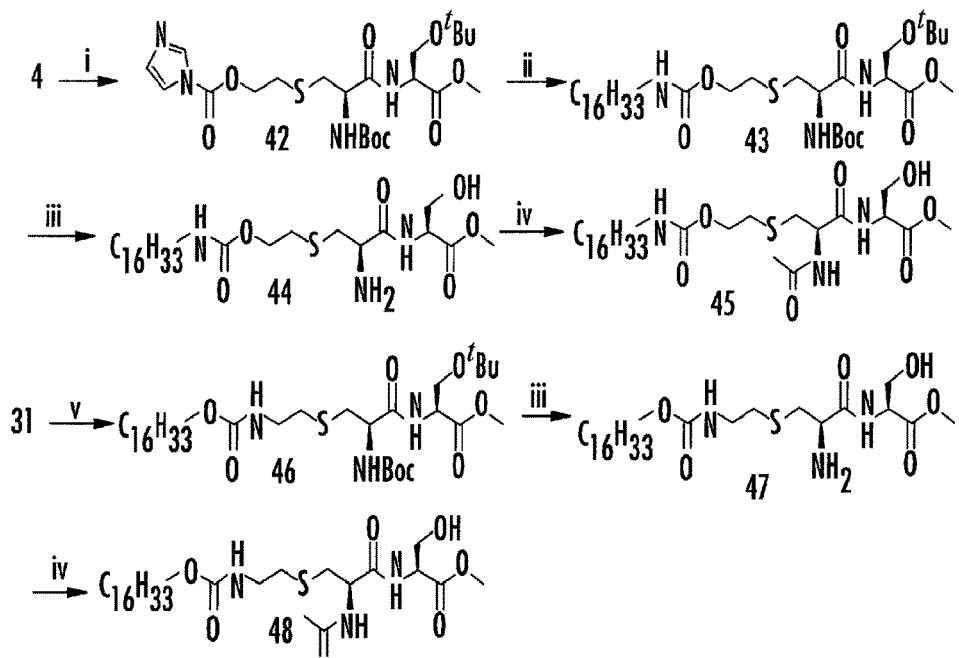
REAGENTS AND CONDITIONS: i. CDI, DCM; ii. $C_{16}H_{33}NH_2$, DCM; iii TFA; iv. $Ac_2O$, PYRIDINE, DCM; v. CETYL CHLOROFORMATE, $Et_3N$, DCM.
GENERAL SCHEME 11:
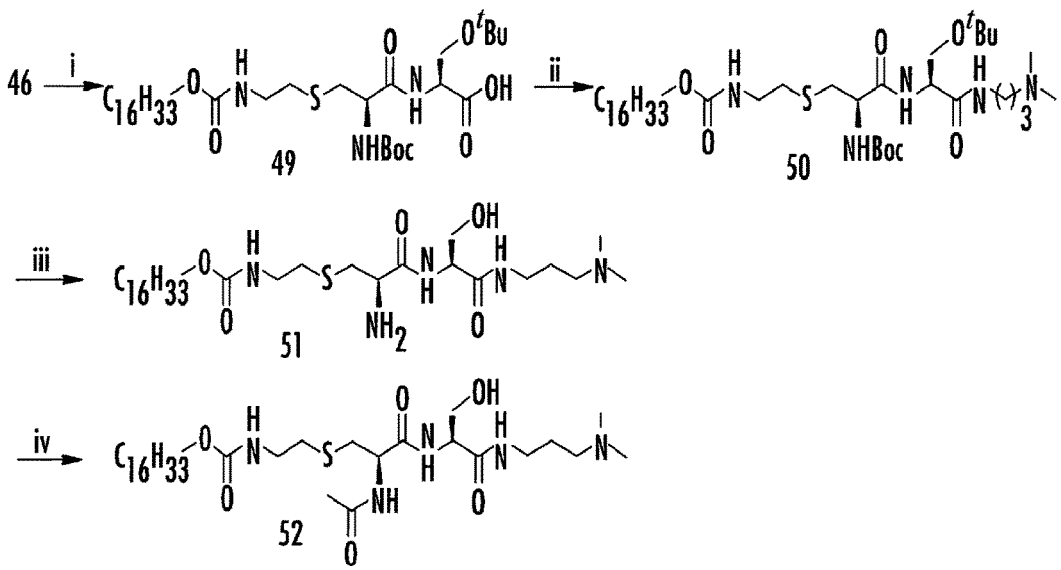
REAGENTS AND CONDITIONS: i.$(CH_3)_3$SnOH, DCE; ii. N,n-DIMETHYLETHYLENEDIAMINE, EDCl, HOBT, NMM, DMF; iii. TFA; iv. $Ac_2O$, $ET_3N$, DCM.
*FIG. 12*

GENERAL SCHEME 12:

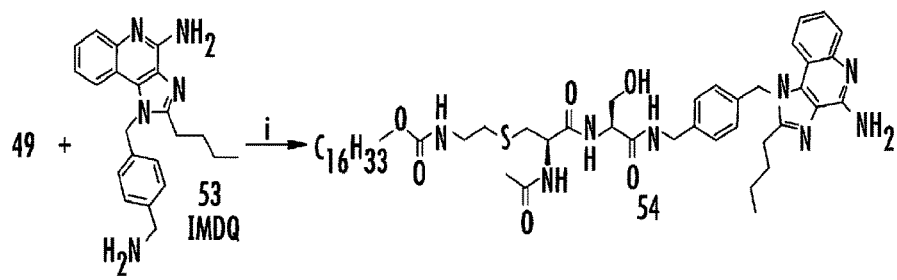

REAGENTS AND CONDITIONS: i. (a) EDCl, HOBt, NMM, DMF (b) TFA (c) Ac₂O, PYRIDINE, DCM.

GENERAL SCHEME 13:

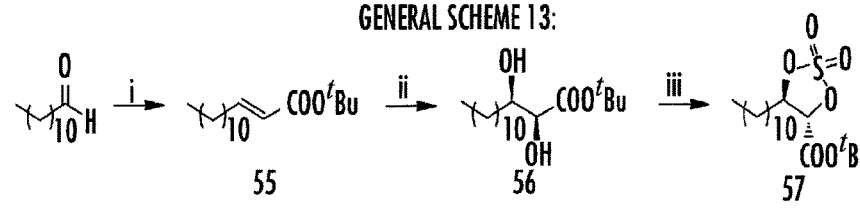

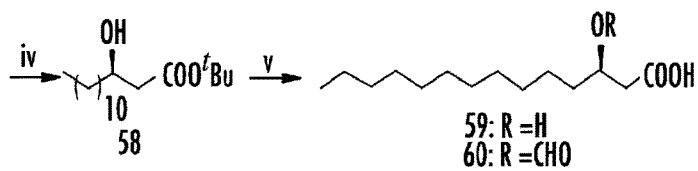

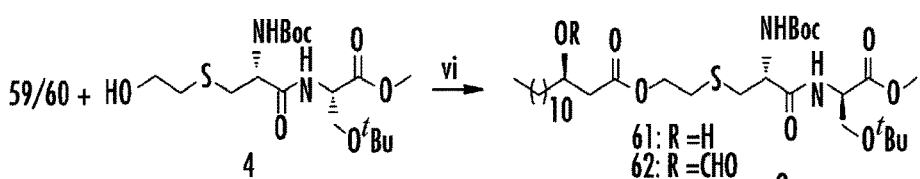

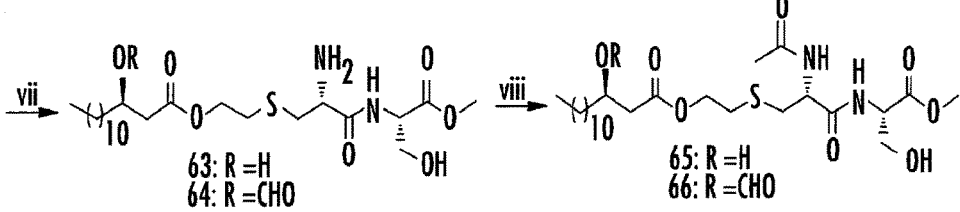

REAGENTS AND CONDITIONS: i. (TERT-BUTOXYCARBONYLMETHYLENE)TRIPHENYLPHOSPHORANE, CH₂Cl₂, OVERNIGHT, E/Z 15:1 ; ii. AD-MIX-, METHANESULFONAMIDE, ᵗBuOH/H₂O 1:1 OVERNIGHT, 92%; iii. (a) SOCl₂, PYRIDINE, 0°C, 30 MIN (b) NaIO₄, CAT. RuCl₃, CH₃CN/H₂O 3:1, 1 h, 74% iv. (a) NaBH₄, DMA, 1 h (b) DIOXANE, aq. HCl, OVERNIGHT 60%; v. FOR 59: TFA AND FOR 60: HCOOH; vi. EDCl, NMM, DMAP; vii. TFA; viii. Ac₂O, PYRIDINE, DCM.

FIG. 13

GENERAL SCHEME 14:
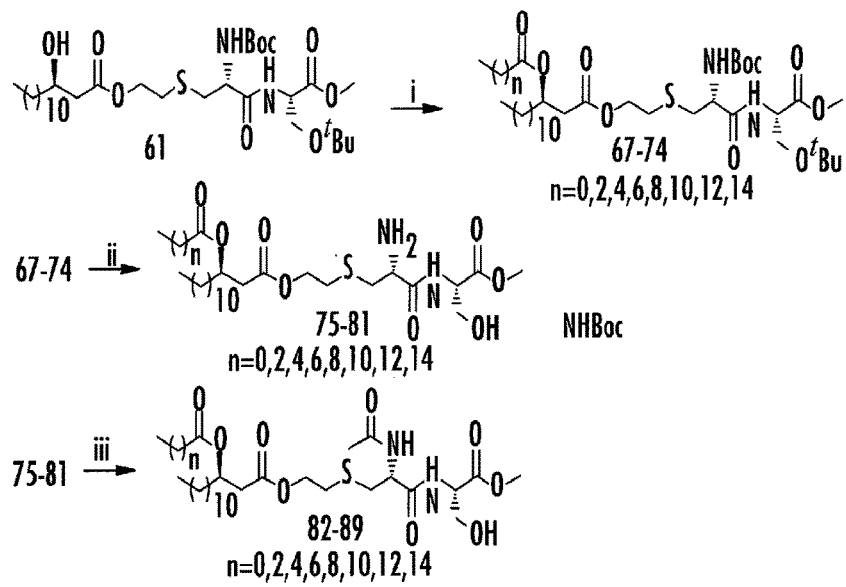
REAGENTS AND CONDITIONS: i. RCOCl, Et3N, DCM; ii. TFA; iii. Ac2O, PYRIDINE, DCM.
GENERAL SCHEME 15:
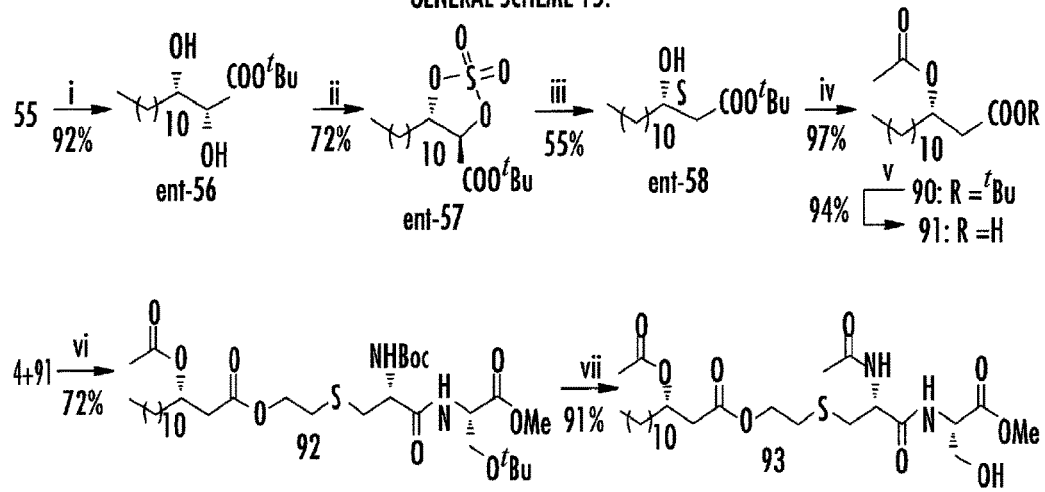
REAGENTS AND CONDITIONS: i. AD-mix-α, METHANESULFONAMIDE, tBuOH/H2O 1:1 0-25°C, 16h; ii. (a) SOCl2, PYRIDINE, 0°C, 30 min (b) NaIO4, CAT. RuCl3, CH3CN/H2O 3:1 25°C, 1h: iii. (a) NaBH4, DMA, 0-25°C, 3h (b) 20% AQ. HCl DIOXANE, 25 C. 24h: iv. Ac2O, Et3N, DCM, DMAP, 25°C, 16h; v. TFA, 25°C, 45 min; vi. EDCl, TRETHYLAMINE, DMAP, DCM, 25°C, 16h: vii. (a) TFA. 25°C, 35 min (b) Ac2O, PYRIDINE, DCM, 25°C, 30 min.
FIG. 14

TOLL-LIKE RECEPTOR 2-AGONISTIC LIPOPEPTIDES, AND METHOD OF MAKING THE SAME

CROSS-REFERENCE TO RELATED APPLICATIONS

This is a national stage filing in accordance with 35 U.S.C. §371 of PCT/US2014/011985, filed Jan. 17, 2014, which claims priority to U.S. provisional application Ser. No. 61/753,690 filed on Jan. 17, 2013 which is incorporated herein by reference in its entirety.

STATEMENT OF FEDERAL FUNDING

This invention was made with government support under federal contract number HHSN272200900033C, awarded by the National Institutes of Health. The government has certain rights in the invention.

FIELD OF THE INVENTION

Embodiments are provided that are directed to synthetic methods for making toll-like receptor 2-agonistic (TLR2) lipopeptides, resulting compounds or compositions comprising TLR2 lipopeptides, and use of such compounds or compositions as vaccine adjuvants.

BACKGROUND

Vaccines are perhaps one of the most successful medical interventions against infectious disease. An important component in the design of effective vaccines is the incorporation of appropriate immune potentiators (also termed adjuvants) along with the antigen; adjuvants initiate early innate immune responses, which lead to the induction of robust and long-lasting adaptive immune responses. More than eight decades have elapsed since the discovery of adjuvanticity of aluminum salts (primarily phosphate and hydroxide) and the repertoire of investigational adjuvants has grown to encompass a very wide range of materials; however, aluminum salt-based mineral salts (generically, and incorrectly, termed "alum") have, until the recent introduction of 3-O-desacyl-4'-monophosphoryl lipid A (MPL), remained the only adjuvants currently approved by the FDA. Aluminum salts have enjoyed a good safety record but are weak adjuvants for antibody induction, promoting a $T_H2$-skewed, rather than a $T_H1$ response. Furthermore, not only are aluminum salts ineffective at inducing cytotoxic T lymphocyte (CTL) or mucosal IgA antibody responses but also have an undesirable propensity to induce IgE isotype switching, which has been associated with allergic reactions in some subjects (Relyveld, E. H., et al. *Vaccine* 1998, 16, 1016-1023; Gupta, R. K. *Adv. Drug Delivery Rev.* 1998, 32, 155-172).

Toll-like receptors (TLRs) are pattern recognition receptors present on diverse cell types. TLRs recognize specific molecular patterns present in molecules that are broadly shared by pathogens but are sufficiently different so as to be distinguishable from host molecules and are collectively referred to as pathogen-associated molecular patterns (PAMPs). There are 10 TLRs in the human genome; these are transmembrane proteins with an extracellular domain having leucine-rich repeats (LRR) and a cytosolic domain called the Toll/IL-1 receptor (TIR) domain (Kumagai, Y. et al. *J. Infect. Chemother.* 2008, 14, 86-92).

The ligands for these receptors are highly conserved microbial molecules such as lipopolysaccharides (LPS) (recognized by TLR4), lipopeptides (TLR2 in combination with TLR1 or TLR6), flagellin (TLR5), single-stranded RNA (TLR7 and TLR8), double-stranded RNA (TLR3), CpG motif-containing DNA (recognized by TLR9), and profilin present on uropathogenic bacteria (TLR 11) (Kumagai, Y. et al *J. Infect. Chemother.* 2008, 14, 86-92; Takeda, K. Akira, S. *Curr. Protoc. Immunol.* 2007, Chapter 14, Unit 14, p 12). TLR1, -2, -4, -5, and -6 respond to extracellular stimuli, while TLR3, -7, -8, and -9 respond to intracytoplasmic PAMPs, being associated with the endolysosomal compartment (Kumagai, Y. et al. *Infect. Chemother.* 2008, 14, 86-92). The activation of TLRs by their cognate ligands leads to production of inflammatory cytokines, and up-regulation of MHC molecules and costimulatory signals in antigen-presenting cells as well as activating natural killer (NK) cells (innate immune response), in addition to priming and amplifying T- and B-cell effector functions (adaptive immune responses) (Akira, S. *Adv. Immunol.* 1902, 78, 1-56; Akira, S. et al. *Nature Immunol.* 2001, 2, 675-680; Cottalorda, A. et al. *Eur. J. Immunol.* 2006, 36, 1684-1693; Kaisho, T. et al. *Biochim. Biophys. Acta* 2002, 1589, 1-13).

SUMMARY

This summary is provided to briefly indicate the nature and substance of the present disclosure. It is submitted with the understanding that it will not be used to interpret or limit the scope or meaning of the claims.

Toll-like receptor (TLR) stimuli serve to link innate and adaptive immunity and can therefore be exploited as powerful adjuvants in eliciting both primary and anamnestic immune responses. Embodiments are directed to a novel class of compounds of toll-like receptor 2-agonistic (TLR2) lipopeptides, resulting compositions comprising such compounds, synthetic methods for making the compounds, and method of use of such compounds or compositions as vaccine adjuvants.

In some embodiments, the present disclosure provides a composition comprising a compound of general formula I:

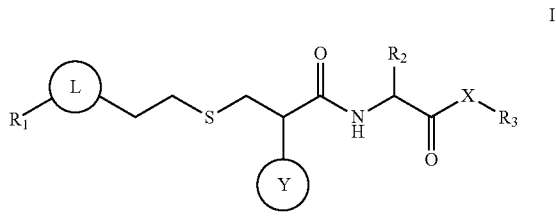

I wherein:

L is a functional group comprising: —C(O)—O—, —O—C(O)—, —C(O)—, —C(O)—NH—, —NH—C(O)—, —NH—C(O)—O—, —O—C(O)—NH—, alkyl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl and $C_{1-20}$ alkyoxyl, urea, esters, inverse esters, a keto group, amides, inverse amides, carbamate groups, inverse carbamate groups, wherein the $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, and the $C_{1-6}$ alkyl is unsubstituted or optionally substituted with a functional group comprising H, —OH, —OR', —NH$_2$, —NHR', —NR'$_2$, —SH, —SR', —O—C(O)R', —C(O)R', —CF$_3$, —OCF$_3$, and an amino acid side chain, the C$_{1-20}$ alkyl, C$_{2-20}$ alkenyl, C$_{2-20}$ alkynyl, C$_{4-20}$ heterocycle, C$_{4-20}$ heteroaryl, C$_{4-20}$ alkyl heterocycle, C$_{7-20}$ alkyl heteroaryl, C$_{1-20}$ alkyoxyl, and the C$_{1-6}$ alkyl is optionally interrupted by one or more O, S, or N atoms, or one or more groups selected from cycloalkyl, —C(O)—O—, —O—C(O)—, —C(O)—, —C(O)—NH—, —NH—C(O)—, —NH—C(O)—O— and —O—C(O)—NH—, and R' is selected from radicals consisting of H, heteroaryl having 1 to 4 N, O and/or S atoms, C$_{1-10}$ alkyl, C$_{2-10}$ alkenyl, C$_{2-10}$ alkynyl, C$_{4-10}$ heterocycle and C$_{4-10}$ heteroaryl;

R$_1$ is H or C$_{1-50}$ alkyl, the C$_{1-50}$ alkyl is unsubstituted or optionally substituted with a functional group selected from the group consisting of H, —OH, —OR', —NH$_2$, —NHR', —NR'$_2$, —SH, —SR', —O—C(O)R', —C(O)R', —CF$_3$, —OCF$_3$, an amino acid side chain or peptide fragment, where R' is selected from radicals consisting of H, heteroaryl having 1 to 4 N, O and/or S atoms, C$_{1-10}$ alkyl, C$_{2-10}$ alkenyl, C$_{2-10}$ alkynyl, C$_{4-10}$ heterocycle and C$_{4-10}$ heteroaryl;

R$_2$ is H, a natural or unnatural amino acid side chain, polar or non-polar groups and S- or R-enantiomers thereof. Examples include, without limitation: beta-alanine, gamma-aminobutyric acid, or α-aminoisobutyric acid.

X comprises —O—, —NH—, or —N(R$_3$)$_2$;

R$_3$ is H or C$_{1-50}$ alkyl, the C$_{1-50}$ alkyl is unsubstituted or optionally substituted with a functional group comprising one or more of: H, —OH, —OR', —NH$_2$, —NHR', —NR'$_2$, —SH, —SR', —O—C(O)R', —C(O)R', —CF$_3$, —OCF$_3$, an amino acid side chain or peptide fragment, where R' is selected from radicals consisting of H, heteroaryl having 1 to 4 N, O and/or S atoms, C$_{1-10}$ alkyl, C$_{2-10}$ alkenyl, C$_{2-10}$ alkynyl, C$_{4-10}$ heterocycle, C$_{4-10}$ heteroaryl, ammonium and salts thereof, sulfates, sulfonates, thiosulfonates, boronates, phosphates, phosphonate, guanidine, amidine, pyridine, pyridium, alkali metal groups, nitrates, chlorates, perchlorates, acetates, chloride, bromide, iodide and salts thereof, an alkali metal salt of sulfonic acid; an alkali metal salt of phosphonic acid; a pharmaceutically acceptable salt; a sugar or a polyhydroxy group;

Y is O, H or nitrogen containing group comprising: —H, —NH$_2$, —NH—C(O)—R$_4$, —NH—R$_5$, —N(R$_4$)R$_5$—SO$_2$—R$_4$, where R$_4$ or R$_5$ is independently selected from H, the C$_{1-20}$ alkyl, C$_{2-20}$ alkenyl, C$_{2-20}$ alkynyl, C$_{4-20}$ heterocycle, C$_{4-20}$ heteroaryl, C$_{4-20}$ alkyl heterocycle, C$_{7-20}$ alkyl heteroaryl, C$_{1-20}$ alkyoxyl, which is unsubstituted or optionally substituted with a functional group selected from the group consisting of H, —OH, —OR', —NH$_2$, —NHR', —NR'$_2$, —SH, —SR', —O—C(O)R', —C(O)R', —CF$_3$, —OCF$_3$, and an amino acid side chain, and is optionally interrupted by one or more O, S, or N atoms, or one or more groups selected from cycloalkyl, —C(O)—O—, —O—C(O)—, —C(O)—, —C(O)—NH—, —NH—C(O)—, —NH—C(O)—O— and —O—C(O)—NH—, and R' is selected from radicals consisting of H, heteroaryl having 1 to 4 N, O and/or S atoms, C$_{1-10}$ alkyl, C$_{2-10}$ alkenyl, C$_{2-10}$ alkynyl, C$_{4-10}$ heterocycle and C$_{4-10}$ heteroaryl.

In some embodiments, L is selected from a group consisting of —C(O)—O—, —O—C(O)—, —C(O)—NH—, —NH—C(O)—, —NH—C(O)—O—, —O—C(O)—NH—, C$_{4-20}$ heteroaryl and C$_{7-20}$ alkyl heteroaryl. L can also comprise a group selected from a group consisting of —C(O)—O—, —O—C(O)—, —C(O)—NH—, —NH—C(O)—, —NH—C(O)—O—, —O—C(O)—NH—, C$_{4-20}$ heteroaryl and C$_{7-20}$ alkyl heteroaryl. L is —C(O)—O— or —NH—C(O)—O— in some embodiments and the C$_{4-20}$ heteroaryl or C$_{7-20}$ alkyl heteroaryl comprises a triazole ring.

In some embodiments, R$_1$ is a C$_{5-20}$ alkyl, or a C$_{5-20}$ alkyl substituted with a functional group selected from the group consisting of —OH, —OR', —NH$_2$, —NHR', —NR'$_2$, —O—C(O)R', —C(O)R', —CF$_3$, and —OCF$_3$. R' is selected from radicals consisting of H and C$_{1-5}$ alkyl. R$_1$ is C$_{14-17}$ alkyl having a formula C$_m$H$_{2m+1}$ where m is an integer from 14 to 17 in some embodiments, for example, C$_{15}$ alkyl or C$_{16}$ alkyl.

In some embodiments, R$_2$ is selected from a group consisting of —C$_p$H$_{2P+1}$—R$_6$, —C$_p$H$_{2P+1}$—O—R$_6$, —C$_p$H$_{2P+1}$—O—C(O)—R$_6$, —C$_p$H$_{2P+1}$—NH—C(O)—R$_6$, and —C$_p$H$_{2P+1}$—SO$_2$—R$_6$, where p is an integer from 1 to 6, and R$_6$ is H or C$_1$-6 alkyl which is unsubstituted or optionally substituted with a functional group selected from the group consisting of —OH, —NH$_2$, —COOH, —C(O)NH$_2$ and a heteroaryl having 1 to 4 N, O and/or S atoms. R$_2$ is a polar group for higher solubility in some embodiments. For example, R$_2$ is selected from a group consisting of —CH$_2$OH, —CH$_2$—O—C(O)—CH$_3$, —CH$_2$—COOH, —CH$_2$—NH$_2$, —CH$_2$—CH$_2$—NH$_2$, and —CH$_2$—O—C(O)—CH$_2$CH$_2$—COOH in some embodiments. R$_2$ is —CH$_2$OH in some embodiments.

In some embodiments, R$_3$ is a C$_{1-10}$ alkyl, or substituted C$_{1-10}$ alkyl. For example, R$_3$ is methyl and X is —O— in some embodiments.

In some embodiments X is an amino acid or a peptide fragment comprising natural amino acids, unnatural amino acids or derivatives thereof.

In some embodiments, Y is a nitrogen containing group selected from the group consisting of —NH$_2$, —NH—C(O)—CH$_3$, —NH—CH$_3$, —NH—C(O)—CF$_3$, —SO$_2$CH$_3$, —SO$_2$CF$_3$, and —SO$_2$C$_6$H$_4$CH$_3$. For example, Y is —NH—C(O)—CH$_3$ in some embodiments.

Embodiments are also directed to methods of synthesizing a compound a general structural formula I as described above. The synthetic methods are discussed in details in the Detailed Description and Examples sections which follow. The methods of synthesizing the compounds include but are not limited to the following exemplary method. In some embodiments, an exemplary method comprises: protecting amine groups of a compound having the structural formula:

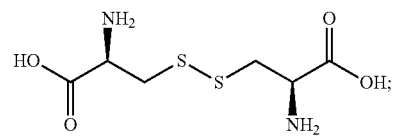 [SMILES: N[C@@H](CSSC[C@H](N)C(=O)O)C(=O)O]

producing a compound of the general structural formula:

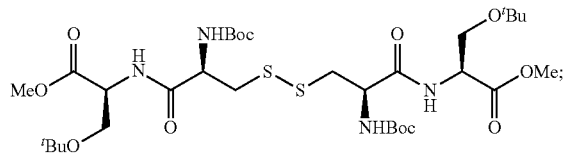 [SMILES: COC(=O)[C@H](COC(C)(C)C)NC(=O)[C@H](CSSC[C@H](NC(=O)OC(C)(C)C)C(=O)N[C@@H](COC(C)(C)C)C(=O)OC)NC(=O)OC(C)(C)C]

cleaving the product by disulfide cleavage and producing a compound of the general formula:

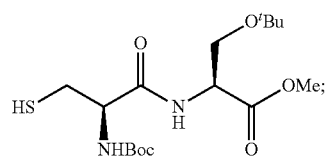

reacting the compound with alkyl halide and producing a compound of the general formula:

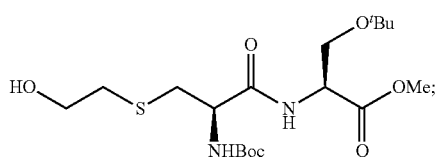

adding acyl chlorides under conditions resulting in O-acylation and producing a compound of the general formula:

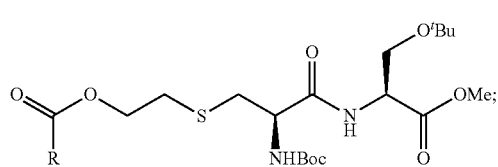

adding trifluoracetic acid to produce a compound of the general formula:

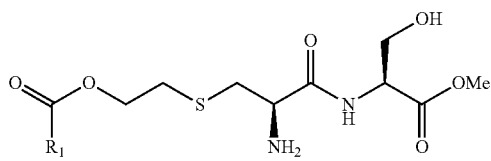

Where L is —C(O)—O—, $R_2$ is —$CH_2$—OH, and X is —O—. In some embodiments, $R_1$ is $C_{4-20}$ alkyl having a formula $C_mH_{2m+1}$ where m is an integer from 4 to 20, for example, 15 or 16.

In some embodiments, a compound produced through this method is

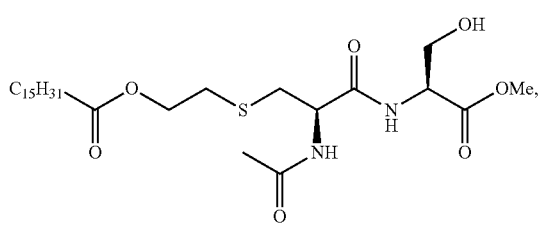

2-(((R)-2-acetamido-3-(((S)-3-hydroxy-1-methoxy-1-oxopropan-2-yl)amino)-3-oxopropyl)thio)ethyl palmitate

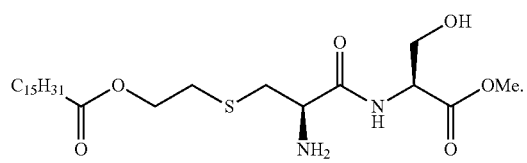

In some embodiments, the method further comprises N-acetylation of

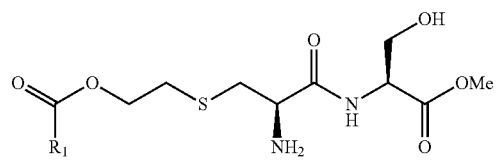

to make a compound having general formula:

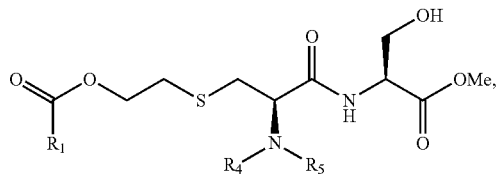

where $R_4$ and $R_5$ are described above.

For example, a compound produced using this method is

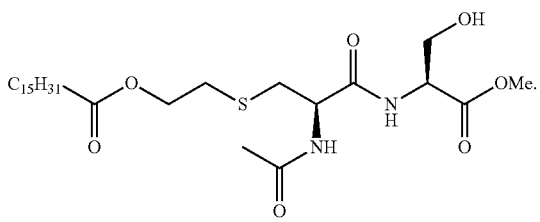

The present disclosure provides a library of compounds and resulting compositions having TLR2 agonistic activity. Some of the exemplary compounds are listed on Table 1. For example, a composition can comprise one of the following selected compounds. The following compounds are listed for demonstration purposes. The compounds in the present disclosure include but are not limited to:

(11d)

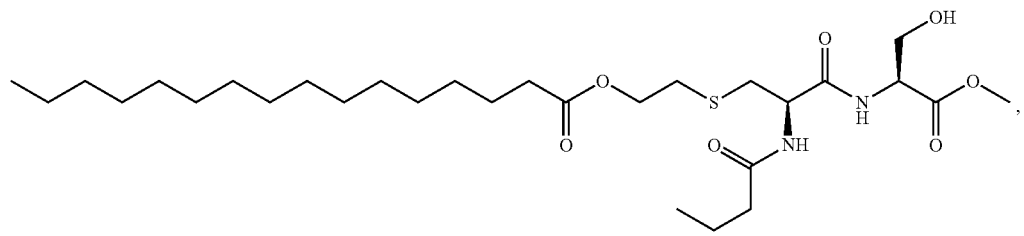
2-(((R)-2-butyramido-3-(((S)-3-hydroxy-1-methoxy-1-oxopropan-2-yl)amino)-3-oxopropyl)thio)ethyl palmitate
(25)
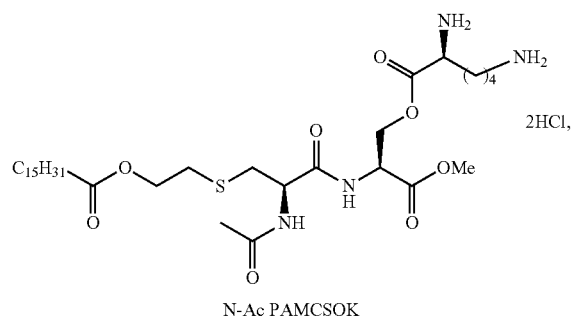
N-Ac PAMCSOK
(27)
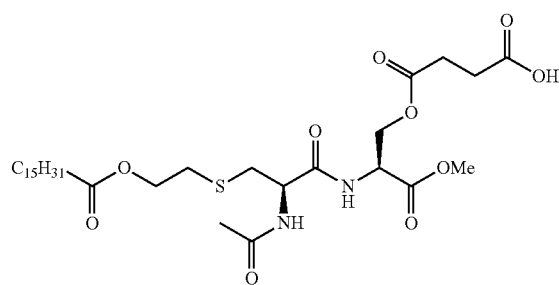
26
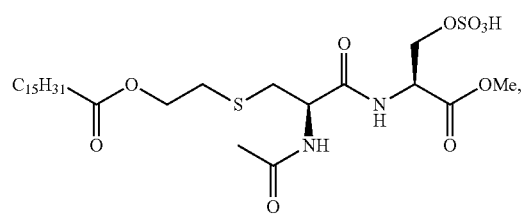
28
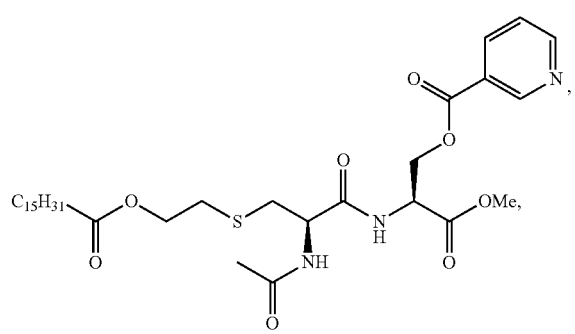
33
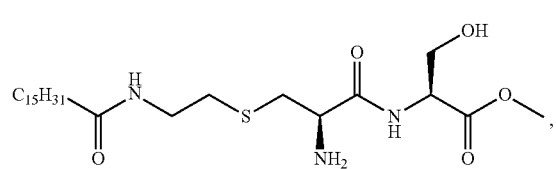
34
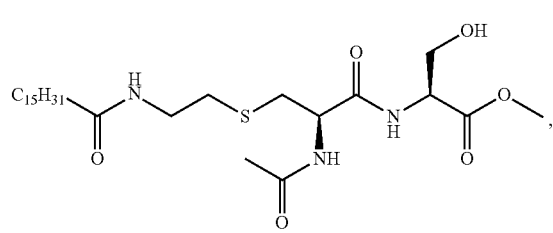
37
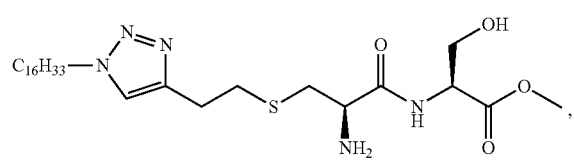
38
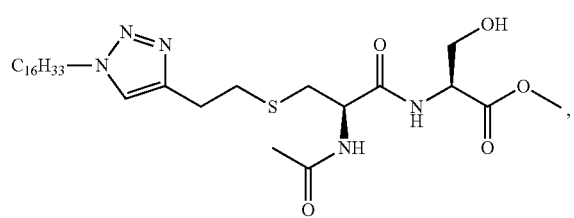

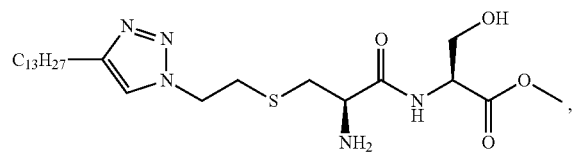
(40)
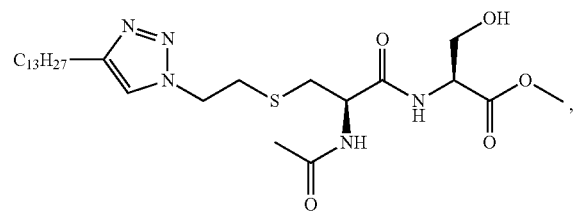
(41)
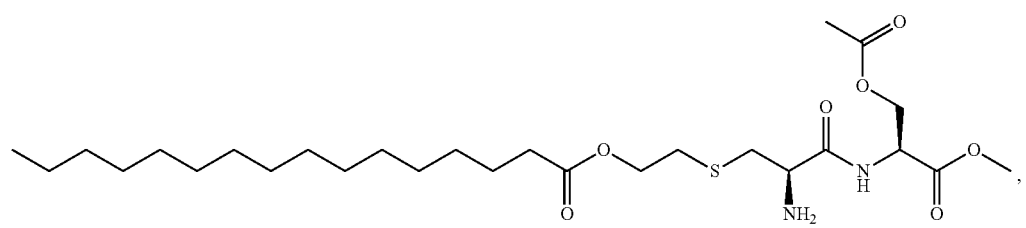
(14a)
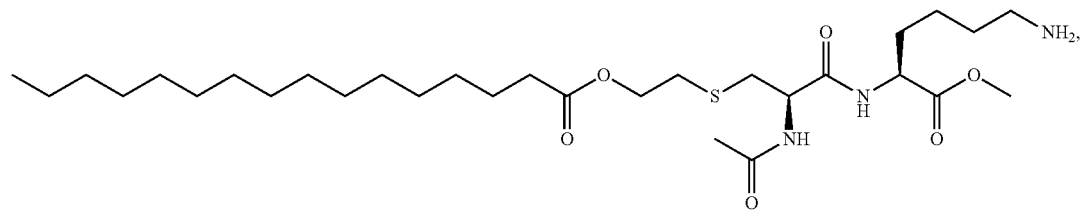
(23)
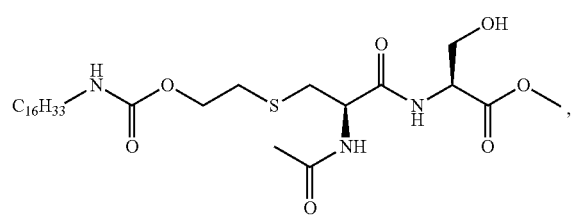
(45)
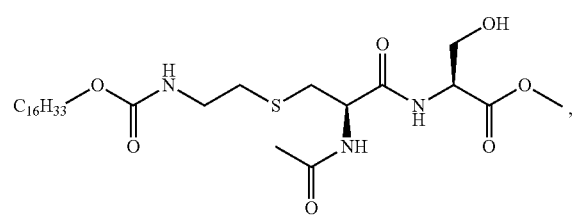
(48)
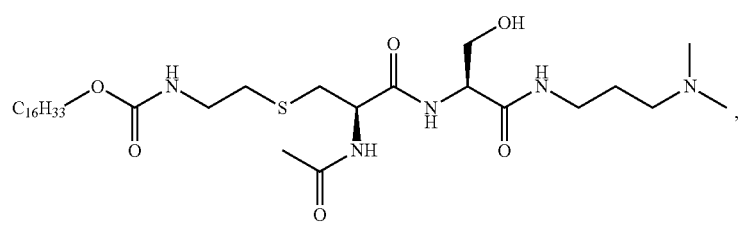
(52)
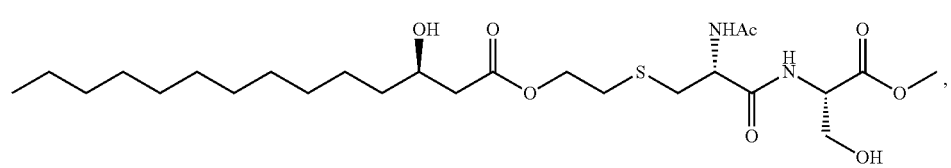
(65)
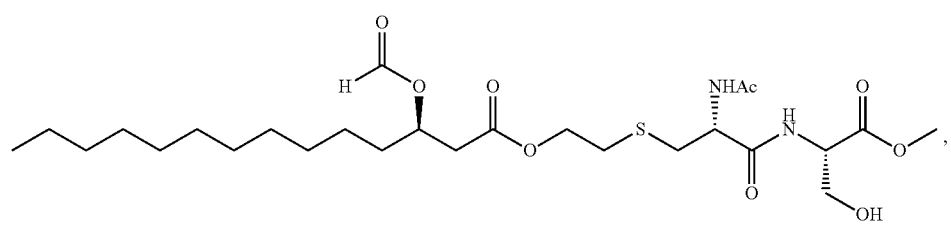
(66)

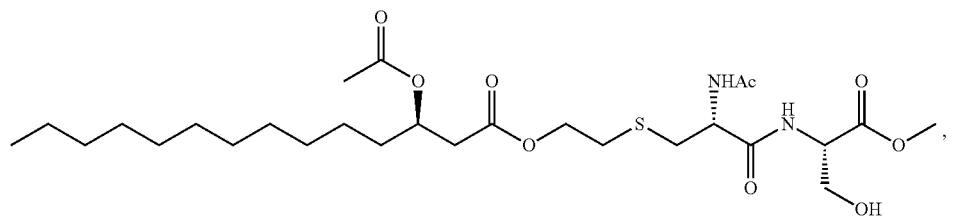
(82)
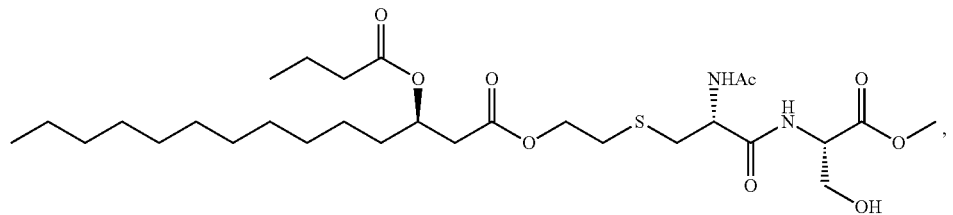
(83)
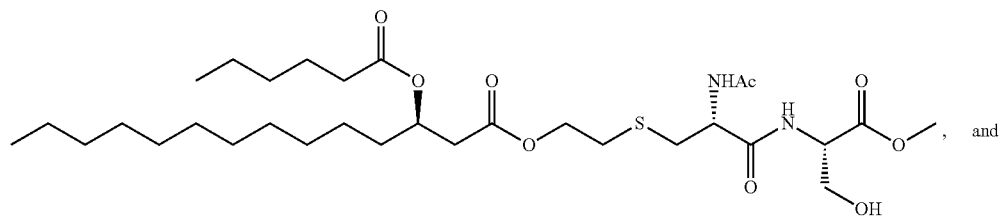
(84)
, and
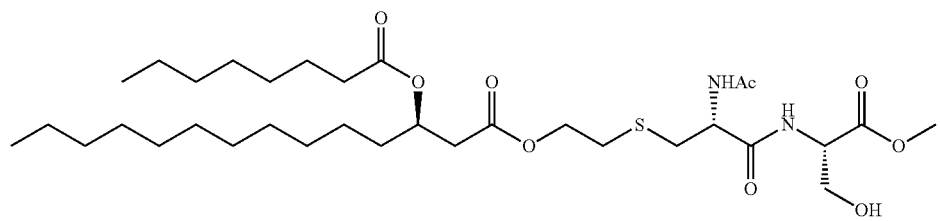
(85)
isomers or pharmaceutically acceptable salts thereof.
In one embodiment, a diastereoisomeric compound comprises:
In another aspect, the present disclosure also provides a method of using a compound or a resulting composition comprising such a compound, as a vaccine adjuvant. These
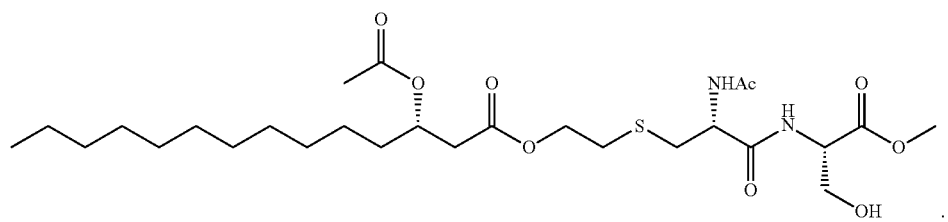
(93)
.

compounds in the present disclosure provide high potency of agonistic activities with human, other than murine, TLR2.

Other aspects are described infra.

BRIEF DESCRIPTION OF THE DRAWINGS

FIG. 7-14 are schematic representations showing an embodiment for each of general schemes 1 to 15. FIG. 7: general schemes 1 and 2; FIG. 8: general schemes 3 and 4; FIG. 9: general schemes 5 and 6; FIG. 10: general scheme 7; FIG. 11: general schemes 8 and 9; FIG. 12: general schemes 10 and 11; FIG. 13: general schemes 12 and 13; FIG. 14: general schemes 14 and 15.

DETAILED DESCRIPTION

Figure 1:
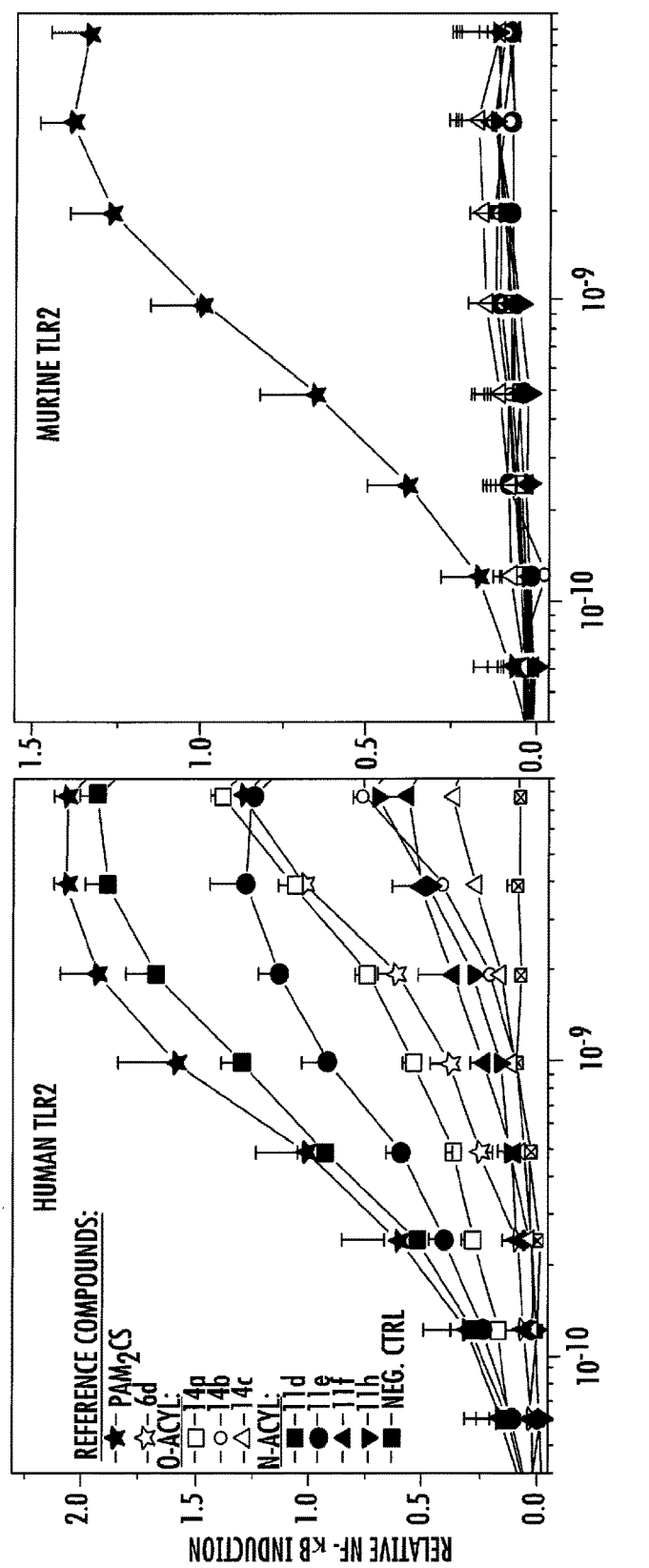
FIG. 1 is a graph showing TLR2-specific NF-κB induction by selected analogues in human and murine TLR2 reporter gene assays. Means and standard deviations of quadruplicate samples are shown.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "determining", "measuring", "evaluating", "detecting", "assessing" and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

"Optional" or "optionally" means that the subsequently described circumstance may or may not occur, such that the description includes instances where the circumstance occurs and instances where it does not.

By the term "modulate," it is meant that any of the mentioned activities of the compounds embodied herein, are, e.g., increased, enhanced, increased, agonized (acts as an agonist), promoted, decreased, reduced, suppressed blocked, or antagonized (acts as an agonist). Modulation can increase activity more than 1-fold, 2-fold, 3-fold, 5-fold, 10-fold, 100-fold, etc., over baseline values. Modulation can also decrease its activity below baseline values.

An "agonist" generally refers to an exogenous compound that binds to a receptor and mimics the effects of an endogenous compound. Further, the term "agonist" refers to both full and/or partial agonists. A full agonist shows full efficacy at a receptor, while a partial agonist shows only partial efficacy at a receptor relative to a full agonist.

"TLR" generally refers to any Toll-like receptor of any species of organism. These include TLR1, TLR2, TLR3, TLR4, TLR5, TLR6, TLR7, TLR8, TLR10, TLR TLR0 and TLR11. A specific TLR may be identified with additional reference to species of origin (e.g., human, murine, etc.), a particular receptor (e.g., TLR6, TLR7, TLR8, etc.), or both.

"TLR agonist" refers to a compound that acts as an agonist of a TLR. This includes TLR1, TLR2, TLR3, TLR4, TLR5, TLR6, TLR7, TLR8, TLR9, TLR10, and TLR11 agonists or a combination thereof. Unless otherwise indicated, reference to a TLR agonist compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers. Also, a compound may be identified as an agonist of one or more particular TLRs (e.g., a TLR7 agonist, a TLR8 agonist, or a TLR7/8 agonist). The TLR agonism for a particular compound may be assessed in any suitable manner. For example, detailed experimental methods are provided in the "Examples" section.

Regardless of the particular assay employed, a compound can be identified as an agonist of a particular TLR if performing the assay with a compound results in at least a threshold modulation, e.g. increase, of some biological activity mediated by the particular TLR. Conversely, a compound may be identified as not acting as an agonist of a specified TLR if, when used to perform an assay designed to detect biological activity mediated by the specified TLR, the compound fails to elicit a threshold modulation, e.g. increase, in the biological activity. Unless otherwise indicated, an increase in biological activity refers to an increase in the same biological activity over that observed in an appropriate control. An assay may or may not be performed in conjunction with the appropriate control. With experience, one skilled in the art may develop sufficient familiarity with a particular assay (e.g., the range of values observed in an appropriate control under specific assay conditions) that performing a control may not always be necessary to determine the TLR agonism of a compound in a particular assay.

The precise threshold increase of TLR-mediated biological activity for determining whether a particular compound is or is not an agonist of a particular TLR in a given assay may vary according to factors known in the art including but not limited to the biological activity observed as the endpoint of the assay, the method used to measure or detect the endpoint of the assay, the signal-to-noise ratio of the assay, the precision of the assay, and whether the same assay is being used to determine the agonism of a compound for multiple TLRs. Accordingly it is not practical to set forth generally the threshold increase of TLR-mediated biological activity required to identify a compound as being an agonist or a non-agonist of a particular TLR for all possible assays. Those of ordinary skill in the art, however, can readily determine the appropriate threshold with due consideration of such factors.

The terms, "compound" and "compounds" as used herein refers to a compound encompassed by the generic formulae disclosed herein, any subgenus of those generic formulae, and any forms of the compounds within the generic and subgeneric formulae. Unless specified otherwise, the term further includes the racemates and stereoisomers, of the compound or compounds. Certain compounds of the invention possess chiral centers and/or double bonds, and/or may have tautomers or atropisomers; the tautomeric, enantiomeric, diastereomeric, atropisomeric, and geometric mixtures of two or more isomers, in any composition, as well as the individual isomers (including tautomers and atropisomers) are encompassed within the scope of the present invention. Whenever the term "isomer" is used, it refers to an atropisomeric, tautomeric, enantiomeric, diastereomeric, and/or geometric isomer or to a mixture of two or more of these isomers, unless the context dictates otherwise.

The term "amino acid" as used herein, includes natural or unnatural amino acids, derivatives, isomers, homologs and the like. "Peptide fragments" as used herein, thus include, one or more "amino acids" as defined herein and peptidomimetics. The term "unnatural amino acid" is intended to represent the D stereoisomer of a naturally occurring amino acid. Encompassed within this term include β-amino acids, derivatives, homologues and any non-naturally occurring amino acid known to those of skill in the art. The term "β-amino acid" refers to those amino acids in which their amino group is bonded to the β-carbon as opposed to the α-carbon represented by the standard biological amino acids. Representative amino acids include, but are not limited to, glycine, alanine, serine, threonine, arginine, lysine, ornithine, aspartic acid, glutamic acid, asparagine, glutamine, phenylalanine, tyrosine, tryptophan, leucine, valine, isoleucine, cysteine, methionine, histidine, 4-trifluoromethyl-phenylalanine, 3-(2-pyridyl)-alanine, 3-(2-furyl)-alanine, 2,4-diaminobutyric acid, and the like. Peptides or amino acid side chains include, without limitation: α-amino acids, β-amino acids and hybrid oligopeptides comprising α- and β-amino acids.

A "derivative" amino acid or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label. A "derivative compound" includes, without limitation, peptide molecules in which free amino groups have been derivatized to form salts or amides, by adding acetyl groups, amine hydrochlorides, carbobenzoxy groups, chloroacetyl groups, formyl groups, p-toluene sulfonyl groups, or t-butyloxycarbonyl groups. Free hydroxyl groups may be derivatized to form O-acyl or O-alkyl derivatives. Furthermore, free carboxyl groups may be derivatized to form salts, esters (e.g., methyl and ethyl esters), or hydrazides. Thus, a "derivative" further includes any pharmaceutically-acceptable salt of a derivative as described herein.

The term "peptidomimetic" refers to a group or moiety that has a structure that is different from the general chemical structure of an amino acid or peptide, but functions in a manner similar to a naturally occurring amino acid or peptide. Therefore, a peptidomimetic is an amino acid mimic or peptide mimic.

The term "lower" as used herein refers to a group having between one and six carbons.

The term "substituted" as used herein refers to substitution with the named substituent or substituents, multiple degrees of substitution being allowed unless otherwise stated.

The term "chiral" is used to describe an object that is nonsuperposable on its mirror image and therefore has the property of chirality.

The term "chirality" refers to the geometric property of a rigid object (or spatial arrangement of points or atoms) of being non-superposable on its mirror image. If the object is superposable on its mirror image the object is described as being achiral.

The term "chirality axis" refers to an axis about which a set of ligands is held so that it results in a spatial arrangement which is not superposable on its mirror image.

The term "chirality center" refers to an atom holding a set of ligands in a spatial arrangement, which is not superposable on its mirror image. A chirality center may be considered a generalized extension of the concept of the asymmetric carbon atom to central atoms of any element. Each chiral center is labeled R or S according to a system by which its substituents are each designated a priority according to the Cahn Ingold Prelog priority rules (CIP), based on atomic number. According to some embodiments, the stereochemistry of the chiral centers represents all possible combinations in terms of relative and absolute chemistry. Accordingly, it may represent either racemates or pure enantiomers.

The term "racemate" as used herein refers to an equimolar mixture of two optically active components that neutralize the optical effect of each other and is therefore optically inactive.

The term, "enantiomer" refers to one of a pair of optical isomers containing one or more asymmetric carbons whose molecular configurations have left- and right-hand (chiral) forms. Enantiomers have identical physical properties, except for the direction of rotation of the plane of polarized light. Enantiomers have identical chemical properties except toward optically active reagents.

The term "isomer" as used herein refers to one of two or more molecules having the same number and kind of atoms and hence the same molecular weight, but differing in chemical structure. Isomers may differ in the connectivities of the atoms (structural isomers), or they may have the same atomic connectivities but differ only in the arrangement or configuration of the atoms in space (stereoisomers). "Stereoisomer" or "stereoisomers" refer to compounds that differ in the chirality of one or more stereocenters. Stereoisomers may include, but are not limited to, E/Z double bond isomers, enantiomers, and diastereomers. Structural moieties that, when appropriately substituted, can impart stereoisomerism include, but are not limited to, olefinic, imine or oxime double bonds; tetrahedral carbon, sulfur, nitrogen or phosphorus atoms; and allenic groups. Enantiomers are non-superimposable mirror images. A mixture of equal parts of the optical forms of a compound is known as a racemic mixture or racemate. Diastereomers are stereoisomers that are not mirror images.

The terms "solvate" or "solvates" of a compound refer to those compounds, where compounds are as defined above, that are bound to a stoichiometric or non-stoichiometric amount of a solvent. Solvates of a compound includes solvates of all forms of the compound. Preferred solvents are volatile, non-toxic, and/or acceptable for administration to humans in trace amounts. Suitable solvates include distilled and pyrogen-free water.

The term "alkyl" as used herein refers to a straight or branched chain monovalent or divalent hydrocarbon radical having, except where specifically indicated otherwise, from one to about fifty carbon atoms, optionally substituted with substituents including, but not limited to: halogens, halides, alkylhalides, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may contain one or more O, S, S(O), or $S(O)_2$ moieties. Examples of "alkyl" as used herein include, but are not limited to, methyl, ethyl, propyl, decyl, undecyl, octadecyl, nonadecyl, eicosyl, heneicosyl, decosyl, tricosyl, tetracosyl, and pentacosyl, n-butyl, t-butyl, n-pentyl, isobutyl, and isopropyl, and the like. In some embodiments the alkyl comprises 1, 2, 3, 4, 5, 6, 7, 8, 9, 10, 11, or 12 carbon atoms.

The term "alkenyl," as used herein, denotes a straight (unbranched) or branched hydrocarbon chain having one or more double bonds therein where the double bond can be unconjugated or conjugated to another unsaturated group (e.g., a polyunsaturated alkenyl) and can be unsubstituted or substituted, with multiple degrees of substitution being allowed. For example, halides, alkylhalides, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl" group may contain one or more O, S, S(O), or $S(O)_2$ moieties. For example, and without limitation, the alkenyl can be vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, decenyl, undecenyl, dodecenyl, heptadecenyl, octadecenyl, nonadecenyl, eicosenyl, heneicosenyl, docosenyl, tricosenyl, tetracisenyl, pentacosenyl, phytyl, the branched chain isomers thereof, and polyunsaturated alkenes including octadec-9,12,-dienyl, octadec-9,12,15-trienyl, and eicos-5,8,11,14-tetraenyl.

The term "alkynyl" refers to a hydrocarbon radical having from about two to about fifty carbons and at least one carbon-carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynyl" group may containing one or more O, S, S(O), or $S(O)_2$ moieties.

The term "aryl" as used herein refers to an optionally substituted benzene ring or to an optionally substituted benzene ring system fused to one or more optionally substituted benzene rings, with multiple degrees of substitution being allowed. Substituents include, but are not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, amino sulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-napthyl, 1-naphthyl, 1-anthracenyl, and the like.

It should be understood that wherever the terms "alkyl" or "aryl" or either of their prefix roots appear in a name of a substituent, they are to be interpreted as including those limitations given above for alkyl and aryl. Designated numbers of carbon atoms (e.g., $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

The terms "carbamates" or "urethanes" as used herein refer to a group of organic compounds sharing a common functional group having the general structure —NHR(CO)O—.

As used herein, "cycloalkyl" (used interchangeably with "aliphatic cyclic") refers to an alicyclic hydrocarbon group optionally possessing one or more degrees of unsaturation, having from about three to about fifty carbon atoms, optionally substituted with substituents, for example: halogens, halides, alkylhalides, selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

The terms "heterocycle" and "heterocyclic" as used herein are used interchangeably to refer to a three to about twelve-membered heterocyclic ring optionally aromatic or possessing zero, one- or more degrees of unsaturation, containing one or more heteroatomic substitutions, for example: —S—, —SO—, —SO$_2$—, —O—, or —N— and substituents including, but not limited to, halogens, halides, alkylhalides lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring optionally may be fused to one or more of another "heterocyclic," cycloalkyl or aryl ring(s).

As used herein, the term "heteroaryl" refers to an optionally substituted aryl ring system wherein, in at least one of the rings, one or more of the carbon atom ring members is independently replaced by a heteroatom group selected from the group consisting of S, O, N, and NH, or NR wherein aryl is as previously defined and R is an optional substituent as defined herein. In some embodiments heteroaryl groups have a total of from about 5 to about 14 carbon atom ring members and heteroatom ring members (and all combinations and subcombinations of ranges and specific numbers of carbon and heteroatom ring members). Heteroaryl groups having a total of from about 5 to about 10 carbon atom ring members and heteroatom ring members (and all combinations and subcombinations of ranges and specific numbers of carbon and heteroatom ring members) are also preferred. Exemplary heteroaryl groups include, but are not limited to, pyrryl, furyl, pyridyl, pyridine-N-oxide, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl may be attached to the rest of the. molecule via a carbon or a heteroatom.

As used herein, the term "heteroarylalkyl" refers to an optionally substituted ring system comprising an alkyl radical bearing a heteroaryl substituent, each as defined above, having from about 6 to about 50 carbon atoms (and all combinations and subcombinations of ranges and specific numbers of carbon atoms therein), with from about 6 to about 25 carbon atoms being preferred. Non-limiting examples include 2-(1H-pyrrol-3-yl)ethyl, 3-pyridylmethyl, 5-(2H-tetrazolyl)methyl, and 3-(pyrimidin-2-yl)-2-methylcyclopentanyl.

As used herein, the term "heterocycloalkyl," "heterocyclic ring" and "heterocyclyl" each refer to an optionally substituted ring system composed of a cycloalkyl radical wherein, in at least one of the rings, one or more of the carbon atom ring members is independently replaced by a heteroatom group selected. From the group consisting of O, S, N, and NH, or NR wherein cycloalkyl is as previously defined and R is an optional substituent as defined herein. Heterocycloalkyl ring systems having a total of from about 3 to about 14 carbon atom ring members and heteroatom ring members (and all combinations and subcombinations of ranges and specific numbers of carbon and heteroatom ring members). In other embodiments, the heterocyclic groups may be fused to one or more aromatic rings. In yet other embodiments, heterocycloalkyl moieties are attached via a ring carbon atom to the rest of the molecule. Exemplary heterocycloalkyl groups include, but are not limited to, azepanyl, tetrahydrofuranyl, hexahydropyrimidinyl, tetrahydrothienyl, piperidinyl, pyrrolidinyl, isoxazolidinyl, isothiazolidinyl, pyrazolidinyl, oxazolidinyl, imidazolidinyl, diazolidinyl, piperazinyl, 2-oxo-morpholinyl, morpholinyl, 2-oxo-piperidinyl, piperadinyl, decahydroquinolyl, octahydrochromenyl, octahydro-cyclopentapyranyl, 1,2,3,4,-tetrahydroquinolyl, 1,2,3,4-tetrahydroquinazolinyl, octahydro-[2]pyridinyl, decahydro-cyclooctafuranyl, 1,2,3,4-tetrahydroisoquinolyl, 2-oxoimidazolidinyl, and imidazolidinyl. In some embodiments, two moieties attached to a heteroatom may be taken together to form a heterocycloalkyl ring. In certain of these embodiments, 1 or 2 of the heterocycloalkyl ring carbon atoms may be replaced by other moieties which contain either one (—O—, —S—, —N($R^9$)—) or two (—N($R^{10}$)—C(=O)—, or —C(=O)N($R^{10}$)—) ring replacement atoms. When a moiety containing one ring replacement atom replaces a ring carbon atom, the resultant ring, after replacement of a ring atom by the moiety, will contain the same number of ring atoms as the ring before ring atom replacement. When a moiety containing two ring replacement atoms replaces a ring carbon atom, the resultant ring after replacement will contain one more ring atom than the ring prior to replacement by the moiety. For example, when a piperidine ring has one of its ring carbon atoms replaced by —N($R^{10}$) C(=O)—, the resultant ring is a 7-membered ring containing 2 ring nitrogen atoms and the carbon of a carbonyl group in addition to 4 other carbon ring atoms (CH$_2$ groups) from the original piperidine ring. In general, the ring system may be saturated or may be partially unsaturated, i.e., the ring system may contain one or more non-aromatic C—C or C—N double bonds.

The term "optionally substituted" means that the group in question may be unsubstituted or it may be substituted one or several times, such as 1 to 3 times or 1 to 5 times. For example, an alkyl group that is "optionally substituted" with 1 to 5 chloro atoms, may be unsubstituted, or it may contain 1, 2, 3, 4, or 5 chlorine atoms. Typically, substituted chemical moieties include one or more substituents that replace hydrogen. Exemplary substituents include, for example, halo (e.g., F, Cl, Br, I), alkyl, cycloalkyl, alkylcycloalkyl, alkenyl, alkynyl, haloalkyl including trifluoroalkyl, aralkyl, aryl, heteroaryl, heteroarylalkyl, spiroalkyl, heterocyclyl, heterocycloalkyl, hydroxyl (—OH), alkoxyl, aryloxyl, aralkoxyl, nitro (—NO$_2$), cyano (—CN), amino (—NH$_2$), N-substituted amino (—NHR"), N,N-disubstituted amino (—N(R")R"), carboxyl (—COOH), —C(=O)R", —OR", —C(=O)OR", —C(=O)NHSO$_2$R", —NHC(=O)R", aminocarbonyl (—C(=O)NH$_2$), N-substituted aminocarbonyl (C(=O)NHR"), N,N-disubstituted aminocarbonyl (—C(=O)N(R")R"), thiolato (SR"), sulfonic acid and its esters (—SO$_3$R"), phosphonic acid and its mono-ester (—P(=O)(OR")(OH) and di-esters (—P(=O)(OR")(OR"), —S(=O)$_2$R", —S(=O)$_2$NH$_2$, —S(=O)$_2$NHR", —S(=O)$_2$NR"R", —SO$_2$NHC(=O)R", NHS(=O)$_2$R", —NR"S(=O)$_2$R", —CF$_3$, —CF$_2$CF$_3$, —NHC(=O)NHR", —NHC(=O)NR"R", —NR"C(=O)NHR", —NR"C(=O)NR"R", —NR"C(=O)R" and the like. In relation to the aforementioned substituents, each moiety "R" can be, independently, any of H, alkyl, cycloalkyl, alkenyl, aryl, aralkyl, heteroaryl, or heterocycloalkyl, or when (R"(R")) is attached to a nitrogen atom, R" and R" can be taken together with the nitrogen atom to which they are attached to form a 4- to 8-membered nitrogen heterocycle, wherein the heterocycloalkyl ring is optionally interrupted by one or more additional —O—, —S—, —SO, —SO$_2$—, —NH—, —N(alkyl)-, or —N(aryl)groups, for example. In certain embodiments, chemical moieties are substituted by at least one optional substituent, such as those provided hereinabove. In the present invention, when chemical moieties are substituted with optional substituents, the optional substituents are not further substituted unless otherwise stated. For example, when an R group is an alkyl moiety, it is optionally substituted, based on the definition of "alkyl" as set forth herein. In some embodiments, when R is alkyl substituted with optional aryl, the optional aryl substituent is not further substituted.

When any variable occurs more than one time in any constituent or formula for a compound, its definition at each occurrence is independent of its definition at every other occurrence. Thus, for example, if the R group is shown to be substituted with 0-2 substituents, then said group may optionally be substituted with up to two substituents and each substituent is selected independently from the definition of optionally substituted defined above. Also, combinations of substituents and/or variables are permissible only if such combinations result in stable compounds.

When a bond to a substituent is shown to cross a bond connecting two atoms in a ring, then such substituent may be bonded to any atom on the ring having an attached hydrogen atom. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The term "water-soluble group" refers to a functional group that is well solvated in aqueous environments and that imparts improved water solubility to the compound to which it is attached. Examples of water-soluble groups include, but are not limited to, polyalcohols, straight chain or cyclic saccharides, primary, secondary, tertiary, or quaternary amines and polyamines, sulfate groups, sulfonate groups, sulfinate groups, carboxylate groups, phosphate groups, phosphonate groups, phosphinate groups, ascorbate groups, glycols, including polyethylene glycols, and polyethers.

As used herein, a "pharmaceutically acceptable" component/carrier etc. is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

The term "prodrug" refers to any derivative of a compound of the embodiments that is capable of directly or indirectly providing a compound of the embodiments or an active metabolite or residue thereof when administered to a subject. Particularly favored derivatives and prodrugs are those that increase the bioavailability of the compounds of the embodiments when such compounds are administered to a subject (e.g., by allowing an orally administered compound to be more readily absorbed into the blood) or which enhance delivery of the parent compound to a biological compartment (e.g., the brain or lymphatic system) relative to the parent species. A general overview of prodrugs is provided in T. Higuchi and V. Stella, *Pro-drugs as Novel Delivery Systems*, Vol. 14 of the A.C.S. Symposium Series, and in Edward B. Roche, ed., Bioreversible.

The term "pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), *Handbook of Pharmaceutical Salts Properties*, Selection, and Use; 2002.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive.

While a particular diagnostic method may not provide a definitive diagnosis of a condition, it suffices if the method provides a positive indication that aids in diagnosis.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

Compounds

Detailed structure-activity relationships (SAR) of several immunostimulatory chemotypes were explored. Attention was focused particularly on agonists of TLR2, exemplified by the S-[2,3-bis(palmitoyloxy)-(2RS)-propyl]-R-cysteinyl-S-serine ($PAM_2CS$) chemotype (Agnihotri, G. et al., *J. Med. Chem.* 2011, 54, 8148-8160; Wu, W. et al., *J. Med. Chem.*, 2010, 53, 3198-3213), which distinguishes itself from virtually all other TLR agonists in that although the lipopeptide is devoid of any detectable pro-inflammatory activity in ex vivo human blood models (as defined by the production of detectable levels of TNF-α, IL-1β, IL-6, or IL-8), or of local reactogenicity and pyrogenicity in rabbit models, it is potently adjuvantic in murine models of immunization, providing evidence that this chemotype may be a safe and effective adjuvant. Extensive SAR on the $PAM_2CS$ class of compounds led to simplified second-generation mono-acyl lipopeptides in which the spacing between the ester-linked acyl group and the thioether was found to play a crucial role in determining activity; homologation of the ethylene-bridged compound (6d in Scheme 1) by one methylene unit resulted in complete abrogation of activity (Agnihotri, G. et al., *J. Med. Chem.* 2011, 54, 8148-8160).

The structurally simpler, synthetically more accessible, and water-soluble 6d with its potent TLR2-agonistic properties in both primary screens employing human TLR2, as well as secondary screens in ex vivo human blood models presented an excellent lead. Prior to commencing immunization studies in rodent and non-rodent models, this compound was subjected to further evaluation. It was surprisingly found, that unlike $PAM_2CS$, 6d showed exquisite specificity in activating human TLR2 (hTLR2), but not murine TLR2 (mTLR2), providing evidence that the binding mode of 6d to TLR2 may be substantially different from that of $PAM_2CS$. This conjecture was strengthened by the observation that N-acylation of 6d with a palmitoyl group resulted in complete loss of hTLR2-agonistic activity, which is unexpected given the pronounced activity of the analogous, N-palmitoylated $PAM_2CS$ compound ($PAM_3CS$), and crystallographic evidence for the engagement of the TLR2/TLR1 heterodimer by $PAM_3CS$ (Jin, M. S. et al., *Cell.* 2007, 130, 1071-1082; Kang, J. Y.; Lee, J. O. *Annu. Rev. Biochem.* 2011, 80, 917-941).

In embodiments, a compound comprises a structure having a general formula I:

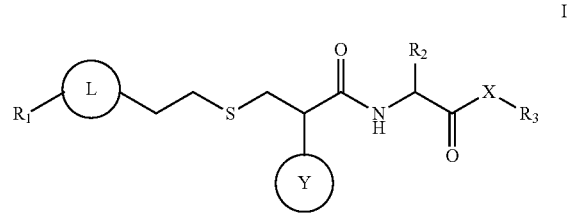

I wherein:

L is a functional group comprising: —C(O)—O—, —O—C(O)—, —C(O)—, —C(O)—NH—, —NH—C(O)—, —NH—C(O)—O—, —O—C(O)—NH—, alkyl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl and $C_{1-20}$ alkyoxyl, urea, esters, inverse esters, a keto group, amides, inverse amides, carbamate groups, inverse carbamate groups, wherein the $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, and the $C_{1-6}$ alkyl is unsubstituted or optionally substituted with a functional group comprising H, —OH, —OR', —$NH_2$, —NHR', —$NR'_2$, —SH, —SR', —O—C(O)R', —C(O)R', —$CF_3$, —$OCF_3$, and an amino acid side chain, the $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, and the $C_{1-6}$ alkyl is optionally interrupted by one or more O, S, or N atoms, or one or more groups selected from cycloalkyl, —C(O)—O—, —O—C(O)—, —C(O)—, —C(O)—NH—, —NH—C(O)—, —NH—C(O)—O— and —O—C(O)—NH—, and R' is selected from radicals consisting of H, heteroaryl having 1 to 4 N, O and/or S atoms, $C_{1-10}$ alkyl, $C_{2-10}$ alkenyl, $C_{2-10}$ alkynyl, $C_{4-10}$ heterocycle and $C_{4-10}$ heteroaryl;

$R_1$ is H or $C_{1-50}$ alkyl, the $C_{1-50}$ alkyl is unsubstituted or optionally substituted with a functional group selected from the group consisting of H, —OH, —OR', —$NH_2$, —NHR', —$NR'_2$, —SH, —SR', —O—C(O)R', —C(O)R', —$CF_3$, —$OCF_3$, an amino acid side chain or peptide fragment, where R' is selected from radicals consisting of H, heteroaryl having 1 to 4 N, O and/or S atoms, $C_{1-10}$ alkyl, $C_{2-10}$ alkenyl, $C_{2-10}$ alkynyl, $C_{4-10}$ heterocycle and $C_{4-10}$ heteroaryl;

$R_2$ is H, a natural or unnatural amino acid side chain, β-amino acids, polar or non-polar groups and S- or R-enantiomers thereof. Examples include, without limitation: beta-alanine, gamma-aminobutyric acid, or α-aminoisobutyric acid;

X comprises —O—, —NH—, or —N($R_3$)$_2$;

$R_3$ is H or $C_{1-50}$ alkyl, the $C_{1-50}$ alkyl is unsubstituted or optionally substituted with a functional group comprising one or more of: H, —OH, —OR', —NH$_2$, —NHR', —NR'$_2$, —SH, —SR', —O—C(O)R', —C(O)R', —CF$_3$, —OCF$_3$, an amino acid side chain or peptide fragment, where R' is selected from radicals consisting of H, heteroaryl having 1 to 4 N, O and/or S atoms, $C_{1-10}$ alkyl, $C_{2-10}$ alkenyl, $C_{2-10}$ alkynyl, $C_{4-10}$ heterocycle, $C_{4-10}$ heteroaryl, ammonium and salts thereof, sulfates, sulfonates, thiosulfonates, boronates, phosphates, phosphonate, guanidine, amidine, pyridine, pyridium, alkali metal groups, nitrates, chlorates, perchlorates, acetates, chloride, bromide, iodide and salts thereof, an alkali metal salt of sulfonic acid; an alkali metal salt of phosphonic acid; a pharmaceutically acceptable salt; a sugar or a polyhydroxy group;

Y is O, H or nitrogen containing group comprising: —H, —NH$_2$, —NH—C(O)—$R_4$, —NH—$R_5$, —NH—$R_5$, —N($R_4$)$R_5$—SO$_2$—$R_4$, where $R_4$ or $R_5$ is independently selected from H, the $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, which is unsubstituted or optionally substituted with a functional group selected from the group consisting of H, —OH, —OR', —NH$_2$, —NHR', —NR'$_2$, —SH, —SR', —O—C(O)R', —C(O)R', —CF$_3$, —OCF$_3$, an amino acid side chain or peptide fragment, and is optionally interrupted by one or more O, S, or N atoms, or one or more groups selected from cycloalkyl, —C(O)—O—, —O—C(O)—, —C(O)—, —C(O)—NH—, —NH—C(O)—, —NH—C(O)—O— and —O—C(O)—NH—, and R' is selected from radicals consisting of H, heteroaryl having 1 to 4 N, O and/or S atoms, $C_{1-10}$ alkyl, $C_{2-10}$ alkenyl, $C_{2-10}$ alkynyl, $C_{4-10}$ heterocycle and $C_{4-10}$ heteroaryl;

isomers or pharmaceutically acceptable salts thereof.

In some embodiments, a method of synthesizing a compound having a general structural formula I:

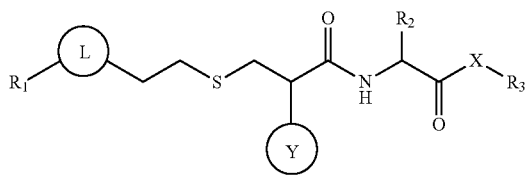

wherein,

L is a functional group comprising —C(O)—O—, —O—C(O)—, —C(O)—, —C(O)—NH—, —NH—C(O)—, —NH—C(O)—O—, —O—C(O)—NH—, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl or $C_{1-20}$ alkyoxyl, wherein, the $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, and the $C_{1-6}$ alkyl is unsubstituted or optionally substituted with a functional group selected from the group consisting of H, —OH, —OR', —NH$_2$, —NHR', —NR'$_2$, —SH, —SR', —O—C(O)R', —C(O)R', —CF$_3$, —OCF$_3$, an amino acid side chain or peptide fragment, the $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, and the $C_{1-6}$ alkyl is optionally interrupted by one or more O, S, or N atoms, or one or more groups selected from cycloalkyl, —C(O)—O—, —O—C(O)—, —C(O)—, —C(O)—NH—, —NH—C(O)—, —NH—C(O)—O— and —O—C(O)—NH—, and R' is selected from radicals consisting of H, heteroaryl having 1 to 4 N, O and/or S atoms, $C_{1-10}$ alkyl, $C_{2-10}$ alkenyl, $C_{2-10}$ alkynyl, $C_{4-10}$ heterocycle and $C_{4-10}$ heteroaryl;

$R_1$ is H or $C_{1-50}$ alkyl, the $C_{1-50}$ alkyl is unsubstituted or optionally substituted with a functional group selected from the group consisting of H, —OH, —OR', —NH$_2$, —NHR', —NR'$_2$, —SH, —SR', —O—C(O)R', —C(O)R', —CF$_3$, —OCF$_3$, an amino acid side chain or peptide fragment, where R' is selected from radicals consisting of H, heteroaryl having 1 to 4 N, O and/or S atoms, $C_{1-10}$ alkyl, $C_{2-10}$ alkenyl, $C_{2-10}$ alkynyl, $C_{4-10}$ heterocycle and $C_{4-10}$ heteroaryl;

$R_2$ comprises H, beta-alanine, gamma-aminobutyric acid, α-aminoisobutyric acid, a natural or unnatural amino acid side chain, polar or non-polar groups, β-amino acids, or S- or R-enantiomers thereof;

X comprises —O—, —NH—, or —N($R_3$)$_2$;

$R_3$ is H or $C_{1-50}$ alkyl, the $C_{1-50}$ alkyl is unsubstituted or optionally substituted with a functional group comprising one or more of: H, —OH, —OR', —NH$_2$, —NHR', —NR'$_2$, —SH, —SR', —O—C(O)R', —C(O)R', —CF$_3$, —OCF$_3$, and an amino acid side chain, where R' is selected from radicals consisting of H, heteroaryl having 1 to 4 N, O and/or S atoms, $C_{1-10}$ alkyl, $C_{2-10}$ alkenyl, $C_{2-10}$ alkynyl, $C_{4-10}$ heterocycle, $C_{4-10}$ heteroaryl, ammonium and salts thereof, sulfates, sulfonates, thiosulfonates, boronates, phosphates, phosphonate, guanidine, amidine, pyridine, pyridium, alkali metal groups, nitrates, chlorates, perchlorates, acetates, chloride, bromide, iodide and salts thereof, an alkali metal salt of sulfonic acid; an alkali metal salt of phosphonic acid; a pharmaceutically acceptable salt; a sugar or a polyhydroxy group; where Y is O, H or nitrogen containing group comprising: —H, —NH$_2$, —NH—C(O)—$R_4$, —NH—$R_5$, —N($R_4$)$R_5$—SO$_2$—$R_4$, where $R_4$ or $R_5$ is independently selected from H, the $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, which is unsubstituted or optionally substituted with a functional group selected from the group consisting of H, —OH, —OR', —NH$_2$, —NHR', —NR'$_2$, —SH, —SR', —O—C(O)R', —C(O)R', —CF$_3$, —OCF$_3$, an amino acid side chain or peptide fragment, and is optionally interrupted by one or more 0, S, or N atoms, or one or more groups selected from cycloalkyl, —C(O)—O—, —O—C(O)—, —C(O)—, —C(O)—NH—, —NH—C(O)—, —NH—C(O)—O— and —O—C(O)—NH—, and R' is selected from radicals consisting of H, heteroaryl having 1 to 4 N, O and/or S atoms, $C_{1-10}$ alkyl, $C_{2-10}$ alkenyl, $C_{2-10}$ alkynyl, $C_{4-10}$ heterocycle and $C_{4-10}$ heteroaryl.

In some embodiments, L is selected from a group consisting of —C(O)—O—, —O—C(O)—, —C(O)—NH—, —NH—C(O)—, —NH—C(O)—O—, —O—C(O)—NH—, $C_{4-20}$ heteroaryl and $C_{7-20}$ alkyl heteroaryl.

In some embodiments, $R_1$ is $C_{5-20}$ alkyl, or $C_{5-20}$ alkyl substituted with a functional group selected from the group consisting of —OH, —OR', —NH$_2$, —NHR', —O—C(O)R', —C(O)R', —CF$_3$, and —OCF$_3$, where R' is selected from radicals consisting of H and $C_{1-5}$ alkyl.

In some embodiments $R_2$ is selected from a group consisting of —$C_pH_{2P+1}$—$R_6$, —$C_pH_{2P+1}$—O—C(O)—$R_6$, —$C_pH_{2P+1}$—O—C(O)—$R_6$, —$C_pH_{2P+1}$—NH—C(O)—$R_6$, and —$C_pH_{2P+1}$—SO$_2$—$R_6$, where p is an integer from 1 to 6, and $R_6$ is H or $C_1$-6 alkyl which is unsubstituted or optionally substituted with a functional group selected from the group consisting of —OH, —NH$_2$, —COOH, —C(O)NH$_2$ and a heteroaryl having 1 to 4 N, O and/or S atoms.

In other embodiments, $R_2$ is selected from a group consisting of —CH$_2$OH, —CH$_2$—O—C(O)—CH$_3$, —CH$_2$—COOH, —CH$_2$—NH$_2$, —CH$_2$—CH$_2$—NH$_2$, and —CH$_2$—O—C(O)—CH$_2$CH$_2$—COOH.

In another embodiment, $R_3$ is a $C_{1-10}$ alkyl, or substituted $C_{1-10}$ alkyl.

In other embodiments, Y is O, H or nitrogen containing group comprising: —H, —NH$_2$, —NH—C(O)—$R_4$, —NH—$R_5$, —N($R_4$)$R_5$—SO$_2$—$R_4$. Examples include: —NH$_2$, —NH—C(O)—CH$_3$, —NH—CH$_3$, —NH—C(O)—CF$_3$, —SO$_2$CH$_3$, —SO$_2$CF$_3$, and —SO$_2$C$_6$H$_4$CH$_3$.

In some embodiments X is an amino acid or a peptide fragment comprising natural amino acids, unnatural amino acids or derivatives thereof.

In some embodiments, the method of synthesizing a compound having a general structural formula I, further comprises protecting amine groups of a compound having the structural formula:

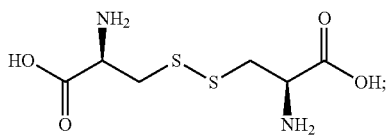 [SMILES: N[C@@H](CSSC[C@H](N)C(=O)O)C(=O)O]

producing a compound of the general structural formula:

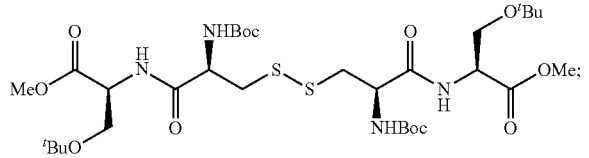 [SMILES: COC(=O)[C@H](COC(C)(C)C)NC(=O)[C@H](CSSC[C@H](NC(=O)OC(C)(C)C)C(=O)N[C@@H](COC(C)(C)C)C(=O)OC)NC(=O)OC(C)(C)C]

deprotecting the product and producing a compound of the general formula:

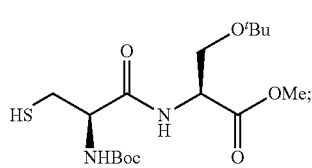

reacting the compound with an amine and producing a compound of the general formula:

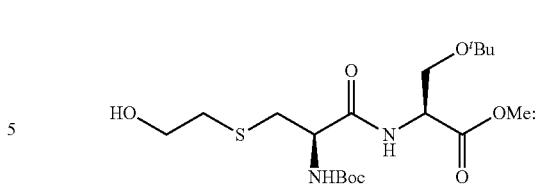

adding pyridine under conditions resulting in O-palmitoylation and producing a compound of the general formula:

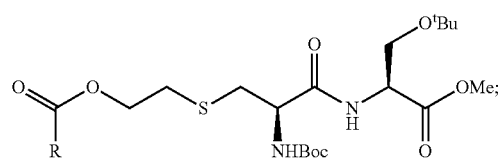

adding trifluoracetic acid to produce a compound of the general formula:

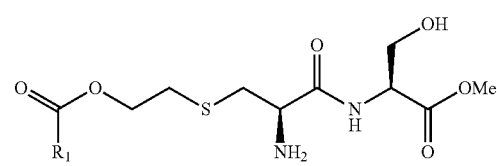

wherein, L is —C(O)—O—, $R_1$ is $C_{14-17}$ alkyl having a formula $C_mH_{2m+1}$ where m is an integer from 14 to 17, $R_2$ is —CH$_2$—OH, and X is —O—.

In some embodiments, a compound produced is

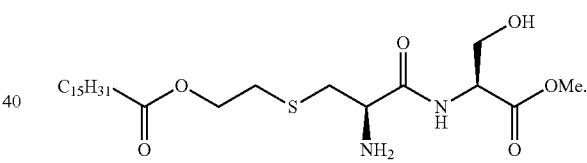

In some embodiments, a method of synthesizing compounds of general formula I, further comprise N-acetylation of

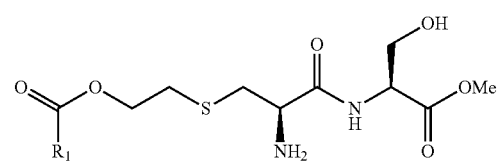

to make a compound having general formula:

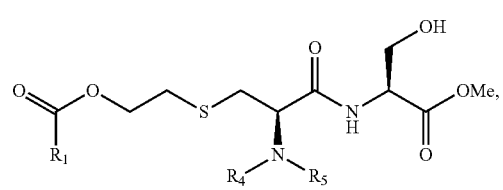

wherein $R_4$ or $R_5$ is independently selected from H, the $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, which is unsubstituted or optionally substituted with a functional group selected from the group consisting of H, —OH, —OR', —NH$_2$, —NHR', —NR'$_2$, —SH, —SR', —O—C(O)R', —C(O)R', —CF$_3$, —OCF$_3$, and an amino acid side chain, and is optionally interrupted by one or more O, S, or N atoms, or one or more groups selected from cycloalkyl, —C(O)—O—, —O—C(O)—, —C(O)—, —C(O)—NH—, —NH—C(O)—, —NH—C(O)—O— and —O—C(O)—NH—, and R' is selected from radicals consisting of H, heteroaryl having 1 to 4 N, O and/or S atoms, $C_{1-10}$ alkyl, $C_{2-10}$ alkenyl, $C_{2-10}$ alkynyl, $C_{4-10}$ heterocycle and $C_{4-10}$ heteroaryl.

In some embodiments, a compound produced is

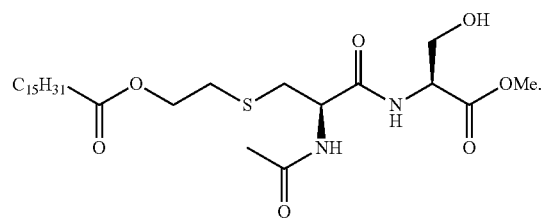

Generalized schemes for synthesis of the compounds are provided herein as examples which are not meant to be construed as limiting in any way.

In one embodiment, compounds are produced by the general scheme 1:

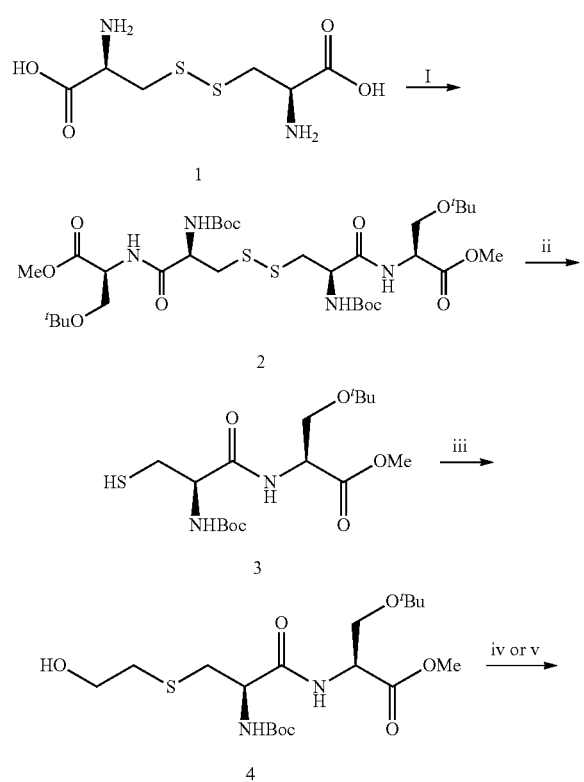

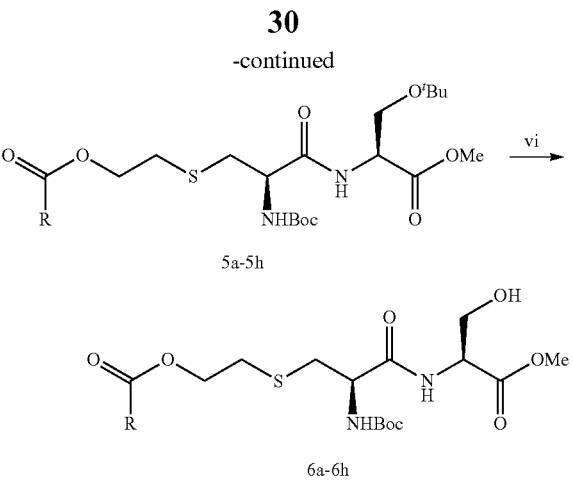

Examples of reagents and conditions employed in scheme 1 comprise: (i) (a) Boc$_2$O, Et$_3$N, H$_2$O (b) H-Ser($^t$Bu)-OMe.HCl, EDCl, HOBt, Et$_3$N, DMF; (ii) Bu$_3$P, CH$_2$Cl$_2$; (iii) 2-iodoethanol, Et$_3$N, DMF; for compounds 5a-5g: (iv) RCOCl, Et$_3$N, DMAP, CH$_2$Cl$_2$; for compound 5h: (v) RCOOH, HBTU, Et$_3$N, DMAP, DMF; (vi) TFA.

Wherein compounds designated (a) R is $C_3H_7$; (b) R is $C_7H_{15}$; (c) R is $C_{11}H_{23}$; (d) R is $C_{15}H_{31}$; (e) R is $C_{17}H_{35}$; (f) R is

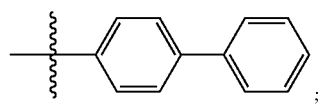 [SMILES: *c1ccc(-c2ccccc2)cc1]

(g) R is

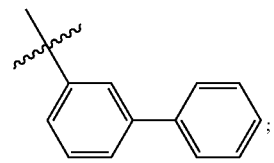 [SMILES: *c1cccc(-c2ccccc2)c1]

(h) R is

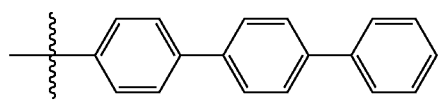

In another embodiment, analogues are synthesized by general scheme 2:

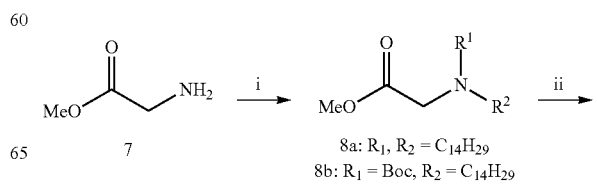

8a: $R_1$, $R_2$ = $C_{14}H_{29}$
8b: $R_1$ = Boc, $R_2$ = $C_{14}H_{29}$

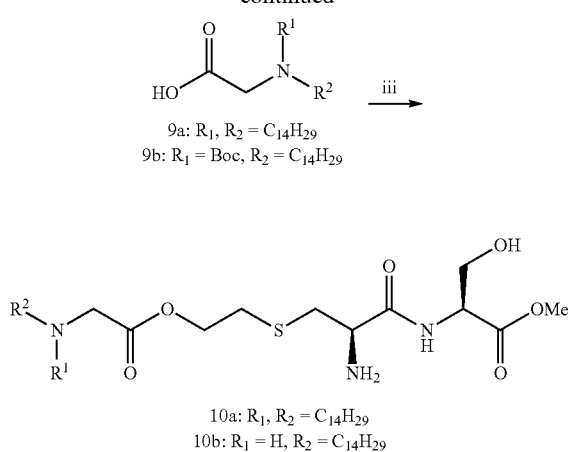

9a: $R_1, R_2 = C_{14}H_{29}$
9b: $R_1 = Boc, R_2 = C_{14}H_{29}$

10a: $R_1, R_2 = C_{14}H_{29}$
10b: $R_1 = H, R_2 = C_{14}H_{29}$

Non-limiting examples of reagents and conditions comprise: (i) (a) 1-bromotetradecane, $Et_3N$, DMF (b) $Boc_2O$, $Et_3N$, $CH_2Cl_2$; (ii) LiOH, $H_2O$, THF; (iii) (a) 4, EDCl, DMAP, NMM, $CH_2Cl_2$ (b) $CF_3COOH$.

In another embodiment, compounds are synthesized by general scheme 3:

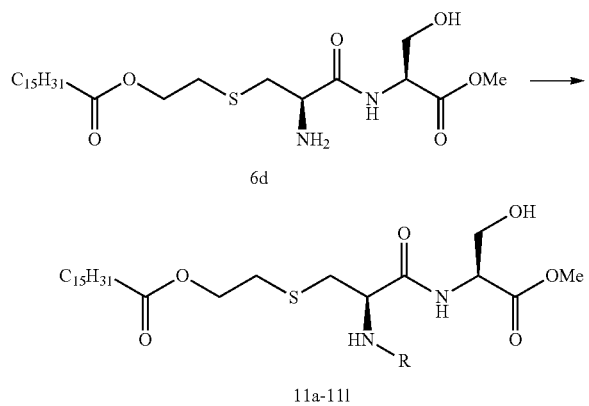

6d 11a-11l

| Compounds | R | Reagents and conditions |
|---|---|---|
| 11a | —$C_2H_5$ | $CH_3CHO$, $CH_3COOH$, MP—$CNBH_3$, $CH_2Cl_2$ |
| 11b | —$C_8H_{17}$ | $C_7H_{15}CHO$, $CH_3COOH$, MP—$CNBH_3$, $CH_2Cl_2$ |
| 11c | —$C_{16}H_{33}$ | $C_{16}H_{33}Br$, $Et_3N$, $CH_2Cl_2$ |
| 11d | —$COCH_3$ | $(CH_3CO)_2O$, $Et_3N$, $CH_2Cl_2$. |
| 11e | —$COC_3H_7$ | $C_3H_7COCl$, pyridine |
| 11f | —$COC_7H_{15}$ | $C_7H_{15}COCl$, pyridine |
| 11g | —$COC_{15}H_{31}$ | $C_{15}H_{31}COCl$, pyridine |
| 11h | —$COCF_3$ | $(CF_3CO)_2O$, $Et_3N$, $CH_2Cl_2$ |
| 11i | —$COCCl_3$ | EDCl•HCl, HOBt, $CCl_3COOH$, $CH_2Cl_2$ |
| 11j | —$SO_2CH_3$ | $(CH_3SO_2)_2O$, $Et_3N$, $CH_2Cl_2$ |
| 11k | —$SO_2CF_3$ | $(CF_3SO_2)_2O$, $Et_3N$, $CH_2Cl_2$ |
| 11l | —$SO_2C_6H_4CH_3$ | $CH_3C_6H_4SO_2Cl$, $Et_3N$, $CH_2Cl_2$ |

In another embodiment, analogues, which are O-acyl derivatives of the compounds described above, are synthesized by general scheme 4:

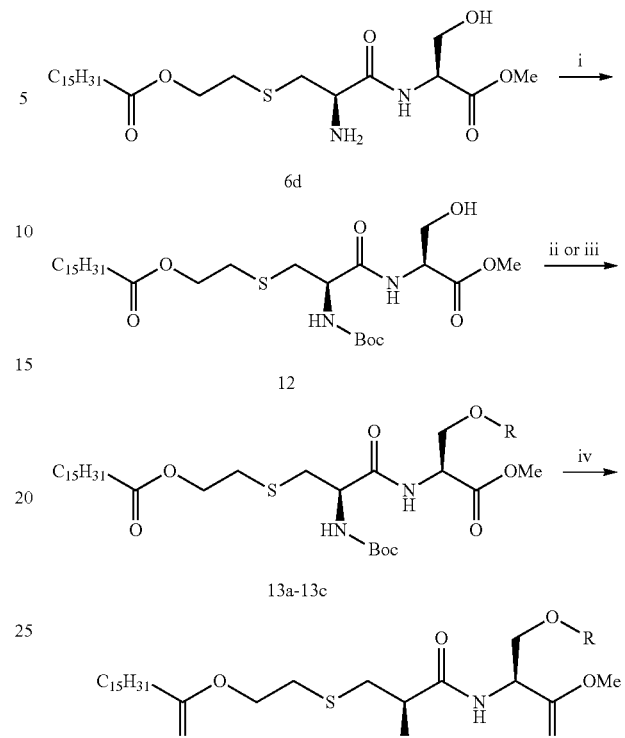

13a-13c 14a-14c a, R = —$COCH_3$; b, R = —$COC_3H_7$; c, R = —$COC_{15}H_{31}$

Examples of reagents and conditions employed in scheme 4 comprise: (i) $(Boc)_2O$, $Et_3N$, $CH_2Cl_2$; For compound 13a: (ii) $(CH_3CO)_2O$, pyridine; For compounds 13b-13c: (iii) RCl, $Et_3N$, THF; (iv) $CF_3COOH$.

In another embodiment, analogues, which are N-acetylated derivatives of the compounds above, are synthesized by an exemplary scheme 5:

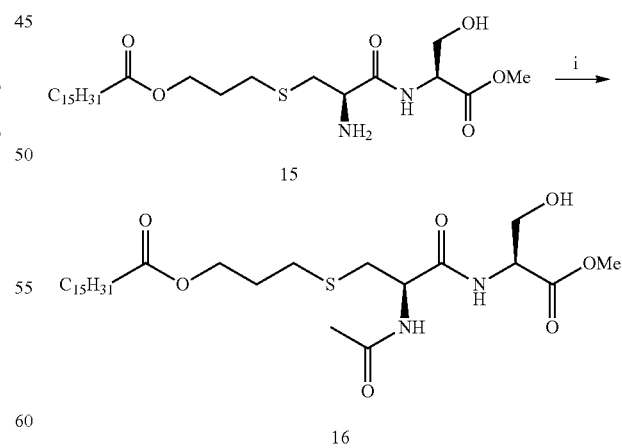

Examples of reagents and conditions employed in scheme 5 comprise: (i) $(CH_3CO)_2O$, $Et_3N$, $CH_2Cl_2$.

In another embodiment, compounds are synthesized by scheme 6:

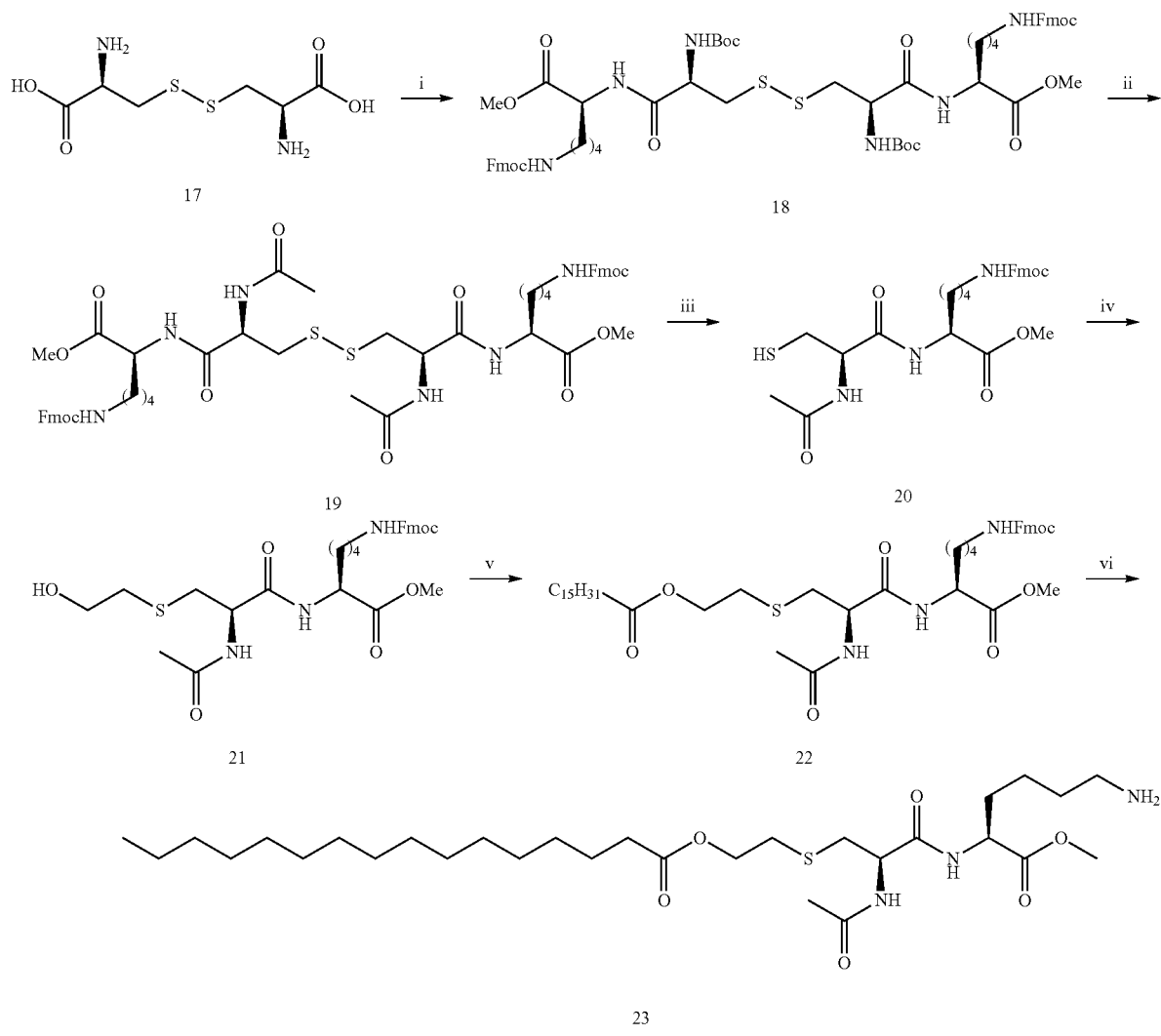
Examples of reagents and conditions employed in scheme 6 comprise: (i) (a) Boc₂O, Et₃N, H₂O (b) H-Lys(Fmoc)-OMe·HCl, EDCl, HOBt, pyridine, DMF, DCM: (ii) (a) HCl, dioxane (b) Ac₂O, pyridine, DCM; (iii) Bu₃P, CH₂Cl₂, H₂O; (iv) 2-iodoethanol, K₂CO₃, DMF; (v) C₁₅H₃₁COCl, pyridine, DCM; (vi) piperazine polymer bound, DMF.
In another embodiment, compounds are synthesized by general scheme 7:
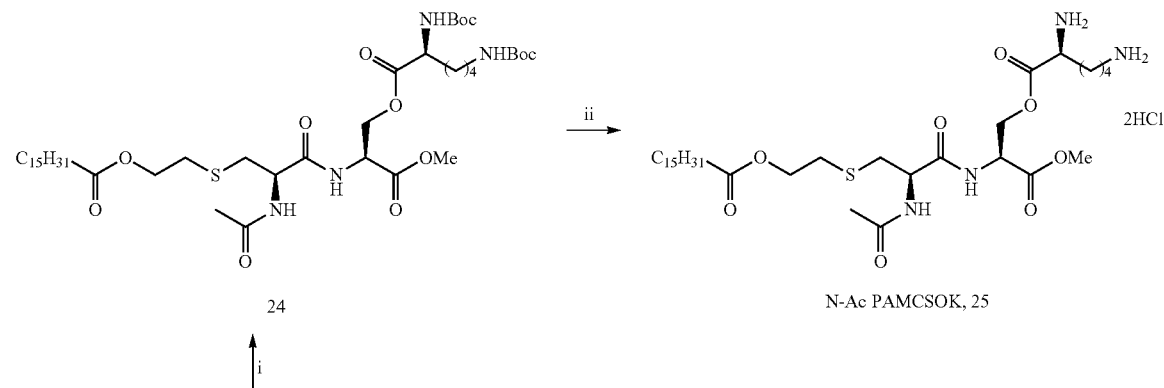

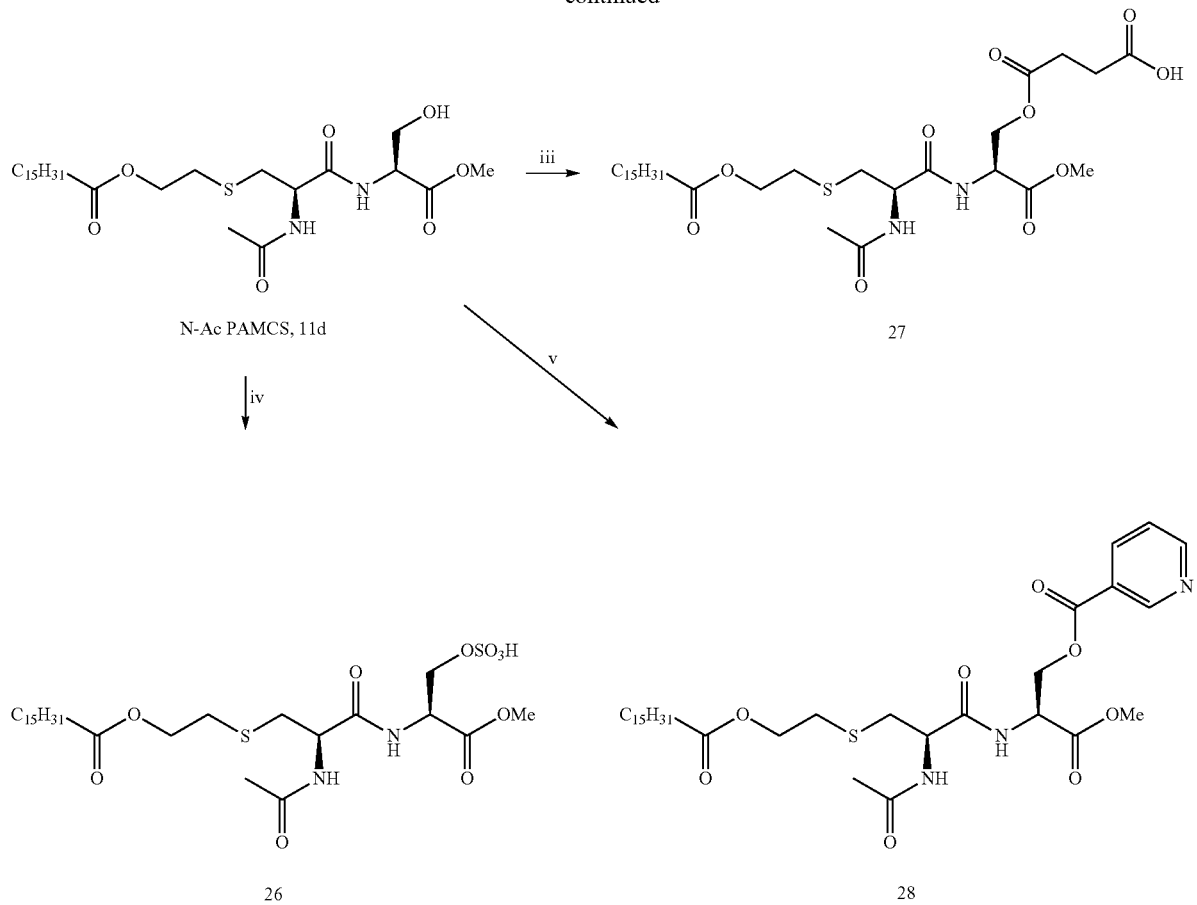
Examples of reagents and conditions employed in scheme 7 comprise: (i) N,N'-Di-Boc-L-Lysine, EDCl, NMM, DMAP, DCM; (ii) HCl, dioxane; (iii) succinic anhydride, Et3N, THF; (iv) SO3-pyridine; (v) nicotinic acid, EDCl, DMAP, NMM.
In another embodiment, compounds such as amide derivatives are synthesized by a process illustrated in scheme 8:
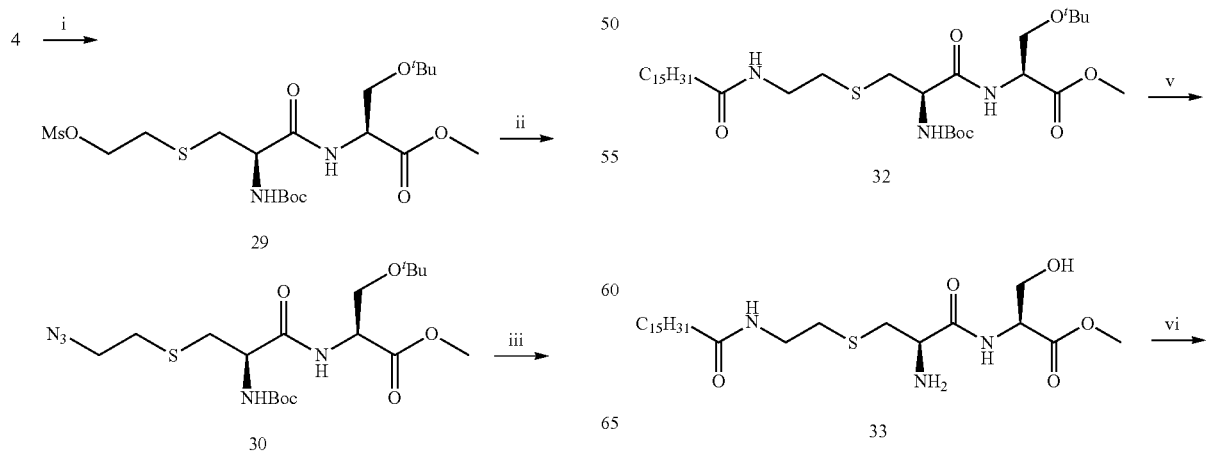

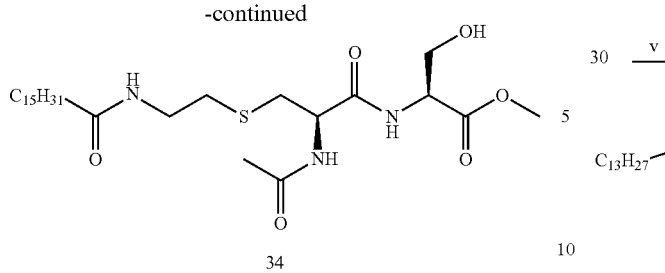

34

Examples of reagents and conditions employed in scheme 8 comprise: (i) MsCl, Et₃N, DCM; (ii) NaN₃, DMF; (iii) PPh₃, THF, H₂O; (iv) C₁₅H₃₁COCl, DCM; (v) TFA; (vi) Ac2O, Et3N, DCM.

In another embodiment, compounds such as 1,2,3-triazole derivatives are synthesized by a method illustrated in general scheme 9:

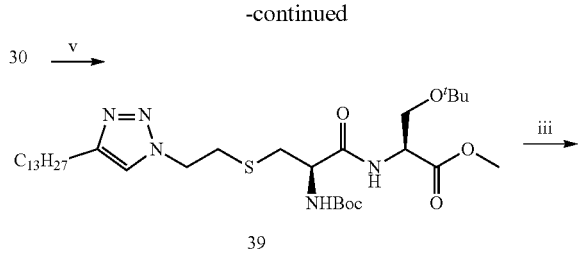

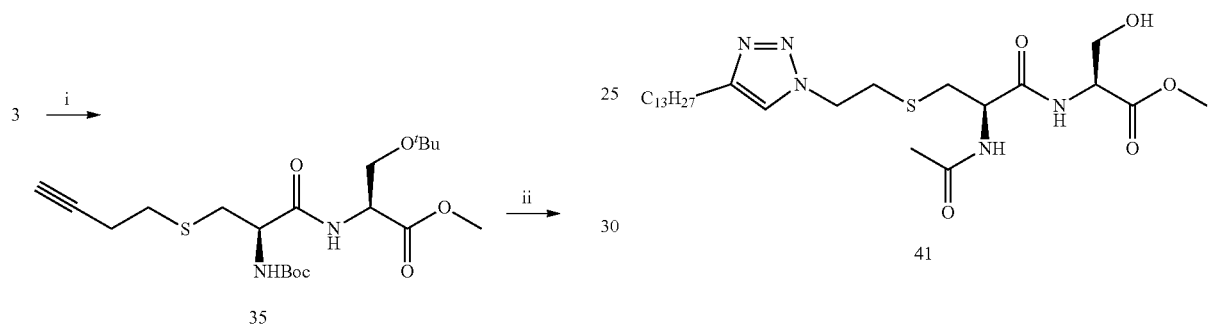

Examples of reagents and conditions employed in scheme 9 comprise: (i) (i) 4-bromobut-1-yne, Et₃N, DMF; (ii) 1-azidohexadecane, CuSO₄, sodium ascorbate, THF, H₂O; (iii) TFA; (iv) Ac₂O, pyridine, DCM; (v) pentadec-1-yne, CuSO₄, sodium ascorbate, THF, H₂O.

In another embodiment, the carbamate derivatives and the water soluble analogue of compound 48 is synthesized by a method illustrated in scheme 10:

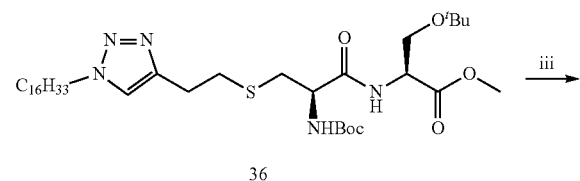

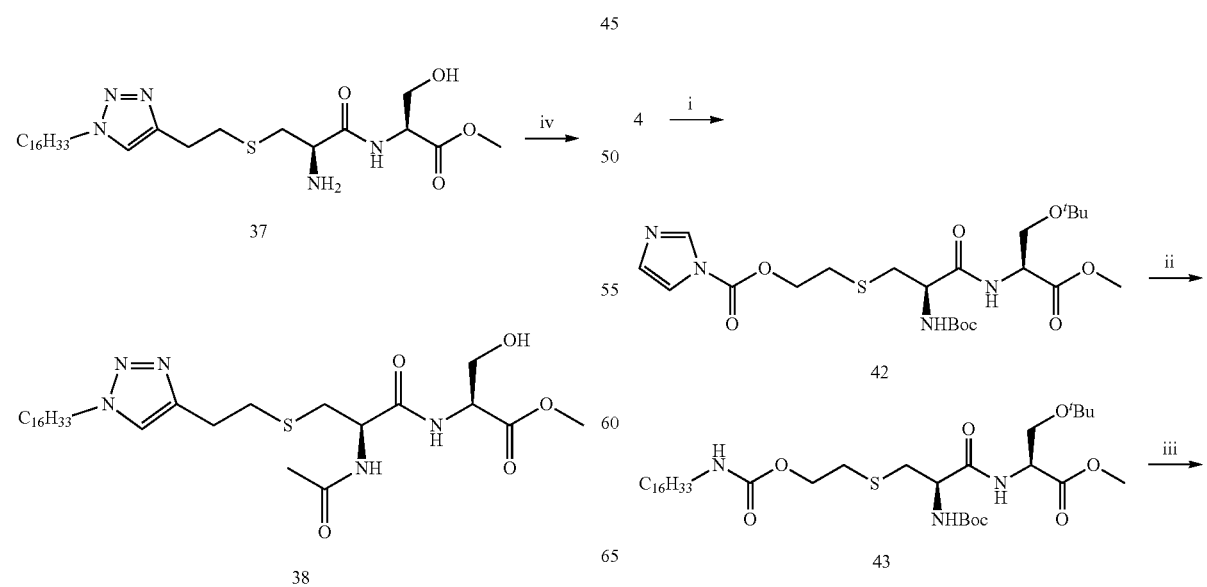

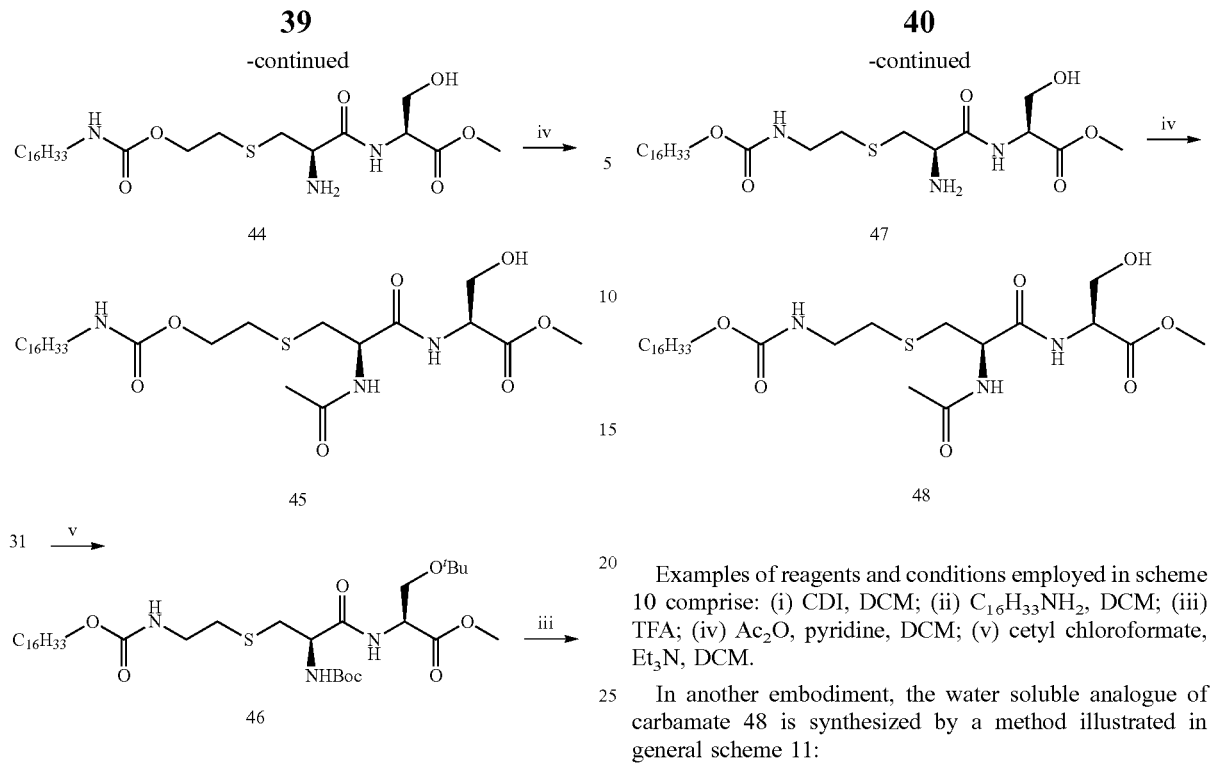
Examples of reagents and conditions employed in scheme 10 comprise: (i) CDI, DCM; (ii) $C_{16}H_{33}NH_2$, DCM; (iii) TFA; (iv) $Ac_2O$, pyridine, DCM; (v) cetyl chloroformate, $Et_3N$, DCM.
In another embodiment, the water soluble analogue of carbamate 48 is synthesized by a method illustrated in general scheme 11:
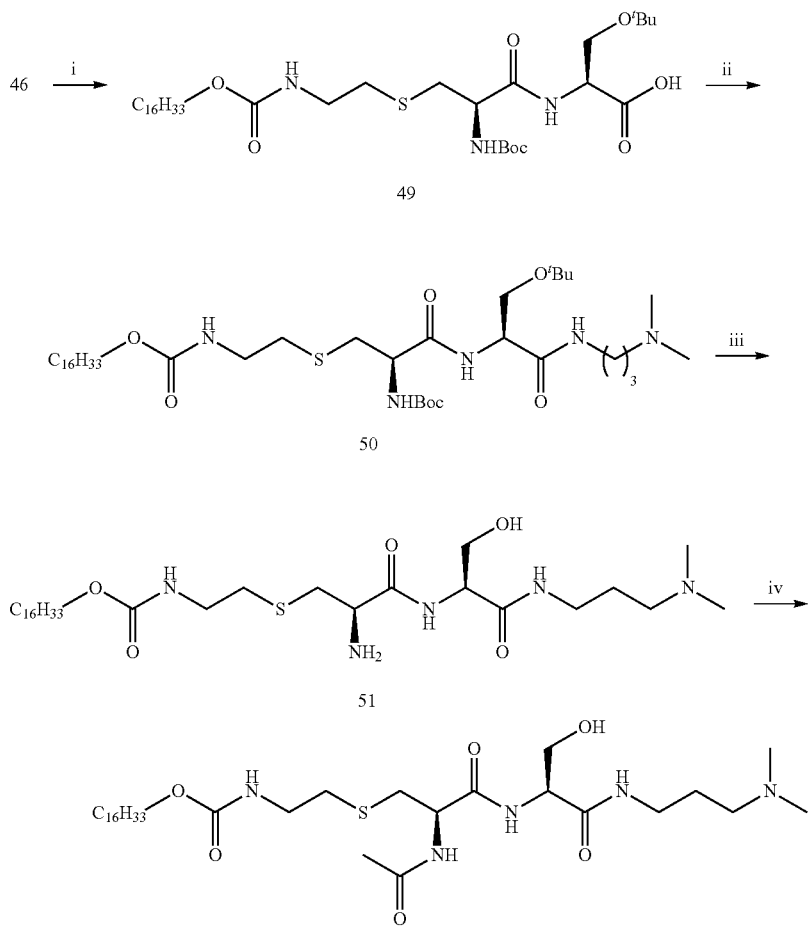

Examples of reagents and conditions employed in scheme 11 comprise: (i) (CH$_3$)$_3$SnOH, DCE; N,N-Dimethylethyl-enediamine, EDCl, HOBT, NMM, DMF; (iii) TFA; (iv) Ac$_2$O, Et$_3$N, DCM.

In another embodiment, compounds are synthesized by an exemplary method illustrated in general scheme 12:

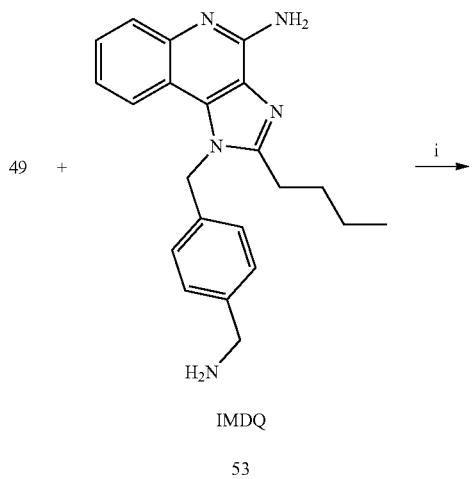

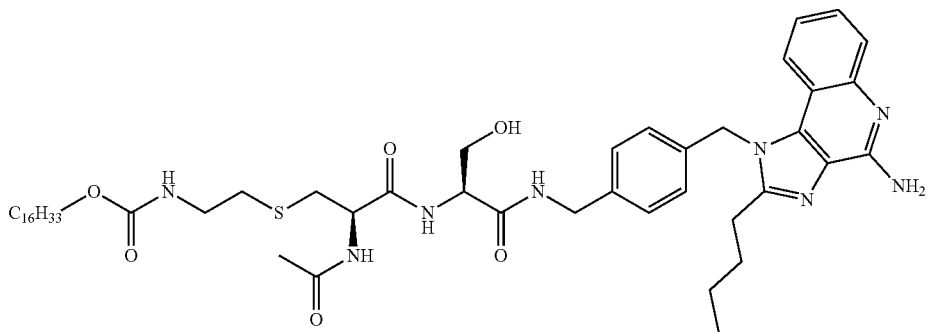

Examples of reagents and conditions employed in scheme 12 comprise: (i) (a) EDCl, HOBt, NMM, DMF (b) TFA (c) Ac$_2$O, pyridine, DCM.

In another embodiment, compounds are synthesized by general scheme 13:

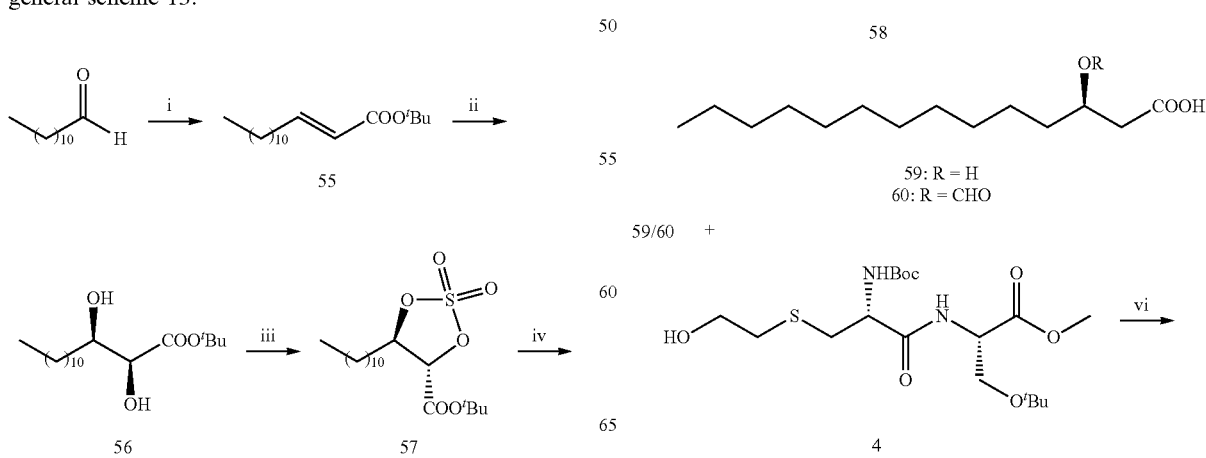

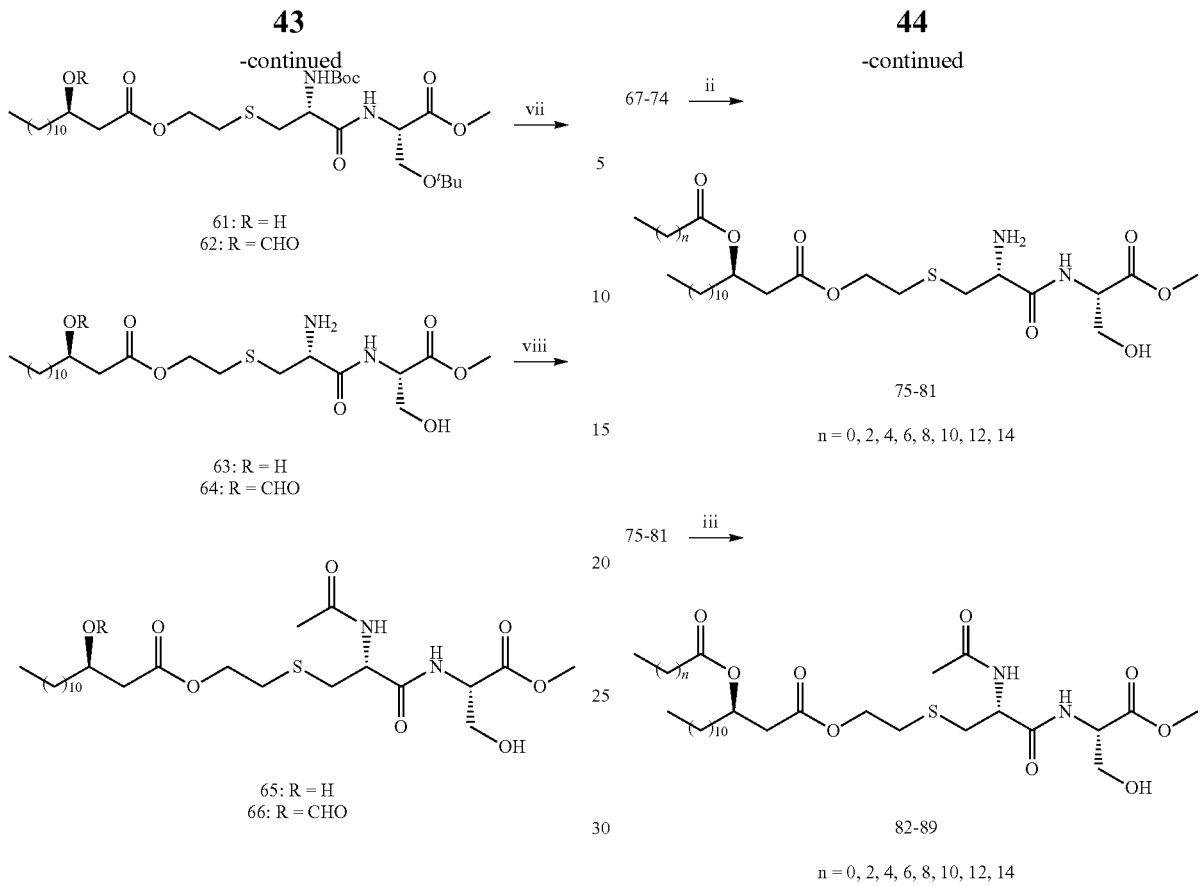

61: R = H
62: R = CHO

63: R = H
64: R = CHO

65: R = H
66: R = CHO 75-81
n = 0, 2, 4, 6, 8, 10, 12, 14

82-89
n = 0, 2, 4, 6, 8, 10, 12, 14

Examples of reagents and conditions employed in scheme 13 comprise: (i) (tert-butoxycarbonylmethylene)triphenylphosphorane, $CH_2Cl_2$, overnight, E/Z 15:1; (ii) AD-mix-β, methanesulfonamide, $^tBuOH/H_2O$ 1:1, overnight, 92%; (iii) (a) $SOCl_2$, pyridine, 0° C., 30 min (b) $NaIO_4$, catalyst $RuCl_3$, $CH_3CN/H_2O$ 3:1, 1 h, 74%; (iv) (a) $NaBH_4$, DMA, 1 h (b) dioxane, aq. HCl, overnight, 60%; (v) for compound 59, TFA and for compound 60: HCOOH; (vi) EDCl, NMM, DMAP; (vii) TFA; (viii) $Ac_2O$, pyridine, DCM.

In another embodiment, compounds are synthesized by general scheme 14:

Examples of reagents and conditions employed in scheme 14 comprise: (i) RCOCl, $Et_3N$, DCM; (ii) TFA; (iii) $Ac_2O$, pyridine, DCM.

In another embodiment, compounds are synthesized by general scheme 15:

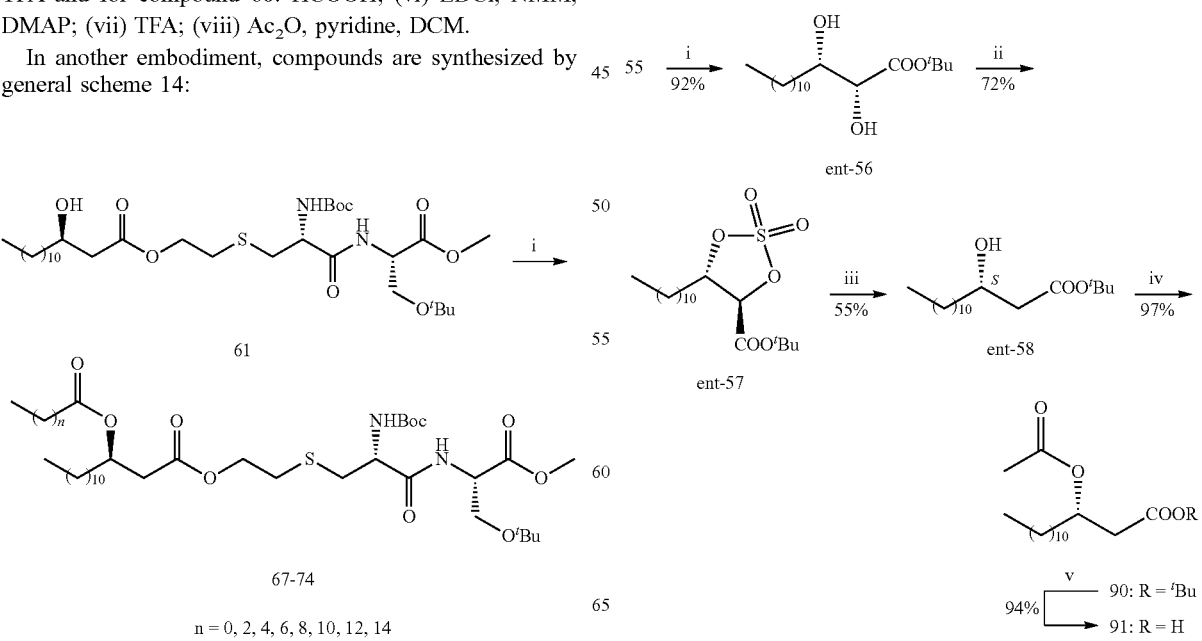

ent-56 ent-57 ent-58

90: R = $^tBu$
91: R = H

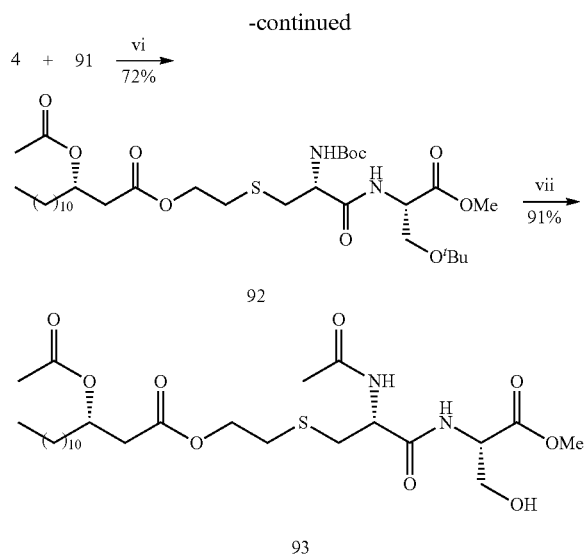

Examples of reagents and conditions employed in scheme 15 comprise: (i) AD-mix-α, methanesulfonamide, $^t$BuOH/H$_2$O 1:1, 0-25° C., 1 h; (iii) (a) NaBH$_4$, DMA, 0-25° C., 3 h (b) 20% aq. HCl, dioxane, 25° C., 24 h; (iv) Ac$_2$O, Et$_3$N, DCM, DMAP, 25° C., 16 h; (v) TFA, 25° C., 45 min.; (vi) EDCl, triethylamine, DMAP, DCM, 25° C., 16 hours (vii) (a) TFA, 25° C., 35 min. (b) Ac$_2$O, pyridine, DCM, 25° C., 30 min.

Examples of the reagents and conditions are provided for illustrative purposes only and are not meant to be limiting. Those of ordinary skill in the art may adapt the conditions and reagents in each of the schemes. For example, the temperatures and times are not meant to be absolute and may be varied.

In another embodiment, one or more compounds of general formula I are administered as a pharmaceutical composition.

In other embodiments, a pharmaceutical composition comprises an effective amount of one or more compounds of formula I.

Uses

In embodiments, one or more compounds of formula I activate TLR molecules. In another preferred embodiment, one or more compounds of formula I modulate an immune response in vitro or in vivo.

In another embodiment, a pharmaceutical composition comprising an effective amount of one or more compounds of formula I are administered to a patient in need thereof, either alone, in combination with another therapeutic agent or as part of a therapy. The therapeutic agent can be, for example, a vaccine, chemotherapy, radiotherapy, immuno therapy, surgery, antibiotics, anti-fungal, etc.

In another embodiment, a pharmaceutical composition comprising an effective amount of one or more compounds of formula I are administered to a patient in need thereof, as an adjuvant. The compounds can, for example, stimulate an immune response to a weakly immunogenic antigen.

In some aspects, a method comprising administering any of the compositions provided herein to a subject in an amount effective to modulate an immune response is provided. In some embodiments, the composition is in an amount effective to induce or enhance an immune response. In some embodiments, the composition is in an amount effective to suppress an immune response. In some embodiments, the composition is in an amount effective to direct or redirect an immune response. In some embodiments, the method is for prophylaxis and/or treatment of the diseases or disorders which would benefit by an enhanced immune response.

In some embodiments, where the method is to induce or enhance an immune response, the subject has or is susceptible to having cancer, an infectious disease, a non-autoimmune metabolic or degenerative disease, an atopic disease, or an addiction. In some embodiments, the subject has been exposed to or may be exposed to a toxin. In some embodiments, the subject has been exposed to or may be exposed to a toxin from a chemical weapon. In some embodiments, the method raises high titer antibodies that bind and neutralize the offending agent before it reaches its effector site (e.g., the brain). In some embodiments, the method is used to modulate cytokines in vivo or in vitro.

In some embodiments, the infectious disease is a chronic viral infection. In some embodiments, the chronic viral infection is HIV, HPV, HBV, or HCV infection. In some embodiments, the infectious disease is or is caused by a bacterial infection. In some embodiments, the subject has or is susceptible to having a *Pseudomonas* infection, a *Pneumococcus* infection, tuberculosis, malaria, leishmaniasis, *H. pylori*, a *Staphylococcus* infection, or a *Salmonella* infection. In some embodiments, the infectious disease is or is caused by a fungal infection. In some embodiments, the infectious disease is or is caused by a parasitic infection. In some embodiments, the infectious disease is or is caused by a protozoan infection. In some embodiments, the subject has or is susceptible to having influenza.

In some aspects, the compositions comprising compounds of formula I are administered with immunomodulatory agents that stimulate various cells of the immune system. For example, B cells, T cells, antigen-presenting cells (APCs).

In some embodiments, an immunomodulatory agent may comprise isolated and/or recombinant proteins or peptides, carbohydrates, glycoproteins, glycopeptides, proteoglycans, inactivated organisms and viruses, dead organisms and virus, genetically altered organisms or viruses, and cell extracts. In some embodiments, an immunomodulatory agent may comprise nucleic acids, carbohydrates, lipids, and/or small molecules. In some embodiments, an immunomodulatory agent is one that elicits an immune response. In some embodiments, an immunomodulatory agent is an antigen. In some embodiments, an immunomodulatory agent is used as a vaccine. In some embodiments, an immunomodulatory agent is any protein and/or other antigen derived from a pathogen. The pathogen may be a virus, bacterium, fungus, protozoan, parasite, etc. In some embodiments, an immunomodulatory agent may be in the form of whole killed organisms, peptides, proteins, glycoproteins, glycopeptides, proteoglycans, carbohydrates, or combinations thereof.

In another embodiment, the compounds can be labeled with a detectable label. Examples of such moieties include radioactive materials, fluorescent proteins, chemiluminescent moieties, fluorophores and the like. A "label" or a "detectable label" is a composition detectable by spectroscopic, photochemical, biochemical, immunochemical, or chemical means. For example, useful labels include $^{32}$P, fluorophores, luminescent compounds, electron-dense reagents, enzymes (e.g., as commonly used in an ELISA), biotin, digoxigenin, or haptens and proteins which can be made detectable.

Fluorophores include any compound, composition or molecule capable of emitting light in response to irradiation. In many instances, fluorophores emit light in the visible region of the spectrum. In other instances, the fluorophores can emit light in the non-visible regions of the spectrum, such as ultraviolet, near-ultraviolet, near-infrared, and infrared. For example and without limitation, examples of fluorophores include: quantum dots; nanoparticles; fluorescent proteins, such as green fluorescent protein and yellow fluorescent protein; heme-based proteins or derivatives thereof; carbocyanine-based chromophores, such as IRDye 800CW, Cy 3, and Cy 5; coumarin-based chromophores, such as (7-diethylamino-3-(4'-maleimidylphenyl)-4-methylcoumarin) (CPM); fluorine-based chromophores, such as fluorescein, fluorescein isothiocyanate (FITC); and numerous ALEXA FLUOR™ chromophores and ALEXA FLUOR™ bioconjugates, which absorb in the visible and near-infrared spectra. The emission from the fluorophores can be detected by any number of methods, including but not limited to, fluorescence spectroscopy, fluorescence microscopy, fluorimeters, fluorescent plate readers, infrared scanner analysis, laser scanning confocal microscopy, automated confocal nanoscanning, laser spectrophotometers, fluorescent-activated cell sorters (FACS), image-based analyzers and fluorescent scanners (e.g., gel/membrane scanners).

Chemiluminescent moieties include any compound, composition or molecule capable of emitting light in response to a chemical reaction. A bioluminescent compound refers to a naturally occurring form of a chemiluminescent compound. Examples of chemiluminescent compounds include: lucigenin, luminol. Examples of bioluminescent compounds include: luciferins, coelenterazines. The emission from chemiluminescent compounds can be detected by luminometers or scanning spectrometers.

The labeled compounds can be used as diagnostics for both in vivo and in vitro use. The compounds can be labeled with a detectable label in order to detect binding.

In another preferred embodiment, a candidate compound has a direct therapeutic effect, that is, without the requirement of any other modifications. The identified compounds can be then used in the prevention or treatment of that disease or disorder. For example, treatment of: inflammatory disease, neuroinflammatory diseases, cancer, neurological diseases, cardiovascular diseases, parasitic or bacterial diseases, viral diseases, central nervous system diseases, brain diseases, autoimmune diseases, transplant rejections, graft-versus-host disease etc.

Effective doses of the compositions of the present invention, for the treatment of the above described diseases, vary depending upon may different factors, including means of administration, physiological state of the patient, whether the patient is human or an animal, other medications administered, and whether treatment is prophylactic or therapeutic. Usually, the patient is a human, but in certain embodiments, a patient is an animal, particularly an animal selected from a mammalian species including rat, rabbit, bovine, ovine, porcine, canine, feline, murine, equine, and primate.

The compounds can be administered on multiple occasions, wherein intervals between single dosages can be daily, weekly, monthly, or yearly. Alternatively, one or more of the compounds of the invention can be administered as a sustained-release formulation, in which case less frequent administration is required. Dosage and frequency may vary depending on the half-life of the compounds of the invention. In therapeutic applications, a relatively high dosage at relatively short intervals is sometimes required until progression of the disease is reduced or terminated, and sometimes until the patient shows partial or complete amelioration of symptoms of the disease. Thereafter, the patient can be administered a prophylactic regime.

Pharmaceutical Compositions

As discussed above, the invention also includes pharmaceutical compositions containing compounds having a general formula I. In some embodiments, the compositions are suitable for internal use and include an effective amount of a pharmacologically active conjugate of the invention, alone or in combination, with one or more pharmaceutically acceptable carriers.

The patient having a pathology, e.g. the patient treated by the methods of this invention can be a mammal, or more particularly, a human. In practice, the agents, are administered in amounts which will be sufficient to exert their desired biological activity.

The pharmaceutical compositions of the invention may contain, for example, more than one specificity. In some examples, a pharmaceutical composition of the invention, containing one or more compounds of the invention, is administered in combination with another useful composition such as an anti-inflammatory agent, an immunostimulator, a chemotherapeutic agent, an antiviral agent, or the like. Furthermore, the compositions of the invention may be administered in combination with a cytotoxic, cytostatic, or chemotherapeutic agent such as an alkylating agent, antimetabolite, mitotic inhibitor or cytotoxic antibiotic. In general, the currently available dosage forms of the known therapeutic agents for use in such combinations will be suitable.

Combination therapy (or "co-therapy") includes the administration of the compositions and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

Combination therapy may, but generally is not, intended to encompass the administration of two or more of these therapeutic agents as part of separate monotherapy regimens that incidentally and arbitrarily result in the combinations of the present invention. Combination therapy is intended to embrace administration of compounds of formula I in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. Combination therapy also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Therapeutic or pharmacological compositions of the present invention will generally comprise an effective amount of the active component(s), dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

For any agent used in the methods of the invention, the therapeutically effective amount or dose can be estimated initially from activity assays in cell cultures and/or animals. For example, a dose can be formulated in animal models to achieve a circulating concentration range that includes the $IC_{50}$ as determined by activity assays (e.g., the concentration of the test compound, which achieves a half-maximal inhibition of the proliferation activity). Such information can be used to more accurately determine useful doses in humans.

Toxicity and therapeutic efficacy of the peptides described herein can be determined by standard pharmaceutical procedures in experimental animals, e.g., by determining the $IC_{50}$ and the $LD_{50}$ (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1). Dosage amount and interval may be adjusted individually to provide plasma levels of the active moiety which are sufficient to maintain therapeutic effects, termed the minimal effective concentration (MEC). The MEC will vary for each preparation, but can be estimated from in vitro and/or in vivo data, e.g., the concentration necessary to achieve 50-90% inhibition of a proliferation of certain cells may be ascertained using the assays described herein. Dosages necessary to achieve the MEC will depend on individual characteristics and route of administration. HPLC assays or bioassays can be used to determine plasma concentrations. Dosage intervals can also be determined using the MEC value. Preparations should be administered using a regimen, which maintains plasma levels above the MEC for 10-90% of the time, preferable between 30-90% and most preferably 50-90%. Depending on the severity and responsiveness of the condition to be treated, dosing can also be a single administration of a slow release composition described hereinabove, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, etc.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or other known methods.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

The pharmaceutical compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

The compositions of the present invention can be administered in intravenous (both bolus and infusion), intraperitoneal, subcutaneous or intramuscular form, all using forms well known to those of ordinary skill in the pharmaceutical arts. Injectables can be prepared in conventional forms, either as liquid solutions or suspensions.

Parenteral injectable administration is generally used for subcutaneous, intramuscular or intravenous injections and infusions. Additionally, one approach for parenteral administration employs the implantation of a slow-release or sustained-released systems, which assures that a constant level of dosage is maintained, according to U.S. Pat. No. 3,710,795, incorporated herein by reference.

Furthermore, preferred compositions for the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, suppositories, ointments, lotions, aerosol sprays and gels, wherein the concentration of active ingredient would typically range from 0.01% to 15%, w/w or w/v.

The active compound defined above, may be also formulated as suppositories, using for example, polyalkylene glycols, for example, propylene glycol, as the carrier. In some embodiments, suppositories are advantageously prepared from fatty emulsions or suspensions.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564. For example, the molecules described herein can be provided as a complex with a lipophilic compound or non-immunogenic, high molecular weight compound constructed using methods known in the art. An example of nucleic-acid associated complexes is provided in U.S. Pat. No. 6,011,020.

The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition to be administered may also contain minor amounts of non-toxic auxiliary substances such as wetting or emulsifying agents, pH buffering agents, and other substances such as for example, sodium acetate, and triethanolamine oleate. The dosage regimen utilizing the molecules is selected in accordance with a variety of factors including type, species, age, weight, sex and medical condition of the patient; the severity of the condition to be treated; the route of administration; the renal and hepatic function of the patient; and the particular molecule or salt thereof employed. An ordinarily skilled physician or veterinarian can readily determine and prescribe the effective amount of the drug required to prevent, counter or arrest the progress of the condition. Compounds of the present invention may be administered in a single daily dose, or the total daily dosage may be administered in divided doses of two, three or four times daily.

The invention has been described in detail with reference to preferred embodiments thereof. However, it will be appreciated that those skilled in the art, upon consideration of this disclosure, may make modifications and improvements within the spirit and scope of the invention. The following non-limiting examples are illustrative of the invention.

EXAMPLES

A detailed SAR on the monoacylated lipopeptide chemotype was conducted, the goals being not only to identify potentially more potent analogues of 6d, but also to attempt to understand the structural correlates determining human versus murine TLR2 specificity.

Materials and Methods

Chemistry.

All of the solvents and reagents used were obtained commercially and used as such unless noted otherwise. Moisture- or air-sensitive reactions were conducted under nitrogen atmosphere in oven-dried (120° C.) glass apparatus. The solvents were removed under reduced pressure using standard rotary evaporators. Flash column chromatography was carried out using RediSep Rf 'Gold' high performance silica columns on CombiFlash Rf instrument unless otherwise mentioned, while thin-layer chromatography was carried out on silica gel CCM pre-coated aluminum sheets. Purity for all final compounds was confirmed to be greater than 97% by LC-MS using a Zorbax Eclipse Plus 4.6 mm×150 mm, 5 μm analytical reverse phase $C_{18}$ column with $H_2O$-isopropanol or $H_2O$—$CH_3CN$ gradients and an Agilent ESI-TOF mass spectrometer (mass accuracy of 3 ppm) operating in the positive ion (or negative ion, as appropriate) acquisition mode.

General Procedure for the Syntheses of Compounds 5a-5g

Synthesis of Compound 5a: 2-(((R)-3-(((S)-3-(tert-butoxy)-1-methoxy-1-oxopropan-2-yl)amino)-2-((tert-butoxycarbonyl)amino)-3-oxopropyl)thio)ethyl butyrate

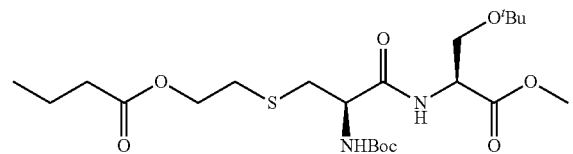 [SMILES: CCCC(=O)OCCSC[C@H](NC(=O)OC(C)(C)C)C(=O)N[C@@H](COC(C)(C)C)C(=O)OC]

To a solution of compound 4 (100 mg, 0.24 mmol) in anhydrous $CH_2Cl_2$ (5 mL), were added triethylamine (49 μL, 0.18 mmol) and 4-dimethylaminopyridine (DMAP, 3.0 mg, 0.024 mmol) and the reaction mixture was stirred at room temperature. After 10 min butyryl chloride (30 μL, 0.28 mmol) was added and the reaction mixture was stirred for further 30 min. The solvent was then removed using vacuum and the residue was purified using column chromatography (5% MeOH/CH$_2$Cl$_2$) to obtain the compound 5a (99 mg, 85%). $^1$H NMR (500 MHz, CDCl$_3$) δ 7.13 (d, J=7.8 Hz, 1H), 5.44 (s, 1H), 4.65 (dt, J=8.1, 3.0 Hz, 1H), 4.33 (d, J=4.5 Hz, 1H), 4.24 (t, J=6.6 Hz, 2H), 3.82 (dd, J=9.1, 2.9 Hz, 1H), 3.74 (s, 3H), 3.57 (dd, J=9.1, 3.2 Hz, 1H), 3.01 (dd, J=13.9, 5.6 Hz, 1H), 2.92 (dd, J=13.9, 6.7 Hz, 1H), 2.84 (dd, J=12.2, 6.1 Hz, 2H), 2.30 (t, J=7.4 Hz, 2H), 1.65 (m, 2H), 1.45 (s, 9H), 1.13 (s, 9H), 0.94 (t, J=7.4 Hz, 3H). $^{13}$C NMR (126 MHz, CDCl$_3$) δ 173.61, 170.59, 170.50, 155.37, 80.40, 77.42, 77.42, 77.16, 76.91, 73.65, 63.15, 61.78, 53.84, 53.32, 52.57, 36.18, 34.98, 31.19, 28.43, 27.43, 18.50, 13.82. MS (ESI) calculated for C$_{22}$H$_{40}$N$_2$O$_8$S, m/z 492.25. found 515.24 (M+Na)$^+$.

Compounds 5b, 5c, 5e-5g were synthesized similarly as compound 5a. Compound 5d was synthesized as published earlier (Agnihotri, G. et al., *J. Med. Chem.* 2011, 54, 8148-8160).

5b: 2-(((R)-3-(((S)-3-(tert-butoxy)-1-methoxy-1-oxopropan-2-yl)amino)-2-((tert-butoxycarbonyl)amino)-3-oxopropyl)thio)ethyl octanoate

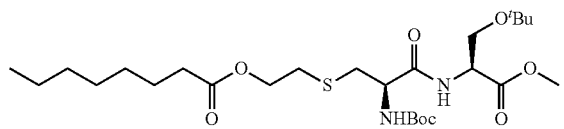 [SMILES: CCCCCCCC(=O)OCCSC[C@H](NC(=O)OC(C)(C)C)C(=O)N[C@@H](COC(C)(C)C)C(=O)OC]

(119 mg, 92%) $^1$H NMR (500 MHz, CDCl3) δ 7.13 (d, J=7.9 Hz, 1H), 5.44 (s, 1H), 4.65 (dt, J=8.1, 3.0 Hz, 1H), 4.32 (s, 1H), 4.24 (t, J=6.6 Hz, 2H), 3.82 (dd, J=9.1, 2.9 Hz, 1H), 3.74 (s, 3H), 3.57 (dd, J=9.1, 3.2 Hz, 1H), 3.01 (dd, J=13.9, 5.5 Hz, 1H), 2.92 (dd, J=13.9, 6.8 Hz, 1H), 2.83 (dd, J=12.6, 6.3 Hz, 2H), 2.31 (t, J=7.6 Hz, 2H), 1.61 (dd, J=14.7, 7.4 Hz, 2H), 1.45 (s, 9H), 1.31-1.24 (m, 8H), 1.14 (s, 9H), 0.87 (t, J=6.9 Hz, 3H). $^{13}$C NMR (126 MHz, CDCl$_3$) δ 174.05, 170.84, 170.76, 155.61, 80.64, 73.91, 63.39, 62.03, 54.09, 53.57, 52.82, 35.22, 34.57, 32.04, 31.42, 29.48, 29.32, 28.69, 27.68, 25.28, 22.99, 14.47. MS (ESI) calculated for C$_{26}$H$_{48}$N$_2$O$_8$S, m/z 548.31. found 571.31 (M+Na)$^+$.

5c: 2-(((R)-3-(((S)-3-(tert-butoxy)-1-methoxy-1-oxopropan-2-yl)amino)-2-((tert-butoxycarbonyl)amino)-3-oxopropyl)thio)ethyl dodecanoate

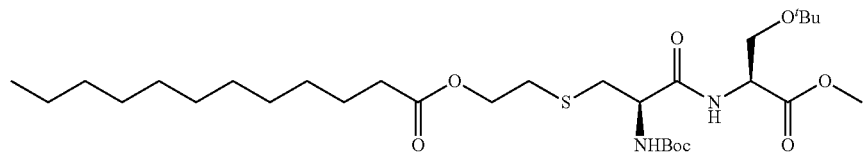 [SMILES: CCCCCCCCCCCC(=O)OCCSC[C@H](NC(=O)OC(C)(C)C)C(=O)N[C@@H](COC(C)(C)C)C(=O)OC]

(124 mg, 87%) $^1$H NMR (500 MHz, CDCl$_3$) δ 7.14 (d, J=7.9 Hz, 1H), 5.44 (s, 1H), 4.65 (dt, J=8.1, 3.0 Hz, 1H), 4.33 (d, J=4.2 Hz, 1H), 4.23 (t, J=6.6 Hz, 2H), 3.82 (dd, J=9.1, 3.0 Hz, 1H), 3.74 (s, 3H), 3.57 (dd, J=9.1, 3.2 Hz, 1H), 3.01 (dd, J=13.9, 5.5 Hz, 1H), 2.92 (dd, J=13.9, 6.8 Hz, 1H), 2.83 (dd, J=12.6, 6.3 Hz, 2H), 2.31 (t, J=7.6 Hz, 2H), 1.60 (dd, J=14.6, 7.3 Hz, 2H), 1.45 (s, 9H), 1.30-1.23 (m, 16H), 1.14 (s, 9H), 0.87 (t, J=7.0 Hz, 3H). $^{13}$C NMR (126 MHz, CDCl$_3$) δ 174.05, 170.84, 170.76, 155.61, 80.65, 73.91, 63.39, 62.03, 54.09, 53.57, 52.82, 35.22, 34.58, 32.30, 31.41, 30.00, 29.86, 29.73, 29.67, 29.54, 28.69, 27.68, 25.28, 23.08, 14.52. MS (ESI) calculated for C$_{30}$H$_{56}$N$_2$O$_8$S, ink 604.38. found 627.37 (M+Na)$^+$.

5e: 2-(((R)-3-(((S)-3-(tert-butoxy)-1-methoxy-1-oxopropan-2-yl)amino)-2-((tert-butoxycarbonyl)amino)-3-oxopropyl)thio)ethyl stearate

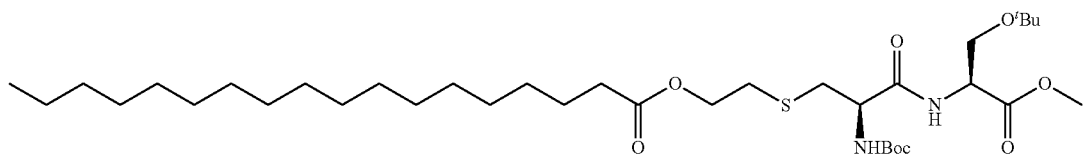 [SMILES: CCCCCCCCCCCCCCCCCC(=O)OCCSC[C@H](NC(=O)OC(C)(C)C)C(=O)N[C@@H](COC(C)(C)C)C(=O)OC]

(142 mg, 87%). $^1$H NMR (500 MHz, CDCl$_3$) δ 7.13 (d, J=7.9 Hz, 1H), 5.44 (s, 1H), 4.65 (dt, J=8.1, 3.0 Hz, 1H), 4.33 (d, J=4.5 Hz, 1H), 4.24 (t, J=6.6 Hz, 2H), 3.82 (dd, J=9.1, 2.9 Hz, 1H), 3.74 (s, 3H), 3.57 (dd, J=9.1, 3.2 Hz, 1H), 3.01 (dd, J=13.9, 5.5 Hz, 1H), 2.92 (dd, J=13.9, 6.8 Hz, 1H), 2.83 (dd, J=12.7, 6.4 Hz, 2H), 2.31 (t, J=7.6 Hz, 2H), 1.63-1.58 (m, 2H), 1.46 (s, 9H), 1.30-1.22 (m, 28H), 1.14 (s, 9H), 0.87 (t, J=6.9 Hz, 3H). $^{13}$C NMR (126 MHz, CDCl$_3$) δ 174.05, 170.84, 170.76, 155.59, 80.65, 73.91, 63.38, 62.03, 54.09, 53.58, 52.82, 35.22, 34.58, 32.32, 31.42, 30.10, 30.06, 30.02, 29.88, 29.76, 29.69, 29.55, 28.69, 27.69, 25.28, 23.09, 14.53. MS (ESI) calculated for C$_{36}$H$_{68}$N$_2$O$_8$S, m/z 688.47. found 711.48 (M+Na)$^+$.

5f: 2-(((R)-3-(((S)-3-(tert-butoxy)-1-methoxy-1-oxopropan-2-yl)amino)-2-((tert-butoxycarbonyl)amino)-3-oxopropyl)thio)ethyl[1,1'-biphenyl]-4-carboxylate

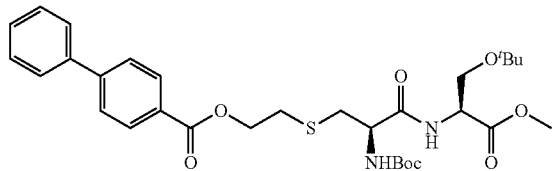 [SMILES: COC(=O)[C@H](COC(C)(C)C)NC(=O)[C@H](CSCCOC(=O)c1ccc(-c2ccccc2)cc1)NC(=O)OC(C)(C)C]

(87 mg, 60%). $^1$H NMR (500 MHz, CDCl$_3$) δ 8.11 (d, J=8.5 Hz, 2H), 7.66 (d, J=8.5 Hz, 2H), 7.63 (dd, J=5.2, 3.3

Hz, 2H), 7.47 (t, J=7.5 Hz, 2H), 7.40 (dt, J=9.3, 4.3 Hz, 1H), 7.17 (d, J=7.9 Hz, 1H), 5.48 (s, 1H), 4.67 (dt, J=8.1, 3.0 Hz, 1H), 4.52 (t, J=6.6 Hz, 2H), 4.38 (s, 1H), 3.83 (dd, J=9.1, 2.9 Hz, 1H), 3.73 (s, 3H), 3.57 (dd, J=9.1, 3.2 Hz, 1H), 3.09 (dd, J=13.9, 5.5 Hz, 1H), 3.04-2.94 (m, 3H), 1.46 (s, 9H), 1.13 (s, 9H). $^{13}$C NMR (126 MHz, CDCl$_3$) δ 170.61, 170.52, 166.42, 155.40, 145.94, 140.13, 130.38, 129.08, 128.79, 128.32, 127.43, 127.23, 80.44, 73.67, 63.79, 61.78, 53.88, 53.34, 52.58, 35.05, 31.28, 28.44, 27.43. MS (ESI) calculated for C$_{31}$H$_{42}$N$_2$O$_8$S, m/z 602.27. found 625.27 (M+Na)$^+$.

5g: 2-(((R)-3-(((S)-3-(tert-butoxy)-1-methoxy-1-oxopropan-2-yl)amino)-2-((tert-butoxycarbonyl)amino)-3-oxopropyl)thio)ethyl[1,1'-biphenyl]-3-carboxylate

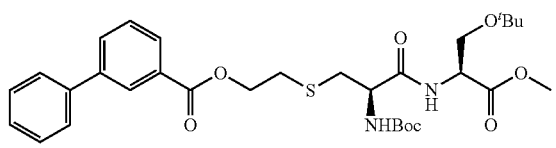 [SMILES: COC(=O)[C@H](COC(C)(C)C)NC(=O)[C@H](CSCCOC(=O)c1cccc(-c2ccccc2)c1)NC(=O)OC(C)(C)C]

(81 mg, 56%). $^1$H NMR (500 MHz, CDCl$_3$) δ 8.28 (t, J=1.6 Hz, 1H), 8.02 (d, J=7.8 Hz, 1H), 7.79 (ddd, J=7.7, 1.8, 1.2 Hz, 1H), 7.62 (d, J=7.1 Hz, 2H), 7.52 (d, J=7.7 Hz, 1H), 7.46 (dd, J=9.9, 3.5 Hz, 2H), 7.38 (t, J=7.4 Hz, 1H), 7.17 (d, J=7.8 Hz, 1H), 5.48 (d, J=3.4 Hz, 1H), 4.66 (dt, J=8.1, 3.0 Hz, 1H), 4.52 (t, J=6.7 Hz, 2H), 4.38 (d, J=3.6 Hz, 1H), 3.82 (dd, J=9.1, 2.9 Hz, 1H), 3.72 (s, 3H), 3.56 (dd, J=9.1, 3.2 Hz, 1H), 3.08 (dd, J=13.9, 5.4 Hz, 1H), 3.03-2.95 (m, 3H), 1.45 (s, 9H), 1.13 (s, 9H). $^{13}$C NMR (126 MHz, CDCl$_3$) δ 170.60, 170.50, 166.48, 155.39, 141.65, 140.21, 131.86, 130.61, 129.04, 128.57, 127.90, 127.32, 80.41, 73.66, 63.83, 61.78, 53.89, 53.34, 52.57, 35.05, 31.23, 28.43, 27.41. MS (ESI) calculated for C$_{31}$H$_{42}$N$_2$O$_8$S, m/z 602.27. found 625.26 (M+Na)$^+$.

General Procedure for Synthesis of Compounds 6a-6g

Synthesis of Compound 6a: 2-(((R)-2-Amino-3-(((S)-3-Hydroxy-1-Methoxy-1-oxopropan-2-yl)amino)-3-oxopropyl)thio)ethyl butyrate

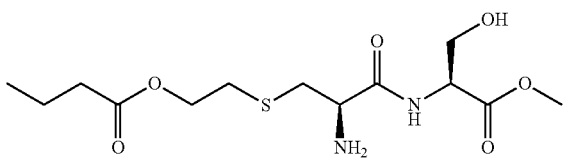 [SMILES: CCCC(=O)OCCSC[C@H](N)C(=O)N[C@@H](CO)C(=O)OC]

Compound 5a (49 mg, 0.1 mmol) was dissolved in 2 mL of trifluoracetic acid and stirred for 30 min, followed by removal of the solvent by purging nitrogen and drying under vacuum to obtain the residue which was further purified using column chromatography to obtain the trifluoroacetate salt of compound 6a in quantitative yield (49 mg). $^1$H NMR (500 MHz, CDCl$_3$) δ 8.52 (d, J=7.7 Hz, 1H), 4.71-4.62 (m, 1H), 4.35 (t, J=6.4 Hz, 1H), 4.28-4.17 (m, 2H), 3.97-3.90 (m, 1H), 3.87 (dd, J=11.6, 5.1 Hz, 1H), 3.76 (s, 3H), 3.17 (dd, J=14.4, 5.4 Hz, 1H), 3.02 (dd, J=14.4, 7.1 Hz, 1H), 2.81 (t, J=6.4 Hz, 2H), 2.31 (t, J=7.4 Hz, 2H), 1.69-1.55 (m, 2H), 0.94 (t, J=7.4 Hz, 3H). $^{13}$C NMR (126 MHz, CDCl$_3$) δ 174.40, 170.35, 168.39, 62.71, 61.83, 55.35, 52.91, 52.86, 36.14, 33.16, 30.90, 18.43, 13.71. MS (ESI) calculated for C$_{13}$H$_{24}$N$_2$O$_6$S, m/z 336.14. found 337.15 (M+H)$^+$.

Compounds 6b, 6c, 6e-6g were synthesized similarly as compound 6a. Compound 6d was synthesized as published earlier (Agnihotri, G. et al., *J. Med. Chem.* 2011, 54, 8148-8160).

6b: 2-(((R)-2-amino-3-(((S)-3-hydroxy-1-methoxy-1-oxopropan-2-yl)amino)-3-oxopropyl)thio)ethyl octanoate

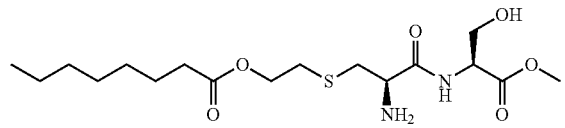 [SMILES: CCCCCCCC(=O)OCCSC[C@H](N)C(=O)N[C@@H](CO)C(=O)OC]

$^1$H NMR (500 MHz, CDCl$_3$) δ 8.49 (d, J=7.7 Hz, 1H), 4.71-4.64 (m, 1H), 4.35 (t, J=6.5 Hz, 1H), 4.26-4.18 (m, 2H), 3.96-3.90 (m, 1H), 3.86 (dd, J=11.7, 5.2 Hz, 1H), 3.75 (s, 3H), 3.48 (s, 1H), 3.16 (dd, J=14.5, 5.6 Hz, 1H), 3.01 (dd, J=14.6, 7.2 Hz, 1H), 2.81 (t, J=6.5 Hz, 2H), 2.31 (t, J=7.6 Hz, 2H), 1.64-1.55 (m, 2H), 1.35-1.18 (m, 8H), 0.87 (t, J=7.0 Hz, 3H). $^{13}$C NMR (126 MHz, CDCl$_3$) δ 174.57, 170.31, 168.25, 62.64, 61.82, 55.38, 52.96, 52.82, 50.99, 34.30, 33.05, 31.78, 30.90, 29.21, 29.04, 24.97, 22.73, 14.19. MS (ESI) calculated for C$_{17}$H$_{32}$N$_2$O$_6$S, m/z 392.20. found 393.21 (M+H)$^+$.

6c: 2-(((R)-2-amino-3-(((S)-3-hydroxy-1-methoxy-1-oxopropan-2-yl)amino)-3-oxopropyl)thio)ethyl dodecanoate

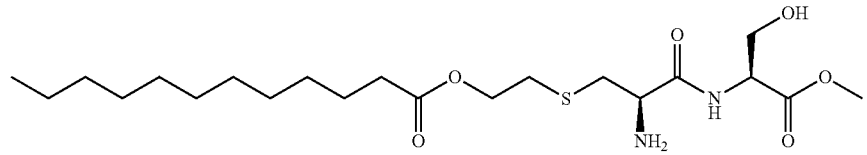 [SMILES: CCCCCCCCCCCC(=O)OCCSC[C@H](N)C(=O)N[C@@H](CO)C(=O)OC]

¹H NMR (500 MHz, CDCl₃) δ 8.49 (d, J=7.3 Hz, 1H), 4.68 (s, 1H), 4.36 (s, 1H), 4.23 (t, J=6.0 Hz, 2H), 3.93 (d, J=9.5 Hz, 1H), 3.86 (dd, J=11.1, 4.7 Hz, 1H), 3.76 (s, 3H), 3.16 (dd, J=14.3, 5.2 Hz, 1H), 3.02 (dd, J=14.2, 6.9 Hz, 1H), 2.81 (t, J=6.4 Hz, 2H), 2.31 (t, J=7.7 Hz, 2H), 1.59 (dd, J=14.3, 7.2 Hz, 2H), 1.31-1.22 (m, 16H), 0.87 (t, J=7.0 Hz, 3H). ¹³C NMR (126 MHz, CDCl₃) δ 174.83, 170.54, 168.51, 62.89, 62.07, 55.65, 53.22, 53.07, 34.57, 33.29, 32.31, 31.15, 30.03, 30.02, 29.90, 29.75, 29.69, 29.55, 25.24, 23.08, 14.52. MS (ESI) calculated for $C_{21}H_{40}N_2O_6S$, m/z 448.26. found 449.27 (M+H)⁺.

6e: 2-(((R)-2-amino-3-(((S)-3-hydroxy-1-methoxy-1-oxopropan-2-yl)amino)-3-oxopropyl)thio)ethyl stearate ¹H NMR (500 MHz, CDCl₃) δ 8.57 (d, J=7.4 Hz, 1H), 8.02 (d, J=8.4 Hz, 2H), 7.58 (d, J=8.4 Hz, 2H), 7.55-7.52 (m, 2H), 7.40 (t, J=7.4 Hz, 2H), 7.36-7.31 (m, 1H), 4.72-4.67 (m, 1H), 4.50-4.42 (m, 3H), 3.94 (d, J=9.2 Hz, 1H), 3.87 (dd, J=11.4, 4.7 Hz, 1H), 3.65 (s, 3H), 3.25 (dd, J=14.3, 5.1 Hz, 1H), 3.10 (dd, J=14.3, 6.9 Hz, 1H), 2.95 (t, J=6.4 Hz, 2H). ¹³C NMR (126 MHz, CDCl₃) δ 170.59, 168.60, 167.20, 146.33, 140.15, 130.62, 129.31, 128.63, 128.60, 127.62, 127.45, 63.57, 62.12, 55.67, 53.18, 51.27, 33.42, 31.25. MS (ESI) calculated for $C_{22}H_{26}N_2O_6S$, m/z 446.15. found 447.16 (M+H)⁺.

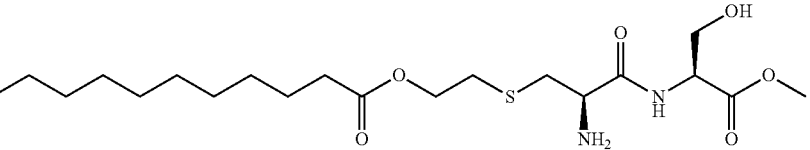

¹H NMR (500 MHz, CDCl₃) δ 8.47 (d, J=7.6 Hz, 1H), 4.72-4.64 (m, 1H), 4.35 (t, J=6.3 Hz, 1H), 4.24-4.16 (m, 2H), 3.94 (d, J=8.9 Hz, 1H), 3.86 (dd, J=11.6, 5.1 Hz, 1H), 3.76 (s, 3H), 3.16 (dd, J=14.4, 5.3 Hz, 1H), 3.03-2.97 (m, 1H), 2.81 (t, J=6.4 Hz, 2H), 2.31 (t, J=7.7 Hz, 2H), 1.59 (dd, J=14.3, 7.1 Hz, 2H), 1.39-1.09 (m, 28H), 0.88 (t, J=7.0 Hz, 3H). ¹³C NMR (126 MHz, CDCl₃) δ 174.43, 170.15, 168.12, 62.49, 61.70, 55.26, 52.83, 52.69, 34.18, 32.94, 31.94, 30.79, 29.73, 29.71, 29.68, 29.54, 29.38, 29.32, 29.18, 24.85, 22.70, 14.13. MS (ESI) calculated for $C_{27}H_{52}N_2O_6S$, m/z 532.35. found 533.37 (M+H)⁺.

6f: 2-(((R)-2-amino-3-(((S)-3-hydroxy-1-methoxy-1-oxopropan-2-yl)amino)-3-oxopropyl)thio)ethyl[1,1'-biphenyl]-4-carboxylate

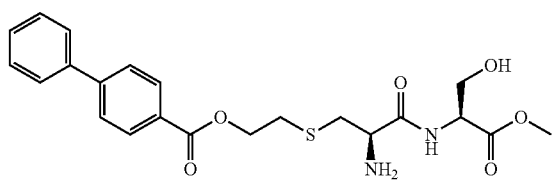 [SMILES: COC(=O)[C@H](CO)NC(=O)[C@@H](N)CSCCOC(=O)c1ccc(-c2ccccc2)cc1]

6g: 2-(((R)-2-amino-3-(((S)-3-hydroxy-1-methoxy-1-oxopropan-2-yl)amino)-3-oxopropyl)thio)ethyl[1,1'-biphenyl]-3-carboxylate

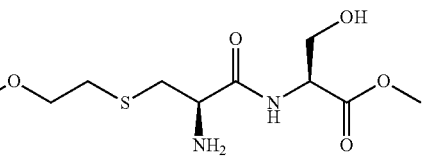

¹H NMR (500 MHz, CDCl₃) δ 8.54 (d, J=7.5 Hz, 1H), 8.21 (s, 1H), 7.94 (d, J=7.8 Hz, 1H), 7.72 (d, J=7.8 Hz, 1H), 7.56 (d, J=7.2 Hz, 2H), 7.42 (dt, J=13.5, 7.8 Hz, 3H), 7.33 (t, J=7.4 Hz, 1H), 4.71-4.64 (m, 1H), 4.48-4.42 (m, 3H), 3.92 (d, J=9.2 Hz, 1H), 3.85 (dd, J=11.5, 4.9 Hz, 1H), 3.63 (s, 3H), 3.48 (s, 2H), 3.23 (dd, J=14.4, 5.3 Hz, 1H), 3.08 (dd, J=14.3, 6.9 Hz, 1H), 2.93 (t, J=6.5 Hz, 2H). ¹³C NMR (126 MHz, CDCl₃) δ 170.55, 168.54, 167.25, 141.87, 140.27, 132.28, 130.50, 129.33, 129.28, 128.84, 128.71, 128.18, 127.50, 63.56, 62.10, 55.67, 53.16, 51.27, 33.38, 31.21. MS (ESI) calculated for $C_{22}H_{26}N_2O_6S$, m/z 446.15. found 447.16 (M+H)⁺.

Synthesis of Compound 6h: 2-(((R)-2-amino-3-(((S)-3-hydroxy-1-methoxy-1-oxopropan-2-yl)amino)-3-oxopropyl)thio)ethyl[1,1'-biphenyl]-3-carboxylate

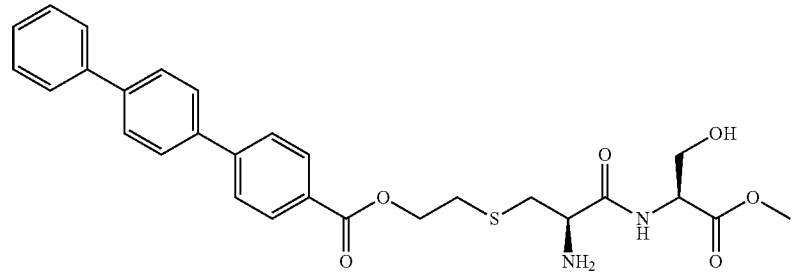 [SMILES: COC(=O)[C@H](CO)NC(=O)[C@@H](N)CSCCOC(=O)c1ccc(-c2ccc(-c3ccccc3)cc2)cc1]

To a solution of p-terphenyl-4-carboxylic acid (33 mg, 0.12 mmol) and compound 4 (100 mg, 0.24 mmol) in anhydrous dimethylformamide (DMF), were added triethylamine (33 μL, 0.24 mmol), DMAP (2.9 mg, 0.024 mmol) and O-benzotriazole-N,N,N',N'-tetramethyl-uronium hexafluorophosphate (HBTU, 55 mg, 0.144 mmol) and the reaction mixture was stirred at room temperature for 14 h, followed by removal of the solvent under reduced pressure. The crude was then dissolved in ethyl acetate and washed with water. The organic fraction was dried over anhydrous sodium sulfate, filtered, concentrated and purified using column chromatography (5% MeOH/CH$_2$Cl$_2$) to obtain the compound 5h. The product obtained was dissolved in 2 mL of trifluoracetic acid and stirred for 30 min, followed by removal of the solvent by purging nitrogen and drying under vacuum to obtain the residue which was further purified using column chromatography to obtain the trifluoroacetate salt of compound 6h (37 mg, 59%). $^1$H NMR (500 MHz, MeOD) δ 8.14 (d, J=8.5 Hz, 2H), 7.83 (d, J=8.5 Hz, 2H), 7.81-7.74 (m, 2H), 7.68 (dd, J=8.3, 1.1 Hz, 1H), 7.46 (t, J=7.7 Hz, 1H), 7.37 (t, J=7.4 Hz, 1H), 4.62 (t, J=5.0 Hz 1H), 4.59-4.53 (m, 1H), 4.17 (dd, J=8.8, 4.7 Hz, 1H), 3.97 (dd, J=11.2, 4.8 Hz, 1H), 3.85 (dd, J=11.2, 3.8 Hz, 1H), 3.74 (s, 3H), 3.35 (d, J=4.6 Hz, 1H), 3.07 (td, J=6.5, 2.5 Hz, 2H), 3.02 (dd, J=14.7, 8.8 Hz, 1H). $^{13}$C NMR (126 MHz, MeOD) δ 171.67, 169.09, 167.76, 146.80, 142.49, 141.63, 139.84, 131.30, 129.98, 129.89, 128.69, 128.66, 128.61, 128.01, 127.92, 64.82, 62.57, 56.41, 53.59, 53.00, 34.29, 31.68. MS (ESI) calculated for C$_{28}$H$_{30}$N$_2$O$_6$S, m/z 522.18. found 523.19 (M+H)$^+$.

Syntheses of 8a and 8b

To a solution of glycine methyl ester 7 (1.0 g, 8 mmol) in DMF (5 mL) triethylamine (4.5 mL, 32 mmol) was added, followed by 1-bromotetradecane (3.6 mL, 12 mmol) and the reaction mixture was stirred at room temperature for 18 h. The solvent was evaporated, water (50 mL) was added and the product was extracted in CH$_2$Cl$_2$ (100 mL) The organic layer was dried over sodium sulfate and evaporated to afford a mixture of methyl 2-(tetradecylamino)acetate and methyl 2-(ditetradecylamino)acetate. Di-tert-butyl dicarbonate (1.0 g) was added to the solution of this crude mixture in anhydrous CH$_2$Cl$_2$ (10 mL) followed by triethylamine (0.7 mL, 5.25 mmol) was added and the reaction mixture was stirred at room temperature for 1 h. The solvent was removed and the product was column purified to furnish compound 8a (330 mg, 9%) and compound 8b (1.01 g, 33%). Spectroscopic evidence for two conformers for 8b was observed in both $^1$H and $^{13}$C NMR.

Methyl 2-(ditetradecylamino)acetate (8a)

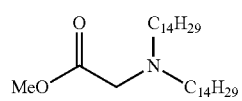

$^1$H NMR (500 MHz, CDCl$_3$) δ 3.69 (s, 3H), 3.32 (s, 2H), 2.53 (dd, J=8.6, 6.7 Hz, 4H), 1.46-1.39 (m, 4H), 1.35-1.15 (m, 44H), 0.88 (t, J=7.0 Hz, 6H). $^{13}$C NMR (126 MHz, CDCl$_3$) δ 172.39, 55.26, 54.71, 51.54, 32.08, 29.85, 29.84, 29.83, 29.81, 29.79, 29.73, 29.52, 27.56, 27.53, 22.85, 14.28. MS (ESI) calculated for C$_{31}$H$_{63}$NO$_2$, m/z 481.49. found 482.67 (M+H)$^+$.

Methyl 2-((tert-butoxycarbonyl)(tetradecyl)amino)acetate (8b)

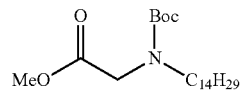

$^1$H NMR (500 MHz, CDCl$_3$) δ 3.95 (s, 1H), 3.86 (s, 1H), 3.73 (d, J=2.6 Hz, 3H), 3.25 (dt, J=19.4, 7.5 Hz, 2H), 1.42-1.50 (m, 11H), 1.34-1.19 (m, 22H), 0.88 (t, J=7.0 Hz, 3H). $^{13}$C NMR (126 MHz, CDCl$_3$) δ 170.91, 170.81, 156.02, 155.27, 80.16, 80.13, 52.11, 52.05, 49.27, 48.60, 48.49, 48.43, 32.06, 29.83, 29.81, 29.79, 29.75, 29.54, 29.50, 29.45, 28.50, 28.44, 28.39, 28.27, 26.93, 26.86, 22.83, 14.27. MS (ESI) calculated for C$_{22}$H$_{43}$NO$_4$, m/z 385.32. found 386.33 (M+H)$^+$.

Synthesis of 2-(ditetradecylamino)acetic acid (9a)

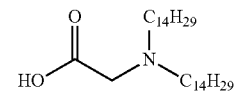

Compound 8a (275 mg, 0.57 mmol) was dissolved in tetrahydrofuran (THF, 10 mL) and LiOH (68 mg, 2.85 mmol) in 2 mL of H$_2$O was added and the reaction mixture was stirred at room temperature for 18 h. The solvent was evaporated, water added, the pH of the aqueous layer was rendered acidic by the addition of 1N HCl, and the product was extracted in CH$_2$Cl$_2$. The organic layer was dried over anhydrous sodium sulfate, evaporated, and column purified to afford compound 9a as white solid (250 mg, 93%). $^1$H NMR (500 MHz, CDCl$_3$) δ 3.29 (s, 2H), 3.13 (s, 1H), 2.72-2.46 (m, 4H), 1.47 (m, 4H), 1.19 (m, 44H), 0.81 (t, J=6.9 Hz, 6H). $^{13}$C NMR (126 MHz, CDCl$_3$) δ 174.66, 58.26, 54.51, 31.94, 29.72, 29.71, 29.68, 29.64, 29.63, 29.51, 29.39, 27.43, 25.00, 22.70, 14.09. MS (ESI) calculated for C$_{30}$H$_{61}$NO$_2$, m/z 467.47. found 468.49 (M+H)$^+$.

Compound 9b was synthesized similarly as compound 9a.

9b: 2-((tert-butoxycarbonyl)(tetradecyl)amino)acetic acid

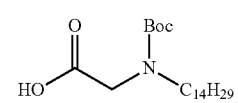

Spectroscopic evidence for two conformers was observed in both $^1$H and $^{13}$C NMR. $^1$H NMR (500 MHz, CDCl$_3$) δ

3.88 (d, J=9.7 Hz, 2H), 3.30-3.18 (m, 2H), 1.52-1.38 (m, 11H), 1.32-1.20 (m, 22H), 0.88 (t, J=7.0 Hz, 3H). $^{13}$C NMR (126 MHz, CDCl$_3$) δ 175.85, 175.28, 156.82, 155.32, 80.83, 80.31, 49.70, 49.16, 48.82, 48.29, 32.07, 29.84, 29.82, 29.81, 29.76, 29.68, 29.64, 29.57, 29.51, 29.46, 28.50, 28.39, 28.35, 28.25, 26.95, 26.84, 22.84, 14.28. MS (ESI) calculated for C$_{21}$H$_{41}$NO$_4$, m/z 371.30. found 394.30 (M+Na)$^+$.

Synthesis of (S)-methyl 2-((R)-2-amino-3-((2-(2-(ditetradecylamino)acetoxy)ethyl)thio)propan-amido)-3-hydroxypropanoate (10a)

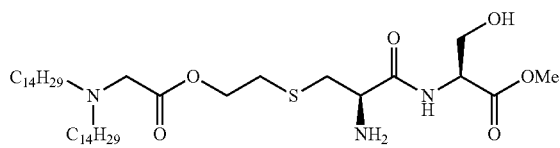

To the solution of compound 4 (80 mg, 0.189 mmol) and 9a (177 mg, 0.379 mmol) in dry CH$_2$Cl$_2$ (5 mL) N-methylmorpholine (41 µL, 0.379 mmol) and DMAP (9.0 mg, 0.076 mmol) were added, and the reaction mixture was stirred in an ice bath. After 20 min 1-ethyl-3-(3-dimethylaminopropyl) carbodiimide hydrochloride (EDCL.HCl, 58 mg, 0.379 mmol) was added and the reaction mixture was stirred at room temperature for 18 h. 50 mL of CH$_2$Cl$_2$ was added to the reaction mixture and the organic layer was washed with water, brine, dried over anhydrous sodium sulfate and evaporated. The crude product was further column purified to furnish the ester intermediate N-Boc, O-$^t$Bu protected 10a. The product obtained was dissolved in 4 mL of trifluoracetic acid and stirred for 30 min, followed by removal of the solvent by purging nitrogen and drying under vacuum to obtain the residue which was further purified using column chromatography to obtain the trifluoroacetate salt of compound 10a in quantitative yield. $^1$H NMR (500 MHz, MeOD) δ 4.60 (t, J=4.1 Hz, 1H), 4.48 (dtd, J=17.9, 11.7, 6.2 Hz, 2H), 4.19 (s, 2H), 4.15 (dd, J=8.4, 4.8 Hz, 1H), 3.97 (dd, J=11.3, 4.6 Hz, 1H), 3.84 (dd, J=11.3, 3.7 Hz, 1H), 3.76 (s, 3H), 3.28 (dd, J=14.8, 4.9 Hz, 1H), 3.20 (dd, J=9.6, 7.1 Hz, 4H), 3.03-2.87 (m, 3H), 1.72 (s, 4H), 1.45-1.25 (m, 44H), 0.90 (t, J=7.0 Hz, 6H). $^{13}$C NMR (126 MHz, MeOD) δ 171.87, 169.24, 167.79, 66.48, 62.57, 56.35, 55.98, 54.39, 53.31, 53.01, 34.00, 33.09, 30.81, 30.79, 30.78, 30.76, 30.64, 30.51, 30.49, 30.19, 27.56, 25.03, 23.75, 14.45. MS (ESI) calculated for C$_{39}$H$_{77}$N$_3$O$_6$S, m/z 715.55. found 716.59 (M+H)$^+$.

Compound 10b was synthesized similarly as compound 10a.

10b: (S)-methyl 2-((R)-2-amino-3-((2-(2-(tetradecylamino)acetoxy)ethyl)thio)propanamido)-3-hydroxypropanoate

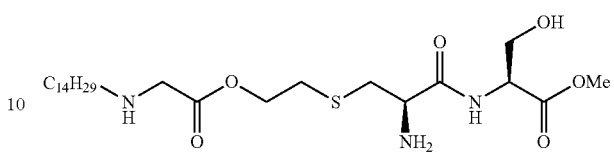

$^1$H NMR (400 MHz, CDCl$_3$) δ 8.26 (d, J=7.7 Hz, 1H), 4.63 (dt, J=7.6, 3.8 Hz, 1H), 4.36-4.24 (m, 2H), 3.95 (ddd, J=17.8, 11.2, 3.8 Hz, 2H), 3.80 (s, 3H), 3.67-3.58 (m, 1H), 3.44 (s, 2H), 3.05 (dd, J=13.6, 4.3 Hz, 1H), 2.95 (dd, J=13.6, 6.9 Hz, 1H), 2.81 (t, J=6.6 Hz, 2H), 2.63-2.55 (m, 2H), 1.72 (bs, 4H), 1.49 (m, 2H), 1.29-1.23 (m, 22H), 0.88 (t, J=6.8 Hz, 3H). $^{13}$C NMR (126 MHz, CDCl$_3$) δ 173.78, 172.27, 170.90, 63.76, 63.14, 54.87, 54.12, 52.87, 50.86, 49.74, 37.99, 32.07, 31.00, 29.96, 29.84, 29.83, 29.82, 29.80, 29.77, 29.74, 29.66, 29.51, 27.35, 22.84, 14.28. MS (ESI) calculated for C$_{25}$H$_{49}$N$_3$O$_6$S, m/z 519.33. found 520.35 (M+H)$^+$.

Synthesis of Compound 11a: 2-(((R)-2-(ethyl-amino)-3-(((S)-3-hydroxy-1-methoxy-1-oxopropan-2-yl)amino)-3-oxopropyl)thio)ethyl palmitate

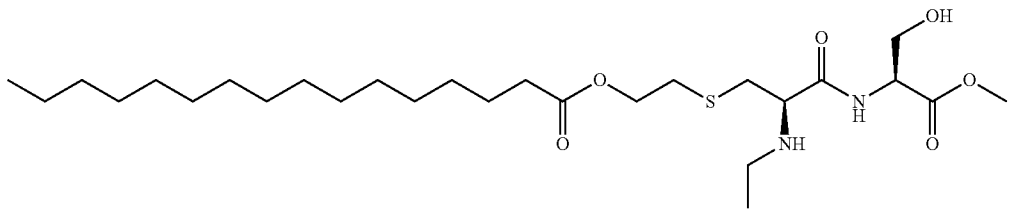 [SMILES: CCCCCCCCCCCCCCCC(=O)OCCSC[C@H](NCC)C(=O)N[C@@H](CO)C(=O)OC]

To a solution of compound 6d (50 mg, 0.081 mmol) in anhydrous CH$_2$Cl$_2$ were added acetaldehyde (3.5 mg, 0.081 mmol), 4 drops of acetic acid and macroporous polystyrene-bound cyanoborohydride (73 mg, 0.162 mmol). The reaction mixture was stirred for 2 h and then filtered to remove the solid resin. The filtrate was evaporated under vacuum to obtain the residue, which was purified using column chromatography (4% MeOH/CH$_2$Cl$_2$), yielding compound 11a (8 mg, 20%). $^1$H NMR (500 MHz, CDCl$_3$) δ 8.28 (d, J=7.7 Hz, 1H), 4.64 (dt, J=7.7, 3.8 Hz, 1H), 4.22 (t, J=6.7 Hz, 2H), 4.01-3.90 (m, 2H), 3.80 (s, 3H), 3.28 (dd, J=8.2, 3.9 Hz, 1H), 3.10 (dd, J=13.5, 3.9 Hz, 1H), 2.84-2.71 (m, 3H), 2.68 (qd, J=7.1, 2.9 Hz, 2H), 2.32 (t, J=7.6 Hz, 2H), 2.08 (s, 2H), 1.66-1.54 (m, 2H), 1.35-1.21 (m, 24H), 1.15 (t, J=7.1 Hz, 3H), 0.87 (d, J=7.1 Hz, 3H). $^{13}$C NMR (126 MHz, CDCl$_3$) δ 173.93, 173.55, 170.77, 63.50, 63.05, 61.55, 54.72, 52.88, 43.30, 35.83, 34.32, 32.07, 30.93, 29.84, 29.83, 29.80, 29.76, 29.62, 29.51, 29.42, 29.28, 25.04, 22.84, 15.50, 14.28. MS (ESI) calculated for C$_{27}$H$_{52}$N$_2$O$_6$S, m/z 532.35. found 533.37 (M+H)$^+$.

Compound 11b was synthesized similarly as compound 11a.

11b: 2-(((R)-3-(((S)-3-hydroxy-1-methoxy-1-oxo-propan-2-yl)amino)-2-(octylamino)-3-oxopropyl)thio)ethyl palmitate

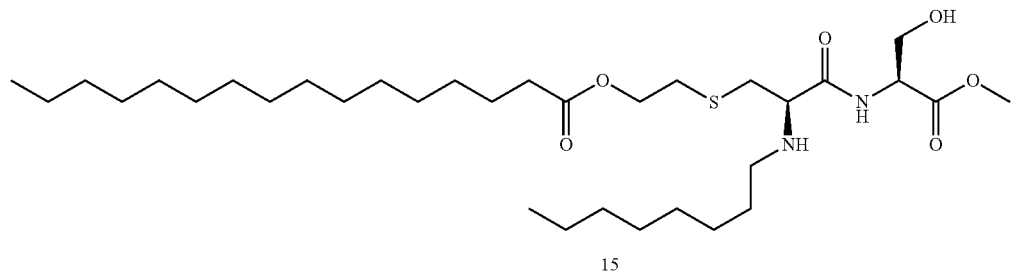

(10 mg, 20%). $^1$H NMR (500 MHz, CDCl$_3$) δ 8.26 (d, J=7.7 Hz, 1H), 4.63 (dt, J=7.7, 3.8 Hz, 1H), 4.22 (t, J=6.7 Hz, 2H), 4.03-3.91 (m, 2H), 3.79 (s, 3H), 3.30 (dd, J=7.8, 3.5 Hz, 1H), 3.10 (dd, J=13.5, 3.9 Hz, 1H), 2.86-2.71 (m, 3H), 2.63 (td, J=7.2, 2.2 Hz, 2H), 2.32 (t, J=7.6 Hz, 2H), 2.05 (s, 2H), 1.67-1.55 (m, 2H), 1.51 (dd, J=14.2, 7.1 Hz, 2H), 1.37-1.19 (m, 34H), 0.92-0.82 (m, 6H). $^{13}$C NMR (126 MHz, CDCl$_3$) δ 173.94, 173.41, 170.67, 63.47, 63.05, 61.57, 54.78, 52.85, 48.95, 35.71, 34.32, 32.07, 31.98, 30.94, 30.19, 29.84, 29.81, 29.77, 29.62, 29.51, 29.43, 29.41, 29.29, 27.32, 25.04, 22.84, 22.81, 14.28, 14.25. MS (ESI) calculated for C$_{33}$H$_{64}$N$_2$O$_6$S, m/z 616.45. found 617.46 (M+H)$^+$.

Synthesis of Compound 11c: 2-(((R)-2-(hexadecylamino)-3-(((S)-3-hydroxy-1-methoxy-1-oxopropan-2-yl)amino)-3-oxopropyl)thio)ethyl palmitate

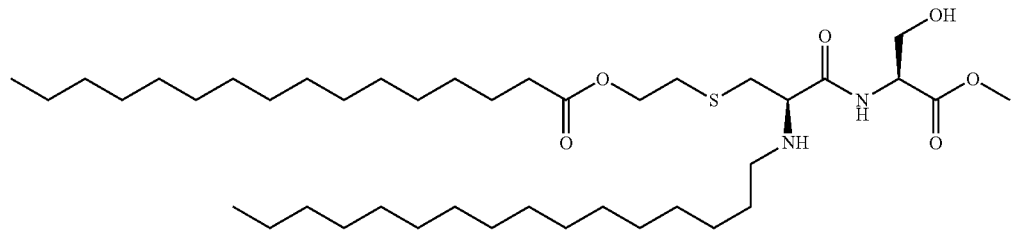 [SMILES: CCCCCCCCCCCCCCCCN[C@@H](CSCCOC(=O)CCCCCCCCCCCCCCC)C(=O)N[C@@H](CO)C(=O)OC]

To a solution of compound 6d (100 mg, 0.162 mmol) in anhydrous DMF, triethylamine (56 μL, 0.405 mmol) was added, followed by 1-bromohexadecane (123 μL, 0.405 mmol). The reaction mixture was stirred at room temperature for 14 h. DMF was evaporated at 50° C. and the crude product obtained was purified using column chromatography to give compound 11c (18 mg, 15%) as white solid. $^1$H NMR (400 MHz, CDCl$_3$) δ 8.26 (d, J=7.7 Hz, 1H), 4.63 (dt, J=7.6, 3.7 Hz, 1H), 4.22 (t, J=6.7 Hz, 2H), 4.00-3.90 (m, 2H), 3.80 (s, 3H), 3.26 (dd, J=8.1, 3.7 Hz, 1H), 3.09 (dd, J=13.5, 3.7 Hz, 1H), 2.83-2.72 (m, 3H), 2.61 (t, J=7.0 Hz, 2H), 2.32 (t, J=7.6 Hz, 2H), 1.88 (bs, 2H), 1.65-1.54 (m, 2H), 1.54-1.45 (m, 2H), 1.25 (s, 50H), 0.88 (t, J=6.7 Hz, 6H). $^{13}$C NMR (126 MHz, CDCl$_3$) δ 173.90, 173.60, 170.69, 63.51, 63.06, 61.66, 54.76, 52.85, 49.01, 35.82, 34.32, 32.07, 30.92, 30.30, 29.86, 29.85, 29.81, 29.78, 29.70, 29.63, 29.51, 29.43, 29.29, 27.36, 25.04, 22.84, 14.28. MS (ESI) calculated for C$_{41}$H$_{80}$N$_2$O$_6$S, m/z 728.57. found 729.58 (M+H)$^+$.

Synthesis of Compound 11d: 2-(((R)-2-acetamido-3-(((S)-3-hydroxy-1-methoxy-1-oxopropan-2-yl)amino)-3-oxopropyl)thio)ethyl palmitate

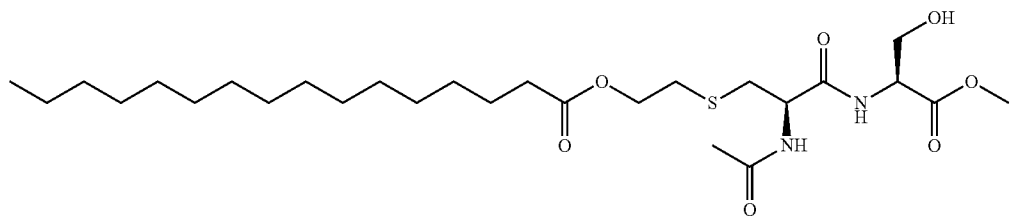 [SMILES: CCCCCCCCCCCCCCCC(=O)OCCSC[C@H](NC(C)=O)C(=O)N[C@@H](CO)C(=O)OC]

To a solution of compound 6d (50 mg, 0.081 mmol) in anhydrous $CH_2Cl_2$ were added triethylamine (17 μL, 0.121 mmol) and acetic anhydride (8 μL, 0.081 mmol). The reaction mixture was stirred for 2 h. The solvent was removed under vacuum to obtain the residue which was purified using column chromatography (6% MeOH/ $CH_2Cl_2$), furnishing compound 11d (35 mg, 79%). $^1$H NMR (400 MHz, CDCl$_3$) δ 7.41 (d, J=7.7 Hz, 1H), 6.63 (d, J=7.1 Hz, 1H), 4.67-4.57 (m, 2H), 4.37-4.17 (m, 2H), 4.01-3.90 (m, 2H), 3.79 (s, 3H), 3.26 (t, J=6.3 Hz, 1H), 2.96 (dd, J=6.4, 3.6 Hz, 2H), 2.83 (t, J=6.6 Hz, 2H), 2.32 (t, J=7.6 Hz, 2H), 2.05 (s, 3H), 1.60 (dd, J=14.4, 7.2 Hz, 2H), 1.25 (s, 24H), 0.87 (t, J=6.8 Hz, 3H). $^{13}$C NMR (126 MHz, CDCl$_3$) δ 174.32, 170.95, 170.58, 170.55, 62.88, 62.76, 55.18, 52.93, 52.89, 34.56, 34.39, 32.06, 31.30, 29.84, 29.80, 29.76, 29.62, 29.50, 29.42, 29.29, 25.02, 23.23, 22.84, 14.27. MS (ESI) calculated for $C_{27}H_{50}N_2O_7S$, m/z 546.33. found 547.35 (M+H)$^+$.

Compounds 11h, 11j and 11k were synthesized similarly as compound 11d.

11h: 2-(((R)-3-(((S)-3-hydroxy-1-methoxy-1-oxopropan-2-yl)amino)-3-oxo-2-(2,2,2-trifluoro-acetamido)propyl)thio)ethyl palmitate

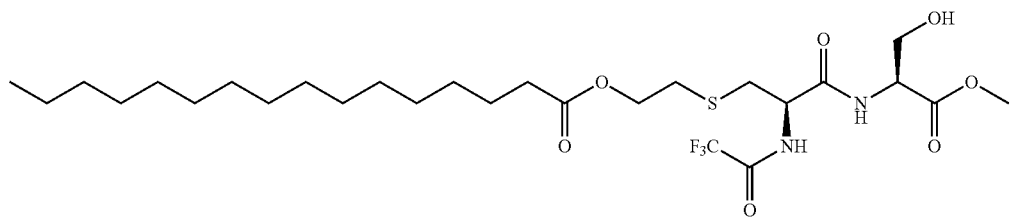

(10 mg, 21%). $^1$H NMR (500 MHz, CDCl$_3$) δ 7.59 (d, J=7.0 Hz, 1H), 7.50 (d, J=7.8 Hz, 1H), 4.72-4.63 (m, 2H), 4.40-4.30 (m, 1H), 4.27 (dd, J=12.0, 5.7 Hz, 1H), 4.00 (ddd, J=54.9, 11.5, 3.3 Hz, 2H), 3.80 (s, 3H), 2.99 (t, J=6.2 Hz, 2H), 2.92-2.80 (m, 2H), 2.77 (s, 1H), 2.38-2.26 (m, 2H), 1.66-1.55 (m, 2H), 1.38-1.18 (m, 24H), 0.87 (t, J=7.0 Hz, 3H). $^{13}$C NMR (126 MHz, CDCl$_3$) δ 174.69, 170.38, 168.95, 157.74, 157.44, 157.13, 156.83, 119.13, 116.85, 114.56, 112.28, 62.81, 62.75, 55.14, 53.06, 52.77, 34.51, 34.41, 32.06, 31.38, 29.84, 29.83, 29.80, 29.76, 29.61, 29.50, 29.40, 29.27, 24.98, 22.83, 14.27. MS (ESI) calculated for $C_{27}H_{47}F_3N_2O_7S$, m/z 600.31. found 601.31 (M+H)$^+$ and 618.34 (M+NH$_4^+$).

11j: 2-(((R)-3-(((S)-3-hydroxy-1-methoxy-1-oxopropan-2-yl)amino)-2-(methylsulfonamido)-3-oxo-propyl)thio)ethyl palmitate

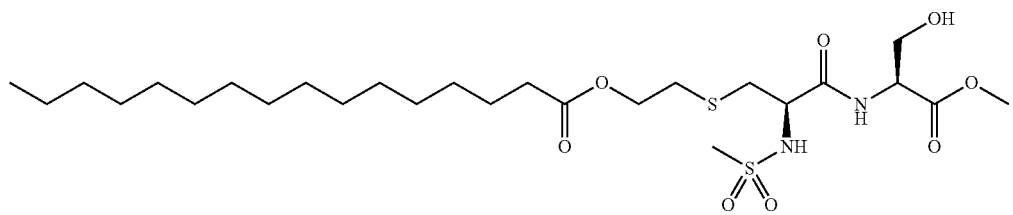 [SMILES: CCCCCCCCCCCCCCCC(=O)OCCSC[C@H](NS(C)(=O)=O)C(=O)N[C@@H](CO)C(=O)OC]

(7 mg, 15%). $^1$H NMR (400 MHz, CDCl$_3$) δ 7.43 (d, J=7.6 Hz, 1H), 5.60 (d, J=7.9 Hz, 1H), 4.71-4.60 (m, 1H), 4.24 (dt, J=14.1, 6.4 Hz, 3H), 4.10-3.92 (m, 2H), 3.80 (s, 3H), 3.09 (s, 3H), 3.05 (t, J=5.7 Hz, 2H), 2.82 (t, J=6.6 Hz, 2H), 2.71 (s, 1H), 2.33 (t, J=7.6 Hz, 2H), 1.60 (q, J=7.3 Hz, 3H), 1.28-1.25 (m, 23H), 0.88 (t, J=6.8 Hz, 3H). $^{13}$C NMR (101 MHz, CDCl$_3$) δ 174.49, 170.46, 170.05, 62.83, 62.78, 56.26, 55.17, 53.06, 41.84, 35.62, 34.40, 32.07, 31.27, 29.84, 29.81, 29.77, 29.63, 29.51, 29.41, 29.29, 25.02, 22.84, 14.27. MS (ESI) calculated for $C_{26}H_{50}N_2O_8S_2$, m/z 582.30. found 583.31 (M+H)$^+$.

11k: 2-(((R)-3-(((S)-3-hydroxy-1-methoxy-1-oxo-propan-2-yl)amino)-3-oxo-2-(trifluoromethyl-sulfonamido)propyl)thio)ethyl palmitate

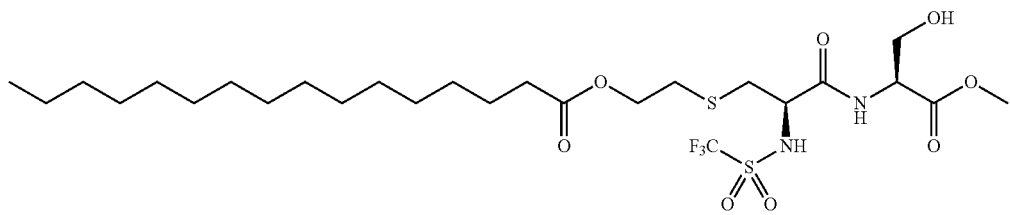 [SMILES: CCCCCCCCCCCCCCCC(=O)OCCSC[C@H](NS(=O)(=O)C(F)(F)F)C(=O)N[C@@H](CO)C(=O)OC]

(39 mg, 78%). $^1$H NMR (500 MHz, CDCl$_3$) δ 7.60 (d, J=7.9 Hz, 1H), 4.75-4.64 (m, 1H), 4.36 (t, J=6.4 Hz, 1H), 4.28-4.20 (m, 2H), 4.05 (dd, J=11.5, 3.5 Hz, 1H), 3.92 (dd, J=11.5, 3.3 Hz, 1H), 3.79 (s. 3H), 3.07-2.94 (m, 2H), 2.86-2.72 (m, 2H), 2.33 (t, J=7.6 Hz, 2H), 1.59 (dd, J=14.5, 7.2 Hz, 2H), 1.33-1.18 (m, 26H), 0.87 (t, J=7.0 Hz, 3H). $^{13}$C NMR (126 MHz, CDCl$_3$) δ 174.71, 170.56, 169.23, 123.42, 120.87, 118.32, 115.77, 62.79, 62.75, 57.35, 54.99, 53.13, 35.73, 34.37, 32.06, 31.29, 29.83, 29.79, 29.76, 29.61, 29.50, 29.40, 29.26, 24.97, 22.83, 14.26. MS (ESI) calculated for C$_{26}$H$_{47}$F$_3$N$_2$O$_8$S$_2$, m/z 636.27. found 637.28 (M+H)$^+$ and 654.31 (M+NH$_4^+$).

Synthesis of Compound 11e: 2-(((R)-2-butyramido-3-(((S)-3-hydroxy-1-methoxy-1-oxopropan-2-yl)amino)-3-oxopropyl)thio)ethyl palmitate

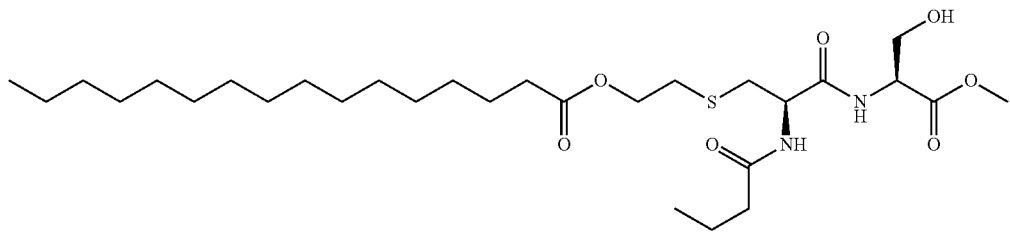 [SMILES: CCCCCCCCCCCCCCCC(=O)OCCSC[C@H](NC(=O)CCC)C(=O)N[C@@H](CO)C(=O)OC]

To a solution of compound 6d (50 mg, 0.081 mmol) in pyridine (1 mL), butyryl chloride (10.2 μL, 0.097 mmol) was added and the reaction mixture was stirred at room temperature for 1 h. The volatiles were removed by evaporation, and the crude product obtained was purified using column chromatography (10% MeOH/CH$_2$Cl$_2$) to obtain compound 11e as a white solid (35 mg, 76%). $^1$H NMR (500 MHz, CDCl$_3$) δ 7.42 (d, J=7.7 Hz, 1H), 6.59 (d, J=7.1 Hz, 1H), 4.63 (dt, J=8.8, 5.0 Hz, 2H), 4.35-4.19 (m, 2H), 3.96 (dt, J=11.5, 8.0 Hz, 2H), 3.78 (s, 3H), 3.02-2.90 (m, 2H), 2.84 (t, J=6.6 Hz, 2H), 2.32 (t, J=7.6 Hz, 2H), 2.27-2.19 (m, 2H), 1.73-1.55 (m, 5H), 1.35-1.19 (m, 24H), 0.95 (t, J=7.4 Hz, 3H), 0.87 (t, J=7.0 Hz, 3H). $^{13}$C NMR (126 MHz, CDCl$_3$) δ 174.31, 173.88, 170.62, 170.57, 62.93, 62.77, 55.19, 52.91, 52.71, 38.45, 34.54, 34.39, 32.06, 31.31, 29.83, 29.80, 29.76, 29.62, 29.50, 29.42, 29.29, 25.02, 22.83, 19.13, 14.27, 13.84. MS (ESI) calculated for C$_{29}$H$_{54}$N$_2$O$_7$S, m/z 574.37. found 575.38 (M+H)$^+$.

Compounds 11f and 11g were synthesized similarly as compound 11e.

11f: 2-(((R)-3-(((S)-3-hydroxy-1-methoxy-1-oxopropan-2-yl)amino)-2-octanamido-3-oxopropyl)thio) ethyl palmitate

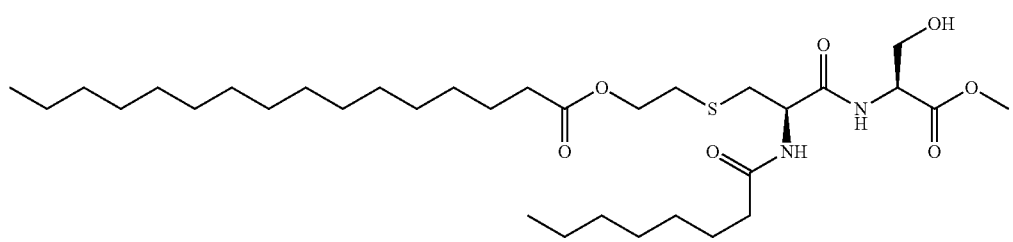 [SMILES: CCCCCCCCCCCCCCCC(=O)OCCSC[C@H](NC(=O)CCCCCCC)C(=O)N[C@@H](CO)C(=O)OC]

(32 mg, 62%). $^1$H NMR (500 MHz, CDCl$_3$) δ 7.39 (d, J=7.6 Hz, 1H), 6.55 (d, J=7.0 Hz, 1H), 4.66-4.55 (m, 2H), 4.35-4.17 (m, 2H), 4.03-3.89 (m, 2H), 3.79 (s, 3H), 3.19 (s, 1H), 2.96 (qd, J=13.9, 6.4 Hz, 2H), 2.84 (t, J=6.6 Hz, 2H), 2.32 (t, J=7.6 Hz, 2H), 2.26-2.22 (m, 2H), 1.77 (s, 1H), 1.61 (dd, J=14.5, 7.5 Hz, 4H), 1.34-1.19 (m, 31H), 0.90-0.83 (m, 6H). $^{13}$C NMR (126 MHz, CDCl$_3$) δ 174.33, 174.01, 170.60, 170.56, 62.93, 62.79, 55.20, 52.92, 52.73, 36.62, 34.54, 34.40, 32.07, 31.80, 31.34, 29.84, 29.80, 29.77, 29.63, 29.51, 29.43, 29.34, 29.30, 29.12, 25.68, 25.03, 22.84, 22.75, 14.27, 14.21. MS (ESI) calculated for C$_{33}$H$_{62}$N$_2$O$_7$S, m/z 630.43. found 631.44 (M+H)$^+$.

11g: 2-(((R)-3-(((S)-3-hydroxy-1-methoxy-1-oxopropan-2-yl)amino)-3-oxo-2-palmitamidopropyl)thio)ethyl palmitate

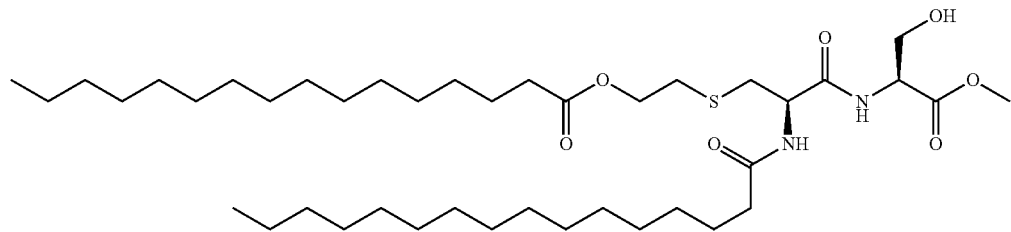 [SMILES: CCCCCCCCCCCCCCCC(=O)N[C@@H](CSCCOC(=O)CCCCCCCCCCCCCCC)C(=O)N[C@@H](CO)C(=O)OC]

(41 mg, 68%). $^1$H NMR (500 MHz, CDCl$_3$) δ 7.37 (d, J=7.6 Hz, 1H), 6.55 (d, J=7.0 Hz, 1H), 4.61 (ddd, J=19.9, 10.3, 5.0 Hz, 2H), 4.33 (dt, J=11.4, 6.7 Hz, 1H), 4.24 (dt, J=11.4, 6.4 Hz, 1H), 3.97 (qd, J=11.6, 3.5 Hz, 2H), 3.79 (s, 3H), 2.95 (ddd, J=30.5, 14.0, 6.5 Hz, 2H), 2.85 (t, J=6.6 Hz, 2H), 2.34-2.30 (m, 2H), 2.27-2.21 (m, 2H), 1.62 (dd, J=14.6, 7.3 Hz, 4H), 1.29-1.23 (m, 49H), 0.87 (t, J=7.0 Hz, 6H). $^{13}$C NMR (126 MHz, CDCl$_3$) δ 174.38, 174.01, 170.63, 170.53, 62.94, 62.80, 55.21, 52.94, 52.76, 36.63, 34.48, 34.41, 32.07, 31.36, 29.85, 29.81, 29.79, 29.78, 29.76, 29.65, 29.64, 29.62, 29.52, 29.49, 29.43, 29.41, 29.30, 25.69, 25.03, 22.84, 14.28. MS (ESI) calculated for C$_{41}$H$_{78}$N$_2$O$_7$S, m/z 742.55. found 743.56 (M+H)$^+$.

Synthesis of Compound 11i: 2-(((R)-3-(((S)-3-hydroxy-1-methoxy-1-oxopropan-2-yl)amino)-3-oxo-2-(2,2,2-trichloroacetamido)propyl)thio)ethyl palmitate

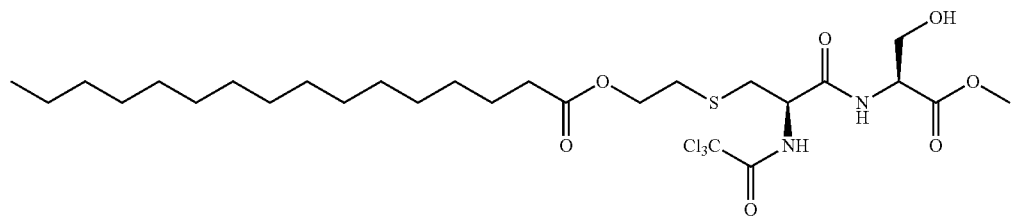

To a solution of compound 6d (40 mg, 0.079 mmol) in anhydrous CH$_2$Cl$_2$ were added triethylamine (11 μL, 0.079 mmol), trichloroacetic acid (13 mg, 0.079 mmol), EDCl.HCl (19 mg, 0.095 mmol) and a catalytic amount of 1-hydroxybenzotriazole (HOBt). The reaction mixture was stirred for 2 h and the solvent was then removed under vacuum. The residue was purified using column chromatography (5% MeOH/CH$_2$Cl$_2$) to obtain compound 11i (6 mg, 12%). $^1$H NMR (500 MHz, DMSO) δ 8.61 (d, J=7.6 Hz, 1H), 5.16 (t, J=5.4 Hz, 1H), 4.57 (dd, J=10.4, 4.0 Hz, 1H), 4.38 (dt, J=7.7, 4.7 Hz, 1H), 4.14 (tt, J=12.9, 5.5 Hz, 2H), 3.75 (dt, J=10.7, 4.0 Hz, 1H), 3.63 (s, 3H), 3.03 (dd, J=13.9, 4.0 Hz, 1H), 2.94 (dd, J=13.9, 10.5 Hz, 1H), 2.81 (qd, J=13.9, 7.2 Hz, 2H), 2.28 (t, J=7.4 Hz, 2H), 1.54-1.47 (m, 2H), 1.23 (s, 24H), 0.85 (t, J=6.9 Hz, 3H). $^{13}$C NMR (126 MHz, DMSO) δ 172.80, 170.72, 169.26, 161.53, 92.55, 63.00, 61.09, 54.79, 54.46, 51.98, 33.42, 33.20, 31.32, 29.81, 29.06, 29.03, 29.00, 28.90, 28.73, 28.71, 28.45, 24.45, 22.13, 13.99. MS (ESI) calculated for C$_{27}$H$_{47}$C$_{13}$N$_2$O$_7$S, m/z 648.22. found 649.22 (M+H)$^+$ and 666.25 (M+NH$_4^+$).

Synthesis of Compound 111: 2-(((R)-3-(((S)-3-hydroxy-1-methoxy-1-oxopropan-2-yl)amino)-2-(4-methylphenylsulfonamido)-3-oxopropyl)thio)ethyl palmitate To a solution of compound 6d (180 mg, 0.29 mmol) in anhydrous CH$_2$Cl$_2$, were added triethylamine (67 µL, 0.49 mmol) and di-tert-butyl dicarbonate (107 mg, 0.49 mmol). The reaction mixture was stirred for 2 h and the solvent was then removed under vacuum. The residue was purified using

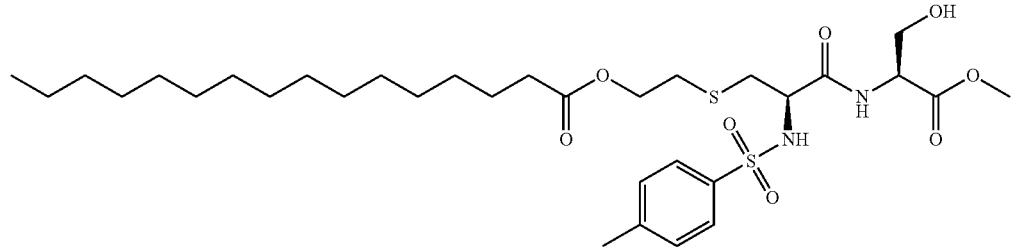 [SMILES: CCCCCCCCCCCCCCCC(=O)OCCSC[C@H](NS(=O)(=O)c1ccc(C)cc1)C(=O)N[C@@H](CO)C(=O)OC]

To a solution of compound 6d (40 mg, 0.079 mmol) in anhydrous CH$_2$Cl$_2$ were added triethylamine (11 µL, 0.079 mmol) and 4-methylbenzene-1-sulfonyl chloride (15 mg, 0.079 mmol). The reaction mixture was stirred for 2 h and the solvent was then removed under vacuum. The residue was purified using column chromatography (5% MeOH/CH$_2$Cl$_2$) to obtain compound 111 (25 mg, 48%). $^1$H NMR (500 MHz, CDCl$_3$) δ 7.78 (d, J=8.3 Hz, 2H), 7.46 (d, J=7.3 Hz, 1H), 7.33 (d, J=8.0 Hz, 2H), 5.82 (d, J=7.6 Hz, 1H), 4.53 (dt, J=7.2, 3.6 Hz, 1H), 4.13 (td, J=6.5, 1.6 Hz, 2H), 3.99-3.90 (m, 2H), 3.90-3.81 (m, 1H), 3.78 (s, 3H), 3.02 (dd, J=14.2, 5.5 Hz, 1H), 2.73-2.56 (m, 4H), 2.43 (s, 3H), 2.31 (t, J=7.6 Hz, 2H), 1.65-1.54 (m, 2H), 1.27 (d, J=16.0 Hz, 24H), 0.88 (t, J=7.0 Hz, 3H). $^{13}$C NMR (126 MHz, CDCl$_3$) δ 174.23, 170.23, 169.91, 144.47, 136.20, 130.06, 127.60, 62.77, 62.73, 55.66, 55.32, 53.01, 34.79, 34.33, 32.07, 31.08, 29.84, 29.80, 29.77, 29.63, 29.51, 29.42, 29.29, 25.00, 22.84, 21.74, 14.28. MS (ESI) calculated for C$_{32}$H$_{54}$N$_2$O$_8$S$_2$, m/z 658.33. found 659.34 (M+H)$^+$ and 676.37 (M+NH$_4$$^+$).

Synthesis of Compound 12: 2-(((2R)-2-((tert-butoxycarbonyl)amino)-3-((3-hydroxy-1-methoxy-1-oxopropan-2-yl)amino)-3-oxopropyl)thio)ethyl palmitate

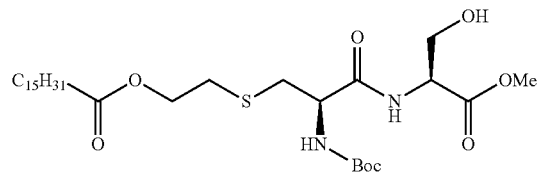

column chromatography (5% MeOH/CH$_2$Cl$_2$) to obtain the compound 12 (160 mg, 91%). $^1$H NMR (400 MHz, CDCl$_3$) δ 7.27 (s, 1H), 5.47 (s, 1H), 4.66 (dt, J=7.0, 3.3 Hz, 1H), 4.28 (ddd, J=10.3, 8.8, 4.4 Hz, 3H), 3.99 (d, J=3.1 Hz, 2H), 3.82 (s, 3H), 3.02 (ddd, J=32.3, 13.9, 6.1 Hz, 2H), 2.84 (t, J=6.6 Hz, 3H), 2.34 (t, J=7.6 Hz, 2H), 1.62 (dd, J=14.3, 7.0 Hz, 2H), 1.48 (s, 9H), 1.27 (s, 24H), 0.90 (t, J=6.7 Hz, 3H). $^{13}$C NMR (126 MHz, CDCl$_3$) δ 174.19, 170.83, 170.57, 155.69, 80.92, 63.09, 62.88, 55.21, 54.17, 52.96, 34.56, 34.36, 32.07, 31.31, 29.84, 29.80, 29.76, 29.62, 29.50, 29.41, 29.28, 28.40, 25.01, 22.84, 14.27. MS (ESI) calculated for C$_{30}$H$_{56}$N$_2$O$_8$S, m/z 604.38. found 605.38 (M+H)$^+$.

Synthesis of Compounds 14a: 2-(((R)-3-(((S)-3-acetoxy-1-methoxy-1-oxopropan-2-yl)amino)-2-amino-3-oxopropyl)thio)ethyl palmitate

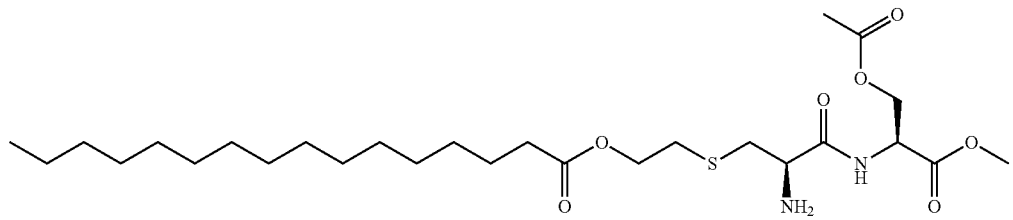 [SMILES: CCCCCCCCCCCCCCCC(=O)OCCSC[C@H](N)C(=O)N[C@@H](COC(C)=O)C(=O)OC]

To a solution of compound 12 (40 mg, 0.079 mmol) in pyridine (1 mL), was added acetic anhydride (15 µL, 0.158 mmol). The reaction mixture was stirred at room temperature for 1 h and the solvent was removed to obtain the crude N-Boc intermediate 13a. The N-Boc group was then removed by stirring compound 13a in 1 mL of trifluoracetic acid for 15 min, followed by removal of solvent by purging nitrogen. The residue was dried under vacuum to obtain compound 14a in quantitative yield. $^1$H NMR (500 MHz, CDCl$_3$) δ 8.18 (d, J=7.7 Hz, 1H), 6.55 (s, 2H), 4.80 (dd, J=7.5, 3.8 Hz, 1H), 4.41 (ddd, J=27.2, 11.6, 3.9 Hz, 2H), 4.35-4.16 (m, 3H), 3.77 (s, 3H), 3.11 (ddd, J=43.7, 14.6, 6.5 Hz, 2H), 2.82 (t, J=6.6 Hz, 2H), 2.31 (t, J=7.6 Hz, 2H), 2.03 (s, 3H), 1.66-1.53 (m, 2H), 1.35-1.09 (m, 24H), 0.87 (t, J=7.0 Hz, 3H). $^{13}$C NMR (126 MHz, CDCl$_3$) δ 174.39, 171.23, 169.23, 63.19, 62.55, 53.13, 52.48, 52.39, 34.31, 33.04, 32.07, 30.89, 29.85, 29.83, 29.81, 29.79, 29.65, 29.51, 29.45, 29.31, 24.99, 22.84, 20.66, 14.27. MS (ESI) calculated for C$_{27}$H$_{50}$N$_2$O$_7$S, m/z 546.33. found 547.34 (M+H)$^+$.

Synthesis of Compound 14b: 2-(((R)-2-amino-3-(((S)-3-(butyryloxy)-1-methoxy-1-oxopropan-2-yl)amino)-3-oxopropyl)thio)ethyl palmitate

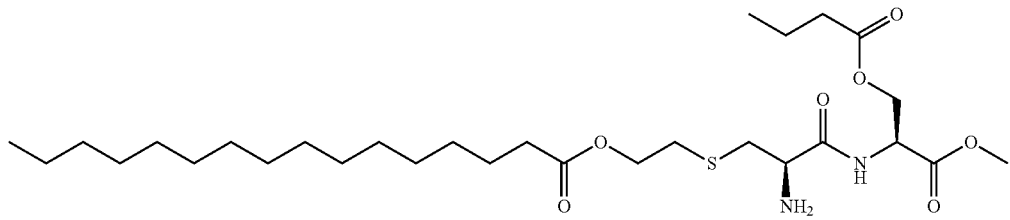 [SMILES: CCCCCCCCCCCCCCCC(=O)OCCSC[C@H](N)C(=O)N[C@@H](COC(=O)CCC)C(=O)OC]

15

To a solution of compound 12 (50 mg, 0.083 mmol) in anhydrous THF were added triethylamine (36 µL, 0.25 mmol) and butyryl chloride (25 µL, 0.25 mmol). The reaction mixture was stirred for 2 h and the solvent was then removed under vacuum. The residue was purified using column chromatography (15% ethylacetate/hexanes) to obtain the N-Boc protected intermediate 13b (25 mg, 45%). The N-Boc group was then removed by stifling compound 13b in 1 mL of trifluoracetic acid for 15 min, followed by removal of the acid by purging nitrogen. The residue was thoroughly dried under vacuum to obtain compound 14b in quantitative yield. $^1$H NMR (400 MHz, CDCl$_3$) δ 7.98 (d, J=7.6 Hz, 1H), 6.17 (s, 4H), 4.79 (dt, J=7.6, 3.7 Hz, 1H), 4.49 (dd, J=11.6, 4.1 Hz, 1H), 4.39-4.30 (m, 2H), 4.31-4.16 (m, 2H), 3.77 (s, 3H), 3.18 (dd, J=14.7, 6.2 Hz, 1H), 3.05 (dd, J=14.7, 7.1 Hz, 1H), 2.82 (t, J=6.5 Hz, 2H), 2.29 (dt, J=19.0, 7.5 Hz, 4H), 1.60 (dd, J=14.7, 7.4 Hz, 4H), 1.25 (s, 24H), 0.89 (dt, J=14.0, 7.2 Hz, 6H). $^{13}$C NMR (126 MHz, CDCl$_3$) δ 174.61, 173.77, 169.15, 167.87, 62.94, 62.39, 53.16, 52.64, 52.47, 35.77, 34.31, 32.80, 32.07, 30.71, 29.85, 29.82, 29.81, 29.78, 29.64, 29.51, 29.42, 29.29, 24.97, 22.84, 18.31, 14.27, 13.62. MS (ESI) calculated for $C_{29}H_{54}N_2O_7S$, m/z 574.37. found 575.37 (M+H)$^+$.

Compound 14c was synthesized similarly as compound 14b.

14c: 2-(((R)-2-amino-3-(((S)-1-methoxy-1-oxo-3-(palmitoyloxy)propan-2-yl)amino)-3-oxopropyl)thio)ethyl palmitate

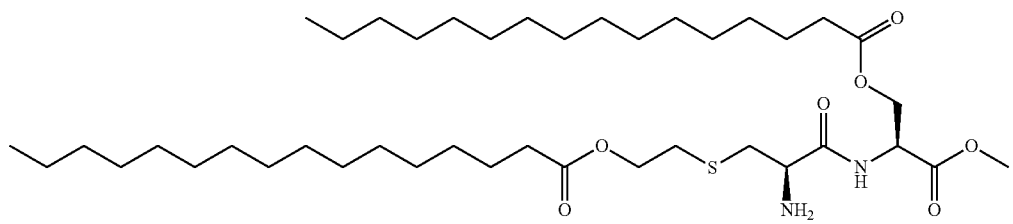 [SMILES: CCCCCCCCCCCCCCCC(=O)OCCSC[C@H](N)C(=O)N[C@@H](COC(=O)CCCCCCCCCCCCCCC)C(=O)OC]

(44 mg, 63%). $^1$H NMR (400 MHz, CDCl$_3$) δ 7.87 (d, J=7.6 Hz, 1H), 6.80 (s, 4H), 4.82-4.73 (m, 1H), 4.49 (dd, J=11.6, 4.1 Hz, 1H), 4.42-4.17 (m, 4H), 3.77 (s, 3H), 3.21 (dd, J=14.7, 5.8 Hz, 1H), 3.02 (dd, J=14.7, 7.7 Hz, 1H), 2.81 (t, J=6.5 Hz, 2H), 2.30 (dt, J=19.4, 7.6 Hz, 4H), 1.68-1.50 (m, 4H), 1.25 (s, 46H), 0.88 (t, J=6.8 Hz, 6H). $^{13}$C NMR (126 MHz, CDCl$_3$) δ 174.85, 174.03, 169.05, 167.77, 62.88, 62.31, 53.20, 52.74, 52.48, 34.34, 33.91, 32.78, 32.08, 30.63, 29.86, 29.83, 29.82, 29.79, 29.65, 29.52, 29.42, 29.29, 29.21, 24.96, 24.85, 22.84, 14.27. MS (ESI) calculated for $C_{41}H_{78}N_2O_7S$, m/z 742.55. found 743.56 (M+H)$^+$.

Synthesis of Compound 16: 3-(((R)-2-acetamido-3-(((S)-3-hydroxy-1-methoxy-1-oxopropan-2-yl)amino)-3-oxopropyl)thio)propyl palmitate

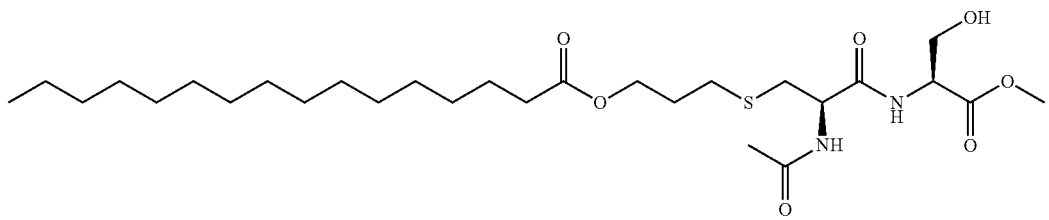 [SMILES: CCCCCCCCCCCCCCCC(=O)OCCCSC[C@H](NC(C)=O)C(=O)N[C@@H](CO)C(=O)OC]

To a solution of compound 15 (20 mg, 0.032 mmol) in anhydrous CH₂Cl₂ were added triethylamine (5 μL, 0.038 mmol) and acetic anhydride (3 μL, 0.032 mmol). The reaction mixture was stirred for 2 h. The solvent was removed under vacuum to obtain the residue which was purified using column chromatography (6% MeOH/CH₂Cl₂), furnishing compound 16 (10 mg, 59%). ¹H NMR (500 MHz, DMSO) δ 8.41 (d, J=7.6 Hz, 1H), 8.12 (d, J=8.5 Hz, 1H), 5.07 (t, J=5.6 Hz, 1H), 4.54 (td, J=8.9, 4.9 Hz, 1H), 4.33 (dt, J=7.7, 4.9 Hz, 1H), 4.10-4.03 (m, 2H), 3.70 (dt, J=11.1, 5.6 Hz, 1H), 3.66-3.58 (m, 4H), 2.82 (dd, J=13.7, 4.9 Hz, 1H), 2.57 (ddd, J=9.2, 5.3, 3.0 Hz, 3H), 2.28 (td, J=7.4, 2.8 Hz, 2H), 1.85 (s, 3H), 1.84-1.76 (m, 2H), 1.57-1.43 (m, 2H), 1.23 (s, 24H), 0.85 (t, J=6.9 Hz, 3H). ¹³C NMR (126 MHz, DMSO) δ 172.96, 170.78, 170.75, 169.25, 62.41, 61.10, 54.75, 51.96, 51.88, 33.66, 33.44, 31.31, 29.06, 29.05, 29.02, 28.98, 28.89, 28.72, 28.69, 28.46, 28.15, 27.69, 24.45, 22.50, 22.12, 13.98. MS (ESI) calculated for C₂₈H₅₂N₂O₇S, m/z 560.35. found 561.35 (M+H)⁺.

Synthesis of Compound 18: (2S,2'S)-Dimethyl 2,2'-(((2R,2'R)-3,3'-disulfanediylbis(2-((tert-butoxycarbonyl)amino)propanoyl))bis(azanediyl))bis(6-((((9H-fluoren-9-yl)methoxy)carbonyl)amino)hexanoate)

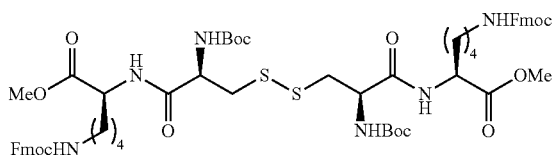

To a solution of L-cystine (500 mg, 2.08 mmol) in water (10 mL) were added triethylamine (870 μL, 6.24 mmol) and di-tert-butyldicarbonate (1.35 g, 6.24 mmol). The reaction mixture was stirred at room temperature for 2 h. After completion of the reaction, the solvent was evaporated under reduced pressure. The residue was dissolved in ethyl acetate and washed with 10% HCl. The organic layer was dried over anhydrous sodium sulfate, filtered, and evaporated under reduced pressure to obtain the crude product which was purified using column chromatography (15% MeOH/CH₂Cl₂) to obtain compound Nα,Nα'-di-Boc-L-cystine (870 mg, 95%). To a solution of Nα,Nα'-di-Boc-L-cystine (500 mg, 1.13 mmol) in anhydrous DMF (15 mL) were added H-Lys(Fmoc)-OMe.HCl (1.05 g, 2.50 mmol), HOBt (338 mg, 2.50 mmol), and pyridine (411 μL, 4.50 mmol). The reaction mixture was stirred at 0° C. for 30 min, followed by addition of EDCL (958 mg, 5.00 mmol) at 0° C. The reaction mixture was stirred at room temperature for 16 h, followed by evaporation of the solvent under reduced pressure. The residue was then dissolved in ethyl acetate and washed with water. The organic solvent was dried over anhydrous sodium sulfate, filtered, and evaporated under reduced pressure to obtain the crude product which was purified using column chromatography (50% EtOAc/hexanes) to obtain compound 18 (1.10 g, 83%). MS (ESI-TOF) for C₆₀H₇₆N₆O₁₄S₂ [M+H]⁺. Found 1169.5011. Calculated 1169.4934; [M+Na]⁺. Found 1191.4834. Calculated 1191.4753.

Synthesis of Compound 19: (2S,2'S)-Dimethyl 2,2'-(((2R,2'R)-3,3'-disulfanediylbis(2-acetamidopropanoyl))bis(azanediyl))bis(6-((((9H-fluoren-9-yl)methoxy)carbonyl)amino)hexanoate)

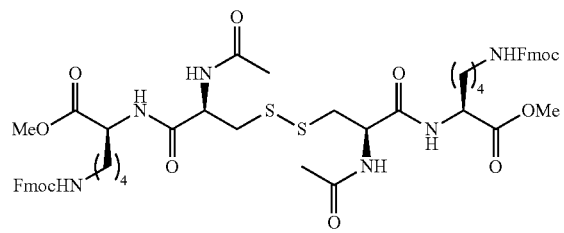

Compound 18 (600 mg, 0.51 mmol) was dissolved in hydrogen chloride solution (10 mL, 4M in dioxane) and the reaction mixture was stirred at room temperature for an hour and the volatilities were removed to afford (2S,2'S)-dimethyl 2,2'-(((2R,2'R)-3,3'-disulfanediylbis(2-aminopropanoyl))bis(azanediyl))bis(6-((((9H-fluoren-9-yl)methoxy)carbonyl)amino)hexanoate)dihydrochloride salt (535 mg, 0.51 mmol). The crude product was dissolved in CH₂Cl₂ (5 mL) and pyridine (5 mL) Acetic anhydride (291 μL, 3.08 mmol) was added and the reaction mixture was stirred at room temperature for 2 h, followed by evaporation of the solvent under reduced pressure. The residue was then dissolved in ethyl acetate and washed with water. The organic solvent was dried over anhydrous sodium sulfate, filtered, and evaporated under reduced pressure to obtain the crude product which was purified using column chromatography (50% EtOAc/hexanes) to obtain compound 19 (425 mg, 79% over two steps). ¹H NMR (500 MHz, CDCl₃) δ 8.46 (d, J=7.1 Hz, 2H), 7.74 (d, J=7.5 Hz, 4H), 7.57 (d, J=7.4 Hz, 4H), 7.38 (t, J=7.4 Hz, 4H), 7.29 (t, J=7.5 Hz, 4H), 6.72 (d, J=9.1 Hz, 2H), 5.45 (td, J=9.9, 3.2 Hz, 2H), 4.94 (t, J=5.4 Hz, 2H), 4.48-4.32 (m, 6H), 4.18 (t, J=6.8 Hz, 2H), 3.71 (s, 6H), 3.20-3.03 (m, 6H), 2.94-2.83 (m, 2H), 2.02 (s, 6H), 1.91-1.68 (m, 4H), 1.58-1.31 (m, 8H). ¹³C NMR (126 MHz, CDCl₃) δ 172.4, 170.7, 156.5, 144.1, 141.4, 127.8, 127.2, 125.1, 120.1, 66.6, 53.2, 52.7, 52.5, 47.4, 46.2, 40.8, 31.2, 29.5, 23.5, 22.8. MS (ESI-TOF) for C₅₄H₆₄N₆O₁₂S₂ [M+H]⁺. Found 1053.4234. Calculated 1053.4096; [M+Na]⁺. Found 1075.4048. Calculated 1075.3916.

Synthesis of Compound 20: (S)-Methyl 6-((((9H-fluoren-9-yl)methoxy)carbonyl)amino)-2-((R)-2-acetamido-3-mercaptopropanamido)hexanoate

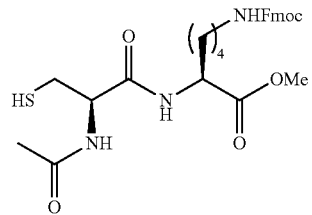

To a solution of 19 (375 mg, 0.356 mmol) in dichloromethane (5 mL) were added water (100 μL) and tributylphosphine (356 μL, 1.43 mmol). The reaction mixture was stirred at room temperature for 2 h. After completion of the reaction, the solvent was removed under reduced pressure to obtain the crude product, which was purified using column chromatography (50% EtOAc/hexanes) to obtain compound 20 (250 mg, 66%). MS (ESI-TOF) for $C_{27}H_{33}N_3O_6S$ [M+H]$^+$. Found 528.2232. Calculated 528.2163; [M+Na]$^+$. Found 550.2061. Calculated 550.1988.

Synthesis of Compound 21: (S)-Methyl 6-((((9H-fluoren-9-yl)methoxy)carbonyl)amino)-2-((R)-2-acetamido-3-((2-hydroxyethyl)thio)propanamido)hexanoate

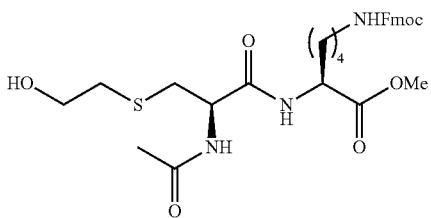

To a solution of compound 20 (245 mg, 0.465 mmol) in DMF (5 mL) were added 2-iodoethanol (182 μL, 2.33 mmol) and potassium carbonate (320 mg, 2.33 mmol). The reaction mixture was stirred at room temperature for an hour. After completion of the reaction, the solid potassium carbonate was filtered out and the solvent was removed under reduced pressure to obtain the crude product, which was purified using column chromatography (5% MeOH/CH$_2$Cl$_2$) to obtain compound 21 as a white solid (111 mg, 42%). MS (ESI-TOF) for $C_{29}H_{37}N_3O_7S$ [M+H]$^+$. Found 572.2427. Calculated 572.2425; [M+Na]$^+$. Found 594.2255. Calculated 594.2244.

Synthesis of Compound 22: (9S,12R)-12-Acetamido-1-(9H-fluoren-9-yl)-9-(methoxycarbonyl)-3,11-dioxo-2-oxa-14-thia-4,10-diazahexadecan-16-yl palmitate

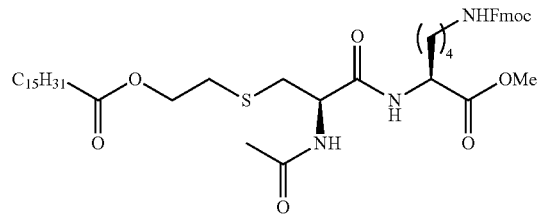

To a solution of compound 21 (100 mg, 0.175 mmol) in CH$_2$Cl$_2$ (1 mL) and pyridine (1 mL) was added palmitoyl chloride (80 μL, 0.262 mmol) and the reaction mixture was stirred at room temperature for 1 h. After completion of the reaction, the solvents were removed under reduced pressure to obtain the crude product, which was purified using column chromatography (50% EtOAc/hexanes) to obtain compound 22 (133 mg, 94%). $^1$H NMR (500 MHz, CDCl$_3$) δ 7.76 (d, J=7.5 Hz, 2H), 7.60 (d, J=7.4 Hz, 2H), 7.40 (t, J=7.4 Hz, 2H), 7.31 (t, J=7.4 Hz, 2H), 7.07 (d, J=7.7 Hz, 1H), 6.54 (d, J=7.2 Hz, 1H), 5.12 (t, J=5.7 Hz, 1H), 4.63-4.50 (m, 2H), 4.46-4.35 (m, 2H), 4.31-4.16 (m, 3H), 3.73 (s, 3H), 3.17 (td, J=13.6, 6.9 Hz, 2H), 2.92 (qd, J=14.0, 6.4 Hz, 2H), 2.82 (td, J=6.6, 1.9 Hz, 2H), 2.30 (t, J=7.6 Hz, 2H), 2.01 (s, 3H), 1.89 (ddd, J=14.9, 10.8, 5.7 Hz, 1H), 1.79-1.66 (m, 1H), 1.65-1.56 (m, 2H), 1.56-1.47 (m, 2H), 1.45-1.33 (m, 2H), 1.33-1.21 (m, 24H), 0.87 (t, J=7.0 Hz, 3H). $^{13}$C NMR (126 MHz, CDCl$_3$) δ 174.05, 172.33, 170.53, 170.38, 156.76, 144.11, 144.08, 141.44, 127.81, 127.17, 125.17, 120.11, 66.67, 62.76, 52.68, 52.64, 52.39, 47.39, 40.53, 34.34, 34.26, 32.06, 31.64, 31.15, 29.83, 29.79, 29.76, 29.62, 29.50, 29.42, 29.36, 29.28, 25.02, 23.20, 22.83, 22.40, 14.27. MS (ESI-TOF) for $C_{45}H_{67}N_3O_8S$ [M+H]$^+$. Found 810.4754. Calculated 810.4722; [M+Na]$^+$. Found 832.4591. Calculated 832.4541.

Synthesis of Compound 23: 2-(((R)-2-Acetamido-3-(((S)-6-amino-1-methoxy-1-oxohexan-2-yl)amino)-3-oxopropyl)thio)ethyl palmitate

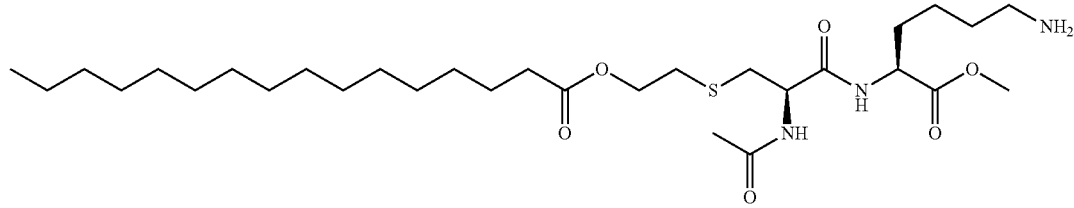 [SMILES: CCCCCCCCCCCCCCCC(=O)OCCSC[C@H](NC(C)=O)C(=O)N[C@@H](CCCCN)C(=O)OC]

To a solution of compound 22 (81 mg, 0.1 mmol) in DMF (1 mL) was added polymer-bound piperazine (1-2 mmol/g loading) (333 mg, ~0.5 mmol) and the reaction mixture was stirred at room temperature for 4 h. After completion of the reaction, the resin was filtered out and the solvents were removed under reduced pressure to obtain the crude product, which was purified using column chromatography (20% MeOH/CH$_2$Cl$_2$) to obtain compound 23 as a white solid (32 mg, 55%). $^1$H NMR (500 MHz, CDCl$_3$) δ 8.03 (d, J=7.9 Hz, 1H), 7.05 (d, J=8.4 Hz, 1H), 4.84 (td, J=8.0, 5.5 Hz, 1H), 4.54 (dd, J=13.8, 7.4 Hz, 1H), 4.31-4.15 (m, 2H), 3.73 (s, 3H), 3.06 (ddd, J=19.2, 13.6, 6.2 Hz, 3H), 2.92-2.72 (m, 3H), 2.34-2.26 (m, 2H), 2.06 (s, 3H), 1.97-1.88 (m, 1H), 1.85 (dd, J=15.0, 7.7 Hz, 2H), 1.77-1.67 (m, 1H), 1.59 (dd, J 14.3, 7.2 Hz, 4H), 1.40-1.17 (m, 24H), 0.87 (t, J=7.0 Hz, 3H). $^{13}$C NMR (126 MHz, CDCl$_3$) δ 174.01, 172.17, 171.42, 170.90, 63.08, 52.63, 52.40, 39.05, 34.97, 34.36, 32.07, 31.19, 30.21, 29.85, 29.82, 29.81, 29.79, 29.66, 29.51, 29.46, 29.33, 26.58, 25.06, 23.41, 22.84, 22.07, 14.28. MS (ESI-TOF) for $C_{30}H_{57}N_3O_6S$ [M+H]$^+$. Found 588.4086. Calculated 588.4041; [M+Na]$^+$. Found 610.3914. Calculated 610.3860.

Synthesis of 25: 2-(((R)-2-Acetamido-3-(((S)-3-(((S)-2,6-diaminohexanoyl)oxy)-1-methoxy-1-oxopropan-2-yl)amino)-3-oxopropyl)thio)ethyl palmitate

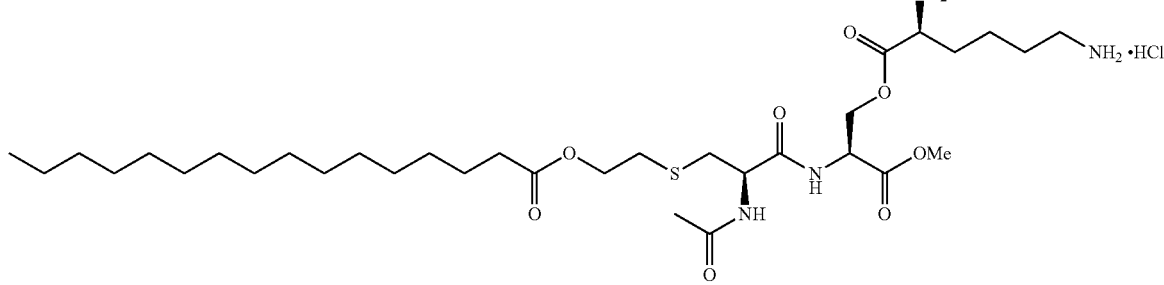

To a solution of N,N'-di-boc-L-lysine (63 mg, 0.183 mmol) and compound 11d (50 mg, 0.091 mmol) in anhydrous $CH_2Cl_2$ (5 mL), were added N-methylmorpholine (20 μL, 0.183 mmol) and catalytic amount of DMAP. The reaction mixture was stirred at 0° C. and EDCL (28 mg, 0.183 mmol) was added after 15 min. The reaction mixture was then stirred at room temperature for 4 h. After the completion of reaction, water (10 mL) was added and the product was extracted in $CH_2Cl_2$. The organic layer was washed with water (10 mL×2), brine (10 mL) and dried over anhydrous sodium sulfate. The solvent was removed under vacuum and the residue was purified using column chromatography (5% MeOH/$CH_2Cl_2$) to obtain the diboc protected intermediate 24 as white solid (40 mg, 50%). $^1$H NMR (500 MHz, $CDCl_3$) δ 7.35 (d, J=7.6 Hz, 1H), 6.74 (d, J=7.6 Hz, 1H), 5.23 (d, J=6.6 Hz, 1H), 4.83 (dt, J=7.7, 3.9 Hz, 1H), 4.77 (s, 1H), 4.66 (d, J=6.3 Hz, 1H), 4.58 (d, J=10.0 Hz, 1H), 4.45 (dd, J=11.2, 3.9 Hz, 1H), 4.32-4.14 (m, 3H), 3.78 (s, 3H), 3.18-3.07 (m, 2H), 2.97 (qd, J=13.9, 6.4 Hz, 2H), 2.85-2.74 (m, 2H), 2.31 (t, J=7.6 Hz, 2H), 2.07 (s, 3H), 1.86-1.55 (m, 6H), 1.55-1.41 (m, 18H), 1.41-1.20 (m, 24H), 0.87 (t, J=7.0 Hz, 3H). $^{13}$C NMR (126 MHz, $CDCl_3$) δ 173.95, 172.59, 170.84, 170.57, 169.19, 156.49, 155.86, 80.25, 79.42, 63.83, 62.93, 53.54, 53.15, 52.66, 52.15, 39.84, 34.35, 33.95, 32.07, 31.67, 31.11, 29.84, 29.80, 29.77, 29.63, 29.51, 29.44, 29.30, 28.59, 28.50, 25.04, 23.25, 22.84, 22.48, 14.28. MS (ESI-TOF) for $C_{43}H_{78}N_4O_{12}S$ $[M+H]^+$. Found 875.5417. Calculated 875.5410; $[M+Na]^+$. Found 897.5232. Calculated 897.5229. Compound 24 was then dissolved in HCl/dioxane (4 M solution, 2 mL) and the reaction mixture was stirred at room temperature for 15 min, followed by removal of the solvent under vacuum to obtain compound 25 as a white solid in quantitative yield. $^1$H NMR (500 MHz, DMSO) δ 8.80 (d, J=8.1 Hz, 1H), 8.63 (s, 3H), 8.31 (d, J=8.3 Hz, 1H), 7.95 (s, 3H), 4.72 (ddd, J=7.9, 6.3, 4.9 Hz, 1H), 4.46 (ddd, J=15.7, 10.0, 4.7 Hz, 2H), 4.38 (dd, J=11.2, 6.4 Hz, 1H), 4.18-4.11 (m, 2H), 3.97 (bs, 1H), 3.73-3.69 (m, 1H), 3.69-3.64 (m, 4H), 3.52-3.48 (m, 1H), 3.46 (ddd, J=6.1, 3.9, 1.2 Hz, 1H), 2.93 (dd, J=13.7, 4.8 Hz, 1H), 2.83-2.72 (m, 4H), 2.67 (dd, J=13.7, 9.4 Hz, 1H), 2.28 (t, J=7.4 Hz, 2H), 1.88 (s, 3H), 1.84-1.77 (m, 2H), 1.62-1.32 (m, 8H), 1.30-1.18 (m, 24H), 0.85 (t, J=6.9 Hz, 3H). $^{13}$C NMR (126 MHz, DMSO) δ 172.81, 170.76, 169.68, 169.23, 168.91, 72.17, 70.53, 63.95, 62.88, 60.18, 52.44, 51.67, 50.78, 43.63, 38.23, 33.53, 33.41, 31.31, 30.01, 29.11, 29.06, 29.03, 29.02, 29.00, 28.90, 28.72, 28.46, 26.19, 24.44, 22.55, 22.12, 21.13, 13.99. MS (ESI-TOF) for $C_{33}H_{62}N_4O_8S$ $[M+H]^+$. Found 675.4181. Calculated 675.4361.

Synthesis of 26: 2-(((R)-2-Acetamido-3-(((S)-1-methoxy-1-oxo-3-(sulfooxy)propan-2-yl)amino)-3-oxopropyl)thio)ethyl palmitate

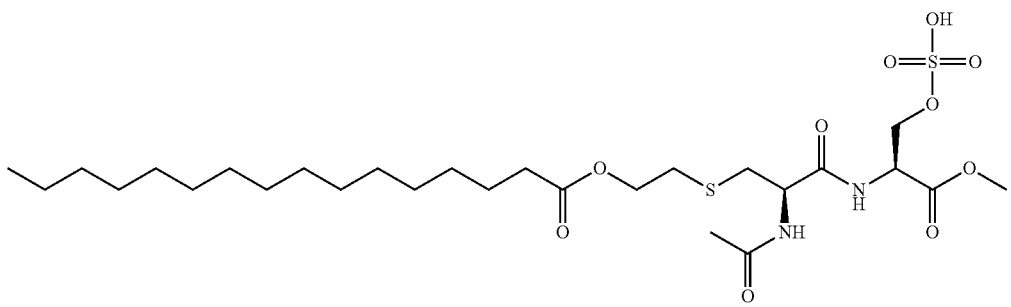 [SMILES: CCCCCCCCCCCCCCCC(=O)OCCSC[C@H](NC(C)=O)C(=O)N[C@@H](COS(=O)(=O)O)C(=O)OC]

To a solution of compound 11d (60 mg, 0.110 mmol) in anhydrous pyridine was added sulfur trioxide pyridine complex (175 mg, 1.10 mmol). The reaction mixture was heated at 80° C. for 16 h. The solvent was removed under vacuum to obtain the residue which was purified using column chromatography (10% MeOH/$CH_2Cl_2$), to furnish compound 26 as a white solid (23 mg, 33%). $^1$H NMR (500 MHz, $CDCl_3$) δ 8.20 (d, J=5.3 Hz, 1H), 7.30 (d, J=1.6 Hz, 1H), 4.92-4.79 (m, 2H), 4.32 (dd, J=33.8, 6.7 Hz, 2H), 4.26-4.14 (m, 2H), 3.76 (s, 3H), 3.00 (d, J=9.1 Hz, 1H), 2.89 (dd, J=12.8, 6.8 Hz, 1H), 2.78 (t, J=6.4 Hz, 2H), 2.36-2.26 (m, 3H), 2.02 (s, 3H), 1.59 (dd, J=14.3, 7.2 Hz, 2H), 1.35-1.22 (m, 24H), 0.88 (t, J=7.0 Hz, 3H). $^{13}$C NMR (126 MHz, CDCl$_3$) δ 174.00, 172.28, 171.43, 170.29, 67.45, 62.92, 53.15, 52.60, 52.19, 34.36, 32.08, 30.97, 29.87, 29.86, 29.82, 29.71, 29.52, 29.51, 29.38, 25.08, 23.01, 22.85, 14.28. MS (ESI-TOF, Negative Mode) for C$_{27}$H$_{50}$N$_2$O$_{10}$S$_2$, [M−H]$^-$ Found 625.2633. Calculated 625.2834.

Synthesis of 27: (7S,10R)-10-Acetamido-7-(methoxycarbonyl)-4,9,16-trioxo-5,15-dioxa-12-thia-8-azahentriacontan-1-oic acid

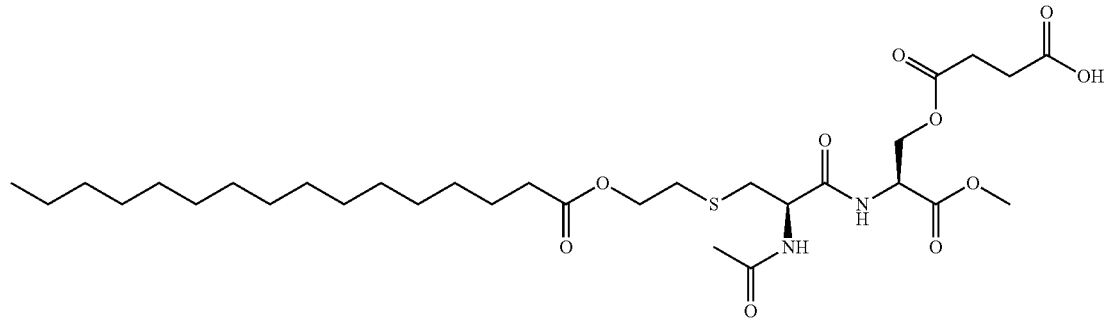 [SMILES: CCCCCCCCCCCCCCCC(=O)OCCSC[C@H](NC(C)=O)C(=O)N[C@@H](COC(=O)CCC(=O)O)C(=O)OC]

To a solution of compound 11d (50 mg, 0.091 mmol) in anhydrous THF were added triethylamine (25 μL, 0.183 mmol) and succinic anhydride (18 mg, 0.183 mmol). The reaction mixture was stifled at 50° C. for 2 h. The solvent was removed under vacuum to obtain the residue which was purified using column chromatography (10% MeOH/CH$_2$Cl$_2$), to furnish compound 27 (37 mg, 62%). $^1$H NMR (500 MHz, CDCl$_3$) δ 7.25 (d, J=7.8 Hz, 1H), 6.77 (d, J=8.5 Hz, 1H), 4.87-4.78 (m, 2H), 4.65 (dd, J=11.4, 3.5 Hz, 1H), 4.39 (dd, J=11.4, 3.4 Hz, 1H), 4.34-4.19 (m, 2H), 3.79 (s, 3H), 2.99 (dd, J=14.0, 5.9 Hz, 1H), 2.87 (dd, J=14.0, 7.2 Hz, 1H), 2.81 (td, J=6.8, 1.0 Hz, 2H), 2.75-2.53 (m, 4H), 2.37-2.29 (m, 2H), 2.08 (s, 3H), 1.66-1.56 (m, 2H), 1.35-1.21 (m, 24H), 0.87 (t, J=7.0 Hz, 3H). $^{13}$C NMR (126 MHz, CDCl$_3$) δ 175.28, 174.54, 171.84, 171.65, 170.25, 169.41, 63.29, 63.04, 53.10, 52.40, 52.03, 34.58, 34.39, 32.06, 30.90, 29.84, 29.80, 29.76, 29.67, 29.61, 29.50, 29.41, 29.39, 29.27, 25.00, 23.36, 22.83, 14.27. MS (ESI-TOF) for C$_{31}$H$_{54}$N$_2$O$_{10}$S [M+H]$^+$. Found 647.3649. Calculated 647.3572; [M+Na]$^+$. Found 669.3476. Calculated 669.3391.

Synthesis of 28: (S)-2-((R)-2-Acetamido-3-((2-(palmitoyloxy)ethyl)thio)propanamido)-3-methoxy-3-oxopropyl nicotinate

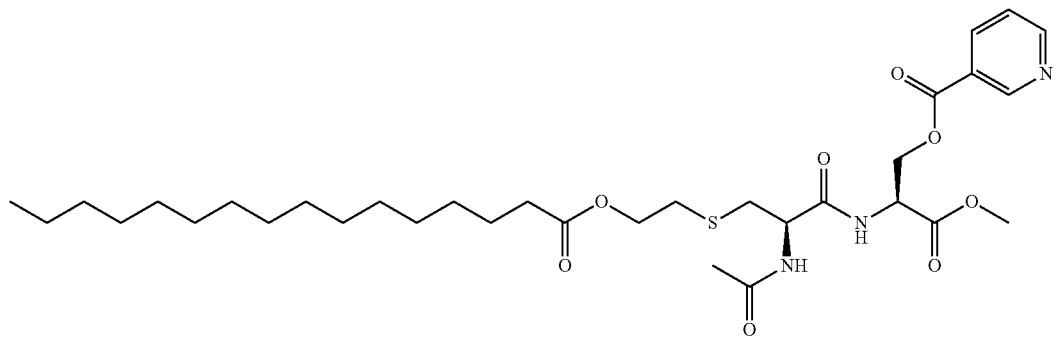 [SMILES: CCCCCCCCCCCCCCCC(=O)OCCSC[C@H](NC(C)=O)C(=O)N[C@@H](COC(=O)c1cccnc1)C(=O)OC]

To a solution of compound 11d (50 mg, 0.091 mmol) and nicotinic acid (23 mg, 0.183 mmol) and in anhydrous CH$_2$Cl$_2$ (5 mL), were added N-methylmorpholine (20 µL, 0.183 mmol) and catalytic amount of DMAP. The reaction mixture was stirred at 0° C. and EDCl (28 mg, 0.183 mmol) was added after 15 min. The reaction mixture was then stirred at room temperature for overnight. After the completion of reaction, water (10 mL) was added and the product was extracted in CH$_2$Cl$_2$. The organic layer was washed with water (10 mL×2), brine (10 mL) and dried over anhydrous sodium sulfate. The solvent was removed under vacuum and the residue was purified using column chromatography (5% MeOH/CH$_2$Cl$_2$) to obtain product 28 as a white solid (41 mg, 68%). $^1$H NMR (500 MHz, CDCl$_3$) δ 9.19 (dd, J=2.2, 0.8 Hz, 1H), 8.80 (dd, J=4.9, 1.7 Hz, 1H), 8.30-8.23 (m, 1H), 7.48 (d, J=7.6 Hz, 1H), 7.41 (ddd, J=8.0, 4.9, 0.8 Hz, 1H), 6.44 (d, J=7.1 Hz, 1H), 4.95 (dt, J=7.7, 3.8 Hz, 1H), 4.77-4.65 (m, 2H), 4.61 (td, J=7.2, 5.7 Hz, 1H), 4.32-4.18 (m, 2H), 3.82 (s, 3H), 2.99 (dd, J=14.0, 5.6 Hz, 1H), 2.93-2.75 (m, 3H), 2.34-2.24 (m, 2H), 2.01 (s, 3H), 1.62 (s, 3H), 1.62-1.53 (m, 2H), 1.36-1.18 (m, 24H), 0.88 (t, J=7.0 Hz, 3H). $^{13}$C NMR (126 MHz, CDCl$_3$) δ 174.05, 170.51, 170.44, 169.36, 164.88, 154.04, 151.18, 137.36, 125.39, 123.56, 64.41, 62.61, 53.28, 52.55, 52.23, 34.35, 33.99, 32.07, 31.20, 29.84, 29.80, 29.77, 29.62, 29.51, 29.42, 29.29, 25.02, 23.21, 22.84, 14.28. MS (ESI-TOF) for C$_{33}$H$_{53}$N$_3$O$_8$S [M+H]$^+$. Found 652.3672. Calculated 652.3626; [M+Na]$^+$. Found 674.3472. Calculated 674.3446.

Synthesis of 30: (S)-Methyl 2-((R)-3-((2-azido-ethyl)thio)-2-((tert-butoxycarbonyl)amino)propanamido)-3-(tert-butoxy)propanoate

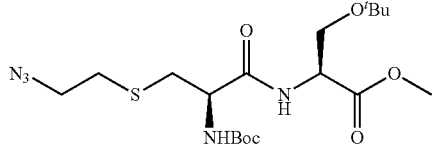 [SMILES: COC(=O)[C@H](COC(C)(C)C)NC(=O)[C@H](CSCCN=[N+]=[N-])NC(=O)OC(C)(C)C]

To a solution of compound 4 (500 mg, 1.185 mmol) in CH$_2$Cl$_2$ (5 mL) were added triethylamine (0.5 mL, 3.56 mmol) and methanesulfonyl chloride (276 µL, 3.55 mmol) and the reaction mixture was stirred at room temperature for 3 h. After the completion of the reaction, water (10 mL) was added to the reaction and the product was extracted in CH$_2$Cl$_2$. The organic layer was washed with water (10 mL×2) and brine (10 mL), dried over anhydrous sodium sulfate and the solvent was removed under reduced pressure to obtain the crude mesylate. This crude product was dissolved in DMF (5 mL) and sodium azide (385 mg, 5.925 mmol) was added and the reaction mixture was stirred at 60 C for 4 h. After the completion of reaction, water (20 mL) was added to the reaction and the product obtained was extracted in EtOAc. The organic layer was washed with water (10 mL×3) and brine (10 mL), dried over anhydrous sodium sulfate and the solvent was removed under reduced pressure to obtain the crude product which was purified using column chromatography (20% EtOAc/hexanes) to obtain compound 30 (390 mg, 73% over two steps). $^1$H NMR (500 MHz, CDCl$_3$) δ 7.14 (d, J=7.8 Hz, 1H), 5.49 (s, 1H), 4.66 (dt, J=8.2, 3.0 Hz, 1H), 4.32 (d, J=4.9 Hz, 1H), 3.83 (dd, J=9.1, 2.9 Hz, 1H), 3.74 (s, 3H), 3.57 (dd, J=9.1, 3.2 Hz, 1H), 3.51 (ddd, J=12.5, 9.0, 6.2 Hz, 2H), 3.02 (dd, J=14.0, 5.1 Hz, 1H), 2.90 (dd, J=14.0, 7.0 Hz, 1H), 2.79 (ddd, J=12.1, 9.5, 3.7 Hz, 2H), 1.46 (s, 9H), 1.14 (s, 9H). $^{13}$C NMR (126 MHz, CDCl$_3$) δ 170.59, 170.41, 155.40, 80.47, 73.70, 61.76, 53.93, 53.31, 52.60, 51.14, 34.89, 31.86, 28.43, 27.41. MS (ESI-TOF) for C$_{18}$H$_{33}$N$_5$O$_6$S [M+Na]$^+$. Found 470.1919. Calculated 470.2044.

Synthesis of 31: (S)-Methyl 2-((R)-3-((2-amino-ethyl)thio)-2-((tert-butoxycarbonyl)amino)propanamido)-3-(tert-butoxy)propanoate

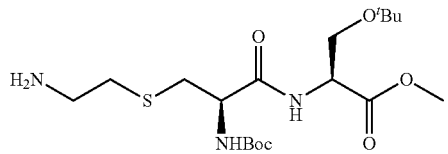 [SMILES: COC(=O)[C@H](COC(C)(C)C)NC(=O)[C@H](CSCCN)NC(=O)OC(C)(C)C]

To a solution of compound 30 (237 mg, 0.53 mmol) in dry THF (5 mL) was added triphenylphosphine (208 mg, 0.795 mmol) and the reaction mixture was heated to reflux for 3 h. Water (1 mL) was added and the heating was continued for 2 more hours. After the completion of reaction, the solvent was removed under reduced pressure to obtain the crude product which was purified using column chromatography (10% MeOH/CH$_2$Cl$_2$) to obtain compound 6 (200 mg, 90%). $^1$H NMR (500 MHz, CDCl$_3$) δ 7.57 (bs, 1H), 5.73 (d, J=7.5 Hz, 1H), 4.74-4.61 (m, 1H), 4.35 (bs, 1H), 3.82 (dd, J=9.1, 3.0 Hz, 1H), 3.73 (s, 3H), 3.57 (dd, J=9.1, 3.3 Hz, 1H), 3.03-2.80 (m, 4H), 2.79-2.63 (m, 2H), 1.45 (s, 9H), 1.13 (s, 9H). $^{13}$C NMR (126 MHz, CDCl$_3$) δ 170.7, 170.6, 155.5, 80.3, 73.6, 61.9, 54.0, 53.3, 52.5, 41.4, 36.4, 34.9, 28.5 (3C), 27.4 (3C). MS (ESI-TOF) for C$_{18}$H$_{35}$N$_3$O$_6$S [M+H]$^+$. Found 470.1919. Calculated 470.2044.

Synthesis of 32: (S)-Methyl 3-(tert-butoxy)-2-((R)-2-((tert-butoxycarbonyl)amino)-3-((2-palmitamido-ethyl)thio)propanamido)propanoate

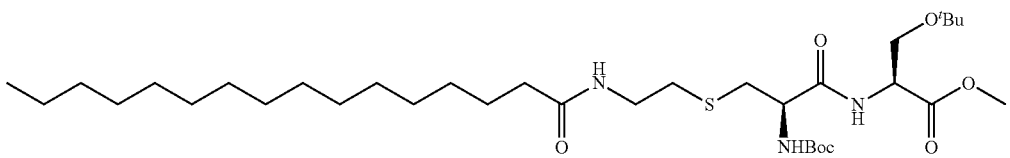 [SMILES: CCCCCCCCCCCCCCCC(=O)NCCSC[C@H](NC(=O)OC(C)(C)C)C(=O)N[C@@H](COC(C)(C)C)C(=O)OC]

To a solution of compound 31 (100 mg, 0.238 mmol) in dry CH$_2$Cl$_2$ (2 mL) were added triethylamine (50 mL, 0.356 mmol) and palmitoyl chloride (109 mL, 0.356 mmol) and the reaction mixture was stirred at room temperature for 30 min. Water (10 mL) was added and the heating was continued for 2 more hours. After the completion of reaction, water (10 mL) was added to the reaction and the product obtained was extracted in CH$_2$Cl$_2$. The organic layer was washed with water (10 mL×3) and brine (10 mL), dried over anhydrous sodium sulfate and the solvent was removed under reduced pressure to obtain the crude product which was purified using column chromatography (40% EtOAc/hexanes) to obtain compound 31 (105 mg, 69%). $^1$H NMR (500 MHz, CDCl$_3$) δ 7.14 (d, J=8.1 Hz, 1H), 6.25 (s, 1H), 5.48 (d, J=4.1 Hz, 1H), 4.66 (dt, J=8.2, 3.1 Hz, 1H), 4.32 (d, J=5.6 Hz, 1H), 3.83 (dd, J=9.1, 3.0 Hz, 1H), 3.74 (s, 3H), 3.57 (dd, J=9.1, 3.2 Hz, 1H), 3.48 (td, J=9.3, 6.0 Hz, 2H), 2.97 (dd, J=13.9, 5.5 Hz, 1H), 2.88 (dd, J=13.9, 6.9 Hz, 1H), 2.82-2.66 (m, 2H), 2.24-2.13 (m, 2H), 1.67-1.56 (m, 2H), 1.45 (s, 9H), 1.37-1.19 (m, 24H), 1.14 (s, 9H), 0.87 (t, J=7.0 Hz, 3H). $^{13}$C NMR (126 MHz, CDCl$_3$) δ 173.53, 170.71, 170.50, 155.50, 80.47, 73.75, 61.76, 53.88, 53.30, 52.62, 38.58, 36.86, 34.55, 32.51, 32.06, 29.84, 29.80, 29.78, 29.71, 29.67, 29.54, 29.50, 28.45, 27.43, 25.88, 22.83, 14.27. MS (ESI-TOF) for C$_{34}$H$_{65}$N$_3$O$_7$S [M+H]$^+$. Found 660.4560. Calculated 660.4616; [M+Na]$^+$. Found 682.4373. Calculated 682.4435.

Synthesis of 34: (S)-Methyl 2-((R)-2-acetamido-3-((2-palmitamidoethyl)thio)propanamido)-3-hydroxypropanoate

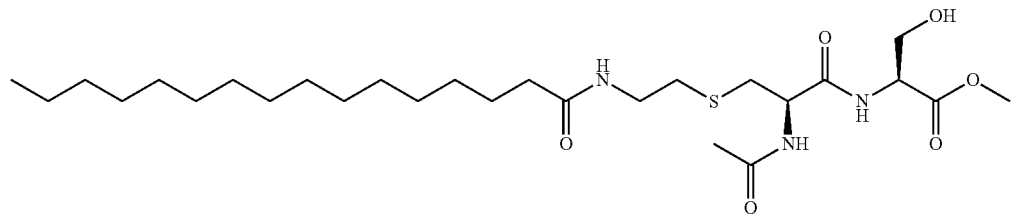 [SMILES: CCCCCCCCCCCCCCCC(=O)NCCSC[C@H](NC(C)=O)C(=O)N[C@@H](CO)C(=O)OC]

To compound 32 (95 mg, 0.183 mmol) was added TFA (2 mL). The reaction mixture was stirred at room temperature for 30 min and then dried by blowing nitrogen through the solution. The crude product was used directly for the next step. To a solution of the crude intermediate in dichloromethane (2 mL) was added pyridine (16 μL, 0.2 mmol) and acetic anhydride (19 μL, 0.2 mmol). The reaction mixture was stirred at room temperature for 30 min and then concentrated. The residue was purified by a flash chromatography (SiO$_2$, MeOH in dichloromethane 0 to 5%) to give product 34 (70 mg, 84%) as a white solid. $^1$H NMR (500 MHz, CDCl$_3$) δ 7.76 (d, J=7.8 Hz, 1H), 6.75 (d, J=7.3 Hz, 1H), 6.07 (s, 1H), 4.71 (d, J=7.1 Hz, 1H), 4.62 (dd, J=7.7, 3.3 Hz, 1H), 4.01 (s, 2H), 3.78 (s, 2H), 3.63-3.48 (m, 2H), 2.95 (dd, J=22.3, 6.2 Hz, 2H), 2.85 (dt, J=14.2, 5.7 Hz, 1H), 2.72 (dt, J=14.5, 7.4 Hz, 1H), 2.23-2.19 (m, 1H), 2.06 (s, 2H), 1.63-1.56 (m, 2H), 1.34-1.22 (m, 18H), 0.88 (t, J=6.9 Hz, 2H). $^{13}$C NMR (126 MHz, CDCl$_3$) δ 175.10, 170.66, 170.61, 170.55, 62.88, 55.43, 52.78, 52.28, 39.22, 37.01, 35.36, 32.75, 32.07, 29.85, 29.84, 29.81, 29.77, 29.63, 29.51, 29.45, 29.40, 25.80, 23.35, 22.84, 14.28. MS (ESI-TOF) for C$_{27}$H$_{51}$N$_3$O$_6$S [M+H]$^+$. Found 546.3474. Calculated 546.3571; [M+Na]$^+$. Found 568.3293. Calculated 568.3391.

Synthesis of Compound 38: (S)-Methyl 2-((R)-2-acetamido-3-((2-(1-hexadecyl-1H-1,2,3-triazol-4-yl)ethyl)thio)propanamido)-3-hydroxypropanoate

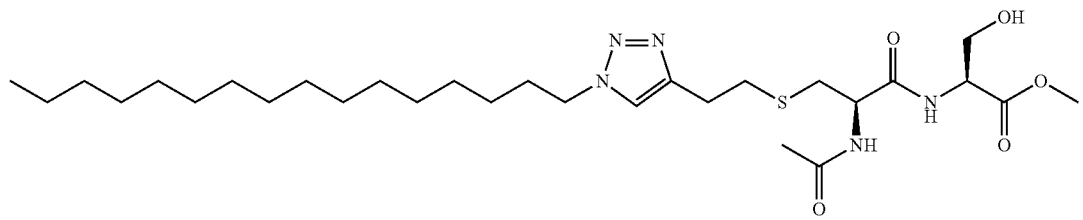 [SMILES: CCCCCCCCCCCCCCCCn1cc(CCSC[C@H](NC(C)=O)C(=O)N[C@@H](CO)C(=O)OC)nn1]

To a solution of compound 3 (200 mg, 0.529 mmol) in dry DMF (5 mL) were added 4-bromobut-1-yne (248 μL, 2.65 mmol) and triethylamine (147 μL, 1.06 mmol) and the reaction mixture was heated to 90° C. for 1 h. After the completion of reaction, water (20 mL) was added to the reaction and the product obtained was extracted in EtOAc. The organic layer was washed with water (10 mL×3) and brine (10 mL), dried over anhydrous sodium sulfate and the solvent was removed under reduced pressure to obtain the crude product 35 as a white solid. The crude product was further washed with hexanes to remove excess 4-bromobut-1-yne, dried and used as it is for the next step. To a stirred solution of compound 35 (150 mg, 0.35 mmol) and 1-azidohexadecane (139 mg, 0.52 mmol) in THF (3 mL), were added CuSO$_4$.5H$_2$O (9 mg in 0.5 mL water, 0.035 mmol) and sodium ascorbate (14 mg in 0.5 mL water, 0.07 mmol) and the reaction mixture was stirred at room temperature for overnight. After the completion of reaction, water (20 mL) was added and the product obtained was extracted in EtOAc. The organic layer was washed with water (10 mL×2) and brine (10 mL), dried over anhydrous sodium sulfate and the solvent was removed under reduced pressure to obtain the crude product 36. MS (ESI-TOF) for C$_{36}$H$_{67}$N$_5$O$_6$S [M+H]$^+$. Found 698.5075. Calculated 698.4885. The crude product was used as it is for the next step. The global deprotection using TFA and further N-acetylation was carried out similarly as compound 34 to furnish compound 38 as white solid. $^1$H NMR (500 MHz, CDCl$_3$) δ 8.11 (d, J=7.5 Hz, 1H), 7.38 (s, 1H), 6.94 (d, J=7.2 Hz, 1H), 4.66 (td, J=7.6, 4.5 Hz, 1H), 4.62 (dt, J=7.3, 3.5 Hz, 1H), 4.38-4.21 (m, 3H), 4.02 (s, 2H), 3.23-2.87 (m, 5H), 2.79 (dd, J=14.3, 7.9 Hz, 1H), 2.06 (s, 3H), 1.91-1.82 (m, 2H), 1.38-1.20 (m, 24H), 0.87 (t, J=7.0 Hz, 3H). MS (ESI-TOF) for C$_{29}$H$_{53}$N$_5$O$_5$S [M+H]$^+$. Found 584.3889. Calculated 584.3840; [M+Na]$^+$. Found 606.3692. Calculated 606.3660.

Synthesis of Compound 39: (S)-methyl 3-(tert-butoxy)-2-((R)-2-((tert-butoxycarbonyl)amino)-3-((2-(4-tridecyl-1H-1,2,3-triazol-1-yl)ethyl)thio)propanamido)propanoate

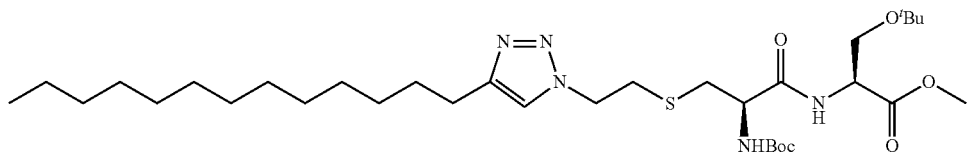 [SMILES: CCCCCCCCCCCCCc1cn(CCSC[C@H](NC(=O)OC(C)(C)C)C(=O)N[C@@H](COC(C)(C)C)C(=O)OC)nn1]

To a stirred solution of compound 30 (60 mg, 0.134 mmol) and pentadec-1-yne (39 μL, 0.147 mmol) in THF (2 mL), were added $CuSO_4.5H_2O$ (3 mg in 0.25 mL water, 0.013 mmol) and sodium ascorbate (5 mg in 0.25 mL water, 0.003 mmol) and the reaction mixture was stirred at room temperature for overnight. After the completion of reaction, water (10 mL) was added and the product obtained was extracted in EtOAc. The organic layer was washed with water (10 mL×2) and brine (10 mL), dried over anhydrous sodium sulfate and the solvent was removed under reduced pressure to obtain the crude product. The residue was further purified by a flash chromatography ($SiO_2$, MeOH in dichloromethane 0 to 5%) to give product 39 (48 mg, 55%) as a white solid. $^1$H NMR (500 MHz, $CDCl_3$) δ 7.43 (s, 1H), 7.12 (d, J=7.6 Hz, 1H), 5.51 (d, J=4.1 Hz, 1H), 4.64 (dt, J=8.2, 3.1 Hz, 1H), 4.54 (t, J=7.0 Hz, 2H), 4.32 (d, J=4.4 Hz, 1H), 3.82 (dd, J=9.1, 3.0 Hz, 1H), 3.73 (s, 3H), 3.56 (dd, J=9.1, 3.2 Hz, 1H), 3.12 (dd, J=13.3, 6.5 Hz, 1H), 3.02 (ddd, J=14.1, 13.1, 5.9 Hz, 2H), 2.84 (dd, J=14.1, 7.2 Hz, 1H), 2.74-2.64 (m, 2H), 1.71-1.59 (m, 3H), 1.46 (s, 9H), 1.39-1.21 (m, 20H), 1.13 (s, 9H), 0.87 (t, J=7.0 Hz, 3H). $^{13}$C NMR (126 MHz, $CDCl_3$) δ 170.56, 170.36, 155.36, 148.63, 121.30, 80.54, 73.75, 61.67, 53.85, 53.35, 52.62, 49.64, 34.44, 32.24, 32.07, 29.84, 29.82, 29.80, 29.72, 29.62, 29.55, 29.50, 29.47, 28.44, 27.42, 25.86, 22.84, 14.28. MS (ESI-TOF) for $C_{33}H_{61}N_5O_6S$ [M+H]$^+$. Found 656.4403. Calculated 656.4415; [M+Na]$^+$. Found 678.4223. Calculated 678.4235.

Synthesis of Compound 41: (S)-Methyl 2-((R)-2-acetamido-3-((2-(4-tridecyl-1H-1,2,3-triazol-1-yl)ethyl)thio)propanamido)-3-hydroxypropanoate

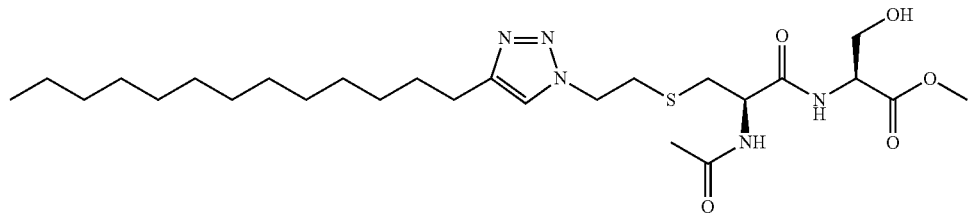 [SMILES: CCCCCCCCCCCCCc1cn(CCSC[C@H](NC(C)=O)C(=O)N[C@@H](CO)C(=O)OC)nn1]

The global deprotection of compound 39 using TFA and further N-acetylation was carried out similarly as compound 34 to furnish compound 41 as white solid. $^1$H NMR (500 MHz, $CDCl_3$) δ 7.86 (d, J=7.8 Hz, 1H), 7.38 (s, 1H), 6.78 (d, J=6.8 Hz, 1H), 5.21 (s, 1H), 4.92 (ddd, J=14.2, 8.9, 4.1 Hz, 1H), 4.63 (ddd, J=7.7, 4.6, 3.0 Hz, 1H), 4.61-4.52 (m, 2H), 4.03 (dd, J=12.2, 3.7 Hz, 2H), 3.75 (s, 3H), 3.24 (ddd, J=14.8, 5.9, 4.2 Hz, 1H), 3.07 (dd, J=9.0, 4.7 Hz, 1H), 2.90 (dd, J=14.5, 4.1 Hz, 1H), 2.72 (dd, J=14.5, 9.1 Hz, 1H), 2.67 (dd, J=8.5, 6.8 Hz, 2H), 2.03 (s, 3H), 1.73-1.54 (m, 2H), 1.39-1.17 (m, 20H), 0.87 (t, J=6.9 Hz, 3H). $^{13}$C NMR (126 MHz, $CDCl_3$) δ 170.40, 170.23, 169.96, 149.51, 121.78, 62.52, 55.79, 53.11, 52.67, 50.05, 36.03, 34.69, 32.06, 29.83, 29.81, 29.79, 29.69, 29.50, 29.48, 29.39, 29.37, 25.57, 23.31, 22.84, 14.28. MS (ESI-TOF) for $C_{26}H_{47}N_5O_5S$ [M+H]$^+$. Found 542.3378. Calculated 542.3371; [M+Na]$^+$. Found 564.3201. Calculated 564.3190.

Synthesis of Compound 44: (2S,5R)-methyl 5-amino-2-(hydroxymethyl)-4,11-dioxo-10-oxa-7-thia-3,12-diazaoctacosan-1-oate

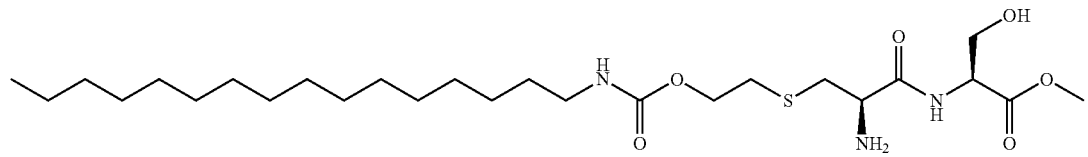 [SMILES: CCCCCCCCCCCCCCCCNC(=O)OCCSC[C@H](N)C(=O)N[C@@H](CO)C(=O)OC]

To a solution of compound 4 (100 mg, 0.237 mmol) in CH$_2$Cl$_2$ (1 mL) was added carbonyldiimidazole (58 mg, 0.355 mmol) and the reaction mixture was stirred at room temperature. Hexadecylamine (146 mg, 0.593 mmol) and DMF (1 mL) were added after 4 h and the reaction was kept stirring for 1 h. After the completion of reaction, water (10 mL) was added and the product obtained was extracted in CH$_2$Cl$_2$. The organic layer was washed with water (10 mL×3) and brine (10 mL), dried over anhydrous sodium sulfate and the solvent was removed under reduced pressure to obtain the crude product. The residue was further purified by a flash chromatography (SiO$_2$, MeOH in dichloromethane 0 to 5%) to give product 43 (110 mg, 67%) as a white solid. MS (ESI-TOF) for C$_{35}$H$_{67}$N$_3$O$_8$S [M+H]$^+$. Found 690.4659. Calculated 690.4722; [M+Na]$^+$. Found 712.4478. Calculated 712.4541. The global deprotection of compound 43 using TFA resulted in compound 44 in quantitative yield. $^1$H NMR (500 MHz, CDCl$_3$) δ 8.53 (d, J=7.6 Hz, 1H), 5.41 (t, J=5.7 Hz, 1H), 4.72-4.63 (m, 1H), 4.36 (t, J=6.5 Hz, 1H), 4.22 (ddd, J=23.1, 11.5, 5.7 Hz, 2H), 3.89 (dt, J=11.7, 7.2 Hz, 2H), 3.75 (s, 3H), 3.24-2.96 (m, 4H), 2.80 (t, J=5.5 Hz, 2H), 1.46 (m, 2H), 1.25 (s, 26H), 0.88 (t, J=7.0 Hz, 3H). $^{13}$C NMR (126 MHz, CDCl$_3$) δ 170.45, 168.42, 156.76, 63.91, 61.89, 55.41, 52.94, 52.89, 41.32, 33.41, 32.08, 31.40, 29.94, 29.87, 29.86, 29.82, 29.77, 29.52, 26.97, 22.84, 14.28. MS (ESI-TOF) for C$_{26}$H$_{51}$N$_3$O$_6$S [M+H]$^+$. Found 534.3524. Calculated 534.3571.

Synthesis of Compound 45: (2S,5R)-Methyl 5-acetamido-2-(hydroxymethyl)-4,11-dioxo-10-oxa-7-thia-3,12-diazaoctacosan-1-oate

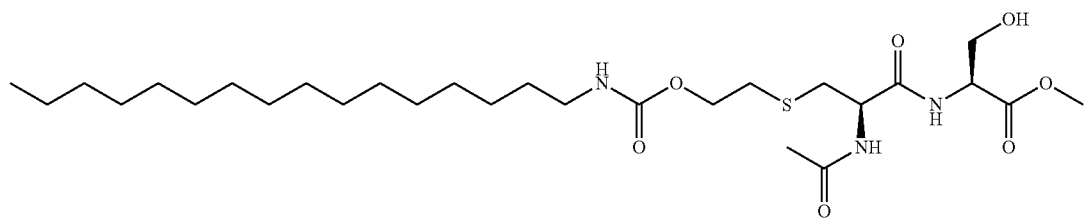 [SMILES: CCCCCCCCCCCCCCCCNC(=O)OCCSC[C@H](NC(C)=O)C(=O)N[C@@H](CO)C(=O)OC]

N-acetylation of compound 44 was carried out similarly as compound 34 to furnish compound 45 as white solid in quantitative yield. $^1$H NMR (500 MHz, CDCl$_3$) δ 7.48 (d, J=7.6 Hz, 1H), 6.66 (d, J=7.1 Hz, 1H), 5.25 (t, J=5.5 Hz, 1H), 4.67 (dd, J=14.1, 7.1 Hz, 1H), 4.63 (dd, J=7.5, 3.6 Hz, 1H), 4.32 (dt, J=12.2, 6.2 Hz, 1H), 4.25 (dt, J=11.7, 6.0 Hz, 1H), 3.97 (q, J=11.4 Hz, 2H), 3.79 (s, 3H), 3.31 (bs, 1H), 3.15 (dd, J=13.4, 6.8 Hz, 2H), 2.96 (qd, J=14.1, 6.6 Hz, 2H), 2.89-2.78 (m, 2H), 2.05 (s, 3H), 1.52-1.44 (m, 2H), 1.34-1.20 (m, 26H), 0.88 (t, J=7.0 Hz, 3H). $^{13}$C NMR (126 MHz, CDCl$_3$) δ 170.83, 170.68, 170.63, 156.79, 64.06, 62.80, 55.23, 52.91, 52.78, 41.31, 34.86, 32.07, 31.87, 29.98, 29.85, 29.81, 29.76, 29.72, 29.51, 29.46, 26.94, 23.29, 22.84, 14.28. MS (ESI-TOF) for $C_{28}H_{53}N_3O_7S$ $[M+H]^+$. Found 576.3594. Calculated 576.3677; $[M+Na]^+$. Found 598.3414. Calculated 598.3496.

Synthesis of Compound 46: (2S,5R)-Methyl 5-((tert-butoxycarbonyl)amino)-2-(tert-butoxymethyl)-4,11-dioxo-12-oxa-7-thia-3,10-diazaoctacosan-1-oate

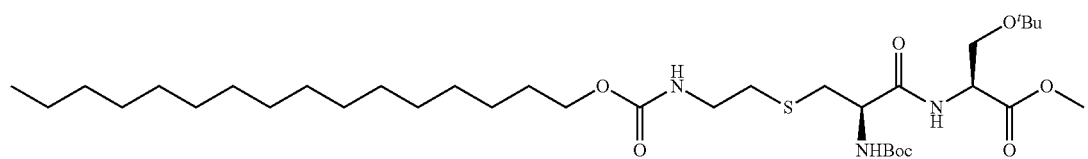 [SMILES: CCCCCCCCCCCCCCCCOC(=O)NCCSC[C@H](NC(=O)OC(C)(C)C)C(=O)N[C@@H](COC(C)(C)C)C(=O)OC]

To a solution of compound 31 (100 mg, 0.238 mmol) in dry $CH_2Cl_2$ (5 mL) were added triethylamine (50 µL, 0.356 mmol) and cetyl chloroformate (117 µL, 0.356 mmol) and the reaction mixture was stirred at room temperature for 30 min. After the completion of reaction, water (10 mL) was added to the reaction and the product obtained was extracted in $CH_2Cl_2$. The organic layer was washed with water (10 mL×2) and brine (10 mL), dried over anhydrous sodium sulfate and the solvent was removed under reduced pressure to obtain the crude product which was purified using column chromatography (50% EtOAc/hexanes) to obtain compound 46 (120 mg, 74%). $^1$H NMR (500 MHz, $CDCl_3$) δ 7.15 (d, J=8.0 Hz, 1H), 5.47 (s, 1H), 5.26 (s, 1H), 4.66 (dt, J=8.2, 3.1 Hz, 1H), 4.32 (s, 1H), 4.03 (t, J=6.6 Hz, 2H), 3.82 (dd, J=9.1, 3.0 Hz, 1H), 3.74 (s, 3H), 3.57 (dd, J=9.1, 3.2 Hz, 1H), 3.39 (d, J=5.4 Hz, 2H), 2.97 (dd, J=13.9, 5.4 Hz, 1H), 2.87 (dd, J=13.8, 6.8 Hz, 1H), 2.80-2.65 (m, 2H), 1.63-1.54 (m, 2H), 1.45 (s, 9H), 1.33-1.23 (m, 26H), 1.14 (s, 9H), 0.87 (t, J=7.0 Hz, 3H). $^{13}$C NMR (126 MHz, $CDCl_3$) δ 170.68, 170.52, 156.92, 155.44, 80.44, 73.73, 65.28, 61.78, 53.79, 53.30, 52.60, 40.15, 34.50, 32.73, 32.06, 29.84, 29.82, 29.80, 29.75, 29.71, 29.50, 29.47, 29.16, 28.44, 27.42, 26.01, 22.83, 14.27. MS (ESI-TOF) for $C_{35}H_{67}N_3O_8S$ $[M+Na]^+$. Found 712.4461. Calculated 712.4547.

Synthesis of Compound 47: (2S,5R)-Methyl 5-amino-2-(hydroxymethyl)-4,11-dioxo-12-oxa-7-thia-3,10-diazaoctacosan-1-oate

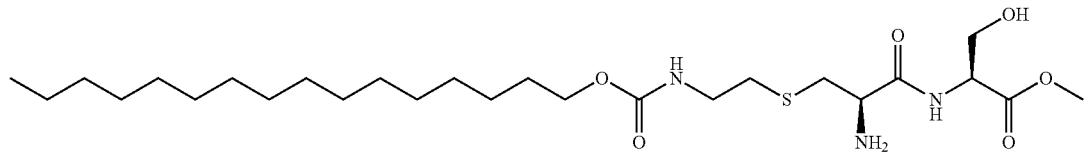 [SMILES: CCCCCCCCCCCCCCCCOC(=O)NCCSC[C@H](N)C(=O)N[C@@H](CO)C(=O)OC]

To compound 46 (110 mg, 0.159 mmol) was added TFA (2 mL). The reaction mixture was stirred at room temperature for 30 min and then dried by blowing nitrogen through the solution. The residue was purified by a flash chromatography (SiO$_2$, MeOH in dichloromethane 0 to 10%) to give product 47 in quantitative yield. $^1$H NMR (500 MHz, DMSO) δ 8.96 (d, J=7.8 Hz, 1H), 8.09 (s, 2H), 7.98 (t, J=5.7 Hz, 1H), 5.26 (t, J=5.4 Hz, 1H), 4.47-4.41 (m, 1H), 4.02 (dd, J=8.9, 4.6 Hz, 1H), 3.79 (dt, J=10.4, 5.1 Hz, 1H), 3.65 (s, 3H), 3.64-3.60 (m, 1H), 3.24 (tt, J=13.7, 7.0 Hz, 2H), 3.03 (dd, J=14.4, 4.5 Hz, 1H), 2.74 (dd, J=14.4, 8.9 Hz, 1H), 2.65 (td, J=6.6, 2.6 Hz, 2H), 2.06 (t, J=7.4 Hz, 2H), 1.51-1.44 (m, 2H), 1.32-1.18 (m, 24H), 0.85 (t, J=6.9 Hz, 3H). $^{13}$C NMR (126 MHz, DMSO) δ 172.57, 170.35, 167.92, 61.06, 54.76, 52.13, 51.68, 38.12, 35.41, 32.82, 31.36, 31.32, 29.08, 29.04, 28.98, 28.84, 28.73, 28.70, 25.28, 22.12, 13.99. MS (ESI-TOF) for C$_{26}$H$_{51}$N$_3$O$_6$S [M+H]$^+$. Found 534.3530. Calculated 534.3571; [M+Na]$^+$. Found 556.3351. Calculated 556.3391.

Synthesis of Compound 48: (2S,5R)-Methyl 5-acetamido-2-(hydroxymethyl)-4,11-dioxo-12-oxa-7-thia-3,10-diazaoctacosan-1-oate

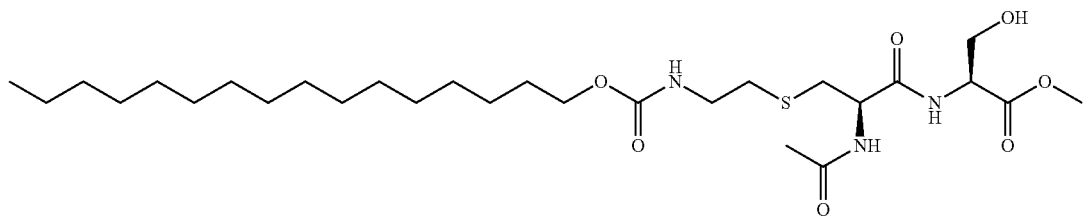 [SMILES: CCCCCCCCCCCCCCCCOC(=O)NCCSC[C@H](NC(C)=O)C(=O)N[C@@H](CO)C(=O)OC]

To a solution of compound 47 (60 mg, 0.093 mmol) in dichloromethane (2 mL) was added pyridine (8 μL, 0.102 mmol) and acetic anhydride (10 μL, 0.102 mmol). The reaction mixture was stirred at room temperature for 30 min and then concentrated. The residue was purified by a flash chromatography (SiO$_2$, MeOH in dichloromethane 0 to 5%) to give product 48. $^1$H NMR (500 MHz, CDCl$_3$) δ 7.56 (d, J=7.4 Hz, 1H), 6.75 (d, J=6.7 Hz, 1H), 5.20 (d, J=5.2 Hz, 1H), 4.74-4.58 (m, 2H), 4.10-3.89 (m, 4H), 3.79 (s, 3H), 3.42 (dd, J=12.5, 6.2 Hz, 3H), 2.94 (d, J=6.1 Hz, 2H), 2.83-2.67 (m, 2H), 2.05 (s, 3H), 1.66-1.53 (m, 2H), 1.36-1.20 (m, 26H), 0.88 (t, J=7.0 Hz, 3H). $^{13}$C NMR (126 MHz, CDCl$_3$) δ 170.87, 170.66, 157.61, 65.69, 62.77, 55.23, 52.90, 52.58, 40.34, 34.48, 32.92, 32.07, 29.85, 29.84, 29.81, 29.75, 29.71, 29.51, 29.45, 29.09, 26.00, 23.27, 22.84, 14.28. MS (ESI-TOF) for C$_{28}$H$_{53}$N$_3$O$_7$S [M+H]$^+$. Found 576.3602. Calculated 576.3677; [M+Na]$^+$. Found 598.3416. Calculated 598.3496.

Synthesis of Compound 49: (2S,5R)-5-((tert-Butoxycarbonyl)amino)-2-(tert-butoxymethyl)-4,11-dioxo-12-oxa-7-thia-3,10-diazaoctacosan-1-oic acid

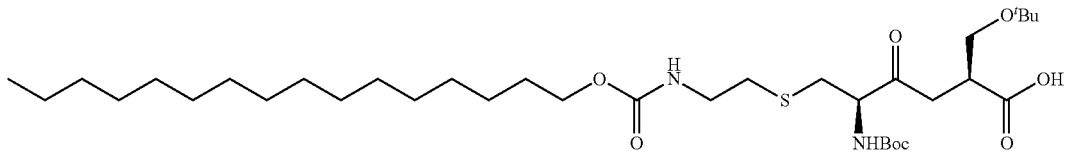 [SMILES: CCCCCCCCCCCCCCCCOC(=O)NCCSC[C@H](NC(=O)OC(C)(C)C)C(=O)C[C@@H](COC(C)(C)C)C(=O)O]

To a solution of compound 46 (100 mg, 0.145 mmol) in dichloroethane (2.5 mL) was added trimethyltin hydroxide (79 mg, 0.435 mmol) and the reaction mixture was heated to reflux for 6 h. After the completion of reaction, the solvent was removed under reduced pressure to obtain the crude product which was purified using column chromatography (50% $CH_2Cl_2$/EtOAc) to obtain compound 49 (72 mg, 73%). $^1$H NMR (500 MHz, $CDCl_3$) δ 7.23 (d, J=6.8 Hz, 1H), 5.55 (d, J=7.3 Hz, 1H), 5.28 (s, 1H), 4.70-4.60 (m, 1H), 4.34 (s, 1H), 4.04 (t, J=6.4 Hz, 2H), 3.90 (dd, J=9.0, 3.5 Hz, 1H), 3.57 (dd, J=8.5, 4.9 Hz, 1H), 3.36 (dd, J=16.2, 10.1 Hz, 2H), 2.93 (qd, J=13.9, 6.2 Hz, 2H), 2.78-2.61 (m, 2H), 1.64-1.54 (m, 2H), 1.45 (s, 9H), 1.35-1.22 (m, 26H), 1.19 (s, 3H), 0.88 (t, J=7.0 Hz, 3H). $^{13}$C NMR (126 MHz, $CDCl_3$) 172.38, 171.01, 157.13, 155.65, 80.69, 74.63, 65.46, 61.26, 53.86, 52.90, 40.17, 34.31, 32.65, 32.07, 29.85, 29.81, 29.76, 29.72, 29.51, 29.48, 29.15, 28.44, 27.45, 26.01, 22.84, 14.28. MS (ESI-TOF) for $C_{34}H_{65}N_3O_8S$ $[M+Na]^+$. Found 698.4272. Calculated 698.4385.

Synthesis of Compound 50: tert-Butyl hexadecyl ((8S,11R)-8-(tert-butoxymethyl)-2-methyl-7,10-dioxo-13-thia-2,6,9-triazapentadecane-11,15-diyl)dicarbamate

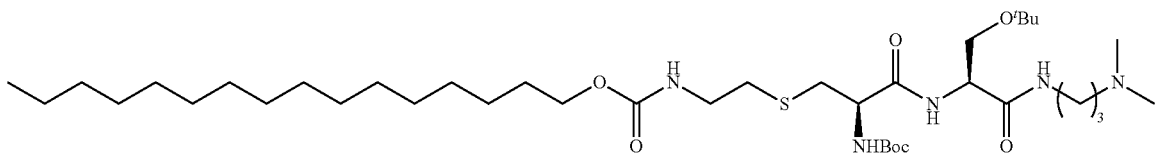

To a solution of acid 49 (563 mg, 0.833 mmol) and $N^1,N^1$-dimethylpropane-1,3-diamine (115 μL, 0.916 mmol) in DMF (5 mL) was added triethylamine (232 μL, 1.67 mmol) and N-hydroxybenzotriazole (HOBt, 56 mg, 0.417 mmol). The reaction mixture was cooled to 0° C. and EDCI (258 mg, 1.67 mmol) was added after 30 min. The resulting mixture was stirred at room temperature for overnight. After the completion of reaction, water (20 mL) was added to the reaction and the product obtained was extracted in EtOAc. The organic layer was washed with water (10 mL×3) and brine (10 mL), dried over anhydrous sodium sulfate and the solvent was removed under reduced pressure to obtain the crude product which was purified using column chromatography (10% MeOH/$CH_2Cl_2$) to obtain compound 10 (530 mg, 84%). MS (ESI-TOF) for $C_{39}H_{77}N_5O_7S$ $[M+H]^+$. Found 760.5486. Calculated 760.5616.

Synthesis of Compound 52: Hexadecyl ((8S,11R)-11-acetamido-8-(hydroxymethyl)-2-methyl-7,10-dioxo-13-thia-2,6,9-triazapentadecan-15-yl)carbamate

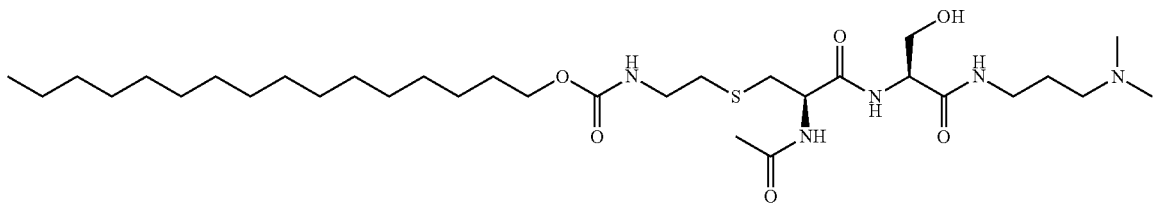 [SMILES: CCCCCCCCCCCCCCCCOC(=O)NCCSC[C@H](NC(C)=O)C(=O)N[C@@H](CO)C(=O)NCCCN(C)C]

To compound 50 (521 mg, 0.685 mmol) was added TFA (5 mL). The reaction mixture was stirred at room temperature for 30 min and then dried by blowing nitrogen through the solution. The crude product was used directly for the next step. To a solution of the crude intermediate in dichloromethane (5 mL) was added pyridine (61 μL, 0.754 mmol) and acetic anhydride (71 μL, 0.754 mmol). The reaction mixture was stirred at room temperature. for 30 min and then concentrated. The residue was purified by a flash chromatography (SiO$_2$, MeOH in dichloromethane 0 to 20%) to give product 52 as a white solid. $^1$H NMR (500 MHz, MeOD) 4.49 (dd, J=8.0, 5.9 Hz, 1H), 4.28 (t, J=5.0 Hz, 1H), 4.02 (t, J=6.6 Hz, 2H), 3.88 (dd, J=11.0, 5.1 Hz, 1H), 3.79 (dd, J=11.0, 5.0 Hz, 1H), 3.40-3.31 (m, 4H), 3.17-3.10 (m, 2H), 3.01 (dd, J=13.7, 5.7 Hz, 1H), 2.89 (s, 6H), 2.83 (dd, J=13.7, 8.1 Hz, 1H), 2.68 (td, J=13.5, 6.6 Hz, 2H), 2.03 (s, 3H), 1.93 (dt, J=13.2, 6.4 Hz, 2H), 1.68-1.55 (m, 2H), 1.42-1.25 (m, 26H), 0.90 (t, J=6.9 Hz, 3H). $^{13}$C NMR (126 MHz, MeOD) δ 173.97, 173.33, 173.25, 159.35, 66.05, 62.44, 57.50, 56.40, 54.92, 43.59, 41.16, 36.65, 33.94, 33.09, 33.02, 30.80, 30.78, 30.72, 30.49, 30.44, 30.23, 27.00, 25.97, 23.75, 22.48, 14.45. MS (ESI-TOF) for C$_{32}$H$_{63}$N$_5$O$_6$S [M+H]$^+$. Found 646.4426. Calculated 646.4572.

Synthesis of Compound 54: Hexadecyl(2-(((R)-2-acetamido-3-(((S)-1-((4-((4-amino-2-butyl-1H-imidazo[4,5-c]quinolin-1-yl)methyl)benzyl)amino)-3-hydroxy-1-oxopropan-2-yl)amino)-3-oxopropyl)thio)ethyl)carbamate dried by blowing nitrogen through the solution. The crude product was used directly for the next step. To a solution of this crude intermediate in dichloromethane (2 mL) was added pyridine (13 μL, 0.168 mmol) and acetic anhydride (15 μL, 0.168 mmol). The reaction mixture was stirred at room temperature for 30 min and then concentrated. The residue was purified by a flash chromatography (SiO$_2$, MeOH in dichloromethane 0 to 10%) to give product 54 as a white solid. $^1$H NMR (500 MHz, MeOD) δ 7.92-7.86 (m, 1H), 7.70 (dd, J=8.4, 0.7 Hz, 1H), 7.58-7.48 (m, 1H), 7.28 (d, J=8.2 Hz, 2H), 7.24 (dd, J=11.4, 4.1 Hz, 1H), 7.03 (d, J=8.2 Hz, 2H), 5.90 (s, 2H), 4.51 (t, J=7.0 Hz, 1H), 4.44-4.36 (m, 3H), 3.98 (t, J=6.6 Hz, 2H), 3.85 (dd, J=11.1, 5.3 Hz, 1H), 3.77 (dd, J=11.1, 5.0 Hz, 1H), 3.19 (t, J=6.9 Hz, 2H), 3.02-2.95 (m, 2H), 2.90 (dd, J=13.7, 6.4 Hz, 1H), 2.75 (dd, J=13.7, 7.7 Hz, 1H), 2.56 (td, J=6.7, 3.1 Hz, 2H), 1.97 (s, 3H), 1.83 (dt, J=15.3, 7.6 Hz, 2H), 1.64-1.52 (m, 2H), 1.46 (dq, J=14.8, 7.4 Hz, 2H), 1.37-1.21 (m, 26H), 0.95 (t, J=7.4 Hz, 3H), 0.89 (t, J=7.0 Hz, 3H). $^{13}$C NMR (126 MHz, MeOD) δ 173.57, 172.98, 172.14, 159.21, 157.56, 151.60, 139.70, 136.57, 135.62, 129.72, 129.30, 126.83, 126.46, 124.93, 123.02, 122.29, 115.05, 66.01, 62.70, 57.20, 54.48, 49.71, 43.56, 41.16, 34.14, 33.09, 32.83, 30.81, 30.79, 30.77, 30.70, 30.69, 30.62, 30.49, 30.41, 30.20, 27.82, 26.97, 23.75, 23.41, 22.41, 14.45, 14.13. MS (ESI-TOF) for C$_{49}$H$_{74}$N$_8$O$_6$S [M+H]$^+$. Found 903.5386. Calculated 903.5525; [M+Na]$^+$. Found 925.5181. Calculated 925.5344.

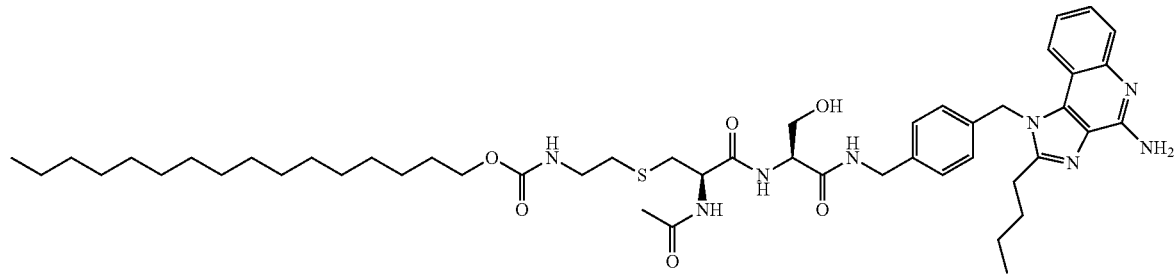 [SMILES: CCCCCCCCCCCCCCCCOC(=O)NCCSC[C@H](NC(C)=O)C(=O)N[C@@H](CO)C(=O)NCc1ccc(Cn2c(CCCC)nc3c(N)nc4ccccc4c32)cc1]

To a solution of acid 49 (100 mg, 0.148 mmol) and 1-(4-(aminomethyl)benzyl)-2-butyl-1H-imidazo[4,5-c]quinolin-4-amine dihydrochloride salt 53 (126 mg, 0.294 mmol) in DMF (4 mL) was added triethylamine (622 μL, 0.444 mmol) and N-hydroxybenzotriazole (10 mg, 0.074 mmol). The reaction mixture was cooled to 0° C. and EDCI (34 mg, 0.222 mmol) was added after 30 min. The resulting mixture was stirred at room temperature for overnight. After the completion of reaction, water (20 mL) was added and the product obtained was extracted in EtOAc. The organic layer was washed with water (10 mL×3) and brine (10 mL), dried over anhydrous sodium sulfate and the solvent was removed under reduced pressure to obtain the crude product. The crude product was used directly for the next step. TFA (2 mL) was added to this crude product and the reaction mixture was stirred at room temperature for 30 min and then Synthesis of Compound 59:
(R)-3-hydroxytetradecanoic acid

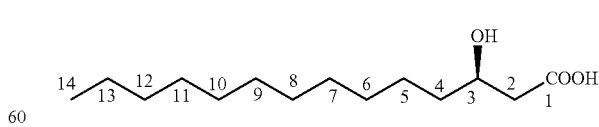

To a solution of (R)-tert-butyl 3-hydroxytetradecanoate 58 (169 mg, 0.563 mmol) in dichloromethane (1 mL) was added triethylsilane (0.1 mL) and TFA (1 mL). The reaction mixture was stirred at room temperature for 45 min then dried by blowing air through the solution. The crude product was purified by a flash chromatography (SiO$_2$, ethyl acetate in hexanes 0 to 50%) to give acid 59 (120 mg, 87%) as a white solid. R$_f$=0.08 (Hexanes/EtOAc 1:1). $^1$H NMR (500 MHz, CDCl$_3$) δ 4.07-3.99 (m, 1H, CH-3), 2.58 (ABqd, 1H, J$_{AB}$=16.6 Hz, J$_{2,3}$=3.0 Hz, CH$_2$-2a), 2.48 (ABqd, 1H, J$_{AB}$=16.6 Hz, J$_{2,3}$=9.0 Hz, CH$_2$-2b), 1.60-1.39 (m, 2H, CH$_2$-4), 1.36-1.20 (m, 18H, CH$_2$-5 to 13), 0.88 (t, 3H, J$_{14,13}$=6.9 Hz, CH$_3$-14). $^{13}$C NMR (126 MHz, CDCl$_3$) δ 177.3, 68.0, 40.9, 36.5, 31.9, 29.6 (4C), 29.5, 29.4, 25.4, 22.7, 14.1. MS (ESI-TOF) for C$_{14}$H$_{28}$O$_3$ [M+Na]$^+$. Found 267.1949. Calculated 267.1931.

Synthesis of Compound 60:
(R)-3-(formyloxy)tetradecanoic acid

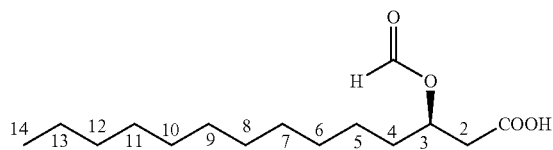 [SMILES: CCCCCCCCCCC[C@H](CC(=O)O)OC=O]

(R)-tert-butyl 3-hydroxytetradecanoate 58 (66 mg, 0.22 mmol) was added to formic acid (2 mL). The reaction mixture was stirred at room temperature for 2 h then concentrated. The crude product was purified by a flash chromatography (SiO$_2$, ethyl acetate in hexanes 0 to 30%) to give acid 60 (39.6 mg, 66%) as a colorless oil. R$_f$=0.14 (Hexanes/EtOAc 1:1). $^1$H NMR (500 MHz, CDCl$_3$) δ 8.06 (s, 1H, formyl), 5.43-5.21 (m, 1H, CH-3), 2.70 (ABqd, 1H, J$_{AB}$=16.2 Hz, J$_{2,3}$=7.7 Hz, CH$_2$-2a), 2.63 (ABqd, 1H, J$_{AB}$=16.2 Hz, J$_{2,3}$=5.0 Hz, CH$_2$-2b), 1.76-1.56 (m, 2H, CH$_2$-4), 1.40-1.16 (m, 18H, CH$_2$-5 to 13), 0.88 (t, 3H, J$_{14,13}$=6.9 Hz, CH$_3$-14). $^{13}$C NMR (126 MHz, CDCl$_3$) δ 175.4, 160.5, 70.2, 38.6, 33.9, 31.9, 29.6, 29.5, 29.4, 29.3, 25.0, 22.7, 14.1. MS (ESI-TOF) for C$_{18}$H$_{28}$O$_4$ [M+Na]$^+$. Found 295.1899. Calculated 295.1880.

Synthesis of Compound 66: Methyl (L-(thio-((R)-ethyl 3-hydroxytetradecanoate)-N-(tert-butoxycarbonyl))cysteyl-L-(3-O-(tert-butyl))serate To a solution of acid 59 (81 mg, 0.331 mmol) and dipeptide 4 (496 mg, 1.17 mmol) in dichloromethane (5 mL) was added 4-methylmorpholine (73 μL, 0.664 mmol), DMAP (7 mg, 0.057 mmol) and EDCI (127 mg, 0.664 mmol). The reaction mixture was stirred at room temperature overnight, then washed with 1N HCl and saturated aqueous NaCl solution, dried over Na$_2$SO$_4$, filtered and concentrated. The residue was purified by a flash chromatography (SiO$_2$, ethyl acetate in hexanes 0 to 30%) to give 61 (135 mg, 63%) as a colorless oil. R$_f$=0.35 (Hexanes/EtOAc 1:1). $^1$H NMR (500 MHz, CDCl$_3$) δ 7.18 (d, 1H, J$_{3,2}$=7.3 Hz, NH-3), 5.45 (brs, 1H, NHBoc), 4.67 (dt, 1H, J$_{2,CH2OtBu}$=8.2 Hz, J$_{2,NH}$=3.1 Hz, CH-2), 4.41-4.24 (m, 3H, CH-5 and CH$_2$-9), 4.07-43.97 (m, 1H, CH-13), 3.82 (ABqd, 1H, J$_{AB}$=9.1 Hz, J$_{CH2OtBu,2}$=3.0 Hz, CH$_2$OtBu), 3.74 (s, 3H, CH$_3$-methyl ester), 3.58 (ABqd, 1H, J$_{AB}$=9.1 Hz, J$_{CH2OtBu,2}$=3.3 Hz, CH$_2$OtBu), 3.02-2.91 (m, 2H, CH$_2$-6), 2.91-2.79 (m, 2H, CH$_2$-8), 2.53 (ABqd, 1H, J$_{AB}$=16.1 Hz, J$_{12a,13}$=3.0 Hz, CH$_2$-12a), 2.44 (ABqd, 1H, J$_{AB}$=16.1 Hz, J$_{12b,13}$=9.2 Hz, CH$_2$-12b), 1.59-1.48 (m, 2H, CH$_2$-14), 1.46 (s, 9H, tBu-Boc), 1.44-1.20 (m, 18H, CH$_2$-15 to 23), 1.14 (s, 9H, tBu), 0.88 (t, 3H, J$_{24,23}$=6.9 Hz, CH$_3$-24). $^{13}$C NMR (126 MHz, CDCl$_3$) δ 172.8, 170.5, 170.4, 68.1, 63.5, 61.7, 53.8, 53.2, 52.5, 41.6, 36.7, 34.7, 31.9, 31.8, 30.9, 29.7 (2C), 29.6 (3C), 29.4, 29.3, 28.3, 27.3 (2C), 25.5, 22.7, 14.1. MS (ESI-TOF) for C$_{32}$H$_{60}$N$_2$O$_9$S [M+H]$^+$. Found 649.4124. Calculated 649.4092; [M+Na]$^+$. Found 671.3948. Calculated 671.3912.

Synthesis of Compound 62: Methyl (L-(thio-((R)-ethyl 3-(formyloxy)tetradecanoate)-N-(tert-butoxycarbonyl))cysteyl-L-(3-O-(tert-butyl))serate

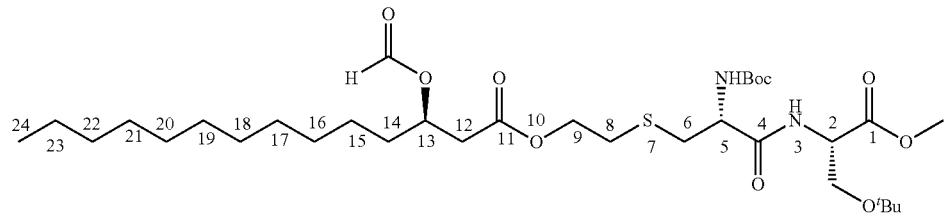

To a solution of acid 60 (39 mg, 0.143 mmol) and dipeptide 4 (60 mg, 0.142 mmol) in dichloromethane (2 mL) was added 4-methylmorpholine (32 μL, 0.291 mmol), catalytic amount of DMAP and EDCI (55 mg, 0.287 mmol). The reaction mixture was stirred at room temperature overnight, then washed with 1N HCl and saturated aqueous NaCl solution, dried over Na$_2$SO$_4$, filtered and concentrated. The residue was purified by a flash chromatography (SiO$_2$, ethyl acetate in hexanes 0 to 30%) to give 62 (15.6 mg, 16%) as a colorless oil. R$_f$=0.24 (Hexanes/EtOAc 7:3). $^1$H NMR (500 MHz, CDCl$_3$) δ 8.07 (s, 1H, formyl), 7.15 (d, 1H, J$_{3,2}$=8.2 Hz, NH-3), 5.44 (br, 1H, NHBoc), 5.39-5.29 (m,

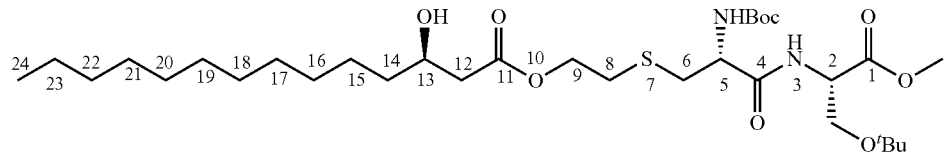 [SMILES: CCCCCCCCCCC[C@@H](O)CC(=O)OCCSC[C@H](NC(=O)OC(C)(C)C)C(=O)N[C@@H](COC(C)(C)C)C(=O)OC]

1H, CH-13), 4.66 (dt, 1H, $J_{2,NH}$=8.2 Hz, $J_{2,CH2OtBu}$=3.1 Hz, CH-2), 4.39-4.30 (m, 1H, CH-5), 4.31-4.19 (m, 2H, CH$_2$-9), 3.83 (ABqd, 1H, $J_{AB}$=9.1 Hz, $J_{CH2OtBu,2}$=2.9 Hz, CH$_2$OtBu), 3.74 (s, 3H, CH$_3$-methylester), 3.57 (ABqd, 1H, $J_{AB}$=9.1 Hz, $J_{CH2OtBu,2}$=3.2 Hz, CH$_2$OtBu), 3.00 (ABqd, 1H, $J_{AB}$=13.9 Hz, $J_{6a,5}$=5.6 Hz, CH$_2$-6a), 2.92 (ABqd, 1H, $J_{AB}$=13.9 Hz, $J_{6b,5}$=6.7 Hz, CH$_2$-6b), 2.88-2.74 (m, 2H, CH$_2$-8), 2.66 (ABqd, 1H, $J_{AB}$=15.8 Hz, $J_{12a,13}$=7.9 Hz, CH$_2$-12a), 2.61 (ABqd, 1H, $J_{AB}$=15.8 Hz, $J_{12b,13}$=4.9 Hz, CH$_2$-12b), 1.74-1.57 (m, 2H, CH$_2$-14), 1.46 (s, 9H, tBu), 1.39-1.19 (m, 18H, CH$_2$-15 to 23), 1.14 (s, 9H, tBu-Boc), 0.88 (t, 3H, $J_{24,23}$=6.9 Hz, CH$_3$-24). $^{13}$C NMR (126 MHz, CDCl$_3$) δ 170.5, 170.3, 170.1, 160.7, 73.5, 70.5, 63.5, 61.7, 61.6, 53.7, 53.2, 52.4, 39.1, 34.8, 34.0, 31.9, 30.8, 29.7, 29.6, 29.6, 29.5, 29.5, 29.3, 29.3, 28.3, 27.3, 25.1, 22.7, 14.1. MS (ESI-TOF) for C$_{33}$H$_{60}$N$_2$O$_{10}$S [M+H]$^+$. Found 677.4095. Calculated 677.4041; [M+Na]$^+$. Found 699.3913. Calculated 699.3861.

General Procedure to Synthesize Compounds 67-74:

To a solution of alcohol 61 (0.10 mmol) in dichloromethane (1 mL) was added acyl chloride (0.16 mmol), triethylamine (56 μL, 0.40 mmol) and catalytic amount of DMAP. The reaction solution was stirred at room temperature for 3 h, then quenched with MeOH and concentrated. The crude product was purified by a flash chromatography to give 67-74 as a colorless oil.

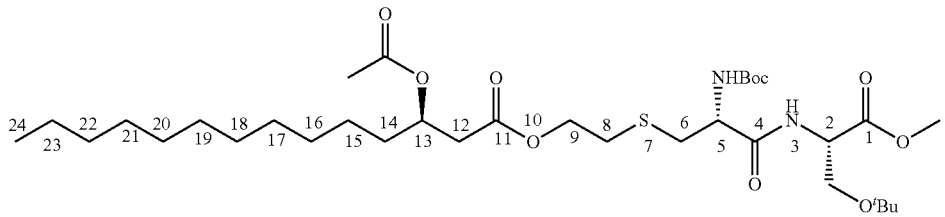 [SMILES: CCCCCCCCCCC[C@H](CC(=O)OCCSC[C@H](NC(=O)OC(C)(C)C)C(=O)N[C@@H](COC(C)(C)C)C(=O)OC)OC=O]

67

67: $^1$H NMR (500 MHz, CDCl$_3$) δ 7.13 (d, 1H, $J_{3,2}$=8.0 Hz, NH-3), 5.53-5.41 (br, 1H, NHBoc), 5.26-5.16 (m, 1H, CH-13), 4.66 (dt, 1H, $J_{2,NH}$=8.2 Hz, $J_{2,CH2OtBu}$=3.1 Hz, CH-2), 4.39-4.29 (m, 1H, CH-5), 4.29-4.17 (m, 2H, CH$_2$-9), 3.83 (ABqd, 1H, $J_{AB}$=9.1 Hz, $J_{CH2OtBu,2}$=3.0 Hz, CH$_2$OtBu), 3.74 (s, 3H, CH$_3$-methylester), 3.57 (ABqd, 1H, $J_{AB}$=9.1 Hz, $J_{CH2OtBu,2}$=3.2 Hz, CH$_2$OtBu), 3.01 (ABqd, 1H, $J_{AB}$=13.9 Hz, $J_{6a,5}$=5.5 Hz, CH$_2$-6a), 2.92 (ABqd, 1H, $J_{AB}$=13.9 Hz, $J_{6b,5}$=6.7 Hz, CH$_2$-6b), 2.88-2.77 (m, 2H, CH$_2$-8), 2.65-2.52 (m, 2H, CH$_2$-12), 2.04 (s, 3H, acetyl), 1.66-1.53 (m, 2H, CH$_2$-14), 1.46 (s, 9H, tBu), 1.35-1.19 (m, 18H, CH$_2$-15 to 23), 1.14 (s, 9H, tBu-Boc), 0.88 (t, 3H, $J_{24,23}$=6.9 Hz, CH$_3$-24). $^{13}$C NMR (126 MHz, CDCl$_3$) δ 170.5, 170.4, 170.3, 170.3, 73.5, 70.5, 63.4, 61.6, 53.8, 53.2, 52.4, 39.1, 34.7, 34.1, 31.9, 30.8, 29.6 (3C), 29.5, 29.4, 29.3 (2C), 28.3, 27.3, 25.1, 22.7, 21.2, 14.1. MS (ESI-TOF) for C$_{34}$H$_{62}$N$_2$O$_{10}$S [M+Na]$^+$. Found 713.3923. Calculated 713.4017.

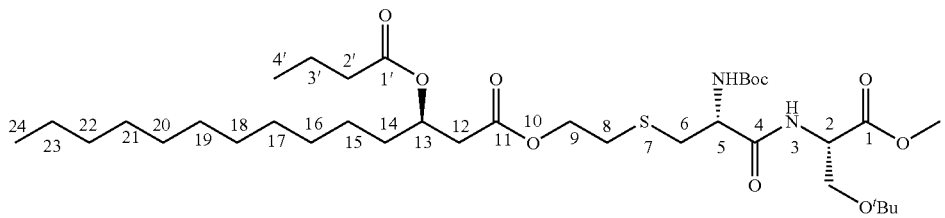

68

68: $^1$H NMR (500 MHz, CDCl$_3$) δ 7.13 (d, 1H, J$_{3,2}$=8.1 Hz, NH-3), 5.51-5.41 (br, 1H, NHBoc), 5.22 (m, 1H, CH-13), 4.66 (dt, 1H, J$_{2,NH}$=8.1 Hz, J$_{2,CH2OtBu}$=3.1 Hz, CH-2), 4.40-4.29 (m, 1H, CH-5), 4.28-4.18 (m, 2H, CH$_2$-9), 3.83 (ABqd, 1H, J$_{AB}$=9.1 Hz, J$_{CH2OtBu,2}$=3.0 Hz, CH$_2$OtBu), 3.74 (s, 3H, CH$_3$-methylester), 3.57 (ABqd, 1H, J$_{AB}$=9.1 Hz, J$_{CH2OtBu,2}$=3.2 Hz, CH$_2$OtBu), 3.01 (ABqd, 1H, J$_{AB}$=13.9 Hz, J$_{6a,5}$=5.6 Hz, CH$_2$-6a), 2.92 (ABqd, 1H, J$_{AB}$=13.9 Hz, J$_{6b,5}$=6.7 Hz, CH$_2$-6b), 2.88-2.74 (m, 2H, CH$_2$-8), 2.60 (ABqd, 1H, J$_{AB}$=15.5 Hz, J$_{12a,13}$=7.4 Hz, CH$_2$-12a), 2.56 (ABqd, 1H, J$_{AB}$=15.5 Hz, J$_{12b,13}$=5.4 Hz, CH$_2$-12b), 2.26 (t, 2H, J$_{2',3'}$=7.4 Hz, CH$_2$-2'), 1.69-1.55 (m, 4H, CH$_2$-14 and CH$_2$-3'), 1.46 (s, 9H, tBu), 1.38-1.19 (m, 18H, CH$_2$-15 to 23), 1.14 (s, 9H, tBu-Boc), 0.94 (t, 3H, J$_{4',3'}$=7.4 Hz, CH$_3$-4'), 0.88 (t, 3H, J$_{24,23}$=6.9 Hz, CH$_3$-24). $^{13}$C NMR (126 MHz, CDCl$_3$) δ 173.0, 170.4, 170.3, 170.3, 155.2, 80.3, 73.5, 61.6, 53.7, 53.2, 52.4, 39.2, 36.4, 34.7, 34.1, 31.9, 30.8, 29.6, 29.5 (2C), 29.4, 29.3, 28.3, 27.3, 25.1, 22.7, 18.5, 14.1, 13.7. MS (ESI-TOF) for C$_{36}$H$_{66}$N$_2$O$_{10}$S [M+H]$^+$. Found 719.4551. Calculated 719.4511; [M+Na]$^+$. Found 741.4373. Calculated 741.4330.

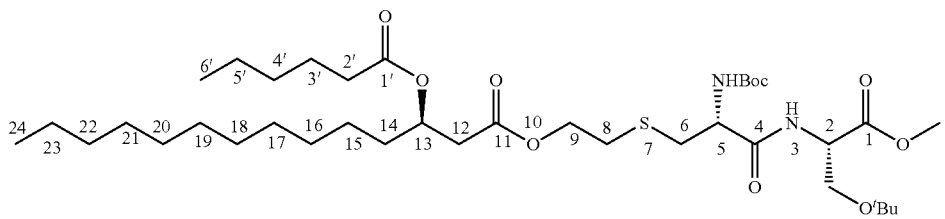

69

69: $^1$H NMR (500 MHz, CDCl$_3$) δ 7.13 (d, 1H, J$_{3,2}$=8.0 Hz, NH-3), 5.51-5.41 (br, 1H, NHBoc), 5.26-5.17 (m, 1H, CH-13), 4.66 (dt, 1H, J$_{2,NH}$=8.2 Hz, J$_{2,CH2OtBu}$=2.9 Hz, CH-2), 4.38-4.28 (m, 1H, CH-5), 4.28-4.17 (m, 2H, CH$_2$-9), 3.83 (ABqd, 1H, J$_{AB}$=9.1 Hz, J$_{CH2OtBu,2}$=2.9 Hz, CH$_2$OtBu), 3.74 (s, 3H, CH$_3$-methylester), 3.58 (ABqd, 1H, J$_{AB}$=9.1 Hz, J$_{CH2OtBu,2}$=3.1 Hz, CH$_2$OtBu), 3.01 (ABqd, 1H, J$_{AB}$=13.9 Hz, J$_{6a,5}$=5.5 Hz, CH$_2$-6a), 2.92 (ABqd, 1H, J$_{AB}$=13.9 Hz, J$_{6b,5}$=6.6 Hz, CH$_2$-6b), 2.88-2.75 (m, 2H, CH$_2$-8), 2.60 (ABqd, 1H, J$_{AB}$=15.5 Hz, J$_{12a,13}$=7.4 Hz, CH$_2$-12a), 2.55 (ABqd, 1H, J$_{AB}$=15.5 Hz, J$_{12b,13}$=5.4 Hz, CH$_2$-12b), 2.27 (t, 2H, J$_{2',3'}$=7.5 Hz, CH$_2$-2'), 1.64-1.56 (m, 4H, CH$_2$-14 and CH$_2$-3'), 1.46 (s, 9H, tBu), 1.38-1.19 (m, 22H, CH$_2$-15 to 23 and CH$_2$-4',5'), 1.14 (s, 9H, tBu-Boc), 0.92-0.85 (m, 6H, CH$_3$-4' and CH$_3$-24). $^{13}$C NMR (126 MHz, CDCl$_3$) δ 173.2, 170.4, 170.3, 170.3, 155.2, 80.3, 70.2, 63.4, 61.6, 53.2, 52.4, 39.2, 34.7, 34.5, 34.1, 31.9, 31.3, 30.8, 29.6 (2C), 29.5 (2C), 29.4, 29.3, 28.3, 27.3, 25.1, 24.7, 22.7, 22.3, 14.1, 13.9. MS (ESI-TOF) for C$_{38}$H$_{70}$N$_2$O$_{10}$S [M+H]$^+$. Found 747.4864. Calculated 747.4824; [M+Na]$^+$. Found 769.4684. Calculated 769.4643.

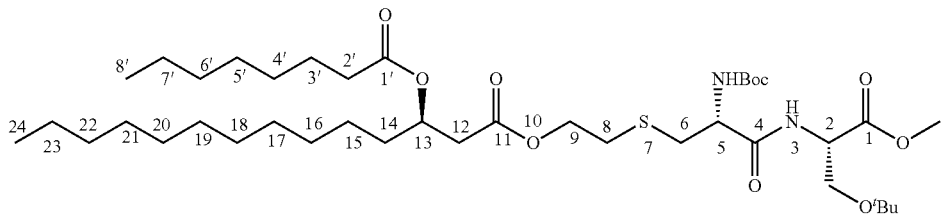

70

70: $^1$H NMR (500 MHz, CDCl$_3$) δ 7.13 (d, 1H, J$_{3,2}$=8.1 Hz, NH-3), 5.52-5.38 (br, 1H, NHBoc), 5.25-5.16 (m, 1H, CH-13), 4.66 (dt, 1H, J$_{2,NH}$=8.1 Hz, J$_{2,CH2OtBu}$=3.0 Hz, CH-2), 4.39-4.29 (m, 1H, CH-5), 4.29-4.18 (m, 2H, CH$_2$-9), 3.83 (ABqd, 1H, J$_{AB}$=9.1 Hz, J$_{CH2OtBu,2}$=3.0 Hz, CH$_2$OtBu), 3.74 (s, 3H, CH$_3$-methylester), 3.57 (ABqd, 1H, J$_{AB}$=9.1 Hz, J$_{CH2OtBu,2}$=3.2 Hz, CH$_2$OtBu), 3.01 (ABqd, 1H, J$_{AB}$=13.9 Hz, J$_{6a,5}$=5.5 Hz, CH$_2$-6a), 2.92 (ABqd, 1H, J$_{AB}$=13.9 Hz, J$_{6b,5}$=6.6 Hz, CH$_2$-6b), 2.88-2.75 (m, 2H, CH$_2$-8), 2.60 (ABqd, 1H, J$_{AB}$=15.5 Hz, J$_{12a,13}$=7.4 Hz, CH$_2$-12a), 2.55 (ABqd, 1H, J$_{AB}$=15.5 Hz, J$_{12b,13}$=5.4 Hz, CH$_2$-12b), 2.27 (t, 2H, J$_{2',3'}$=7.5 Hz, CH$_2$-2'), 1.64-1.56 (m, 4H, CH$_2$-14 and CH$_2$-3'), 1.46 (s, 9H, tBu), 1.38-1.19 (m, 26H, CH$_2$-15 to 23 and CH$_2$-4' to 7'), 1.14 (s, 9H, tBu-Boc), 0.92-0.84 (m, 6H, CH$_3$-8' and CH$_3$-24). $^{13}$C NMR (126 MHz, CDCl$_3$) δ 173.2, 170.4, 170.3, 170.3, 155.2, 80.3, 73.5, 70.2, 63.4, 61.7, 60.4, 53.7, 53.2, 52.4, 39.2, 34.7, 34.5, 34.1, 31.9, 31.7, 30.8, 29.7, 29.6 (2C), 29.5, 29.4 (2C), 29.1, 29.0, 28.3, 27.3, 25.1, 25.0, 22.7, 22.6, 14.1, 14.1. MS (ESI-TOF) for C$_{40}$H$_{74}$N$_2$O$_{10}$S [M+H]$^+$. Found 775.5175. Calculated 775.5137; [M+Na]$^+$. Found 797.4982. Calculated 797.4956.

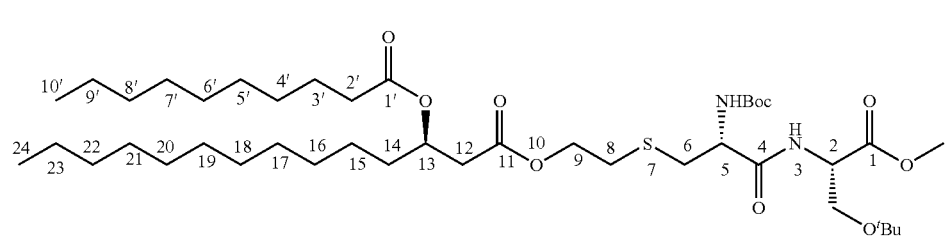

71

71: $^1$H NMR (500 MHz, CDCl$_3$) δ 7.14 (d, 1H, J$_{3,2}$=8.1 Hz, NH-3), 5.53-5.37 (br, 1H, NHBoc), 5.27-5.16 (m, 1H, CH-13), 4.66 (dt, 1H, J$_{2,NH}$=8.2 Hz, J$_{2,CH2OtBu}$=3.1 Hz, CH-2), 4.39-4.29 (m, 1H, CH-5), 4.29-4.18 (m, 2H, CH$_2$-9), 3.83 (ABqd, 1H, J$_{AB}$=9.1 Hz, J$_{CH2OtBu,2}$=3.0 Hz, CH$_2$OtBu), 3.74 (s, 3H, CH$_3$-methylester), 3.57 (ABqd, 1H, J$_{AB}$=9.1 Hz, J$_{CH2OtBu,2}$=3.2 Hz, CH$_2$OtBu), 3.01 (ABqd, 1H, J$_{AB}$=13.9 Hz, J$_{6a,5}$=5.6 Hz, CH$_2$-6a), 2.92 (ABqd, 1H, J$_{AB}$=13.9 Hz, J$_{6b,5}$=6.7 Hz, CH$_2$-6b), 2.88-2.75 (m, 2H, CH$_2$-8), 2.60 (ABqd, 1H, J$_{AB}$=15.5 Hz, J$_{12a,13}$=7.4 Hz, CH$_2$-12a), 2.55 (ABqd, 1H, J$_{AB}$=15.5 Hz, J$_{12b,13}$=5.5 Hz, CH$_2$-12b), 2.27 (t, 2H, J$_{2',3'}$=7.6 Hz, CH$_2$-2'), 1.69-1.52 (m, 4H, CH$_2$-14 and CH$_2$-3'), 1.46 (s, 9H, tBu), 1.35-1.20 (m, 30H, CH$_2$-15 to 23 and CH$_2$-4' to 9'), 1.14 (s, 9H, tBu-Boc), 0.90-0.85 (m, 6H, CH$_3$-10' and CH$_3$-24). $^{13}$C NMR (126 MHz, CDCl$_3$) δ 173.2, 170.4 (2C), 170.3, 155.2, 80.3, 73.5, 70.2, 63.4, 61.7, 53.7, 53.2, 52.4, 39.2, 34.7, 34.5, 34.1, 31.9 (2C), 30.8, 29.7, 29.7, 29.6, 29.6, 29.6, 29.5 (2 C), 29.4 (4C), 29.3 (3C), 29.2 (2C), 29.1, 28.3, 27.3, 25.1, 25.0, 24.8, 22.7, 22.7, 14.1. MS (ESI-TOF) for C$_{42}$H$_{78}$N$_2$O$_{10}$S [M+H]$^+$. Found 803.5485. Calculated 803.5450; [M+Na]$^+$. Found 825.5302. Calculated 825.5269.

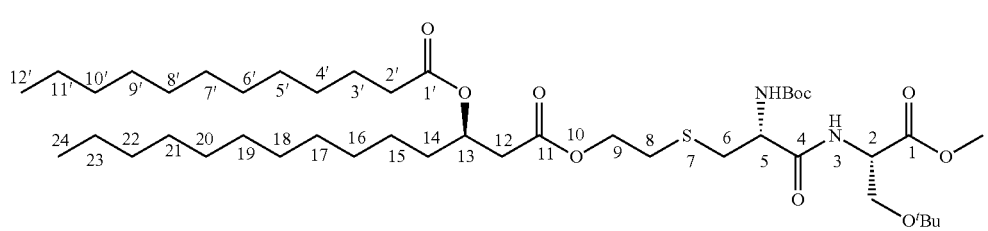

72

72: $^1$H NMR (500 MHz, CDCl$_3$) δ 7.14 (d, 1H, $J_{3,2}$=8.1 Hz, NH-3), 5.55-5.37 (br, 1H, NHBoc), 5.26-5.15 (m, 1H, CH-13), 4.66 (dt, 1H, $J_{2,NH}$=8.2 Hz, $J_{2,CH2OtBu}$=3.1 Hz, CH-2), 4.39-4.28 (m, 1H, CH-5), 4.29-4.17 (m, 2H, CH$_2$-9), 3.83 (ABqd, 1H, $J_{AB}$=9.1 Hz, $J_{CH2OtBu,2}$=3.0 Hz, CH$_2$OtBu), 3.74 (s, 3H, CH$_3$-methylester), 3.58 (ABqd, 1H, $J_{AB}$=9.1 Hz, $J_{CH2OtBu,2}$=3.2 Hz, CH$_2$OtBu), 3.01 (ABqd, 1H, $J_{AB}$=13.9 Hz, $J_{6a,5}$=5.6 Hz, CH$_2$-6a), 2.92 (ABqd, 1H, $J_{AB}$=13.9 Hz, $J_{6b,5}$=6.6 Hz, CH$_2$-6b), 2.88-2.75 (m, 2H, CH$_2$-8), 2.60 (ABqd, 1H, $J_{AB}$=15.5 Hz, =7.5 Hz, CH$_2$-12a), 2.55 (ABqd, 1H, $J_{AB}$=15.5 Hz, $J_{12b,13}$=5.4 Hz, CH$_2$-12b), 2.27 (t, 2H, $J_{2',3'}$=7.6 Hz, CH$_2$-2'), 1.64-1.54 (m, 4H, CH$_2$-14 and CH$_2$-3'), 1.46 (s, 9H, tBu), 1.33-1.21 (m, 34H, CH$_2$-15 to 23 and CH$_2$-4' to 11'), 1.14 (s, 9H, tBu-Boc), 0.88 (t, 6H, $J_{12',11'}$=$J_{24,23}$=6.9 Hz, CH$_3$-12' and CH$_3$-24). $^{13}$C NMR (126 MHz, CDCl$_3$) δ 173.2, 170.4 (2C), 170.3, 155.2, 80.3, 73.5, 70.2, 63.4, 61.7, 53.7, 53.2, 52.4, 39.2, 34.7, 34.5, 34.1, 33.7, 31.9, 30.8, 29.7 (2C), 29.6 (4 C), 29.5 (2C), 29.4 (3C), 29.3 (2C), 29.2, 29.1, 28.3, 27.3, 25.1, 25.0, 24.8, 22.7, 14.1. MS (ESI-TOF) for C$_{44}$H$_{82}$N$_2$O$_{10}$S [M+H]$^+$. Found 831.5806. Calculated 831.5763; [M+Na]$^+$. Found 853.5625. Calculated 853.5582.

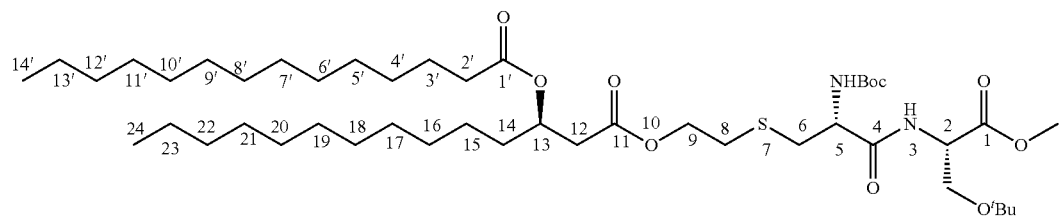

73

73: $^1$H NMR (500 MHz, CDCl$_3$) δ 7.14 (d, 1H, $J_{3,2}$=8.2 Hz, NH-3), 5.54-5.40 (br, 1H, NHBoc), 5.26-5.16 (m, 1H, CH-13), 4.66 (dt, 1H, $J_{2,NH}$=8.2 Hz, $J_{2,CH2OtBu}$=3.1 Hz, CH-2), 4.38-4.28 (m, 1H, CH-5), 4.28-4.18 (m, 2H, CH$_2$-9), 3.83 (ABqd, 1H, $J_{AB}$=9.1 Hz, $J_{CH2OtBu,2}$=3.0 Hz, CH$_2$OtBu), 3.74 (s, 3H, CH$_3$-methylester), 3.58 (ABqd, 1H, $J_{AB}$=9.1 Hz, $J_{CH2OtBu,2}$=3.2 Hz, CH$_2$OtBu), 3.01 (ABqd, 1H, $J_{AB}$=13.9 Hz, $J_{6a,5}$=5.6 Hz, CH$_2$-6a), 2.92 (ABqd, 1H, $J_{AB}$=13.9 Hz, $J_{6b,5}$=6.7 Hz, CH$_2$-6b), 2.88-2.74 (m, 2H, CH$_2$-8), 2.60 (ABqd, 1H, $J_{AB}$=15.5 Hz, $J_{12a,13}$=7.5 Hz, CH$_2$-12a), 2.55 (ABqd, 1H, $J_{AB}$=15.5 Hz, $J_{12b,13}$=5.5 Hz, CH$_2$-12b), 2.27 (t, 2H, $J_{2',3'}$=7.5 Hz, CH$_2$-2'), 1.63-1.56 (m, 4H, CH$_2$-14 and CH$_2$-3'), 1.46 (s, 9H, tBu), 1.33-1.21 (m, 38H, CH$_2$-15 to 23 and CH$_2$-4' to 13'), 1.14 (s, 9H, tBu-Boc), 0.88 (t, 6H, $J_{14',13'}$=$J_{24,23}$=6.9 Hz, CH$_3$-14' and CH$_3$-24). $^{13}$C NMR (126 MHz, CDCl$_3$) δ 173.2, 170.4 (2C), 170.3, 155.2, 80.3, 73.5, 70.2, 63.4, 61.7, 53.7, 53.2, 52.4, 39.2, 34.7, 34.5, 34.1, 31.9, 30.8, 29.7 (3C), 29.6 (3C), 29.5 (2C), 29.4 (3C), 29.3 (2C), 29.2, 29.1, 28.3, 27.3, 25.1, 25.0, 24.8, 22.7, 14.1. MS (ESI-TOF) for C$_{46}$H$_{86}$N$_2$O$_{10}$S [M+H]$^+$. Found 859.6129. Calculated 859.6076; [M+Na]$^+$. Found 881.5944. Calculated 881.5895.

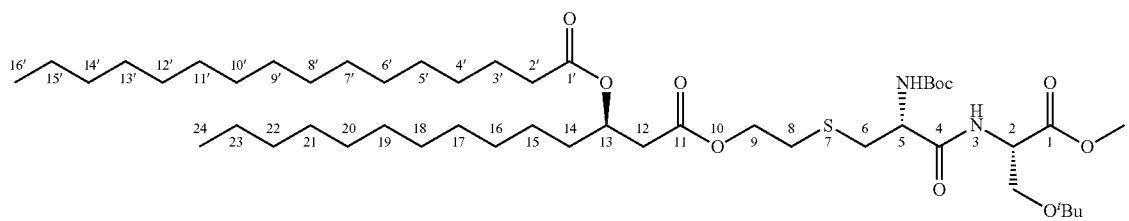

74

74: $^1$H NMR (500 MHz, CDCl$_3$) δ 7.14 (d, 1H, J$_{3,2}$=8.1 Hz, NH-3), 5.46 (d, 1H, J$_{NH,5}$=7.9 Hz, NHBoc), 5.26-5.16 (m, 1H, CH-13), 4.66 (dt, 1H, J$_{2,NH}$=8.2 Hz, J$_{2,CH2OtBu}$=3.1 Hz, CH-2), 4.40-4.28 (m, 1H, CH-5), 4.28-4.18 (m, 2H, CH$_2$-9), 3.83 (ABqd, 1H, J$_{AB}$=9.1 Hz, J$_{CH2OtBu,2}$=3.0 Hz, CH$_2$OtBu), 3.74 (s, 3H, CH$_3$-methylester), 3.58 (ABqd, 1H, J$_{AB}$=9.1 Hz, J$_{CH2OtBu,2}$=3.2 Hz, CH$_2$OtBu), 3.01 (ABqd, 1H, J$_{AB}$=13.9 Hz, J$_{6a,5}$=5.6 Hz, CH$_2$-6a), 2.92 (ABqd, 1H, J$_{AB}$=13.9 Hz, J$_{6b,5}$=6.7 Hz, CH$_2$-6b), 2.88-2.73 (m, 2H, CH$_2$-8), 2.60 (ABqd, 1H, J$_{AB}$=15.5 Hz, J$_{12a,13}$=7.4 Hz, CH$_2$-12a), 2.55 (ABqd, 1H, J$_{AB}$=15.5 Hz, J$_{12b,13}$=5.4 Hz, CH$_2$-12b), 2.27 (t, 2H, J$_{2',3'}$=7.5 Hz, CH$_2$-2'), 1.63-1.55 (m, 4H, CH$_2$-14 and CH$_2$-3'), 1.46 (s, 9H, tBu), 1.37-1.19 (m, 42H, CH$_2$-15 to 23 and CH$_2$-4' to 15'), 1.14 (s, 9H, tBu-Boc), 0.88 (t, 6H, J$_{14',15'}$=J$_{24,23}$=6.9 Hz, CH$_3$-16' and CH$_3$-24). $^{13}$C NMR (126 MHz, CDCl$_3$) δ 173.2, 170.4 (2C), 170.3, 155.2, 80.3, 73.5, 70.2, 63.4, 61.7, 53.7, 53.2, 52.4, 39.2, 34.7, 34.5, 34.1, 33.7, 31.9, 30.8, 29.7 (4C), 29.6 (3C), 29.5 (2C), 29.4 (3C), 29.3 (2C), 29.2, 29.1, 28.3, 27.3, 25.1, 25.0, 24.8, 22.7, 14.1. MS (ESI-TOF) for C$_{48}$H$_{90}$N$_2$O$_{10}$S [M+H]$^+$. Found 887.6446. Calculated 887.6389; [M+Na]$^+$. Found 909.6257. Calculated 909.6208.

General Procedure to Synthesize Compounds 65, 66, 82-89:

To compound 61/62/67-74 (0.01 mmol) was added TFA (0.2 mL). The reaction mixture was stirred at room temperature for 25 min and then dried by blowing air through the solution. The crude product was used directly for the next step. To a solution of the crude intermediate in dichloromethane (0.5 mL) was added pyridine (2.4 µL, 0.03 mmol) and acetic anhydride (0.95 µt, 0.01 mmol). The reaction mixture was stirred at room temperature for 30 min and then concentrated. The residue was purified by a flash chromatography (SiO$_2$, MeOH in dichloromethane 0 to 5%) to give product 65/66/82-89 as a colorless oil.

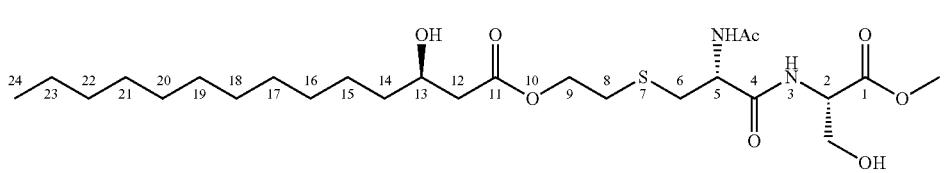

65

65: $^1$H NMR (500 MHz, CDCl$_3$) δ 7.65 (d, J=7.9 Hz, 1H), 6.80 (d, J=7.5 Hz, 1H), 4.68 (dd, J=14.0, 6.9 Hz, 1H), 4.66-4.62 (dt, J=8.0, 3.0 Hz, 1H), 4.40 (dt, J=12.0, 6.2 Hz, 1H), 4.29 (dt, J=11.8, 6.1 Hz, 1H), 4.12-4.01 (m, 1H), 3.97 (dd, J=11.6, 3.6 Hz, 1H), 3.91 (dd, J=11.6, 3.0 Hz, 1H), 3.78 (s, 3H), 3.00 (dd, J=14.0, 6.3 Hz, 1H), 2.92 (dd, J=14.0, 6.8 Hz, 1H), 2.85 (td, J=6.2, 1.9 Hz, 2H), 2.54 (dd, J=15.7, 2.8 Hz, 1H), 2.45 (dd, J=15.7, 9.4 Hz, 1H), 2.04 (s, 3H), 1.58-1.48 (m, 1H), 1.42 (dt, J=13.2, 6.5 Hz, 2H), 1.35-1.19 (m, 15H), 0.87 (t, J=7.0 Hz, 3H). $^{13}$C NMR (126 MHz, CDCl$_3$) δ 172.9, 171.2, 170.7 (2C), 68.5, 63.7, 62.7, 55.1, 52.9, 52.8, 42.0, 36.9, 34.6, 32.1, 31.2, 29.80, 29.77, 29.75, 29.73, 29.66, 29.5, 25.7, 23.2, 22.8, 14.3. MS (ESI-TOF) for C$_{25}$H$_{47}$N$_2$O$_8$S [M+H]$^+$. Found 535.2938. Calculated 535.3048; [M+Na]$^+$. Found 557.2748. Calculated 557.2873.

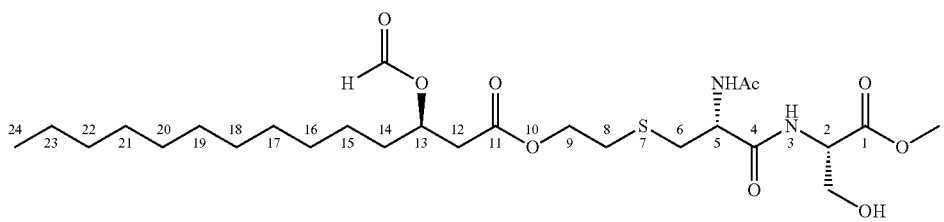

66

66: $^1$H NMR (500 MHz, CDCl$_3$) δ 8.08 (s, 1H, formyl), 7.38 (d, 1H, J$_{3,2}$=7.6 Hz, NH-3), 6.62 (d, 1H, J$_{NH,5}$=7.1 Hz, NHAc), 5.40-5.31 (m, 1H, CH-13), 4.68-4.58 (m, 2H, CH-2 and CH-5), 4.36-4.25 (m, 2H, CH$_2$-9), 4.01 (ABqd, 1H, J$_{AB}$=11.5 Hz, J$_{CH2OH,2}$=3.5 Hz, CH$_2$OH), 3.96 (ABqd, 1H, J$_{AB}$=11.5 Hz, J$_{CH2OH,2}$=3.3 Hz, CH$_2$OH), 3.79 (s, 3H, CH$_3$-methylester), 2.98 (ABqd, 1H, J$_{AB}$=14.0 Hz, J$_{6a,5}$=6.2 Hz, CH$_2$-6a), 2.94 (ABqd, 1H, J$_{AB}$=14.0 Hz, J$_{6b,5}$=6.5 Hz, CH$_2$-6b), 2.85 (t, 2H, J$_{8,9}$=6.4 Hz, CH$_2$-8), 2.67 (ABqd, 1H, J$_{AB}$=15.8 Hz, J$_{12a,13}$=7.9 Hz, CH$_2$-12a), 2.62 (ABqd, 1H, J$_{AB}$=15.8 Hz, J$_{12b,13}$=4.9 Hz, CH$_2$-12b), 2.06 (s, 3H, Ac), 1.72-1.56 (m, 3H, CH$_2$-14 and OH), 1.35-1.18 (m, 18H, CH$_2$-15 to 23), 0.88 (t, 3H, J$_{24,23}$=6.9 Hz, CH$_3$-24). $^{13}$C NMR (126 MHz, CDCl$_3$) δ 170.7, 170.4 (3C), 161.0, 70.8, 63.3, 62.6, 55.0, 52.8, 52.7, 39.2, 34.4, 34.1, 31.9, 31.0, 29.7, 29.6 (2C), 29.5, 29.4, 29.3 (2C), 25.1, 23.1, 22.7, 14.1. MS (ESI-TOF) for C$_{26}$H$_{46}$N$_2$O$_9$S [M+H]$^+$. Found 563.3033. Calculated 563.2997; [M+Na]$^+$. Found 585.2848. Calculated 585.2816.

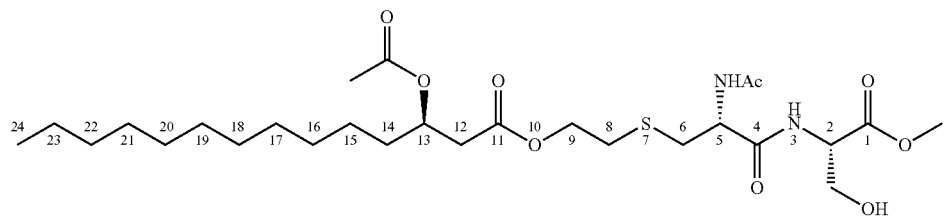

82: $^1$H NMR (500 MHz, CDCl$_3$) δ 7.45 (d, 1H, J$_{3,2}$=7.7 Hz, NH-3), 6.74 (d, 1H, J$_{NH,5}$=7.0 Hz, NHAc), 5.23 (m, 1H, CH-13), 4.70-4.59 (m, 2H, CH-2 and CH-5), 4.35-4.22 (m, 2H, CH$_2$-9), 4.00 (ABqd, 1H, J$_{AB}$=11.5 Hz, J$_{CH2OH,2}$=3.5 Hz, CH$_2$OH), 3.94 (ABqd, 1H, J$_{AB}$=11.5 Hz, J$_{CH2OH,2}$=3.2 Hz, CH$_2$OH), 3.79 (s, 3H, CH$_3$-methylester), 3.44 (brs, 1H, OH), 2.99 (ABqd, 1H, J$_{AB}$=12.9 Hz, J$_{6a,5}$=5.2 Hz, CH$_2$-6a), 2.95 (ABqd, 1H, J$_{AB}$=12.9 Hz, J$_{6b,5}$=5.4 Hz, CH$_2$-6b), 2.83 (t, 2H, J$_{8,9}$=6.4 Hz, CH$_2$-8), 2.62 (ABqd, 1H, J$_{AB}$=15.5 Hz, J$_{12a,13}$=7.4 Hz, CH$_2$-12a), 2.58 (ABqd, 1H, J$_{AB}$=15.5 Hz, J$_{12b,13}$=5.4 Hz, CH$_2$-12b), 2.06 (s, 3H, N—Ac), 2.04 (s, 3H, O—Ac), 1.65-1.52 (m, 2H, CH$_2$-14), 1.35-1.19 (m, 18H, CH$_2$-15 to 23), 0.88 (t, 3H, J$_{24,23}$=6.9 Hz, CH$_3$-24). $^{13}$C NMR (126 MHz, CDCl$_3$) δ 170.9, 170.8, 170.6, 170.5, 170.4, 70.7, 63.4, 62.5, 55.0, 52.8, 52.7, 39.4, 34.5, 34.2, 31.9, 31.1, 29.7, 29.6 (3C), 29.5, 29.4, 29.3, 25.1, 23.1, 22.7, 21.2, 14.1. MS (ESI-TOF) for C$_{27}$H$_{48}$N$_2$O$_9$S [M+H]$^+$. Found 577.3178. Calculated 577.3153; [M+Na]$^+$. Found 599.3000. Calculated 585.2816.

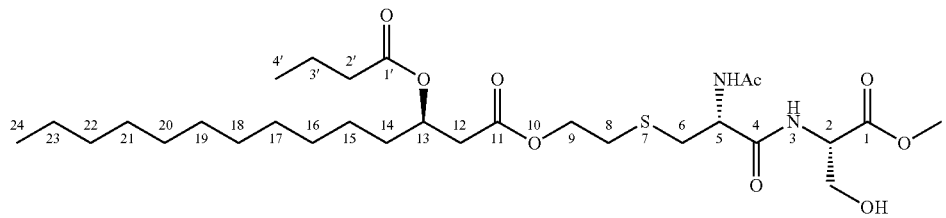

83: $^1$H NMR (500 MHz, CDCl$_3$) δ 7.43 (d, 1H, J$_{3,2}$=7.7 Hz, NH-3), 6.71 (d, 1H, J$_{NH,5}$=7.2 Hz, NHAc), 5.30-5.18 (m, 1H, CH-13), 4.69-4.59 (m, 2H, CH-2 and CH-5), 4.37-4.20 (m, 2H, CH$_2$-9), 4.00 (ABqd, 1H, J$_{AB}$=11.5 Hz, J$_{CH2OH,2}$=3.6 Hz, CH$_2$OH), 3.95 (ABqd, 1H, J$_{AB}$=11.5 Hz, J$_{CH2OH,2}$=3.3 Hz, CH$_2$OH), 3.79 (s, 3H, CH$_3$-methylester), 3.00 (ABqd, 1H, J$_{AB}$=14.0 Hz, J$_{6a,5}$=6.2 Hz, CH$_2$-6a), 2.95 (ABqd, 1H, J$_{AB}$=14.0 Hz, J$_{6b,5}$=6.2 Hz, CH$_2$-6b), 2.83 (t, 2H, J$_{8,9}$=6.4 Hz, CH$_2$-8), 2.61 (ABqd, 1H, J$_{AB}$=15.5 Hz, J$_{12a,13}$=7.5 Hz, CH$_2$-12a), 2.58 (ABqd, 1H, J$_{AB}$=15.5 Hz, J$_{12b,13}$=5.4 Hz, CH$_2$-12b), 2.27 (t, 2H, J$_{2',3'}$=7.4 Hz, CH$_2$-2'), 2.06 (s, 3H, Ac), 1.69-1.52 (m, 4H, CH$_2$-14 and CH$_2$-3'), 1.36-1.16 (m, 18H, CH$_2$-15 to 23), 0.94 (t, 3H, J$_{4',3'}$=7.4 Hz, CH$_3$-4'), 0.88 (t, 3H, J$_{24,23}$=6.9 Hz, CH$_3$-24). $^{13}$C NMR (126 MHz, CDCl$_3$) δ 173.5, 170.7, 170.6, 170.4 (2C), 70.4, 63.4, 62.5, 55.0, 52.8, 52.7, 39.4, 36.4, 34.5, 34.2, 31.9, 31.2, 29.7, 29.6 (2C), 29.5 (2C), 29.4, 29.3, 25.1, 23.1, 22.7, 18.5, 14.1, 13.7. MS (ESI-TOF) for C$_{29}$H$_{52}$N$_2$O$_9$S [M+H]$^+$. Found 605.3487. Calculated 605.3466; [M+Na]$^+$. Found 627.3307. Calculated 627.3286.

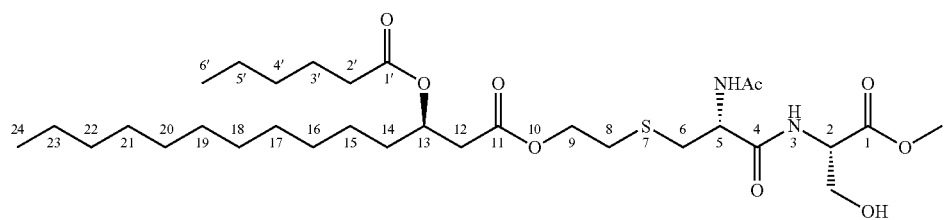

84

84: $^1$H NMR (500 MHz, CDCl$_3$) δ 7.37 (d, 1H, J$_{3,2}$=7.5 Hz, NH-3), 6.65 (d, 1H, J$_{NH,5}$=6.8 Hz, NHAc), 5.29-5.17 (m, 1H, CH-13), 4.66-4.58 (m, 2H, CH-2 and CH-5), 4.33 (ABqt, 1H, J$_{AB}$=11.3 Hz, J$_{9a,8}$=6.4 Hz, CH$_2$-9a), 4.27 (ABqt, 1H, J$_{AB}$=11.7 Hz, J$_{9b,8}$=6.4 Hz, CH$_2$-9b), 4.01 (ABqd, 1H, J$_{AB}$=11.1 Hz, J$_{CH2OH,2}$=3.4 Hz, CH$_2$OH), 3.96 (ABqd, 1H, J$_{AB}$=11.4 Hz, J$_{CH2OH,2}$=3.2 Hz, CH$_2$OH), 3.79 (s, 3H, CH$_3$-methylester), 3.20 (brs, 1H, OH), 3.01 (ABqd, 1H, J$_{AB}$=13.9 Hz, J$_{6a,5}$=5.9 Hz, CH$_2$-6a), 2.94 (ABqd, 1H, J$_{AB}$=13.9 Hz, J$_{6b,5}$=6.6 Hz, CH$_2$-6b), 2.84 (t, 2H, J$_{8,9}$=6.3 Hz, CH$_2$-8), 2.62 (ABqd, 1H, J$_{AB}$=15.4 Hz, J$_{12a,13}$=7.6 Hz, CH$_2$-12a), 2.58 (ABqd, 1H, J$_{AB}$=15.4 Hz, J$_{12b,13}$=5.4 Hz, CH$_2$-12b), 2.28 (t, 2H, J$_{2',3'}$=7.6 Hz, CH$_2$-2'), 2.06 (s, 3H, Ac), 1.65-1.54 (m, 4H, CH$_2$-14 and CH$_2$-3'), 1.39-1.08 (m, 22H, CH$_2$-15 to 23 and CH$_2$-4',5'), 0.93-0.84 (m, 6H, CH$_3$-6' and CH$_3$-24). $^{13}$C NMR (126 MHz, CDCl$_3$) δ 173.7, 170.3, 170.6, 170.4 (2C), 70.4, 63.4, 62.5, 55.0, 52.9, 52.8, 39.4, 34.5 (2C), 34.2, 31.9, 31.3, 31.2, 29.7, 29.6 (2C), 29.5 (2C), 29.4, 29.3, 25.1, 24.7, 23.1, 22.7, 22.3, 14.1, 13.9. MS (ESI-TOF) for C$_{31}$H$_{56}$N$_2$O$_9$S [M+H]$^+$. Found 633.3802. Calculated 633.3779; [M+Na]$^+$. Found 655.3621. Calculated 655.3599.

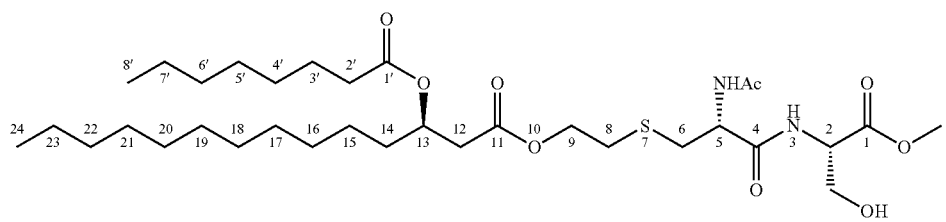

85

85: $^1$H NMR (500 MHz, CDCl$_3$) δ 7.41 (d, 1H, $J_{3,2}$=7.6 Hz, NH-3), 6.69 (d, 1H, $J_{NH,5}$=7.2 Hz, NHAc), 5.28-5.17 (m, 1H, CH-13), 4.69-4.57 (m, 2H, CH-2 and CH-5), 4.32 (ABqt, 1H, $J_{AB}$=11.5 Hz, $J_{9a,8}$=6.5 Hz, CH$_2$-9a), 4.26 (ABqt, 1H, $J_{AB}$=11.4 Hz, $J_{9b,8}$=6.3 Hz, CH$_2$-9b), 4.00 (ABqd, 1H, $J_{AB}$=11.5 Hz, $J_{CH2OH,2}$=3.6 Hz, CH$_2$OH), 3.95 (ABqd, 1H, $J_{AB}$=11.4 Hz, $J_{CH2OH,2}$=3.2 Hz, CH$_2$OH), 3.79 (s, 3H, CH$_3$-methylester), 3.32 (brs, 1H, OH), 3.00 (ABqd, 1H, $J_{AB}$=14.0 Hz, $J_{6a,5}$=6.1 Hz, CH$_2$-6a), 2.95 (ABqd, 1H, $J_{AB}$=13.9 Hz, $J_{6b,5}$=6.6 Hz, CH$_2$-6b), 2.84 (t, 2H, $J_{8,9}$=6.4 Hz, CH$_2$-8), 2.62 (ABqd, 1H, $J_{AB}$=15.4 Hz, $J_{12a,13}$=7.6 Hz, CH$_2$-12a), 2.57 (ABqd, 1H, $J_{AB}$=15.4 Hz, $J_{12b,13}$=5.5 Hz, CH$_2$-12b), 2.28 (t, 2H, $J_{2',3'}$=7.6 Hz, CH$_2$-2'), 2.06 (s, 3H, Ac), 1.65-1.53 (m, 4H, CH$_2$-14 and CH$_2$-3'), 1.36-1.18 (m, 26H, CH$_2$-15 to 23 and CH$_2$-4' to 7'), 0.88 (t, 6H, $J_{24,23}$=$J_{8',7'}$=6.9 Hz, CH$_3$-8' and CH$_3$-24). $^{13}$C NMR (126 MHz, CDCl$_3$) δ 173.7, 170.7, 170.6, 170.4 (2C), 70.0, 64.4, 62.5, 55.0, 52.8, 52.8, 39.4, 34.6, 34.5, 34.2, 31.9, 31.7, 31.2, 29.7 (2C), 29.6 (2C), 29.5, 29.4, 29.3, 29.1, 28.9, 25.1, 25.0, 23.1, 22.7, 22.6, 14.1 (2 C). MS (ESI-TOF) for C$_{33}$H$_{60}$N$_2$O$_9$S [M+H]$^+$. Found 661.4115. Calculated 661.4092; [M+Na]$^+$. Found 683.3936. Calculated 683.3912.

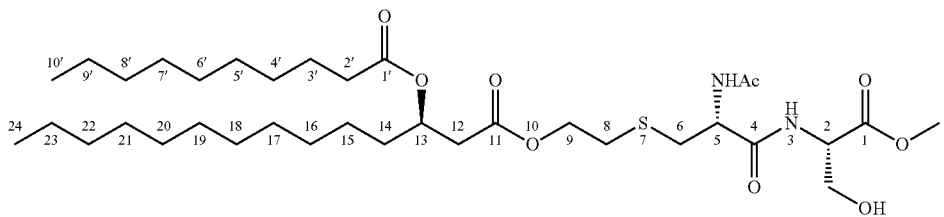

86

86: $^1$H NMR (500 MHz, CDCl$_3$) δ 7.37 (d, 1H, $J_{3,2}$=7.6 Hz, NH-3), 6.65 (d, 1H, $J_{NH,5}$=7.1 Hz, NHAc), 5.28-5.17 (m, 1H, CH-13), 4.68-4.57 (m, 2H, CH-2 and CH-5), 4.33 (ABqt, 1H, $J_{AB}$=11.3 Hz, $J_{9a,8}$=6.4 Hz, CH$_2$-9a), 4.27 (ABqt, 1H, $J_{AB}$=11.7 Hz, $J_{9b,8}$=6.3 Hz, CH$_2$-9b), 4.01 (ABqd, 1H, $J_{AB}$=11.5 Hz, $J_{CH2OH,2}$=3.6 Hz, CH$_2$OH), 3.96 (ABqd, 1H, $J_{AB}$=11.5 Hz, $J_{CH2OH,2}$=3.3 Hz, CH$_2$OH), 3.79 (s, 3H, CH$_3$-methylester), 3.21 (brs, 1H, OH), 3.01 (ABqd, 1H, $J_{AB}$=14.0 Hz, $J_{6a,5}$=6.1 Hz, CH$_2$-6a), 2.94 (ABqd, 1H, $J_{AB}$=14.0 Hz, $J_{6b,5}$=6.7 Hz, CH$_2$-6b), 2.84 (t, 2H, $J_{8,9}$=6.4 Hz, CH$_2$-8), 2.62 (ABqd, 1H, $J_{AB}$=15.4 Hz, $J_{12a,13}$=7.6 Hz, CH$_2$-12a), 2.58 (ABqd, 1H, $J_{AB}$=15.4 Hz, $J_{12b,13}$=5.5 Hz, CH$_2$-12b), 2.28 (t, 2H, $J_{2',3'}$=7.6 Hz, CH$_2$-2'), 2.06 (s, 3H, Ac), 1.63-1.51 (m, 4H, CH$_2$-14 and CH$_2$-3'), 1.35-1.17 (m, 30H, CH$_2$-15 to 23 and CH$_2$-4' to 9'), 0.88 (t, 6H, $J_{24,23}$=$J_{10',9'}$=6.9 Hz, CH$_3$-10' and CH$_3$-24). $^{13}$C NMR (126 MHz, CDCl$_3$) δ 173.7, 170.7, 170.6, 170.4 (2C), 70.4, 63.4, 62.5, 55.0, 52.9, 52.8, 39.5, 34.6, 34.4, 34.2, 31.9 (2C), 31.2, 29.7 (2C), 29.6 (2C), 29.5 (2C), 29.4 (2C), 29.3, 29.1, 25.1, 25.1, 23.1, 22.7 (2C), 14.1 (2 C). MS (ESI-TOF) for C$_{35}$H$_{64}$N$_2$O$_9$S [M+H]$^+$. Found 689.4477. Calculated 689.4405; [M+Na]$^+$. Found 711.4288. Calculated 711.4225.

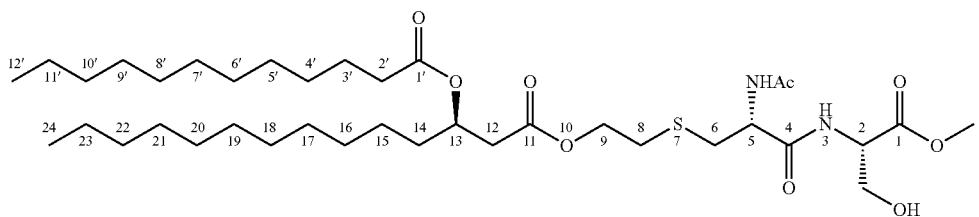

87

87: $^1$H NMR (500 MHz, CDCl$_3$) δ 7.33 (d, 1H, $J_{3,2}$=7.6 Hz, NH-3), 6.61 (d, 1H, $J_{NH,5}$=7.0 Hz, NHAc), 5.29-5.19 (m, 1H, CH-13), 4.66-4.56 (m, 2H, CH-2 and CH-5), 4.35 (ABqt, 1H, $J_{AB}$=11.5 Hz, $J_{9a,8}$=6.4 Hz, CH$_2$-9a), 4.27 (ABqt, 1H, $J_{AB}$=11.4 Hz, $J_{9b,8}$=6.2 Hz, CH$_2$-9b), 4.04-3.94 (m, 2H, CH$_2$OH), 3.79 (s, 3H, CH$_3$-methylester), 3.06 (brs, 1H, OH), 3.02 (ABqd, 1H, $J_{AB}$=14.0 Hz, $J_{6a,5}$=5.9 Hz, CH$_2$-6a), 2.93 (ABqd, 1H, $J_{AB}$=14.0 Hz, $J_{6b,5}$=6.8 Hz, CH$_2$-6b), 2.85 (t, 2H, $J_{8,9}$=6.3 Hz, CH$_2$-8), 2.63 (ABqd, 1H, $J_{AB}$=15.4 Hz, $J_{12a,13}$=7.6 Hz, CH$_2$-12a), 2.58 (ABqd, 1H, $J_{AB}$=15.4 Hz, $J_{12b,13}$=5.4 Hz, CH$_2$-12b), 2.28 (dd, 2H, $J_{2',3'a}$=8.1 Hz, $J_{2',3'b}$=7.1 Hz, CH$_2$-2'), 2.06 (s, 3H, Ac), 1.67-1.53 (m, 4H, CH$_2$-14 and CH$_2$-3'), 1.37-1.17 (m, 34H, CH$_2$-15 to 23 and CH$_2$-4' to 11'), 0.88 (t, 6H, $J_{24,23}$=$J_{12',11'}$=7.0 Hz, CH$_3$-12' and CH$_3$-24). $^{13}$C NMR (126 MHz, CDCl$_3$) δ 173.8, 170.7, 170.5, 170.4, 70.4, 63.4, 62.5, 55.0, 52.9, 52.8, 39.5, 34.6, 34.5, 34.2, 31.9, 31.3, 29.7 (2C), 29.6 (4C), 29.5, 29.4 (2C), 29.3, 29.2, 25.1, 25.1, 23.1, 22.7, 14.1. MS (ESI-TOF) for C$_{37}$H$_{68}$N$_2$O$_9$S [M+H]$^+$. Found 717.4775. Calculated 717.4718; [M+Na]$^+$. Found 739.4597. Calculated 739.4538.

89: $^1$H NMR (500 MHz, CDCl$_3$) δ 7.34 (d, 1H, $J_{3,2}$=7.6 Hz, NH-3), 6.63 (d, 1H, $J_{NH,5}$=7.0 Hz, NHAc), 5.28-5.20 (m, 1H, CH-13), 4.67-4.56 (m, 2H, CH-2 and CH-5), 4.34 (ABqt, 1H, $J_{AB}$=11.4 Hz, $J_{9a,8}$=6.5 Hz, CH$_2$-9a), 4.27 (ABqt, 1H, $J_{AB}$=11.4 Hz, $J_{9b,8}$=6.3 Hz, CH$_2$-9b), 4.04-3.93 (m, 2H, CH$_2$OH), 3.79 (s, 3H, CH$_3$-methylester), 3.14 (brs, 1H, OH), 3.01 (ABqd, 1H, $J_{AB}$=14.0 Hz, $J_{6a,5}$=6.0 Hz, CH$_2$-6a), 2.93 (ABqd, 1H, $J_{AB}$=14.0 Hz, $J_{6b,5}$=6.8 Hz, CH$_2$-6b), 2.85 (t, 2H, $J_{8,9}$=6.4 Hz, CH$_2$-8), 2.63 (ABqd, 1H, $J_{AB}$=15.4 Hz, $J_{12a,13}$=7.6 Hz, CH$_2$-12a), 2.58 (ABqd, 1H, $J_{AB}$=15.4 Hz, $J_{12b,13}$=5.5 Hz, CH$_2$-12b), 2.28 (dd, 2H, $J_{2',3'a}$=8.1 Hz, $J_{2',3'b}$=7.0 Hz, CH$_2$-2'), 2.06 (s, 3H, Ac), 1.62-1.51 (m, 4H, CH$_2$-14 and CH$_2$-3'), 1.35-1.19 (m, 42H, CH$_2$-15 to 23 and CH$_2$-4' to 15'), 0.88 (t, 6H, $J_{24,23}$=$J_{16',15'}$=6.9 Hz, CH$_3$-16' and CH$_3$-24). $^{13}$C NMR (126 MHz, CDCl$_3$) δ 173.8, 170.7, 170.6, 170.4 (2C), 70.4, 63.4, 62.5, 55.0, 52.9, 52.8, 39.5, 34.6, 34.4, 34.2, 31.9, 31.3, 29.7 (4C), 29.6 (2C), 29.5, 29.4 (2C), 29.3, 29.2, 25.1, 25.0, 23.1, 22.7, 14.1. MS (ESI-TOF) for C$_{41}$H$_{76}$N$_2$O$_9$S [M+H]$^+$. Found 773.5413. Calculated 773.5344; [M+Na]$^+$. Found 795.5243. Calculated 795.5164.

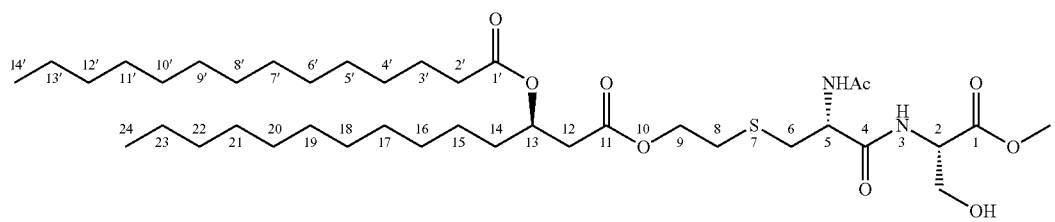

88

88: $^1$H NMR (500 MHz, CDCl$_3$) δ 7.32 (d, 1H, $J_{3,2}$=7.5 Hz, NH-3), 6.60 (d, 1H, $J_{NH,5}$=6.9 Hz, NHAc), 5.30-5.19 (m, 1H, CH-13), 4.68-4.55 (m, 2H, CH-2 and CH-5), 4.35 (ABqt, 1H, $J_{AB}$=11.4 Hz, $J_{9a,8}$=6.4 Hz, CH$_2$-9a), 4.27 (ABqt, 1H, $J_{AB}$=11.4 Hz, $J_{9b,8}$=6.2 Hz, CH$_2$-9b), 4.01 (ABqd, 1H, $J_{AB}$=11.5 Hz, $J_{CH2OH,2}$=3.7 Hz, CH$_2$OH), 3.97 (ABqd, 1H, $J_{AB}$=11.5 Hz, $J_{CH2OH,2}$=3.2 Hz, CH$_2$OH), 3.79 (s, 3H, CH$_3$-methylester), 3.03 (brs, 1H, OH), 3.02 (ABqd, 1H, $J_{AB}$=14.0 Hz, $J_{6a,5}$=5.9 Hz, CH$_2$-6a), 2.93 (ABqd, 1H, $J_{AB}$=14.0 Hz, $J_{6b,5}$=6.8 Hz, CH$_2$-6b), 2.85 (t, 2H, $J_{8,9}$=6.3 Hz, CH$_2$-8), 2.63 (ABqd, 1H, $J_{AB}$=15.4 Hz, $J_{12a,13}$=7.6 Hz, CH$_2$-12a), 2.58 (ABqd, 1H, $J_{AB}$=15.4 Hz, $J_{12b,13}$=5.4 Hz, CH$_2$-12b), 2.28 (dd, 2H, $J_{2',3'a}$=8.1 Hz, $J_{2',3'b}$=7.0 Hz, CH$_2$-2'), 2.06 (s, 3H, Ac), 1.66-1.53 (m, 4H, CH$_2$-14 and CH$_2$-3'), 1.33-1.21 (m, 38H, CH$_2$-15 to 23 and CH$_2$-4' to 13'), 0.88 (t, 6H, $J_{24,23}$=$J_{14',13'}$=6.9 Hz, CH$_3$-14' and CH$_3$-24). $^{13}$C NMR (126 MHz, CDCl$_3$) δ 173.8, 170.7, 170.5, 170.4, 70.4, 63.4, 62.5, 55.0, 52.9, 52.8, 39.5, 34.6, 34.4, 34.2, 31.9, 31.3, 29.7 (3C), 29.6 (2C), 29.5, 29.4, 29.3, 29.2, 25.1, 25.0, 23.1, 22.7, 14.1. MS (ESI-TOF) for C$_{39}$H$_{72}$N$_2$O$_9$S [M+H]$^+$. Found 745.5093. Calculated 745.5031; [M+Na]$^+$. Found 767.4916. Calculated 767.4851.

Synthesis of compound 90: (S)-tert-butyl 3-acetoxytetradecanoate

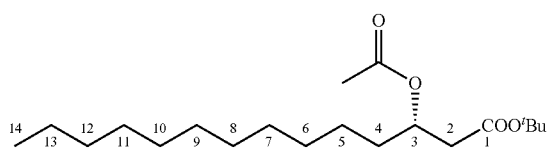

90

To a solution of ent-58 (254 mg, 0.85 mmol) in DCM (4 mL) were added acetic anhydride (161 µL, 1.70 mmol), triethyl amine (237 µL, 1.70 mmol) and 4-dimethylaminopyridine (DMAP, 21 mg, 0.17 mmol). The resulting reaction mixture was stirred at room temperature for 16 h and then concentrated. The residue was purified by a flash chromatography (SiO$_2$, ethyl acetate in hexanes 0 to 5%) to give product 90 (281 mg, 97%). $R_f$=0.45 (Hexanes/EtOAc 9:1). $^1$H NMR (500 MHz, CDCl$_3$) δ 5.28-5.09 (m, 1H),

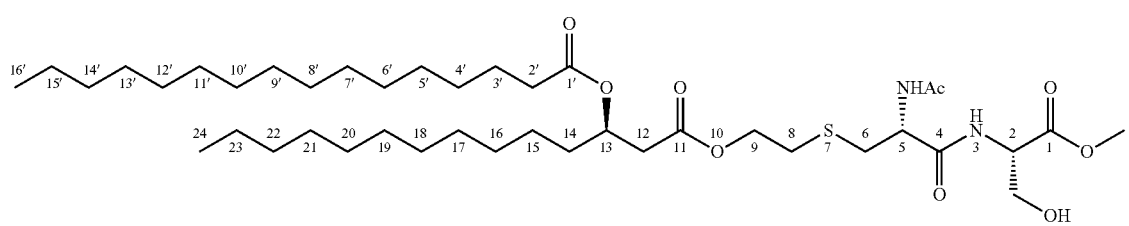

89

2.56-2.34 (m, 1H), 2.03 (s, 3H), 1.67-1.49 (m, 2H), 1.43 (s, 9H), 1.35-1.22 (m, 16H), 0.87 (t, J=6.9 Hz, 3H). $^{13}$C NMR (126 MHz, CDCl$_3$) δ 170.47, 169.86, 80.92, 70.99, 40.76, 34.20, 32.06, 29.78, 29.77, 29.69, 29.63, 29.55, 29.49, 28.16, 25.27, 22.84, 21.28, 14.28. MS (ESI-TOF) for C$_{20}$H$_{38}$O$_4$ [M+Na]$^+$. Found 365.3117. Calculated 365.2668.

Synthesis of compound 91:
(S)-3-acetoxytetradecanoic acid

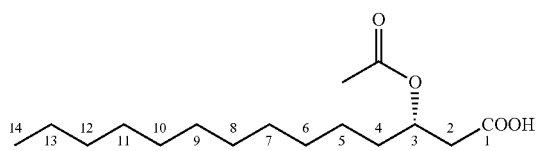

91

To compound 90 (250 mg, 0.73 mmol) was added TFA (2 mL) The reaction mixture was stirred at room temperature for 45 min and then dried by blowing air through the solution. The residue was purified by a flash chromatography (SiO$_2$, ethyl acetate in hexanes 0 to 50%) to give product 91 (197 mg, 94%). R$_f$=0.18 (Hexanes/EtOAc 1:1). $^1$H NMR (500 MHz, CDCl$_3$) δ 8.36 (bs, 1H), 5.20 (dq, J=12.7, 7.1, 6.4 Hz, 1H), 2.70-2.52 (m, 2H), 2.04 (s, 3H), 1.62 (dt, J 14.0, 8.1 Hz, 2H), 1.35-1.15 (m, 18H), 0.88 (t, J=6.9 Hz, 3H). $^{13}$C NMR (126 MHz, CDCl$_3$) δ 176.33, 170.73, 70.42, 38.93, 34.09, 32.06, 29.76, 29.68, 29.61, 29.49, 25.26, 22.84, 21.25, 14.27. MS (ESI-TOF) for C$_{16}$H$_{30}$O$_4$[M+Na]$^+$. Found 309.2073. Calculated 309.2042.

Synthesis of compound 92: (S)-2-(((R)-3-(((S)-3-(tert-butoxy)-1-methoxy-1-oxopropan-2-yl)amino)-2-((tert-butoxycarbonyl)amino)-3-oxopropyl)thio) ethyl 3-acetoxytetradecanoate

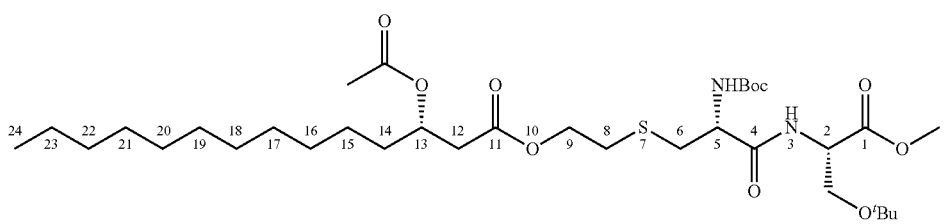

92

To a solution of acid 91 (190 mg, 0.663 mmol) and dipeptide 4 (336 mg, 0.796 mmol) in dichloromethane (5 mL) was added triethylamine (203 μL, 1.459 mmol), catalytic amount of DMAP and EDCI (279 mg, 1.459 mmol). The reaction mixture was stirred at room temperature overnight, then washed with 1N HCl and saturated aqueous NaCl solution, dried over Na$_2$SO$_4$, filtered and concentrated. The residue was purified by a flash chromatography (SiO$_2$, ethyl acetate in hexanes 0 to 30%) to give 92 (330 mg, 72%) as a colorless oil. R$_f$=0.25 (Hexanes/EtOAc 7:3). $^1$H NMR (500 MHz, CDCl$_3$) δ 7.13 (d, J=7.7 Hz, 1H), 5.44 (s, 1H), 5.21 (dq, J=12.7, 7.1, 6.4 Hz, 1H), 4.65 (dt, J=7.8, 2.9 Hz, 1H), 4.32 (s, 1H), 4.24 (t, J=6.0 Hz, 2H), 3.74 (s, 3H), 3.00 (dd, J=13.9, 5.5 Hz, 1H), 2.91 (dd, J=13.9, 6.7 Hz, 1H), 2.86-2.76 (m, 2H), 2.65-2.50 (m, 2H), 2.03 (s, 3H), 1.61-1.55 (m, 2H), 1.45 (s, 9H), 1.34-1.20 (m, 16H), 1.14 (s, 9H), 0.87 (t, J=6.9 Hz, 3H). $^{13}$C NMR (126 MHz, CDCl$_3$) δ 170.58, 170.48, 170.41, 155.35, 80.39, 73.66, 70.63, 63.51, 61.79, 53.85, 53.31, 52.56, 39.27, 34.91, 34.22, 32.06, 31.01, 29.78, 29.77, 29.70, 29.64, 29.53, 29.49, 28.44, 27.44, 25.28, 22.84, 21.30, 14.28. MS (ESI-TOF) for C$_{34}$H$_{62}$N$_2$O$_{10}$S [M+H]$^+$. Found 691.6327. Calculated 691.4198; [M+Na]$^+$. Found 713.6264. Calculated 713.4023.

Synthesis of compound 93: (S)-2-(((R)-2-acetamido-3-(((S)-3-hydroxy-1-methoxy-1-oxopropan-2-yl)amino)-3-oxopropyl)thio)ethyl 3-acetoxytetradecanoate

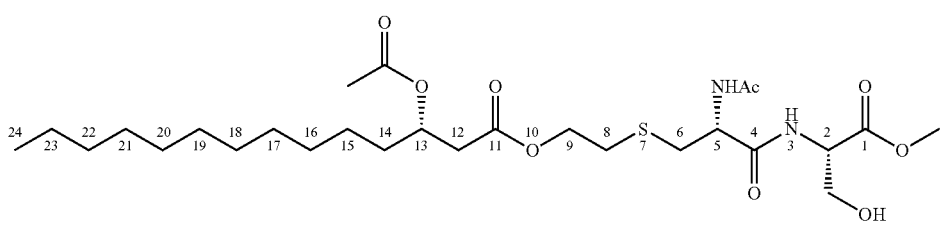

93

To compound 92 (100 mg, 0.145 mmol) was added TFA (2 mL). The reaction mixture was stirred at room temperature for 35 min and then dried by blowing air through the solution. The crude product was used directly for the next step. To a solution of the crude intermediate in dichloromethane (5 mL) was added pyridine (23 µL, 0.29 mmol) and acetic anhydride (15 µL, 0.16 mmol). The reaction mixture was stirred at room temperature for 30 min and then concentrated. The residue was purified by a flash chromatography ($SiO_2$, MeOH in dichloromethane 0 to 5%) to give product 93 as white solid (76 mg, 91% yield). $^1$H NMR (500 MHz, $CDCl_3$) δ 7.44 (d, J=7.8 Hz, 1H), 6.68 (d, J=7.3 Hz, 1H), 5.25 (dq, J=12.8, 7.4, 6.5 Hz, 1H), 4.64 (td, J=7.1, 3.5 Hz, 2H), 4.29 (hept, J=5.9, 5.2 Hz, 2H), 3.97 (tdd, J=15.1, 6.9, 3.4 Hz, 2H), 3.78 (s, 3H), 3.43 (t, J=6.4 Hz, 1H), 2.95 (qd, J=14.0, 6.4 Hz, 2H), 2.83 (hept, J=7.4, 6.8 Hz, 2H), 2.66-2.54 (m, 2H), 2.05 (s, 6H), 1.67-1.50 (m, 2H), 1.32-1.20 (m, 19H), 0.87 (t, J=6.9 Hz, 3H). $^{13}$C NMR (126 MHz, $CDCl_3$) δ 171.30, 170.94, 170.80, 170.61, 70.73, 63.28, 62.72, 55.17, 52.87, 52.53, 39.46, 34.60, 34.35, 32.05, 31.02, 29.77, 29.75, 29.68, 29.62, 29.52, 29.48, 25.25, 23.23, 22.83, 21.37, 14.27. MS (ESI-TOF) for $C_{27}H_{48}N_2O_9S$ $[M+H]^+$. Found 577.4645. Calculated 576.3081; $[M+Na]^+$. Found 599.4581. Calculated 599.2978.

TLR2-Specific NF-κB Induction:

The induction of NF-κB in a TLR2-specific reporter gene assay was quantified using HEK-BLUE™ cells as previously described (Wu, W. et al., *J. Med. Chem.* 2010, 53, 3198-3213). HEK293 cells stably transfected with either human TLR2 or murine TLR2 and alkaline phosphatase (sAP) were obtained from InvivoGen (San Diego, Calif.), and were maintained in HEK-BLUE™ Selection medium containing zeocin and normocin. Stable expression of secreted alkaline phosphatase (sAP) under control of NF-κB promoters is inducible by TLR2 agonists, and extracellular sAP in the supernatant is proportional to NF-κB induction. HEK-Blue cells were incubated at a density of ~$10^5$ cells/mL in a volume of 80 µL/well, in 384-well, flat-bottomed, cell culture-treated microtiter plates until confluency was achieved, and then stimulated with serially-diluted aliquots of compounds for 12 h. sAP was assayed spectrophotometrically using an alkaline phosphatase-specific chromogen (present in the HEK-detection medium as supplied by the vendor) at 620 nm. For antagonist assays, HEK-Blue cells were incubated at a density of ~$10^5$ cells/mL in a volume of 80 µL/well and stimulated with either $PAM_2CS$ (1 µg/mL) or lipoteichoic acid (1 µg/mL) in the presence of graded concentrations of the test compounds as described for TLR7 previously (Shukla, N. M.; et al., *Bioorg. Med. Chem. Lett.* 2009, 19, 2211-2214; Shukla, N. M. et al., *Bioorg. Med. Chem.* 2011, 19, 3801-3811).

Rabbit Immunization:

All experiments were performed in accordance with institutional guidelines (University of Kansas IACUC permit #119-06) which specifically approved this study. All antigen/adjuvant preparations were entirely aqueous; no liposomal or emulsifying agents were used. Cohorts of adult female New Zealand White rabbits (n=4) were immunized intramuscularly in the flank region with (a) 100 µg of bovine α-lactalbumin in 0.2 mL saline, or (b) 100 µg of bovine α-lactalbumin plus 100 µg of compound 25 in 0.2 mL saline, or (d) 100 µg of bovine α-lactalbumin plus 100 µg of dual TLR2-agonistic $PAM_2CSK_4$ (control). Pre-immune test-bleeds were first obtained via venipuncture of the marginal vein of the ear. Animals were immunized on Days 1, 15 and 28. A final test-bleed was performed via the marginal vein of the ear on Day 38. Sera were stored at −80° C. until used.

Enzyme-Linked Immunosorbent Assays (ELISA):

Bovine α-lactalbumin-specific ELISAs were performed in 384-well format using automated liquid handling methods as described (Shukla, N. M. et al. *Bioorg. Med. Chem. Lett.* 2011, 21, 3232-3236). Examination of the affinity of antigen-specific IgG using chaotropic ELISA (Pullen, G. R. et al. *J. Immunol. Methods* 1986, 86, 83-87 and Macdonald, R. A. et al. *J. Immunol. Methods* 1988, 106, 191-194). A precision 2000 liquid handler (Bio-Tek, Winooski, Vt.) was used for all serial dilution and reagent addition steps, and a Bio-Tek ELx405 384-well plate washer was employed for plate washes; 100 mM phosphate-buffered saline (PBS) pH 7.4, containing 0.1% Tween-20 was used as wash buffer. Nunc-Immuno MaxiSorp (384-well) plates were coated with 30 mL of α-lactalbumin in 100 mM carbonate buffer, pH 9.0 overnight at 4° C. After 3 washes, the plates were blocked with 3% bovine serum albumin (in PBS, pH 7.4) for 1 h at rt. Serum samples (in quadruplicate) were serially diluted in a separate 384-well plate using the liquid handler. After three additional washes of the assay plate, 30 µL of the serum dilutions were transferred using the liquid handler, and the plate incubated at 37° C. for 2 h in the absence or presence of graded (2M and 4M) concentrations of sodium thiocyanate. The assay plate was washed three times, and 30 µl of 1:10,000 diluted appropriate anti-mouse immunoglobulin (IgG [γ chain], IgM [µ chain], IgG1, IgG2a) conjugated with horseradish peroxidase was added to all wells. Following an incubation step at 37° C. for 1 h, and three washes, tetramethylbenzidine substrate was added at concentrations recommended by vendor (Sigma). The chromogenic reaction was terminated at 30 min by the addition of 2M $H_2SO_4$. Plates were then read at 450 nm using a SpectraMax M4 device (Molecular Devices, Sunnyvale, Calif.).

TABLE 1

$EC_{50}$ values of compounds in human TLR2-specific reporter gene assay$^a$

| Structure | Compound Number | TLR2-Agonistic Activity ($EC_{50}$ in nM) |
|---|---|---|
| [chemical structure] | 6a | ND |

TABLE 1-continued

EC$_{50}$ values of compounds in human TLR2-specific reporter gene assay[a]

| Structure | Compound Number | TLR2-Agonistic Activity (EC$_{50}$ in nM) |
|---|---|---|
| 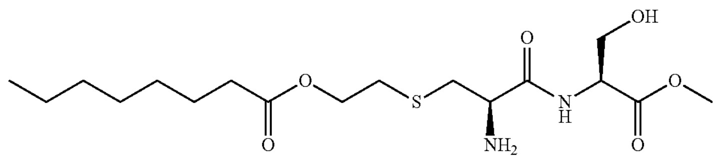 [SMILES: CCCCCCCC(=O)OCCSC[C@H](N)C(=O)N[C@@H](CO)C(=O)OC] | 6b | ND |
| 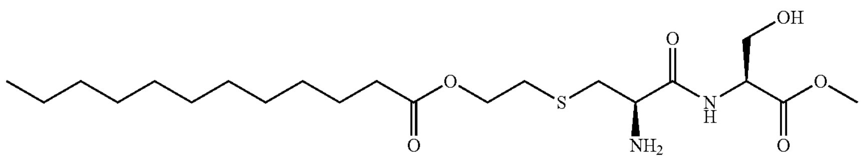 [SMILES: CCCCCCCCCCCC(=O)OCCSC[C@H](N)C(=O)N[C@@H](CO)C(=O)OC] | 6c | ND |
| 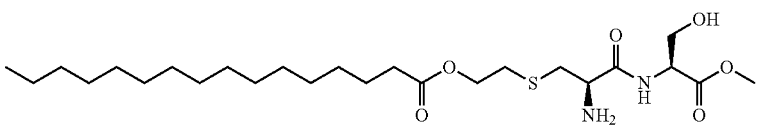 [SMILES: CCCCCCCCCCCCCCCC(=O)OCCSC[C@H](N)C(=O)N[C@@H](CO)C(=O)OC] | 6d | 3.63 (Low potency) |
| 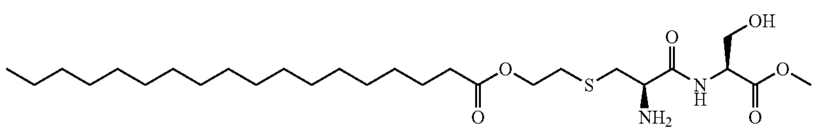 [SMILES: CCCCCCCCCCCCCCCCCC(=O)OCCSC[C@H](N)C(=O)N[C@@H](CO)C(=O)OC] | 6e | 4.79 (Low potency) |
| 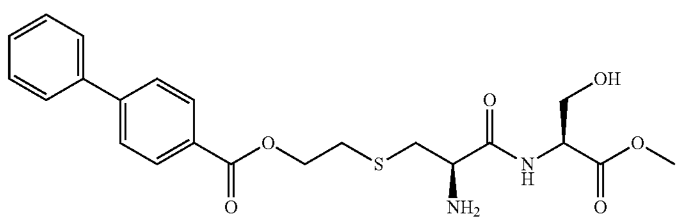 [SMILES: COC(=O)[C@H](CO)NC(=O)[C@@H](N)CSCCOC(=O)c1ccc(-c2ccccc2)cc1] | 6f | ND |
| 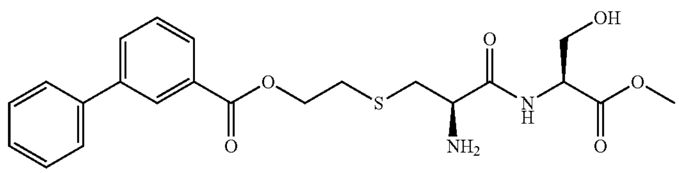 [SMILES: COC(=O)[C@H](CO)NC(=O)[C@@H](N)CSCCOC(=O)c1cccc(-c2ccccc2)c1] | 6g | ND |
| 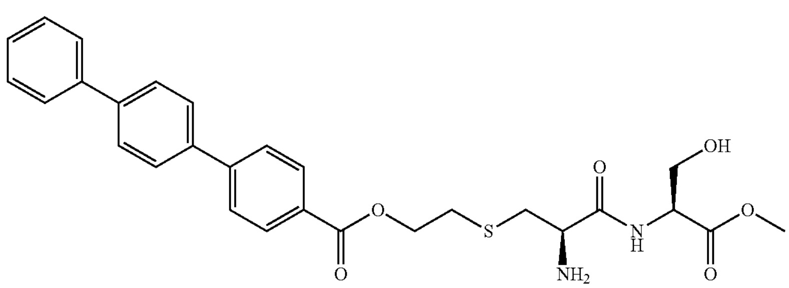 [SMILES: COC(=O)[C@H](CO)NC(=O)[C@@H](N)CSCCOC(=O)c1ccc(-c2ccc(-c3ccccc3)cc2)cc1] | 6h | ND |
| 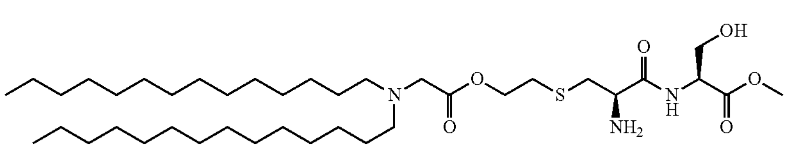 [SMILES: CCCCCCCCCCCCCCN(CCCCCCCCCCCCCC)CC(=O)OCCSC[C@H](N)C(=O)N[C@@H](CO)C(=O)OC] | 10a | ND |

TABLE 1-continued

EC$_{50}$ values of compounds in human TLR2-specific reporter gene assay$^a$

| Structure | Compound Number | TLR2-Agonistic Activity (EC$_{50}$ in nM) |
|---|---|---|
| 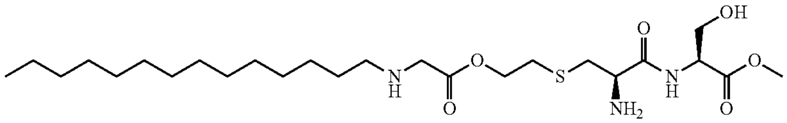 [SMILES: CCCCCCCCCCCCCCNCC(=O)OCCSC[C@H](N)C(=O)N[C@@H](CO)C(=O)OC] | 10b | ND |
| 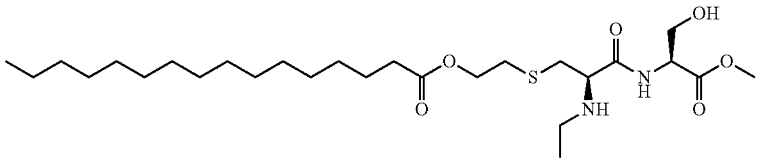 [SMILES: CCCCCCCCCCCCCCCC(=O)OCCSC[C@H](NCC)C(=O)N[C@@H](CO)C(=O)OC] | 11a | ND |
| 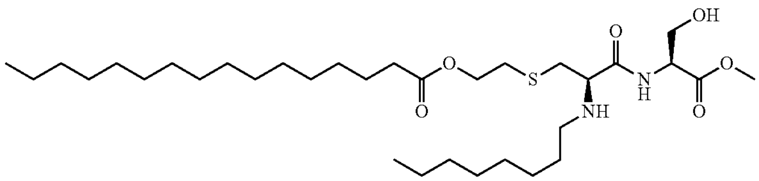 [SMILES: CCCCCCCCCCCCCCCC(=O)OCCSC[C@H](NCCCCCCCC)C(=O)N[C@@H](CO)C(=O)OC] | 11b | ND |
| 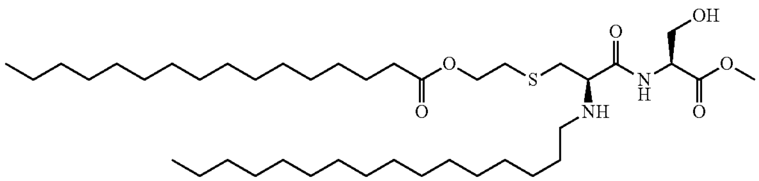 [SMILES: CCCCCCCCCCCCCCCCN[C@@H](CSCCOC(=O)CCCCCCCCCCCCCCC)C(=O)N[C@@H](CO)C(=O)OC] | 11c | ND |
| 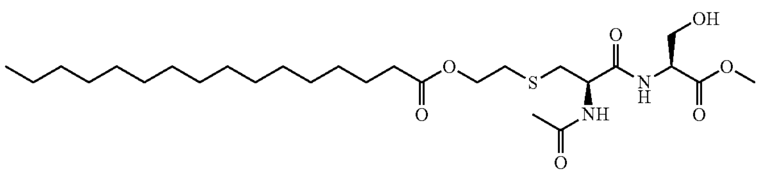 [SMILES: CCCCCCCCCCCCCCCC(=O)OCCSC[C@H](NC(C)=O)C(=O)N[C@@H](CO)C(=O)OC] | 11d | 1.01 |
| 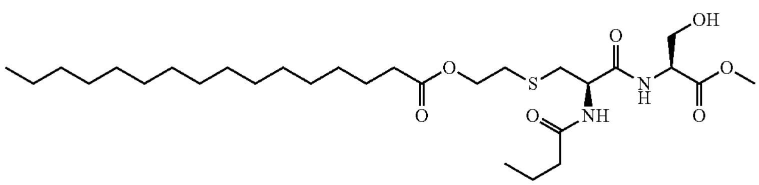 [SMILES: CCCCCCCCCCCCCCCC(=O)OCCSC[C@H](NC(=O)CCC)C(=O)N[C@@H](CO)C(=O)OC] | 11e | 1.64 |
| 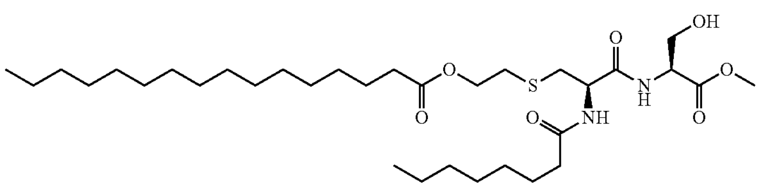 [SMILES: CCCCCCCCCCCCCCCC(=O)OCCSC[C@H](NC(=O)CCCCCCC)C(=O)N[C@@H](CO)C(=O)OC] | 11f | 3.80 |
| 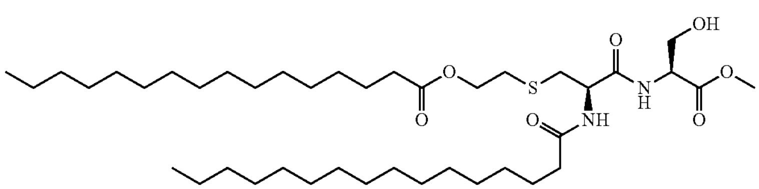 [SMILES: CCCCCCCCCCCCCCCC(=O)N[C@@H](CSCCOC(=O)CCCCCCCCCCCCCCC)C(=O)N[C@@H](CO)C(=O)OC] | 11g | ND |

TABLE 1-continued

EC$_{50}$ values of compounds in human TLR2-specific reporter gene assay$^a$

| Structure | Compound Number | TLR2-Agonistic Activity (EC$_{50}$ in nM) |
|---|---|---|
| (structure) | 11h | 4.45 |
| (structure) | 11i | ND |
| (structure) | 11j | ND |
| (structure) | 11k | ND |
| (structure) | 11l | ND |
| (structure) | 14a | 2.97 |
| (structure) | 14b | 5.47 |
| (structure) | 14c | 5.95 |

TABLE 1-continued

EC$_{50}$ values of compounds in human TLR2-specific reporter gene assay[a]

| Structure | Compound Number | TLR2-Agonistic Activity (EC$_{50}$ in nM) |
|---|---|---|
| 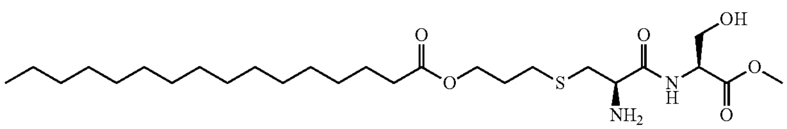 [SMILES: CCCCCCCCCCCCCCCC(=O)OCCCSC[C@H](N)C(=O)N[C@@H](CO)C(=O)OC] | 15 | ND |
| 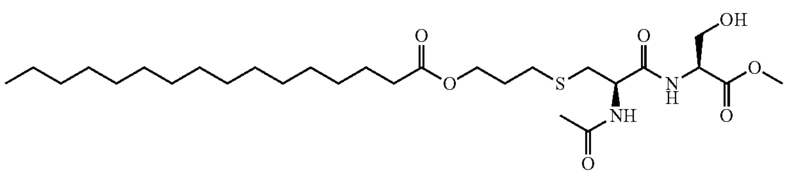 [SMILES: CCCCCCCCCCCCCCCC(=O)OCCCSC[C@H](NC(C)=O)C(=O)N[C@@H](CO)C(=O)OC] | 16 | 5.52 |
| 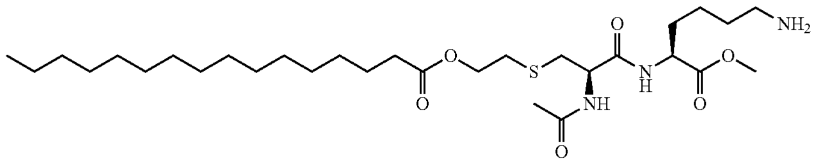 [SMILES: CCCCCCCCCCCCCCCC(=O)OCCSC[C@H](NC(C)=O)C(=O)N[C@@H](CCCCN)C(=O)OC] | 23 | 0.225 |
| 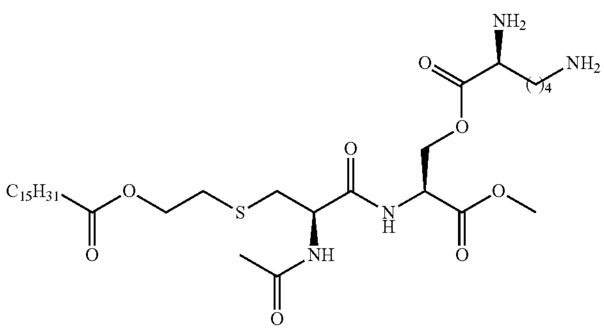 | 25 | 6.81 |
| 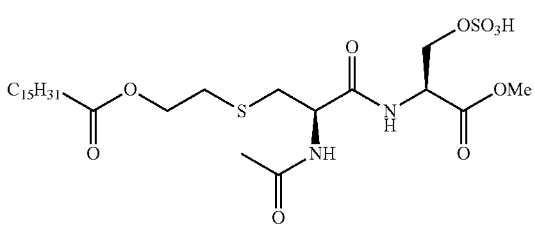 | 26 | 7.10 |
| 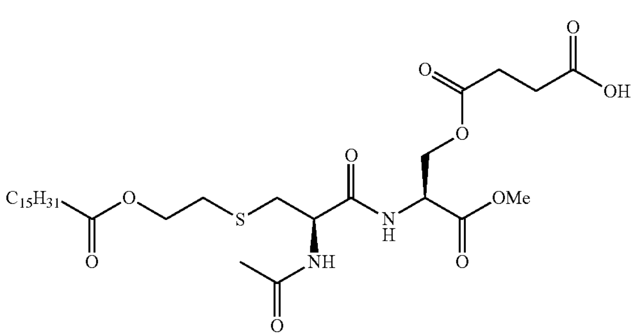 | 27 | 0.518 |

TABLE 1-continued

EC$_{50}$ values of compounds in human TLR2-specific reporter gene assay[a]

| Structure | Compound Number | TLR2-Agonistic Activity (EC$_{50}$ in nM) |
|---|---|---|
| 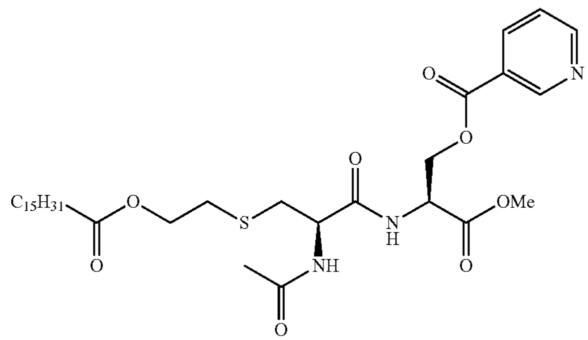 | 28 | 1.27 |
| 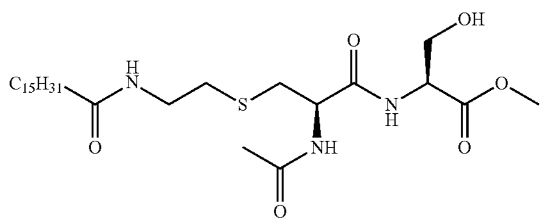 | 34 | 11.8 |
| 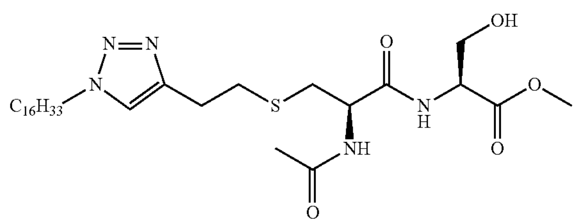 | 38 | 641 |
| 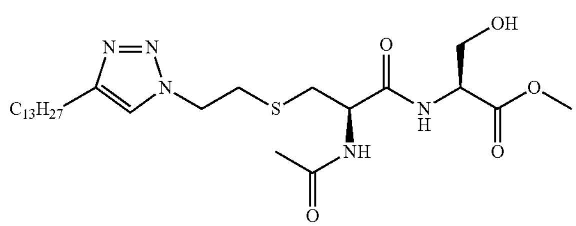 | 41 | 260 |
| 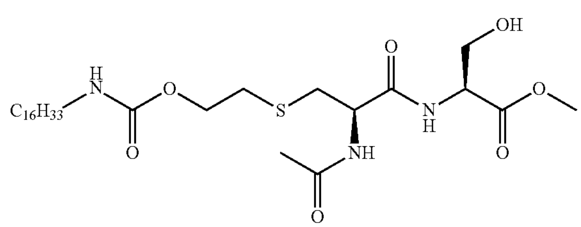 | 45 | 0.323 |
| 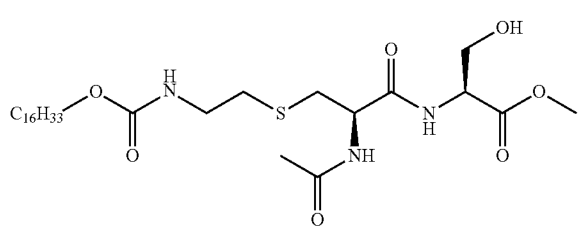 | 48 | 0.0615 |

TABLE 1-continued

EC$_{50}$ values of compounds in human TLR2-specific reporter gene assay[a]

| Structure | Compound Number | TLR2-Agonistic Activity (EC$_{50}$ in nM) |
|---|---|---|
| 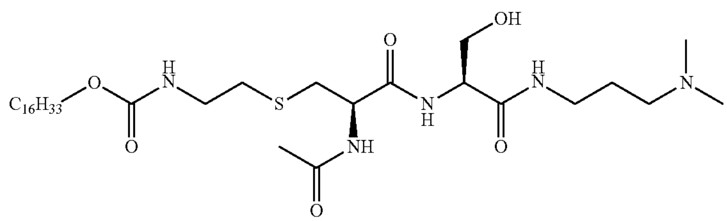 | 52 | 0.279 |
| 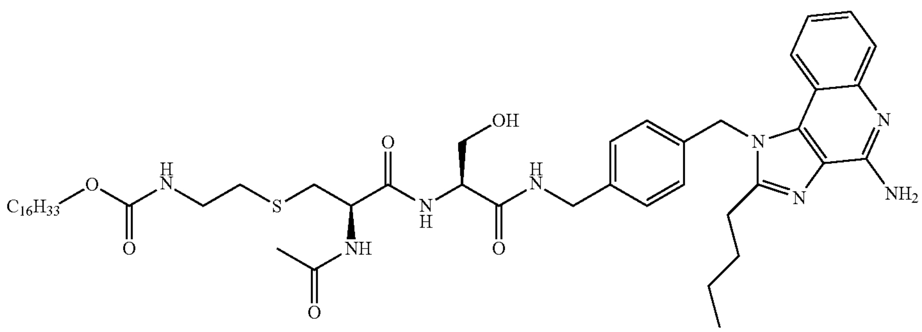 | 54 | 221 |
| 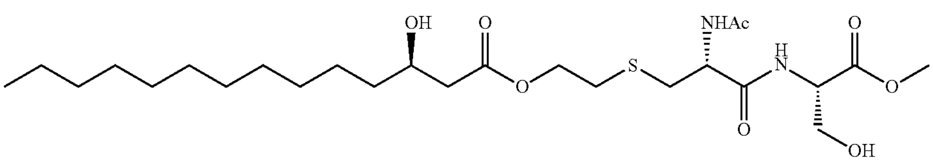 [SMILES: CCCCCCCCCCC[C@@H](O)CC(=O)OCCSC[C@H](NC(C)=O)C(=O)N[C@@H](CO)C(=O)OC] | 65 | 1.13 |
| 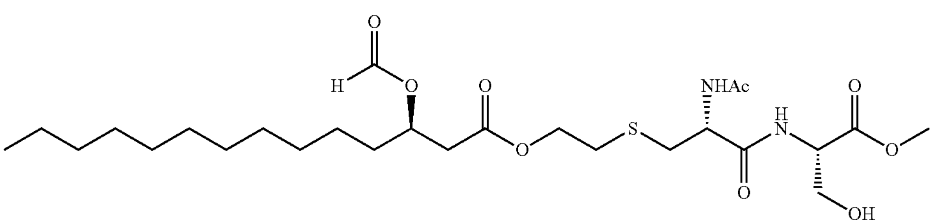 [SMILES: CCCCCCCCCCC[C@H](CC(=O)OCCSC[C@H](NC(C)=O)C(=O)N[C@@H](CO)C(=O)OC)OC=O] | 66 | 0.808 |
| 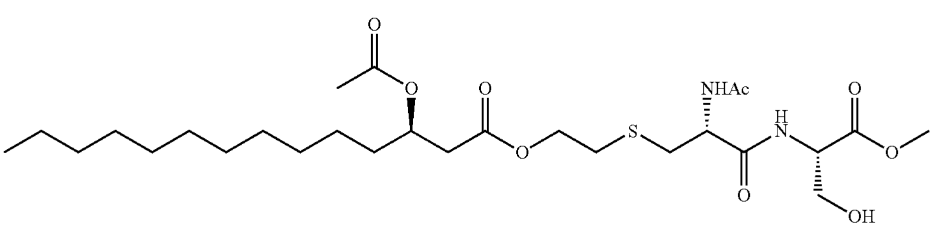 [SMILES: CCCCCCCCCCC[C@H](CC(=O)OCCSC[C@H](NC(C)=O)C(=O)N[C@@H](CO)C(=O)OC)OC(C)=O] | 82 | 0.182 |
| 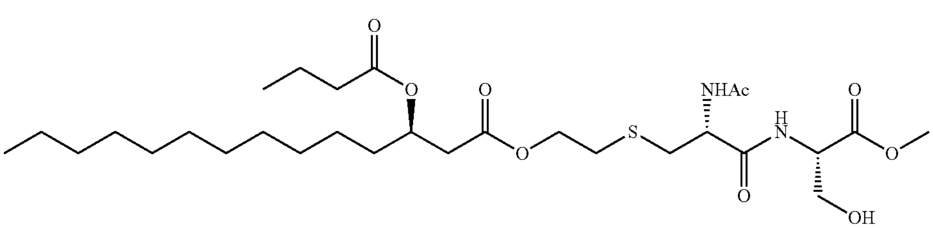 [SMILES: CCCCCCCCCCC[C@H](CC(=O)OCCSC[C@H](NC(C)=O)C(=O)N[C@@H](CO)C(=O)OC)OC(=O)CCC] | 83 | 0.345 |

TABLE 1-continued

EC$_{50}$ values of compounds in human TLR2-specific reporter gene assay$^a$

| Structure | Compound Number | TLR2-Agonistic Activity (EC$_{50}$ in nM) |
|---|---|---|
| 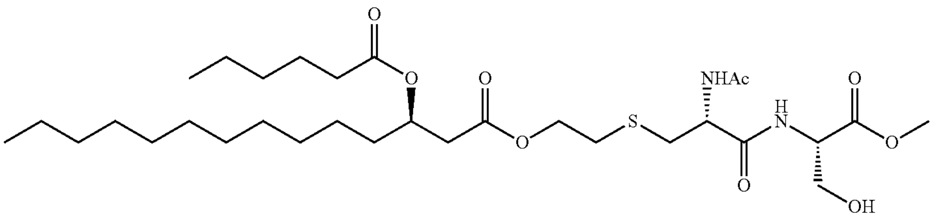 [SMILES: CCCCCCCCCCC[C@H](CC(=O)OCCSC[C@H](NC(C)=O)C(=O)N[C@@H](CO)C(=O)OC)OC(=O)CCCCC] | 84 | 1.50 |
| 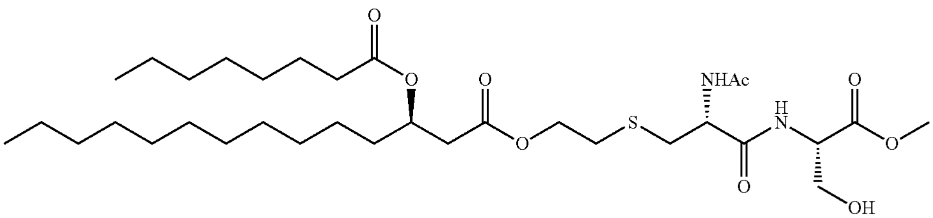 [SMILES: CCCCCCCCCCC[C@H](CC(=O)OCCSC[C@H](NC(C)=O)C(=O)N[C@@H](CO)C(=O)OC)OC(=O)CCCCCCC] | 85 | 3.08 |
| 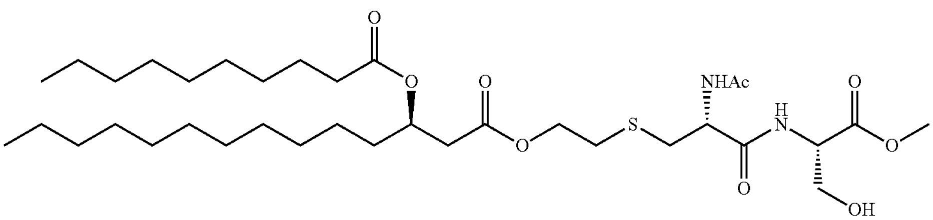 [SMILES: CCCCCCCCCCC[C@H](CC(=O)OCCSC[C@H](NC(C)=O)C(=O)N[C@@H](CO)C(=O)OC)OC(=O)CCCCCCCCC] | 86 | 12.9 |
| 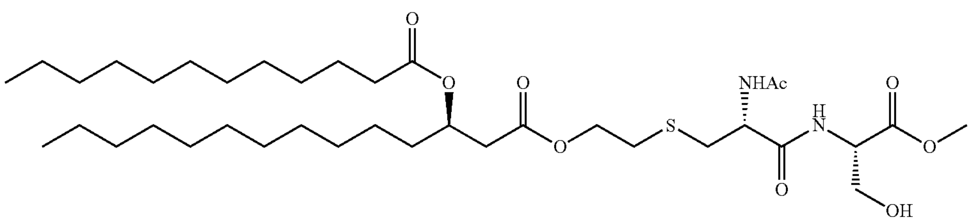 [SMILES: CCCCCCCCCCCC(=O)O[C@H](CCCCCCCCCCC)CC(=O)OCCSC[C@H](NC(C)=O)C(=O)N[C@@H](CO)C(=O)OC] | 87 | 20.7 |
| 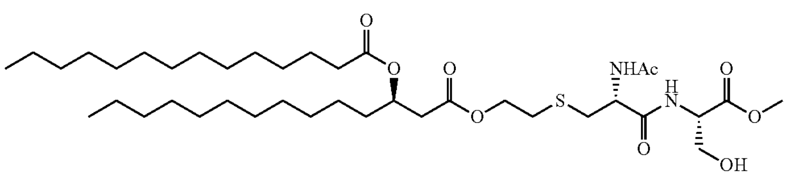 [SMILES: CCCCCCCCCCCCCC(=O)O[C@H](CCCCCCCCCCC)CC(=O)OCCSC[C@H](NC(C)=O)C(=O)N[C@@H](CO)C(=O)OC] | 88 | 9.52 |
| 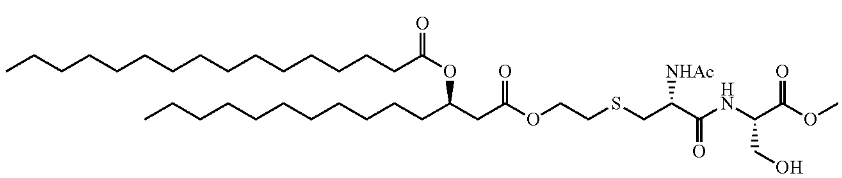 [SMILES: CCCCCCCCCCCCCCCC(=O)O[C@H](CCCCCCCCCCC)CC(=O)OCCSC[C@H](NC(C)=O)C(=O)N[C@@H](CO)C(=O)OC] | 89 | 4.78 |

$^a$ND denotes no activity detected at 10 μM.

Results:

The SAR of the mono-acyl derivatives began with a careful exploration of the nature of the ester-linked acyl group on the mercaptoethanol fragment of the lipopeptide; specifically, the goal was to determine the optimal chain length corresponding to maximal TLR2-stimulatory activity, and whether aryl groups could substitute for the palmitoyl group. The syntheses of these analogues were accomplished (Scheme 1) using the strategy previously described (Agnihotri, G. et al., *J. Med. Chem.* 2011, 54, 8148-8160), 6d, with a palmitoyl group (Scheme 1) was the point of departure. Examination of this series of compounds showed a clear-cut and straightforward SAR: 6d (palmitoyl) and 6e (stearoyl) were active in engaging hTLR2 (3.63 nM and 4.79 nM, respectively, Table 1), but entirely inactive in assays using mTLR2 (FIG. 1). The shorter-chain analogues were completely inactive (Table 1). Aryl substituents were found to abrogate activity as exemplified by the complete absence of activity in the biphenyl-4-carboxylate (6f) and biphenyl-3-carboxylate (6g), as well as the p-terphenyl-4-carboxylate (6h) derived analogues. The latter results were not unexpected given the dimensions of the hydrophobic tunnel in the crystal structure of TLR2 (Jin, M. S. et al., Cell 2007, 130, 1071-1082; Jin, M. S.; Lee, J. O. Curr. Opin. Immunol. 2008, 20, 414-419); however, there was also an interest in examining the possibility of these inactive analogues behaving as antagonists of TLR2, since there is only one known report of a low-potency lanthionine-derived antagonist (Seyberth, T. et al., J. Med. Chem. 2006, 49, 1754-1765). None of the above-mentioned inactive compounds were antagonistic in homotypic (using PAM$_2$CS as stimulus) or heterotypic (using lipoteichoic acid as stimulus) assays in mTLR2 and hTLR2 assays.

The previous SAR on the lipopeptides demonstrated the absolute requirement of the ester-linked long-chain group, and of the importance of the orientation of the carbonyl group of the ester; in these earlier studies, it was found that replacement of the long-chain hydrocarbon functional group with polar poly-ether or polyamine moieties were not tolerated. A more conservative modification was examined. It was hypothesized that the replacement of the palmitoyl group by a 2-(ditetradecylamino) acetate fragment (10a, Scheme 2) may confer to the molecule dual hTLR2/mTLR2 activity by mimicking PAM$_2$CS. This assumption was incorrect since both 10a and its mono-alkyl homologue, 10b, were completely inactive (Table 1).

As mentioned earlier, N-palmitoylation of 6d (11g, Scheme 3) resulted in an unanticipated loss of TLR2-agonistic activity (Table 1). A variety of alkyl and acyl substituents on the cysteine amine were examined in detail. The N-alkyl derivatives 11a (ethyl), 11b (octyl), and 11c (hexadecyl) analogues (obtained by either reductive amination using appropriate aldehydes for 11a and 11b, or by direct alkylation in the case of 11c using hexadecyl bromide) were inactive (Table 1). In contradistinction, the short-chain N-acyl analogues were found to be highly active, with a clear dependence on the chain-length: the N-acetyl analogue 11d was found to be the most potent (1 nM), followed by the N-butyryl analogue 11e, and N-octanoyl compound 11f (3.8 nM). Further homologation (11g, palmitoyl) resulted in complete loss of activity. Two points are to be noted; first, the active analogues (11d-11f) retained specificity toward hTLR2 and displayed no agonistic activity in mTLR2; second, while the EC$_{50}$ of the lead compound (6d: 3.6 nM) is, at first glance, comparable to that of the N-acetyl derivative (11d: 1 nM), the absolute magnitude of TLR2-induced nuclear translocation of NF-κB is far greater for 11d and approaches that of PAM$_2$CS (FIG. 1), indicating the higher potency of 11d.

The progressive decrease in activity with increasing N-acyl chain length provided evidence for steric issues. It was desired to confirm this hypothesis and also evaluate replacements of the N-acetyl group with functionalities differing in electron-withdrawing properties. The trifluoroacetamido derivative 11h retained weaker activity (EC$_{50}$: 4.5 nM, but low magnitude of NF-κB activation, FIG. 1), while the trichloroacetamido analogue 11i was inactive; consistent with these results were the observations that the methanesulfonamide (11j), trifluoromethanesulfonamide (11k) and p-toluenesulfonamide (11l) derivatives were all inactive. Taken together, these results highlight the simultaneous influence of electronic and steric effects of the substituents on the amine.

Given that the cysteine N-acyl substituents showed dramatic differences in activity as described above, it was of interest to explore serine O-acyl substituents as well. The syntheses of these analogues (Scheme 4) required the protection of the cysteine amine as the t-butyl carbamate, followed by O-acylation with either anhydride (14a) or acyl chlorides (14b, 14c). The activity of the O-acetyl analogue 14a was virtually indistinguishable from that of 6d; progressive loss in activity was evident with increasing acyl chain lengths (FIG. 1 and Table 1). As was observed for all of the compounds described above, the O-acyl analogues were also found to be specific for hTLR2.

Given that N-acetylation appeared to specifically enhance TLR2-agonistic potency while preserving specificity for human TLR2, it was of interest to examine if this modification on an inactive homologue of 6d would also result in augmented agonistic activity. The propylene-bridged 3-((R)-2-amino-3-((S)-3-hydroxy-1-methoxy-1-oxopropan-2-ylamino)-3-oxopropylthio)propyl palmitate compound 15 was N-acetylated to furnish 16 as depicted in Scheme 5. The N-acetylated derivative was found to be active, albeit much weaker in potency than 11d (Table 1, FIG. 1), clearly emphasizing the role of N-acetyl group in determining TLR2-agonistic potency, although the structural basis for this observation remains to be elucidated.

Figure 2:
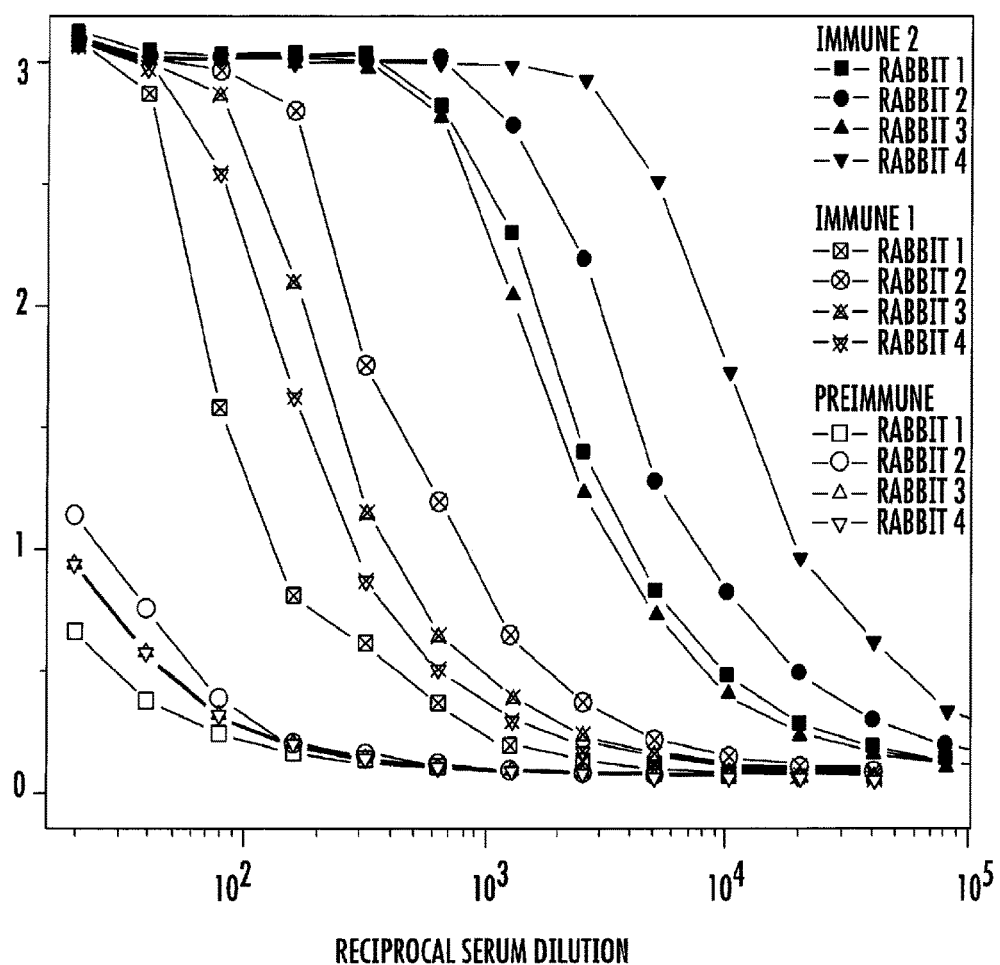
FIG. 2 is a graph showing anti-lactalbumin IgG titers for compound 25 on rabbits.
Figure 3:
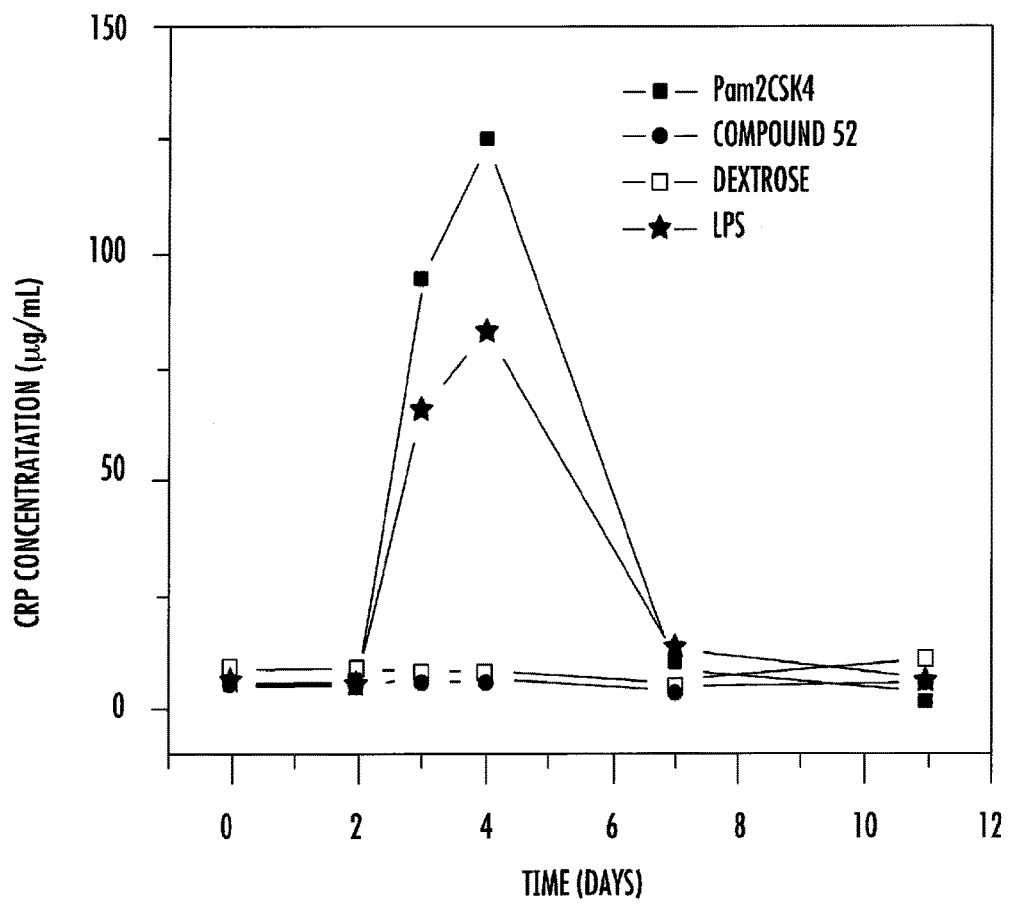
FIG. 3 is a graph showing that the monoacyl compounds (such as DBS-2-217 are non-inflammatory, while the PAM2CS compounds induce C-reactive protein (CRP), indicative of systemic inflammation. The fundamental advantage in this monoacyl compounds compared to the canonical PAM2CS compounds is that these compounds are not reactogenic whilst the PAM2CS compounds are reactogenic. Rabbits were challenged intramuscularly (bolus) with 1.0 mg of compounds. C-reactive protein levels were measured longitudinally. The monoacyl compounds (such as DBS-2-217 are non-inflammatory, while the PAM2CS compounds induce CRP, indicative of systemic inflammation.
Figure 4:
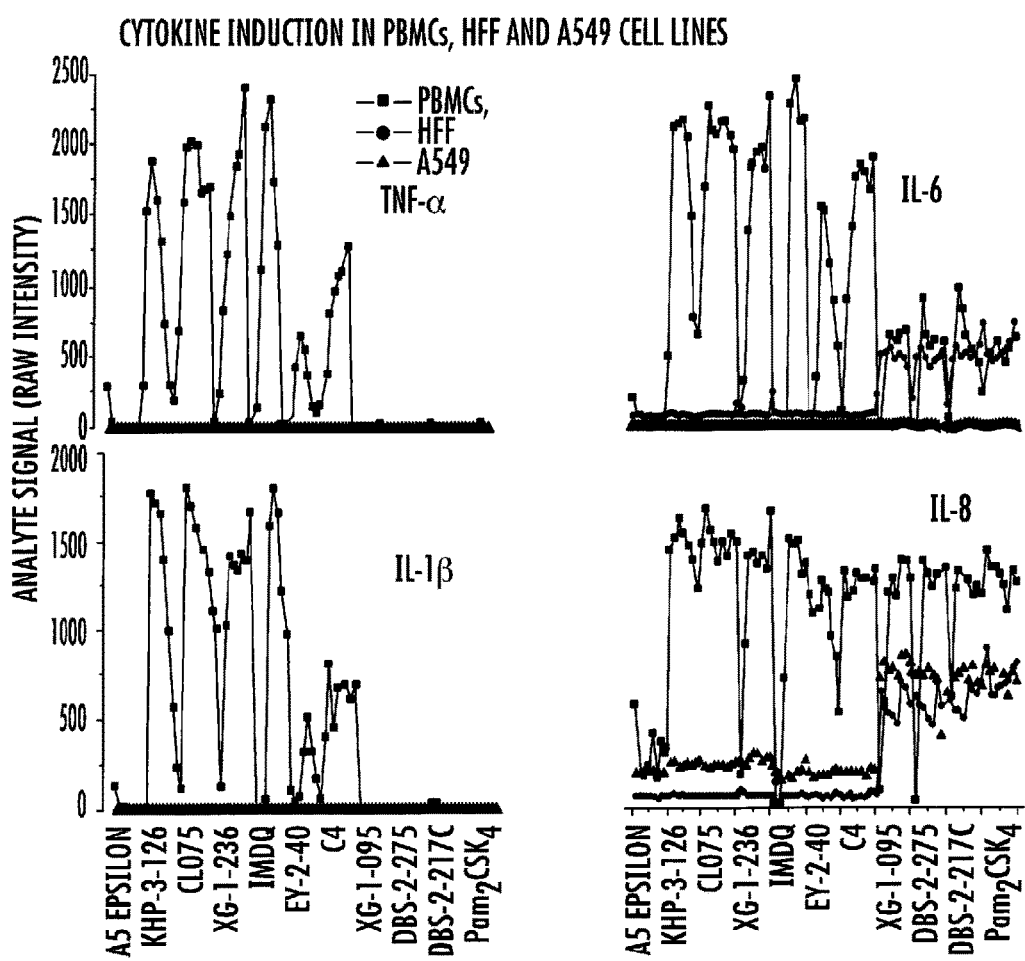
FIG. 4 are graphs showing the results from cytokine induction of representative TLR agonist compounds in peripheral blood mononuclear cells (PBMCs), HFF and A549 cell lines. A variety of agonists, were assayed for modulation of cytokines in various cells and cell lines, for example, A5 epsilon and KHP-3-126 are pure TLR8 agonists; XG-1-236, CL075 and IMDQ are dual TLR7/TLR8 agonists; EY-2-40 and C4 are pure TLR7 agonists; XG-1-095, DBS-2-275, DBS-2-217C and PAM2CSK4 are TLR2 agonists. The TLR8/TLR7 compounds induced high levels of TNF-alpha and IL-1beta in hPBMCs, while TLR2 agonists did not. However, only TLR2 agonists induced IL-6 and IL-8 in human foreskin fibroblasts (DBS-2-217C=Compound 52; XG-1-095=Compound 82 (R— stereochemistry); DBS-2-275=Compound 93 (S-stereoisomer of XG-1-095).
Figure 5:
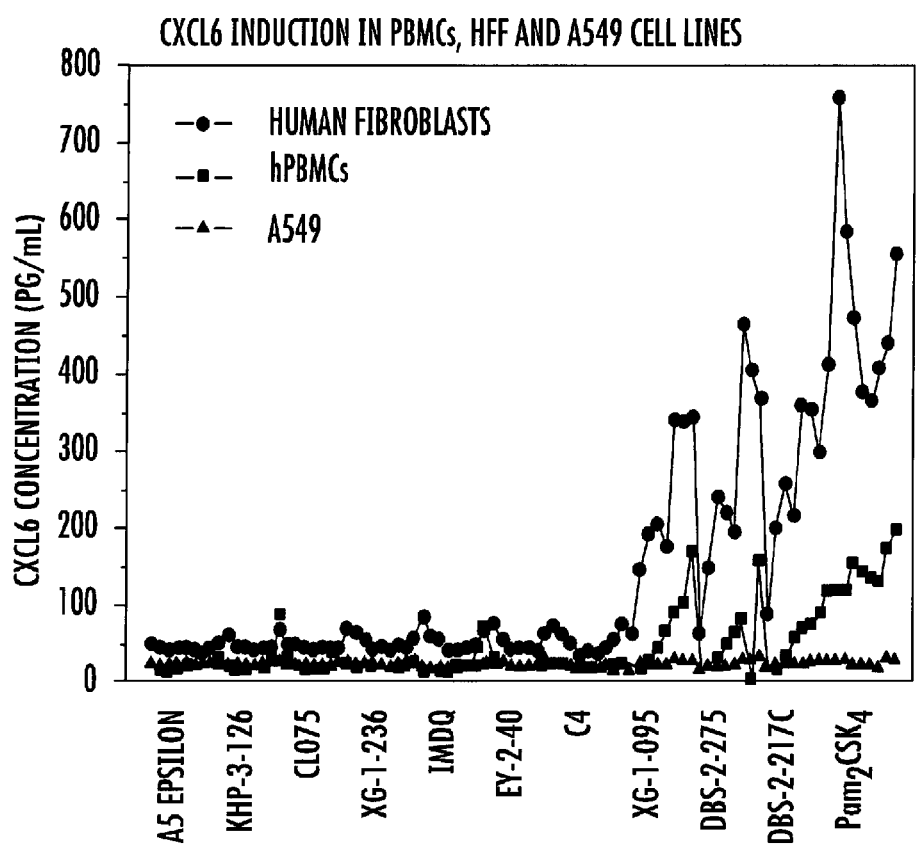
FIG. 5. is a graph showing CXCL6 induction in PBMCs, HFF and A549 cell lines. CXCL6 production was triggered only by TLR2 agonists (DBS-2-217C=Compound 52; XG-1-095=Compound 82 (R— stereochemistry); DBS-2-275=Compound 93 (S-stereoisomer of XG-1-095).
Figure 6:
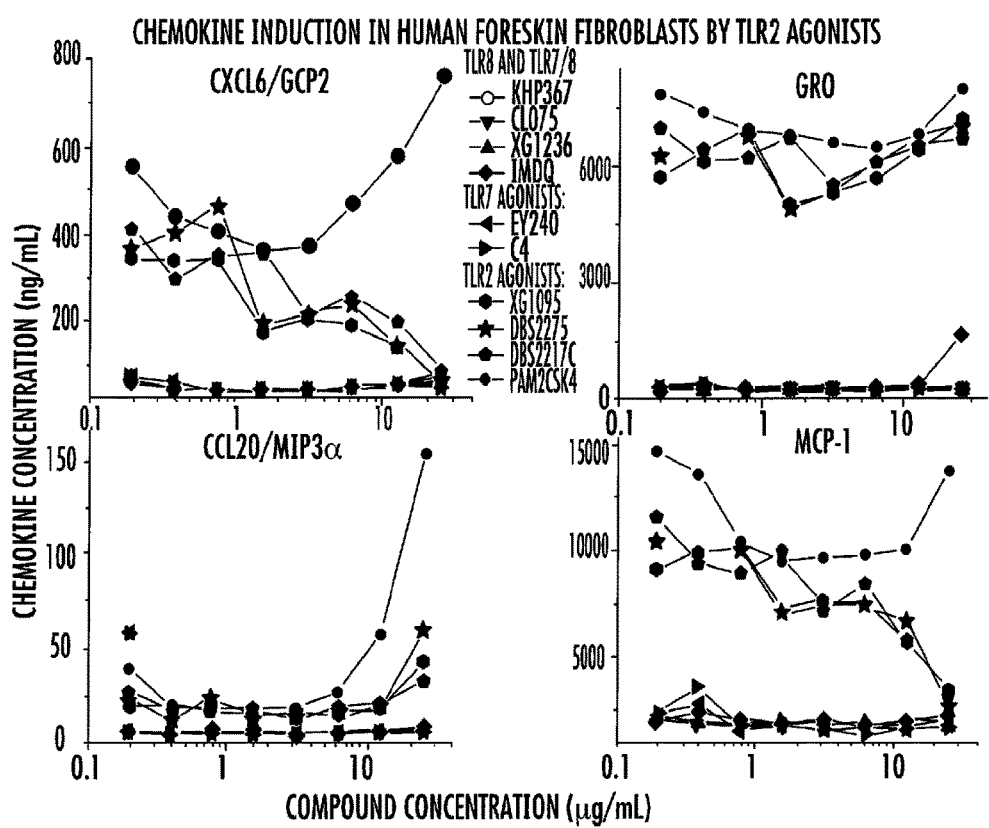
FIG. 6. are graphs showing induction of other cytokines by TLR2 agonists (DBS-2-217C=Compound 52; XG-1-095=Compound 82 (R— stereochemistry); DBS-2-275=S-stereoisomer of XG-1-095).
Figure 9:
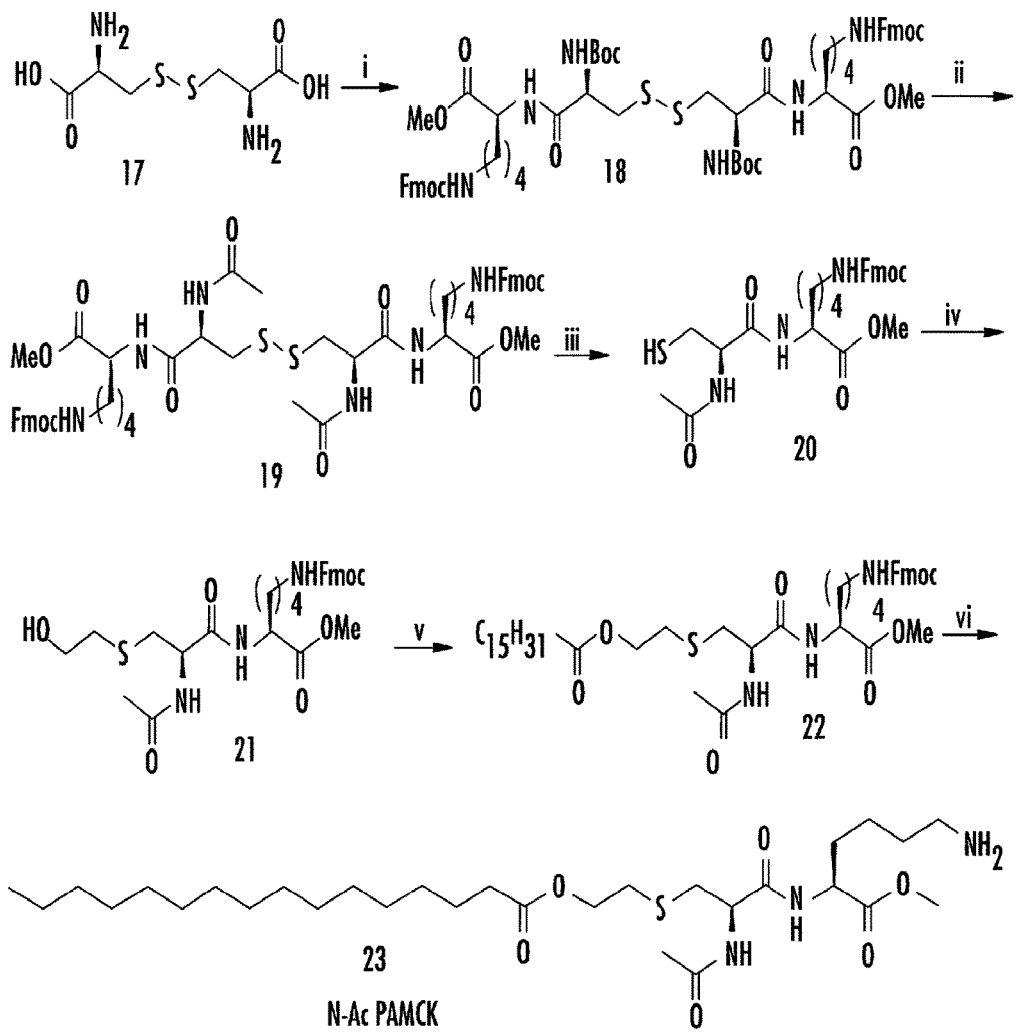
Figure 10:
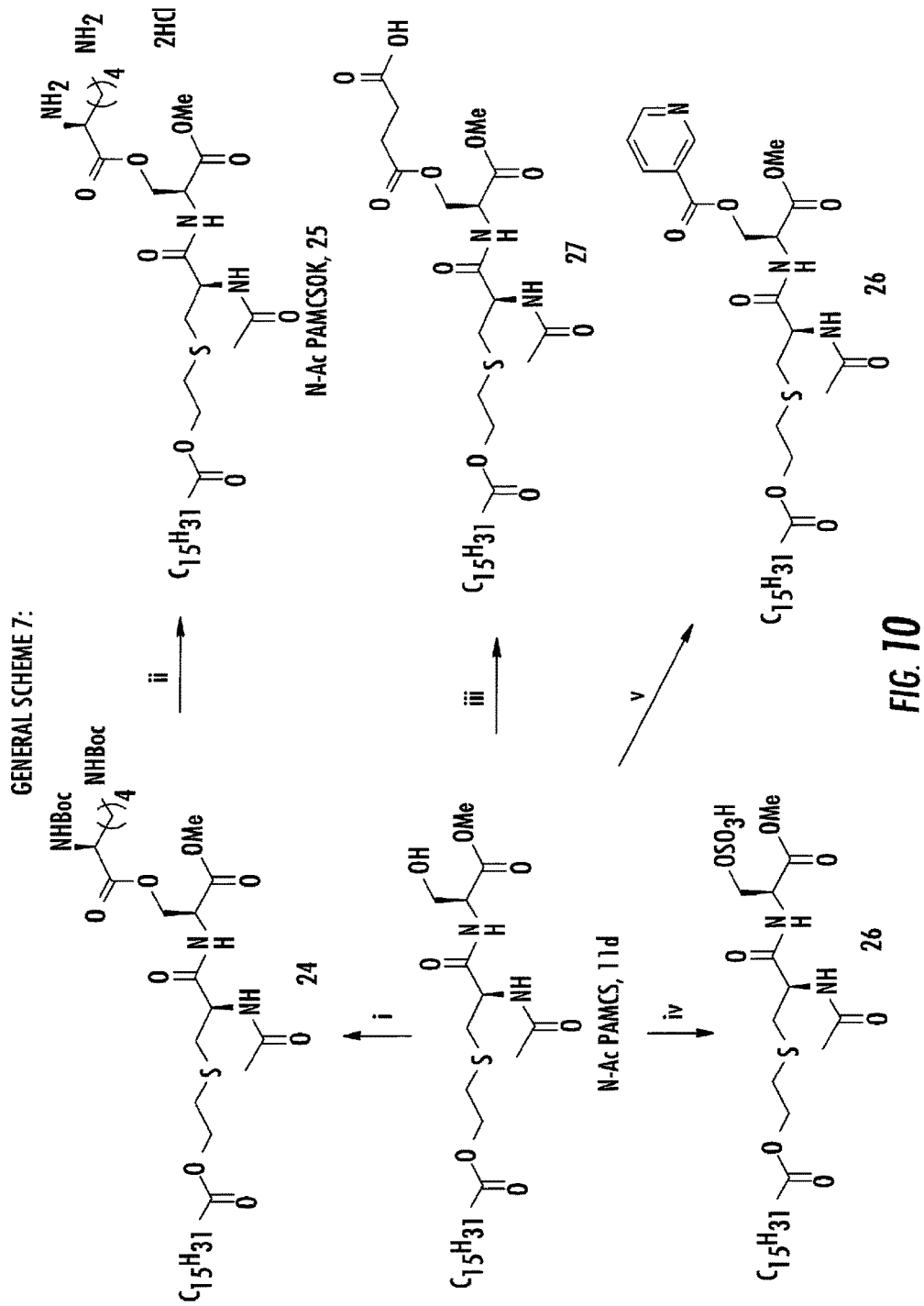

The acetylation of the cysteine amine of compound 6d, however, led to the loss of an ionizable group and, consequently, to the loss of aqueous solubility. An analogue was synthesized with the terminal serine methyl ester replaced with a lysine methyl ester (Compound 23, Scheme 6), reasoning that the ε-amine of lysine would restore water solubility. While the lysine analogue was indeed highly water soluble, a significant loss of activity of aqueous stocks within about a week was observed; mass spectrometry revealed hydrolysis of the methyl ester, presumably via an intramolecular attack of the ε-amine of lysine. To confer water solubility to compound 11d, the serine hydroxyl functionality was esterified with L-lysine, or converted to the sulfate using sulfur trioxide/pyridine complex, or converted to the meisuccinate using succinic anhydride, or coupled with nicotinic acid to furnish compounds 25-28, respectively. All the compounds retained the human specific TLR2-agonistic activity (Table 1). The lysine conjugate 25, the sulfonate 26, as well as hemisuccinate 27 were found to be exceptionally water soluble. In a direct comparison with glucopyranosyl lipid A with the diacyl, water-soluble PAM$_2$CSK$_4$ parent compound (dual murine/human TLR2-agonist) was found to be highly adjuvantic in New Zealand White rabbits. Given that the mono-acyl lipopeptides are human TLR2-specific, it was of importance to verify if we could use rabbit model for examining their adjuvanticity. It was found that the water soluble monoacyl lipopeptide 25 showed excellent induction of anti-bovine α-lactalbumin IgG responses in rabbits using a prime+single-boost model (FIG. 2).

As observed in compound 23, aqueous stocks of compound 25 were found to be unstable, and within few days a white precipitate of its parent compound 11d was observed (confirmed by TLC and LC-MS), indicating that compound 25 is a water-soluble prodrug of compound 11d.

The ester-linked palmitoyl group in 11d is also potentially hydrolytically labile. It was therefore set out to design out all of the hydrolytically labile groups in the lead molecule 11d. The ester-linked palmitoyl group was replaced with an amide (compound 34, Scheme 8), triazole (compounds 38 and 41, Scheme 9) and carbamate (compounds 45 and 48, Scheme 10)-linked long-chain alkyl groups.

Aqueous solubility in the most active carbamate derivative 48 was restored by using a dimethylaminopropylamine appended to the carboxyl group of serine in stable amide linkage (compound 52, Scheme 11, Table 1).

This human specific TLR2-agonistic lipopeptide was further covalently coupled with the highly adjuvantic, TLR7/8-active imidazoquinoline (IMDQ 53, U.S. patent application Ser. No. 13/475,284). In examining this hybrid (compound 54, Scheme 12) in primary human TLR-specific reporter gene assays, we noted that the hybrid 54 was less active than their parent compounds in both TLR2 and TLR7 cell lines.

Lipid A has been demonstrated to activate cells via Toll-like receptor 4 (TLR4), MD-2 and CD14 on the cell surface. Lipid A consists of two glucosamine units with six attached acyl chains. Among these, the four acyl chains attached directly to the glucosamine sugars are β-acyloxyacyl groups, derived from β-hydroxymyristic acid. With this observation, novel β-hydroxymyristic acid grafted lipopeptides were synthesized (Scheme 13, 14) and their TLR2/4-agonistis activities were investigated.

These continuing SAR studies on the TLR2-agonistic lipopeptide chemotype have led to the identification of new analogues possessing strong TLR2-agonistic activity that is exquisitely human TLR2-specific. It is being increasingly appreciated that significant differences between murine and non-rodent species exist not only in receptor specificity to TLR ligands, but also in the cellular responses to them. As has been observed with TLR4 ligands such as taxol, lipid IVa, and E5531, a synthetic lipid A analogue, recent evidence suggests that inter-species differences exist for TLR2 also, as exemplified by variations in specificities for lipopeptide recognition in chimeric TLR constructs. Furthermore, the coupling of these pattern recognition receptors to downstream adaptor molecules also appear to be distinct as shown by disparities in clinical outcomes in humans with IRAK-4 (interleukin-1 receptor-associated kinase 4) deficiency versus the susceptibility to pathogens in knockout mice.

As discussed above, TLR2 agonists appear unique amongst all other TLR agonists in that although the lipopeptides are devoid of any detectable pro-inflammatory activity in ex vivo human blood models (Hood, J. D. et al. *Hum. Vaccines* 2010, 6, 1-14.), or of local reactogenicity and pyrogenicity in rabbit models, it is potently adjuvantic in murine models of immunization, evidencing that this chemotype may be a safe and effective adjuvant. The human-specific TLR2-agonistic properties of the monoacyl lipopeptides precludes its evaluation in murine models, and it remains to be examined if non-rodent animal models (including non-human primates) would be suitable surrogates to evaluate the safety and efficacy of these analogues. These studies are currently underway.

What is claimed is:

1. A composition comprising a compound wherein the compound comprises the following structural formula (52)

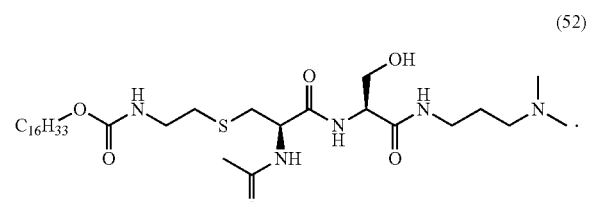

2. A method of synthesizing a compound comprising the structural formula:

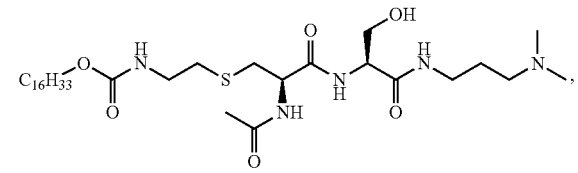

compromising protecting amines of the formula:

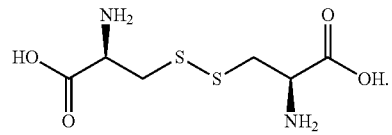

3. The method of claim 1, comprising:

protecting amine groups of a compound having the structural formula:

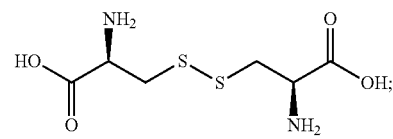 [SMILES: N[C@@H](CSSC[C@H](N)C(=O)O)C(=O)O]

producing a compound of the general structural formula:

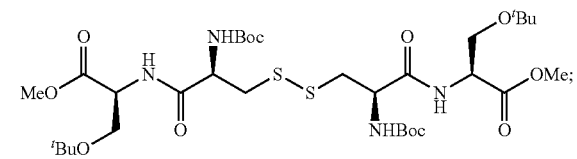 [SMILES: COC(=O)[C@H](COC(C)(C)C)NC(=O)[C@H](CSSC[C@H](NC(=O)OC(C)(C)C)C(=O)N[C@@H](COC(C)(C)C)C(=O)OC)NC(=O)OC(C)(C)C]

cleaving the product by a disulfide cleavage and producing a compound of the general formula:

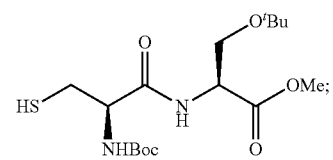

reacting the compound with an amine and producing a compound of the general formula:

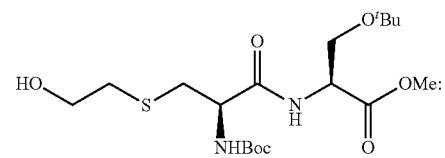

adding pyridine under conditions resulting in O-palmitoylation and producing a compound of the general formula:

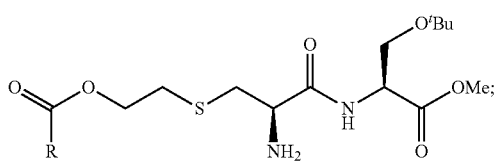

adding trifluoracetic acid to produce a compound of the general formula:

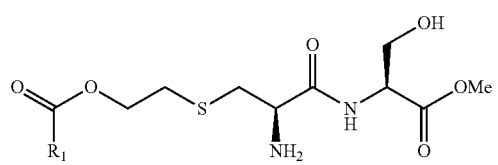

wherein
L is —C(O)—O—,
R$_1$ is C$_{14-17}$ alkyl having a formula C$_m$H$_{2m+1}$ where m is an integer from 14 to 17 R$_2$ is —CH$_2$—OH, and X is —O—.

4. The method of claim 3, wherein a compound produced is

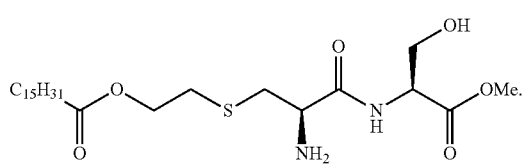

5. The method of 3, further comprising N-acetylation of

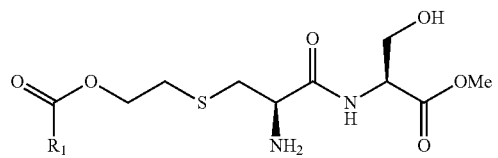

to make a compound having general formula:

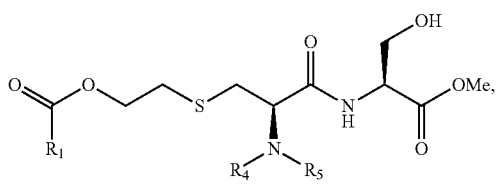

wherein R$_4$ or R$_5$ is independently selected from H, the C$_{1-20}$ alkyl, C$_{2-20}$ alkenyl, C$_{2-20}$ alkynyl, C$_{4-20}$ heterocycle, C$_{4-20}$ heteroaryl, C$_{4-20}$ alkyl heterocycle, C$_{7-20}$ alkyl heteroaryl, C$_{1-20}$ alkyoxyl, which is unsubstituted or optionally substituted with a functional group selected from the group consisting of H, —OH, —OR', —NH$_2$, —NHR', —NR'$_2$, —SH, —SR', —O—C(O)R', —C(O)R', —CF$_3$, —OCF$_3$, an amino acid side chain or peptide fragment, and is optionally interrupted by one or more O, S, or N atoms, or one or more groups selected from cycloalkyl, —C(O)—O—, —O—C(O)—, —C(O)—, —C(O)—NH—, —NH—C(O)—, —NH—C(O)—O— and —O—C(O)—NH—, and R' is selected from radicals consisting of H, heteroaryl having 1 to 4 N, O and/or S atoms, C$_{1-10}$ alkyl, C$_{2-10}$ alkenyl, C$_{2-10}$ alkynyl, C$_{4-10}$ heterocycle and C$_{4-10}$ heteroaryl.

6. The method of claim 2, wherein a compound produced is (52)

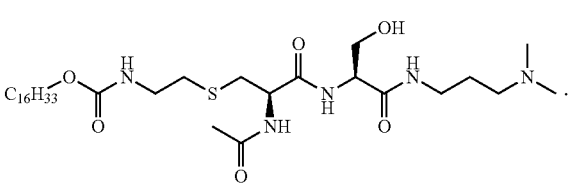

7. A composition comprising a pharmaceutically effective amount of a compound comprising:

(52)

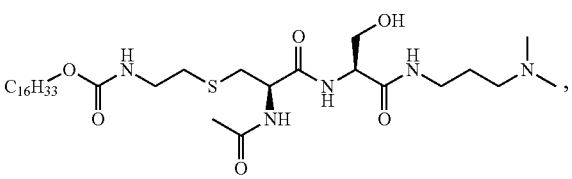

isomers or pharmaceutically acceptable salts thereof.

8. A method of using the composition according to claims 1 or 7 as a vaccine adjuvant.

9. A toll-like receptor (TLR) agonist comprising a composition of claim 1 or 7.

* * * * *